United States Patent
Yang et al.

(10) Patent No.: US 7,632,484 B2
(45) Date of Patent: *Dec. 15, 2009

(54) ETHYLENEDICYSTEINE (EC)-DRUG CONJUGATES, COMPOSITIONS AND METHODS FOR TISSUE SPECIFIC DISEASE IMAGING

(75) Inventors: David J. Yang, Sugarland, TX (US); Chun W. Liu, Sugarland, TX (US); Dong-Fang Yu, Houston, TX (US); E. Edmund Kim, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 222 days.

This patent is subject to a terminal disclaimer.

(21) Appl. No.: 11/405,334

(22) Filed: Apr. 17, 2006

(65) Prior Publication Data

US 2006/0188438 A1 Aug. 24, 2006

Related U.S. Application Data

(60) Division of application No. 09/599,152, filed on Jun. 21, 2000, now Pat. No. 7,067,111, and a continuation-in-part of application No. 09/587,583, filed on Jun. 2, 2000, now abandoned, which is a continuation-in-part of application No. 09/434,313, filed on Oct. 25, 1999, now Pat. No. 6,692,724.

(51) Int. Cl.
*A61K 51/00* (2006.01)
*A61M 36/14* (2006.01)

(52) U.S. Cl. .............. 424/1.65; 424/1.11; 424/1.73; 424/1.69; 206/569; 534/14

(58) Field of Classification Search .......... 424/1.11, 424/1.37, 1.49, 1.65, 1.73, 1.81, 1.85, 1.89, 424/9.1, 9.2, 9.3, 9.4, 9.5, 9.6, 9.7, 9.8; 206/223, 206/569, 570; 534/7, 10–16; 530/300, 311, 530/312, 317
See application file for complete search history.

(56) References Cited

U.S. PATENT DOCUMENTS

| | | | |
|---|---|---|---|
| 4,141,654 A | 2/1979 | Wardlaw et al. .......... 356/243.1 |
| 4,181,654 A | 1/1980 | Weitl et al. ................... 260/239 |
| 4,279,992 A | 7/1981 | Boguslasi et al. .......... 435/7.72 |
| 4,418,068 A | 11/1983 | Jones ......................... 514/337 |
| 4,507,466 A | 3/1985 | Tomalia et al. .............. 528/332 |
| 4,558,120 A | 12/1985 | Tomalia et al. .............. 528/363 |
| 4,568,737 A | 2/1986 | Tomalia et al. .............. 528/332 |
| 4,587,329 A | 5/1986 | Tomalia et al. .............. 528/363 |
| 4,631,337 A | 12/1986 | Tomalia et al. .............. 528/391 |
| 4,694,064 A | 9/1987 | Tomalia et al. .............. 528/332 |
| 4,713,975 A | 12/1987 | Tomalia et al. ............. 73/865.8 |
| 4,730,968 A | 3/1988 | Diperstein et al. .......... 411/178 |
| 4,732,863 A | 3/1988 | Tomasi et al. .............. 424/1.53 |
| 4,737,550 A | 4/1988 | Tomalia ..................... 525/418 |
| 4,789,542 A | 12/1988 | Goodman et al. .......... 424/1.73 |
| 4,824,659 A | 4/1989 | Hawthorne ................. 424/1.53 |
| 4,832,940 A | 5/1989 | Ege ............................ 424/1.41 |
| 4,857,599 A | 8/1989 | Tomalia et al. .............. 525/259 |
| 4,861,869 A | 8/1989 | Nicolotti et al. ............ 424/1.53 |
| 4,871,779 A | 10/1989 | Killat et al. .................... 521/28 |
| 4,925,650 A | 5/1990 | Nosco et al. ................ 424/1.65 |
| 4,965,392 A | 10/1990 | Fritzberg et al. ............ 558/254 |
| 4,988,496 A * | 1/1991 | Srinivasan et al. ......... 424/1.53 |
| 5,013,556 A | 5/1991 | Woodle et al. ............... 424/450 |
| 5,071,965 A | 12/1991 | Dunn et al. .................... 534/14 |
| 5,087,616 A | 2/1992 | Myers et al. ................... 514/21 |
| 5,108,921 A | 4/1992 | Low et al. .................... 435/375 |
| 5,164,294 A | 11/1992 | Skold et al. .................. 435/7.5 |
| 5,242,679 A * | 9/1993 | Fritzberg et al. ............ 424/1.53 |
| 5,268,163 A | 12/1993 | Verbruggen ................... 534/14 |
| 5,279,811 A | 1/1994 | Bergstein et al. ........... 424/1.65 |
| 5,356,793 A | 10/1994 | Koezuka et al. ............... 435/32 |
| 5,412,072 A | 5/1995 | Sakurai et al. .............. 530/322 |
| 5,416,016 A | 5/1995 | Low et al. .................... 435/375 |
| 5,474,756 A | 12/1995 | Tweedle et al. ........... 424/9.363 |
| 5,517,993 A | 5/1996 | Unger et al. ................ 600/410 |
| 5,534,241 A | 7/1996 | Torchilin et al. ......... 424/9.321 |
| 5,541,287 A | 7/1996 | Yau et al. .................... 530/317 |

(Continued)

FOREIGN PATENT DOCUMENTS

EP 1156091 11/2001

(Continued)

OTHER PUBLICATIONS

Mang'era et al, Journal of Labelled Compounds & Radiopharmaceuticals (Aug. 5, 1999), 42(7), pp. 683-699.*

(Continued)

*Primary Examiner*—D L Jones
(74) *Attorney, Agent, or Firm*—Fulbright & Jaworski LLP

(57) ABSTRACT

The invention provides, in a general sense, a new labeling strategy employing $^{99m}$Tc chelated with ethylenedicysteine (EC). EC is conjugated with a variety of ligands and chelated to $^{99m}$Tc for use as an imaging agent for tissue-specific diseases. The drug conjugates of the invention may also be used as a prognostic tool or as a tool to deliver therapeutics to specific sites within a mammalian body. Kits for use in tissue-specific disease imaging are also provided.

38 Claims, 89 Drawing Sheets

U.S. PATENT DOCUMENTS

| | | | |
|---|---|---|---|
| 5,601,800 A | 2/1997 | Katti et al. | 424/1.77 |
| 5,605,671 A | 2/1997 | Lyle et al. | 424/1.41 |
| 5,605,672 A | 2/1997 | Bogdanov et al. | 424/1.65 |
| 5,608,060 A | 3/1997 | Axworthy et al. | 540/474 |
| 5,620,675 A | 4/1997 | McBride et al. | 424/1.69 |
| 5,635,382 A | 6/1997 | Low et al. | 435/458 |
| 5,635,603 A | 6/1997 | Hansen et al. | 530/391.5 |
| 5,643,883 A | 7/1997 | Marchase et al. | 514/23 |
| 5,648,063 A | 7/1997 | Gries et al. | 424/9.363 |
| 5,670,132 A | 9/1997 | Griffiths et al. | 424/1.11 |
| 5,674,470 A | 10/1997 | Tweedle et al. | 424/9.363 |
| 5,688,487 A | 11/1997 | Linder et al. | 424/1.65 |
| 5,688,488 A | 11/1997 | Low et al. | 424/1.69 |
| 5,716,596 A | 2/1998 | Dean et al. | 424/1.69 |
| 5,730,968 A | 3/1998 | Butterfield et al. | 424/78.37 |
| 5,820,847 A | 10/1998 | Low et al. | 424/9.1 |
| 5,830,431 A | 11/1998 | Srinivasan et al. | 424/1.69 |
| 5,834,266 A | 11/1998 | Crabtree et al. | 435/456 |
| 5,846,519 A | 12/1998 | Tweedle et al. | 424/9.363 |
| 5,847,121 A | 12/1998 | Yau et al. | 540/474 |
| 5,877,289 A | 3/1999 | Thorpe et al. | 530/387.1 |
| 5,880,281 A | 3/1999 | Argese et al. | 540/474 |
| 5,891,468 A | 4/1999 | Martin et al. | 424/450 |
| 5,908,777 A | 6/1999 | Lee et al. | 435/320.1 |
| 5,951,964 A | 9/1999 | Dean et al. | 424/1.69 |
| 5,955,053 A | 9/1999 | Marzilli et al. | 424/1.11 |
| 5,958,374 A | 9/1999 | Meares et al. | 424/1.65 |
| 5,977,163 A | 11/1999 | Li et al. | 514/449 |
| 5,986,074 A | 11/1999 | Marzilli et al. | 534/14 |
| 6,033,884 A | 3/2000 | Woo et al. | 435/455 |
| 6,054,436 A | 4/2000 | Crabtree et al. | 514/31 |
| 6,071,490 A | 6/2000 | Griffiths et al. | 424/1.49 |
| 6,071,533 A | 6/2000 | Papahadjopoulos et al. | 424/450 |
| 6,083,741 A | 7/2000 | Hart et al. | 435/320.1 |
| 6,113,946 A | 9/2000 | Szoka, Jr. et al. | 424/486 |
| 6,143,274 A | 11/2000 | Tweedle et al. | 424/1.65 |
| 6,177,551 B1 | 1/2001 | Kasina | 534/10 |
| 6,187,286 B1 | 2/2001 | Elmaleh et al. | 424/1.73 |
| 6,197,278 B1 | 3/2001 | Bainkenberg et al. | 424/1.69 |
| 6,232,295 B1 | 5/2001 | Kayyem et al. | 514/44 |
| 6,251,866 B1 | 6/2001 | Prakash et al. | 514/17 |
| 6,262,107 B1 | 7/2001 | Li et al. | 514/449 |
| 6,440,389 B1 | 8/2002 | Rabito | 424/9.6 |
| 6,521,209 B1 | 2/2003 | Meade et al. | 424/9.3 |
| 6,613,305 B1 | 9/2003 | Collins et al. | 424/1.73 |
| 6,656,450 B2 | 12/2003 | Hubin et al. | 424/9.363 |
| 6,692,724 B1* | 2/2004 | Yang et al. | 424/1.49 |
| 6,713,046 B1 | 3/2004 | Meade | 424/9.363 |
| 6,737,247 B2 | 5/2004 | Bogdanov et al. | 435/25 |
| 7,067,111 B1* | 6/2006 | Yang et al. | 424/9.1 |
| 7,121,926 B2 | 10/2006 | Sabde | 451/41 |
| 7,223,380 B2* | 5/2007 | Yang et al. | 424/9.4 |
| 7,229,604 B2* | 6/2007 | Yang et al. | 424/9.1 |
| 7,261,875 B2* | 8/2007 | Li et al. | 424/1.69 |
| 2001/0034363 A1 | 10/2001 | Li et al. | 514/449 |
| 2001/0041189 A1 | 11/2001 | Xu | 424/488 |
| 2003/0013772 A1 | 1/2003 | Murphy et al. | 514/674 |
| 2003/0152512 A1 | 8/2003 | Rajopadhye et al. | 424/1.49 |
| 2003/0206865 A1 | 11/2003 | Platzek et al. | 424/9.363 |
| 2006/0182687 A1 | 8/2006 | Yang et al. | 424/9.364 |

FOREIGN PATENT DOCUMENTS

| | | |
|---|---|---|
| WO | WO 91/16076 | 10/1991 |
| WO | WO 99/56792 | 10/1991 |
| WO | WO 95/28966 | 11/1995 |
| WO | WO 97/33552 | 9/1997 |
| WO | WO 98/08859 | 3/1998 |
| WO | WO 99/39748 | 8/1999 |
| WO | WO 99/49901 | 10/1999 |
| WO | WO 99/61512 | 12/1999 |
| WO | WO 00/45857 | 8/2000 |
| WO | WO 00/53233 | 9/2000 |
| WO | WO 00/61788 | 10/2000 |
| WO | WO 01/80906 | 11/2001 |
| WO | WO 01/91807 | 12/2001 |
| WO | WO 02/06209 | 1/2002 |
| WO | WO 02/43775 | 6/2002 |
| WO | WO 03/009874 | 2/2003 |
| WO | WO 03/051403 | 6/2003 |
| WO | WO 2006/016784 | 5/2006 |

OTHER PUBLICATIONS

Qu et al, Radiochemica Acta, 1993, vol. 63, pp. 209-212.*

Skrzypczak-Jankun et al, "Structure of the hirugen and hirulog 1 complexes of α-thrombin," *J. Mol. Biol.*, 221:1379-1393, 1991.

Tjuvajev et al., "Comparison of radiolabeled nucleoside probes (FIAU, FHGB, and FHPG) for PET imaging of HSV1-tk gene expression," *J. Nucl. Med.*, 43:1072-1083, 2002.

Walsh et al., "Noninvasive estimation of regional myocardial oxygen consumption by positron emission tomography with carbon-11 acetate in patients with myocardial infaction," *J. Nucl. Med.*, 30:1798-1808, 1989.

Weir et al, "Prognostic value of single-photon emission tomography in acute ischaemic strike," *Eur. Journ. Nuc. Med.*, 24:21-26, 1989.

Israeli Office Action, issued in International Application No. PCT/US01/180602, dated Dec. 7, 2007.

Polish Office Action, issued in International Application No. PCT/US01/180602, dated Dec. 7, 2007.

Yang et al., "Noninvasive Assessment of tumor hypoxia with 99-m-tc labeled metronidazole," *Pharm. Res.*, 16:743-750, 1999.

U.S. Appl. No. 10/627,763, filed Jul. 28, 2003, Lin.

U.S. Appl. No. 11/737,694, filed Apr. 19, 2007, Yang.

U.S. Appl. No. 60/828,347, filed Oct. 5, 2006, Yang.

Aime et al., "Ternary Gd(III)L-HAS adducts: evidence for the replacement of inner-sphere water molecules by coordinating groups of the protein, implications for the design of contrast agents for MRI," *J. of Biol. Inorg. Chem.*, 5:488-497, 2000.

Alper et al., "Assessment of renal functional changes following transurethral prostatectomy suing tc-99m ethylenedicysteine," *J. Nuclear Med.*, 37:289P, Abstract No. 1292, 1996.

Angello et al., "Effect of eating on thallium-201 myocardial redistribution after myocardial ischemia," *Am. J. Cardiol.*, 60:528-533, 1987.

Benveniste and Davies, "Aminoglycoside antibiotic-inactivating enzymes in actinomycetes similar to those present in clinical isolates of antibiotic-resistant bacteria," *Proc. Natl. Acad. Sci USA*, 70:2276-2280, 1973.

Borchardt et al., "Targeted actinium-225 in vivo generators for therapy of ovarian cancer," *Cancer Research*, 63:5084-5090, 2003.

Borodina et al., "Metabolic network analysis of Streptomyces tenebrarius, a Streptomyces species with an active entner-doudoroff pathway," *Appl. Environ. Microb.*, 71:2294-2302, 2005.

Boschi et al., "A CD(4)/T(4) receptor peptide ligand labeled with technetium-99m: synthesis and biological activity," *Nucl. Med. Biol.*, 27:791-795, 2000.

Botta et al., "NMR relaxometric study of new $Gd^{III}$ macrocyclic complexes and their interaction with human serum albumin," *Organic & Biomolecular Chemistry*, 2:570-577, 2004.

Brouwers et al., "Optimization of radioimmunotherapy of renal cell carcinoma: labeling of monoclonal antibody cG250 with $^{131}I$, $^{90}I$, $^{177}Lu$, or $^{186}Re$," *J. Nucl. Med.*, 45:327-337, 2004.

Canet et al., "Kinetic characterization of CMD-A2-Gd-DOTA as an intravascular contrast agent for myocardial perfusion measurement with MRI," *Magentic Resonance in Medicine*, 43:403-409, 2000.

Chappell et al., "Synthesis, characterization, and evaluation of a novel bifunctional chelating agent for the lead isotopes $^{203}Pb$ and $^{212}Pb$," *Nucl. Med. Biol.*, 27:93-100, 2000.

Chmura et al., "Electrophilic chelating agents for irreversible binding of metal chelates to engineered antibodies," *J. of Controlled Release*, 78:249-258, 2002.

Connett et al., "Maximum tolerated dose and large tumor radioimmunotherapy studies of 64Cu-labeled monoclonal antibody 1A3 in a colon cancer model," *Clin. Cancer Res.*, 5(10 Suppl):3207s-3212s, 1999.

Connett et al., "Radioimmunotherapy with a 64Cu-labeled monoclonal antibody: a comparison with 67Cu," *Proc. Natl. Acad. Sci. USA*, 93:6814-6818, 1996.

Corsi et al., "Inulin as a carrier for contrast agents in magnetic resonance imaging," *Chem.*, 7:64-71, 2001.

Cronin et al., "A new class of macrocycle capable of binding exogenous metals: synthesis, structure, magnetic and electrochemical properties of a Cu(II) trinuclear complex based upon 1,4,8,11-tetraazacyclotetradecane-2,3-dione [exoO(2)]cyclam," *J. Chem. Soc., Dalton Transactions*, 12:1925-1927, 1999.

Cutler et al., "Dosimetry of copper-64-labeled monoclonal antibody 1A3 as determined by PET imaging of the torso," *J. Nucl. Med.*, 36:2363-2371, 1995.

Das et al., "[186/188 Re] rhenium-ethylene dicysteine (Re-Ec): preparation and evaluation for possible use in endovascular brachytherapy," *Nucl. Med. Biol.*, 27:189-197, 2000.

DeNardo et al., "Enhancement of 67Cu-2IT-BAT-LYM-1 therapy in mice with human Burkitt's lymphoma (Raji) using interleukin-2," *Cancer*, 80(12 Suppl):2576-2582, 1997.

Diamond et al., "Glycolysis in quiescent cultures of 3T3 cells. Stimulation by serum, epidermal growth factor, and insulin in intact cells and persistence of the stimulation after cell homogenization," *J. Biol. Chem.*, 253:866-871, 1978.

Drapé et al., "Intraarticular diffusion of Gd-DOTA after intravenous injection in the kneww: MR imaging evaluation," *Radiology*, 188:227-234, 1993.

Edreira et al., "Optimization of the small-scale synthesis of DOTA-Tyr$^3$-octreotide," *Nuclear Medicine Communications*, 23:493-499, 2002.

Ellis and Sharma, "Co, Fe and Ga chelates for cell labelling: a potential use in PET imaging?" *Nuclear Medicine Communications*, 20:1017-1021, 1999.

Froidevaux et al., "Preclinical comparison in AR4-2J tumore bearing mice of four radiolabeled 1,4,7,10-tetraazacyclododecane-1,4,7,10-tetraacetic acid somatostatin analogs for tumor diagnosis and internal radiotherapy," *Endocrinology*, 141:3304-3312, 2000.

Green and Wuts, Chapter 1, 1999.
Green and Wuts, Chapter 2, 1999.
Green and Wuts, Chapter 4, 1999.
Green and Wuts, Chapter 5, 1999.
Green and Wuts, Chapter 6, 1999.
Green and Wuts, Chapter 7, 1999.

Gregson et al., "meso-5,5,7,12,14-Hexamethyl-1,4,8,11-tetraazacyclotetradecane as a building block in supramolecular chemistry; salts formed with 2,2'-biphenol, 4,4'-thiodiphenol, 4,4'-sulfonyldiphenol, 3-and 4-hydroxybenzoic acids, 3,5-dihydroxybenzoic acid and phenylphosphonic acid; supramolecular structures in zero, one, two and three dimensions," *Acta Crystallogr.*, B56:39-57, 2000.

Griffiths et al., "$^{90}$Y-DOTA-hLL2: an agent for radioimmunotherapy of Non-Hodgkin's lymphoma," *J. Nucl. Med.*, 44:77-84, 2003.

Gutman et al., Time to completed redistribution of thallium-201 in exercise myocardial scintigraphy: relationship to the degree of coronary artery stenosis, *Am. Heart J.*, 106:989-995, 1983.

Henson et al., "Gadolinium-enhanced CT angiography of the circle of Willis and neck," *AJNR Am. J. Neuroradiol.*, 25:969-972, 2004.

Hoelscher et al., "Effects of very high antibiotic concentrations on human intervertebral disc cell proliferation, viability, and metabolism in vitro," *Spine*, 25:1871-1877, 2000.

Honess et al., "Preclinical evaluation of the novel hypoxic marker $^{99m}$Tc-HL91 (prognox) in murine and xenograft systems in vivo," *Int. J. Radiation Oncology Biol. Phys.*, 42:731-735, 1998.

Hostetler and Hall, "Inhibition of kidney lysosomal phospholipases A and C by aminoglycoside antibiotics: possible mechanism of aminoglycoside toxicity," PNAS, 79:1663-1667, 1982.

Hu, "Neomycin inhibits angiogenin-induced angiogenesis," *Proc. Natl. Acad. Sci. USA*, 95:9791-9795, 1998.

Im et al., "Formation, properties, and characterization of a fully reduced Fe(II)Fe(II) form of spinach (and parsley) [2Fe-2S] ferredoxin with the macrocyclic complex [Cr(15-aneN(4))(H(2)O)(2)](2+) as reductant," *Inorg. Chem.*, 36:1388-1396, 1997.

Im et al., "The Cr$^{II}$L reduction of [2Fe-2S] ferredoxins and site of attachment of Cr$^{III}$ using $^1$H NMR and site-directed mutagenesis," *Inorg. Chem.*, 39:1755-1764, 2000.

Ito et al., "PET and planar imaging of tumor hypoxia with labeled metronidazole," *Acad. Radiol.*, 13:598-609, 2006.

Kao et al., "Role of radioisotope penile plethysmigraphy in the evaluation of penile hemodynamic of impotent patients," *J. Nuclear Med.*, 37:292P, Abstract No. 1304, 1996.

Kao et al., "Technetium-99m methoxyisobutylisonitrile chest imaging of small cell lung carcinoma," *Cancer*, 83:64-68, 1998.

King et al., "Imaging of bone infection with labelled white bloo cells: role of contemporaneous bone marrow imaging," *European Journal of Nuclear Medicine*, 17:18-151, 1990.

Kitamura and Shibata, "Preparation and the covalent hydration of a hexafluoro-2,4-pentanedionatotetraaminecobalt(III) complex," *Inorganica Chimica Acta*, 203:37-42, 1993.

Knight et al., "Radiolabeling of fibrinogen using the Iodogen technique," *Throm. Res. Cen. Dept. Biochem.*, pp. 593-596, 1982.

Kundra et al., "Noninvasive monitoring of somatostatin receptor type 2 chimeric gene transfer," *J. Nucl. Med.*, 43:406-412, 2002.

Laissy et al., "Functional evaluation of normal and ischemic kidney by means of gadolinium-DOTA enhanced TurboFLASH MR imaging: a preliminary comparison with 99Tc-MAG3 dynamic scintigraphy," *Magn. Reson. Imaging*, 12:413-419, 1994.

Lewis et al., "Conjugation of monoclonal antibodies with TETA using activated esters: biological comparison of 64Cu-TETA-1A3 with 64Cu-BAT-2IT-1A3," Cancer Biother. Radiopharm., 16:483-94, 2001.

Li et al., "N,N' Ethylenedi-$_L$-cysteine (EC) and its metal complexes: synthesis, characterization, crystal structures, and equilibrium constants," *Inorg. Chem.*, 35:404-414, 1996.

Li et al., "Vinyl sulfone bifunctional derivatives of DOTA allow sulfhydryl- or amino-directed coupling to antibodies. Conjugates retain immunoreactivity and have similar biodistributions," *Bioconjugate Chem.*, 13:110-115, 2002.

Luckay et al., "Synthesis and structure of a complex of bismuth(III) with nitrogen donor macrocycle," *Journal of the Chemical Society, Chem. Comm.*, 2365-2366, 1995.

Michalik et al., "Effect of various aminoglycoside antibiotics on glucose formation in isolated rabbit kidney-cortex tubules ," *Pharmacol. Res.*, 21:405-414, 1989.

Murakami et al., "Calcium hydroxide ameliorates tobramycin toxicity in cultured chick tibiae," *Bone*, 21:411-418, 1997.

Murakami et al., "Interaction of tobramycin and pH in cultured chick tibiae," *J. Orthop. Res.*, 14:742-748, 1996.

Myszka et al., "Synthesis and induction of apoptosis in B cell chronic leukemia by diosgenyl 2-amino-2-deoxy-beta-D-glucopyranoside hydrochloride and its derivatives," *Carb. Res.*, 338:133-141, 2003.

Nakae and Nakae, "Diffusion of aminoglycoside antibiotics across the outer membrane of Escherichia coli," *Antimicrobial Agents and Chemo.*, 22:554-559, 1982.

Ohtsuki et al., "Technetium-99m HYNIC-annexin V: a potential radiopharmaceutical for the in-vivo detection of apoptosis," *Eur. J. Nucl. Med.*, 26:1251-1258, 1999.

Ozmen et al., "Effects of some antibiotics on activity of glucose-6-phosphate dehydrogenase from human erythrocytes in vitro and effect of isepamicin sulfate on activities of antioxidant enzymes in rat erythrocytes," *Drug Chem. Toxicol.*, 28:433-445, 2005.

Panneerselvam et al., "(12-hydroxymethyl-5,5,7,12,14-pentamethyl-1,4,8,11-tetraazacyclo-tetradecane-$N$-acetato-$N,N',N'',N'''$, $0,0'$)cobalt(III) chloride perchlorate monohydrate," *Acta Crystallogr.,C* 56:659-660, 2000.

Philpott et al., "RadioimmunoPET: detection of colorectal carcinoma with positron-emitting copper-64-labeled monoclonal antibody," *J. Nucl. Med.*, 36:1818-1824, 1995.

Pohost et al., "Differentiation of transiently ischemic from infarcted myocardium by serial imaging after a single dose of thallium-201 ," *Circulation*, 55:294-302, 1977.

Ranganathan et al., "Polymethylated DOTA ligands. 2. synthesis of rigified lanthanide chelates and studies on the effect of alkyl substitution on conformational mobility and relaxivity," *Inorg. Chem.*, 41:6856-6866, 2002.

Ruegg et al., "Improved in vivo stability and tumor targeting of bismuth-labeled antibody," *Cancer research*, 50:4221-4226, 1990.

Schechter et al., "Assessment of epidermal growth factor receptor with 99mTc-ethylenedicysteine-C225 monoclonal antibody," *Anticancer Drugs*, 14:49-56, 2003.

Schechter et al., "Radiation dosimetry of 99mTc-labeled C225 in patients with squamous .cell carcinoma of the head and neck," *J. Nucl. Med.*, 45:1683-1687.

Sharkey et al., "Radioimmunotherapy of Non-Hodgkin's lymphoma with $^{90}$Y-DOTA humanized anti-CD22 IgG ($^{90}$Y-Epratuzumab): do tumor targeting and dosimetry predict therapeutic response?" *J. Nucl. Med.*, 44:2000-2018, 2003.

Silverman et al., "Evaluating tumor biology and oncological disease with positron-emission tomography," *Seminars in Radiation Oncology*, 8:183-196, 1998.

Smith et al., "Radiochemical investigations of $^{177}$Lu-DOTA-8-Aoc-BBN[7-14]NH$_2$: an in vitro/in vivo assessment of the targeting ability of this new radiopharmaceutical for PC-3 human prostate cancer cells," *Nuclear Medicine and Biol.*, 30:101-109, 2003.

Song et al., "Prognostication of recovery in patients with acute ischemic stroke through the use of brain SPECT with Technetium-99m—labeled metronidazole," *Stroke*, 34:982-986, 2003.

Srivastava et al., "Comparative evaluation of chelating agents on the mobilization of cadmium: a mechanistic approach," *J. Toxicology and Environmental Health*, 47:173-182, 1996.

Stein et al., "Radioimmunotherapy of a human lung cancer xenograft with monoclonal antibody RS7: evaluation of $^{177}$Lu and comparison of its efficacy with that of $^{90}$Y and residualizing $^{131}$I," *J. Nucl. Med.*, 42:967-974, 2001.

Tachibana et al., "Inhibitory effects of kanamycin on glycolysis in cochlea and kidney-possible involvement in the formation of oto- and nephrotoxicities," *Biochem. Pharmacol.*, 25:2297-2301, 1976.

Tod et al., "Clinical pharmacokinetics and pharmacodynamics of isepamicin," *Clin. Pharmacokinet.*, 38:205-223, 2000.

Vogler et al., "Pre-clinical evaluation of gadobutrol: a new, neutral, extracellular contrast agent for magnetic resonance imaging," *Eur. J. Radiol.*, 21:1-10, 1995.

Vriens et al., "The use of technetium $^{99m}$Tc annexin V for in vivo imaging of apoptosis during cardiac allograft rejection," *J. Thorac. Cardiovasc. Surg.*, 116.844-853,1998.

Wang et al., "[Cu(L)Mn(N$_3$)2]$_n$: the first complex containing both macrocyclic oxamido and alternate (mu-1,1 and mu-1,3) azido bridges," *Inorg. Chem.*, 43:852-854, 2004.

Wu et al., "High-resolution microPET imaging of carcino-embryonic antigen-positive xenografts by using a copper-64-labeled engineered antibody fragment," *Proc. Nat. Acad. Sci. USA*, 97:8495-8500, 2000.

Wu et al., "Investigations of N-linked macrocycles for 111In and 90Y labeling of proteins," *Nucl. Med. & Biol.*, 19:239-244, 1992.

Wu et al., "Using Tc-99m DMSA renal cortex scan to detect renal damage in women with type 2 diabetes," *J. Diabetes Complications*, 17:297-300, 2003.

Yanai et al., "Amplification of the entire kanamycin biosynthetic gene cluster during empirical strain improvement of Streptomyces kanamyceticus," *Proc. Natl. Acad. Sci. USA*, 103:9661-9666, 2006.

Yang and Kim, "Tracer development and hybrid imaging," *Eur. J. Nucl. Med. Mol. Imaging*, 32:1001-1002, 2005.

Yang et al., "(99m)Tc-EC-guanine: synthesis, biodistribution, and tumor imaging in animals," *Pharm. Res.*, 22:1471-1479, 2005.

Yang et al., "Assessment of antiangiogenic effect using 99mTc-EC-endostatin," *Cancer Biother. Radiopharm.*, 17:233-245, 2002.

Yang et al., "Assessment of cyclooxygense-2 expression with 99mTc-labeled celebrex," *Anticancer drugs*, 15:255-263, 2004.

Yang et al., "Imaging with 99mTc ECDG targeted at the multifunctional glucose transport system: feasibility study with rodents," *Radiology*, 226:465-473, 2003.

Yang et al., "In vivo and in vitro measurement of apoptosis in breast cancer cells using (99m)Tc-EC-annexin V," *Cancer Biotherapy*, 16:73-83, 2001.

Yang et al., "Metabolic pathways that mediate inhibition of hypothalamic neurons by glucose," *Diabetes*, 53:67-73, 2004.

Yang et al., "Targeted molecular imaging in oncology," *Ann. Nucl. Med.*, 20:1-11, 2006.

Zhang et al., "A ferromagnetically coupled CrCu$_3$ tetramer and GdCu$_4$ pentamer with a [15]N$_4$ macrocylic ligand incorporating an oxamido bridge," *Inorg. Chem.*, 42:1462-1466, 2003.

Zhao et al., "Effects of Dextranation on the pharmacokinetics of short peptides. a PET study on mEGF," *Bioconjugate Chem.*, 10:938-946, 1999.

Zhou et al., "Efficient intracellular delievery of oligonucleotides formulated in folate receptor-targeted lipid vesicles," *Bioconjugate Chem.*, 13:1220-1225, 2002.

Abrams et al., "Technetium-*99m*-human polyclonal IgG radiolabeled via the hydrazino nicotinamide derivative for imaging focal sites of infection in rats," *J. Nucl. Med.*, 31:2022-2028, 1990.

Alauddin and Conti, "Synthesis and preliminary evaluationo f9-(4-{18F]-Fluoro-3-Hydroxymethylbutyl)guanine ([18F]FHBG): a new potential imaging agent for viral infection and gene therapy," *Nucl. Med. Biol.*, 25:175-180, 1998.

Alauddin et al., "9-[(3-18F]-fluoro-1-hydroxy-2-propoxy)methyl]guanine ([18F]-FHPG): a potential imaging agent of viral infection and gene therapy using PET," *Nucl. Med. Biol.*, 23:787-792, 1996.

Alauddin et al., "Evaluation of 9-[(3-18F]-fluoro-1-hydroxy-2-propoxy)methyl]guanine ([18F]-FHPG) in vitro and in vivo as probe for PET imaging of gene incorporation and expression in tumors," *Nucl. Med. Biol.*, 26:371-376, 1999.

Alauddin et al., "Receptor mediated uptake of a radiolabeled contrast agent sensitive to β-galactosidase activity," *Nucl. Med Biol.*, 30:261-265, 2002.

Alper et al., "Assessment of renal functional changes following transurethral prostatectomy suing tc-99m ethylenedicysteine," *J. Nuclear Med.*, 37:289P, Abstract No. 1292, 1996.

Anderson et al., "Copper-64-Labeled Antibodies for PET Imaging," *J. Nuclear Medicine*, 33:1685-1691, 1992.

Anderson et al., "N,N'-ethylene-di-1-cysteine (ec) complexes of ga(III) and In (III): molecular modeling, thermodynamic stability and in vivo studies," *Nucl. Med. Biol.*, 22:165-173, 1995.

Anderson et al., "Preparation, Biodistribution and Dosimetry of Copper-64-Labeled Anti-Colorectal Carcinoma Monoclonal Antibody Fragments 1A3-F(ab')2," *J. Nuclear Medicine*, 36:850-858, 1995.

Anderson et al., "Radiometal-labeled agents (non-technetium) for diagnostic imaging," *Chem. Rev.*, 99:2219-2234, 1999.

Antony, "Folate receptors," *Ann. Rev.*, 16:501-521, 1996.

Aoi et al., "Globular carbohydrate macromolecule 'sugar balls' 3. 'radical-growth polymerization' of sugar-substituted α-amino acid N-carboxyanhydrides (glycoNCAs) with a dendritic initiator," *Tetrahedron, Elsevier Science Publishers*, 53(45):15415-15427, 1997.

Appelbaum et al., "The use of radiolabeled anti-CD33 antibody to augment marrow irridation prior to marrow transplantation for acute myelogenous leukemia," *Transplantation*, 54(5):829-833, 1992.

Auzeloux et al., "Technetium-99m Radiolabelling of an N-Amino-Alkyl-Benzamide Nitrido-and Oxo-Technetium Bis(Aminoethanethiol) Derivative Synthesis and Biological Results. Potential Melanoma Tracer Agents," *J. Labelled Compounds and Radiopharmaceuticals*, 42:567-579, 1999.

Baidoo and Lever, "Evaluation of a diaminedithiol-based bifunctional chelate for labeling small molecules with $^{99m}$Tc," *Technetitum and Rhenium in Chemsitry and Nuclear Medicine*, 1990.

Baidoo et al., "Synthesis of a new diaminedithiol bifunctional chelate for the preparation of nuetral technetium complexes," *J. Nuclear Med.*, 31:806, Abstract No. 414, 1990.

Bajorin et al., *Proc. Annu. Meet. Am. Soc. Clin. Oncol.*, 7:250, A967, 1988.

Bakker et al., "Receptor scintigraphy with a radioiodinated somatostatin analogue: radiolabeling, purification, biologic activity and in vivo application in animals," *J. Nucl. Med.*, 31:1501-1509, 1990.

Bar-Sever et al., "Comparison of living related donor and recipient renograms in predicting the early postransplantation course," *J. Nuclear Med.*, 37:292P, Abstract No. 1305, 1996.

Baselga et al, "Phase I studies of anti-epidermal growth factor receptor cheimeric antibody C225 alone and in combination with cisplatin," *J. Clinical Oncology*, 18(4):904-914, 2000.

Baselga et al., "Recombinant humanized anti-HER2 antibody (herceptin) enhances the antitumor activity of paciltazel and doxorubicin against HER2/new overexpressing human breast cancer xenografts," *Cancer Research*, 58:2825-2831, 1998.

Becker et al., "Analysis of E-cadherin in diffuse-type gastric cancer using a mutation-specific monoclonal antibody," *American Journal of Pathology*, 155(6):1803-1809.

Benns et al., "Tailoring new gene delivery designs for specific targets," *Journal of Drug Targeting*, 8(1), Database Medline on STN International, Accession No. 2000222278, 2 pages, 2000.

Bertolini et al., "Angiogenic growth factors and endostatin in non-Hodgkin's lymphoma," *Br. J. Haematol.*, 106:5045, 1999.

Blackenberg et al., "Apoptosis: the importance of nuclear medicine," *Nucl. Med. Comm.*, 21:241-250, 2000.

Blackenberg et al., "In vivo detection and imaging of phosphatidylserine expression during programmed cell death," *Proc. Natl. Acad. Sci., USA*, 95:6349-6354, 1998.

Blair et al., "Linkage of cytotoxin agents to immunoglobulins," *Journal of Immunological Methods*, 59:129-143, 1983.

Biakenberg et al., "Imaging of apoptosis (programmed cell death) with $^{99m}$Tc annexin V," *J. Nucl. Med*, 40:184-191, 1999.

Block, "Poly(g-benzyl-L-glutamate) and other glutamic acid containing polymers," Gordon and Breach Science Publishers, New York, 11-31, 1983.

Blondeau et al., "Dimerization of an intermediate during the sodium in liquid ammonia reduction of L-thiazolidine-4-carboxylic acid," *Can J. Chem*, 45:49-52, 1967.

Boersma et al., "Quantification of apoptotic cells with fluorescein isothiocyanate-labeled annexin V in Chinese hamster ovary cell cultures treated with cisplatin," *Cytometry*, 24:123-130, 1996.

Bohdiewicz et al., "Indium-111 satumomab pendetide: the first FDA-approved monoclonal antibody for tumor imaging," *J. Nuclear Medicine Technology*, 26(3):155-163, 1998.

Bormans et al., "Synthesis and biological characteristics of the fourn stereoisomers of 99mTc-N, N'-bis-(mercaptoacetyl)2,3-diaminopropanoate," *Int. J. Rad. Appl. Instrum. B.*, 17(5);499-506, 1990.

Brechbiel et al., "Synthesis of 1 (P-isothiocyanatobenzyl) derivatives of DTPA and EDTA: antibody labeling and tumor-imaging studies," *Inorg. Chem.*, 25:2772-2781, 1986.

Brogi et al., "Hypoxia-induced paracrine regulation of vascular endothelial growth factor receptor expression," *J. Clin. Invest.*, 97(2):469-476, 1996.

Brokx et al., "Designing peptide-based scaffolds as drug delivery vehicles," *Science*, 78(1-3):115-123, 2002.

Budihardjo et al.," Biochemical pathways of caspase activation during apoptosis," *Annu. Rev. Cell Dev. Biol.*, 15:269-290, 1999.

Burgen, "Targets of drug action," *Ann. Rev. Pharmacol. Toxicol.*, 40:1-16, 2000.

Burian et al., "Angiogenic factors in laryngeal carcinomas: do they have prognostic relevance?," *Acta Otolaryngol.*, 119:289-292, 1999.

Bush et al., "Definitive evidence for hypoxic cells influencing cure in cancer therapy," *Br J Cancer*, (Suppl. III) 37:302-306, 1978.

Cafaggi et al., "Synthesis and antitumor activity of a new cis-diammineplatinum (III) complex containing procaine hydrochloride," *Anticancer Research*, 12:2285-2292, 1992.

Cammisuli et al., "SDZ 281-977: a modified partial structure of lavendustin A that exerts potent and selective antiproliferative activities in vitro and in vivo," *Int J Cancer*, 65:351-359, 1996.

Campbell et al., "Folate-binding protein is a marker for ovarian cancer," *Cancer Res*, 51:5329-5338, 1991.

Cao, "Therapeutic potentials of angiostatin in the treatment of cancer," *Haematologica*. 84:643-650, 1999.

Chakrabarti et al., "Interaction of the antitumor antibiotic chromomycin A3 with glutathione, a sulfhydryl agent, and the effect upon its DNA binding properties," *Biochemical Pharmacology*, 56:1471-1479, 1998.

Chapman et al., "Therapeutic antibody fragments with prolonged in vivo half-lives," *Nature Biotech.*, 17:780-783, 1999.

Chen et al., "Biological and pharmacokinetic evaluation of tc-99m ma2g2-b: a potential renal agent," *J. Nuclear Med.*, 35:263P, Abstract No. 1082, 1994.

Cherif et al., "Rapid synthesis of [$^{18}$F]Fluoro-1-(2'-Nitro-1'-Imidazolyl)-2-Propanol ([$^{18}$F]Fluoromisonidazole)," *Pharm Res.*, 11:466-469, 1994.

Cleynhens et al., "Synthesis and biological evaluation in mice of a monoamide derivative of tc-99m-l,l-ec," *J. Nuclear Med.*, 38:186P, Abstract No. 799, 1997.

Collier et al. "Immunoscintigraphy performed with In-111-labeled CYT-103 in the management of colorectal cancer: comparison with CT," *Radiology*, 185:179-186, 1992.

Coney et al., "Chimeric murine-human antibodies directed against folate binding receptor are efficient mediators of ovarian carcinoma cell killing," *Cancer Res*, 54:2448-2455, 1994.

Connors, "Anticancer drug development: the way forward," *The Oncologist*, 1:180-181, 1996.

Co-Pending U.S. Appl. No. 10/672,142, filed Sep. 26, 2003.
Co-Pending U.S. Appl. No. 10/703,405, filed Nov. 7, 2003.
Co-Pending U.S. Appl. No. 10/672,763, filed Sep. 26, 2003.
Co-Pending U.S. Appl. No. 10/732,919, filed Dec. 10, 2003.

Corlija et al., "Contribution of radiolytically induced dissociation of 99mtc-d,1-hmpao in aqueous solutions," *J. Nuclear Med.*, 31:806, Abstract No. 413, 1990.

Craig et al., "Renal outcomes for children on year after urinary tract infection," *J. Nuclear Med.*, 37:46P, Abstract No. 175, 1996.

Culver et al., "In vivo gene transfer with retroviral vector-producer cells for treatment of experimental brain tumors," *Science*, 256:1550-1552, 1992.

Dagli et al., "Analysis of the complete dynamic scan data for camera-based determination of renal function," *J. Nuclear Med.*, 37:91P, Abstract No. 354, 1996.

Davison et al., "A new class of oxotechnetium(5+) chelate complexes containing a TcON$_2$S$_2$ Core," *Inorg Chem*, 20:1629-1632, 1981.

de Klerk et al., "Aspirin versus captopril renography in the diagnosis of renal artery stenosis," *J. Nuclear Med.*, 37:289P, Abstract No. 1291, 1996.

Deguchi et al., "Retention of biologic activity of human epidermal growth factor following conjugation to a blood-brain barrier drug delivery vector via an extended poly(ethylene glycol) linker," *Bioconjugate Chem.*, 10:32-37, 1999.

DeNardo et al., "Pharmacokinetics of chimeric L6 conjugated to indium 111- and yttrium-90-DOTA-peptide in tumor-bearing mice," *J. Nuclear Medicine*, 36:829-836, 1995.

DeNardo et al., "Yttrium-90/indoum-111-DOTA-peptide-chimeric L6: Pharmacokinetics, dosimetry and initial results in patients with incurable breast cancer," *Anticancer Research*, 17(3B):1735-1744, 1997.

Deutsch et al., "Synthesis of congeners and prodrugs, water-soluble prodrugs of taxol with potent antitumor activity," *J. Med. Chem.*, 32:788-792, 1989.

Deveraux and Reed, "IAP family proteins-suppressors of apoptosis," *Genes and Development*, 13:239-252, 1999.

Dewanjee et al., "Labeling antisense oligodeoxynucleotide (on) with tc-99m and hybridization with c-myc oncogene mrna in p388 leukemic cells," *J. Nuclear Med.*, 35:263P, Abstract No. 1081, 1994.

Dezutter et al., "Preparation and biological evaluation of technetium-$^{99m}$-L,L-propylenedicysteine" *J. of Labelled Cpd. Radiopharm.*, 42:553-565, 1999.

Dische, "A review of hypoxic-cell radiosensitization," *Int J Radiat Oncol Biol Phys*, 20:147-152, 1991.

Divgi et al., "Phase I and imaging trial of indium 111-labeled anti-epidermal growth factor receptor monoclonal antibody 225 in patients with squamous cell lung carcinoma," *J. National Cancer Institute*, 83(2):97-104, 1991.

Drobnik et al., "Soluble synthetic polymers in biological systems," *Adv. Polym. Sci.*, 57:1-50, 1984.

Dunn et al., "Receptor-mediated endocytosis of epidermal growth factor by hepatocytes in the perfused rat liver: ligand and receptor dynamics," *J. Cell Biol.*, 98:2148-2159, 1984.

Eary et al., "Radiochemistry of halogenated antibodies," *Antibodies in Radiodiagnosis and Therapy*, Boca Ratan, Florida, CPC Press, 83-100, 1988.

Eiseman et al., "Plasma pharmacokinetics and tissue distribution of paclitaxel in CD2F1 mice," *Cancer Chemother, Pharmacol.*, 34:465-471, 1994.

Eisenhut et al., "Synthesis and In Vivo Testing of a bromobutyl substituted 1,2-Dithia-5,9-diazacycloundecane: a versatile precursor for new $^{99m}$Tc-bis(aminoethanethiol) complexes," *Nucl. Med. Biol.*, 16:805-811, 1989.

Ennis et al., "Anti-epidermal growth factor receptor antibodies inhibit the autosrine-stimulated growth of MDA-468 human breast cancer cells," *Mol. Endocrinology*, 3(11):1830-1838, 1989.

Eshima et al., "Evaluating the role of protein binding on the renal extraction of tc-99m tubular agents utilizing an isolated perfused rat kidney model," *J. Nuclear Med.*, 37:47P, Abstract No. 178, 1996.

Ethier, "Growth factor synthesis and human breast cancer progression," *J. Natl. Cancer Inst.*, 87(13):964-973, 1995.

Fan et al., "Antitumor effect of anti-epidermal growth factor receptor monoclonal antibodies plus cis-diamminedichloroplatinum on well established A431 cell xenografts," *Cancer Research*, 53:4637-4642, 1993.

Fan et al., "Blockade of epidermal growth factor receptor function by bivalent and monovalent fragments of 225 anti-epidermal growth factor receptor monoclonal antibodies," *Cancer Research*, 53:4322-4328, 1993.

Fanciulli et al., "Glycolysis and growth rate in normal and in hexokinase-transfected NIH-3T3 cells," *Oncology Res.*, 6:405-409, 1994.

Fang et al., "Involvement of p21 Wafl in mediating inhibition of paclitaxel-induced apoptosis by epidermal growth factor in MDA-MB-468 human breast cancer cells," *Anticancer Research*, 20(1A):103-112, 2000.

Fidler et al., "The biology of cancer invasion and metastasis," *Adv. Cancer Res.*, 28:149-250, 1987.

Foa et al., "Taxol (paclitaxel): a novel anti-microtubule agent with remarkable anti-neoplastic activity," *J. Clin. Lab. Res.*, 24:6-14, 1994.

Frankel et al., "Targeted toxins," *Clin. Cancer Res.*, 6:326-334, 2000.

Franklin et al., "New anti-lung-cancer antibody cluster 12 reacts with human folate receptors present on adenocarcinoma," *Int J Cancer-Supplement*, 8:89-95, 1994.

Frisch and Screaton, "Anoikis mechanisms," *Curr. Opin. Cell Biol.*, 13:555-562, 2001.

Fuertges et al., "The clinical efficacy of poly(ethylene glycol)-modified porteins," *J. Controlled Release*, 11:139-148, 1990.

Fuller et al., "A procedure for the facile synthesis of amino-acid N-carboxyanhydride," *Biopolymers*, 15:1869, 1976.

Gabizon, "Selective tumor localization and improved therapeutic index of anthracyclines encapsulated in long-circulating liposomes," *Cancer Research*, 52:891-896, 1992.

Gambhir et al., "A mutant herpes simplex virus type 1 thymidine kinase reporter gene shows improved sensitivity for imaging reporter gene expression with positron emission tomography," *Proc. Natl. Acad. Sci., USA*, 97(6):2785-2790, 2000.

Gambhir et al., "Imaging adenoviral-directed reporter gene expression in living animals with positron emission tomography," *Proc. Natl. Acad. Sci., USA*, 96:2333-2338, 1999.

Gambhir et al., "Imaging of adenoviral-directed herpes simplex virus type 1 thymidine kinase reporter gene expression in mice with radiolabeled ganciclovir," *J. Nucl. Med.*, 39:2003-2011, 1998.

Garayoa et al., "Hypoxia-inducible factor-1 (HIF-1) up-regulates adrenomedullin expression in human tumor cell lines during oxygen deprivation: a possible promotion mechanism of carcinogenesis," *Molecular Endocrinology*, 14:848-862, 2000.

Gariepy et al., "Vectorial delivery of macromolecules into cells using peptide-based vehicles," *Trends in Biotechnology*, 19(1):21-28, 2001.

Ginobbi et al., "Folic acid- polylysine carrier improves efficacy of c-myc antisense oligodeoxynucleotides on human melanoma (M14) cells," *Anticancer Res*, 17:29-35, 1997.

Girard, "Mechanisms by which carbohydrates regulate expression genes for clycolytic and lipogenic enzymes," *Ann. Rev. Nutr.*, 17:325-352, 1997.

Giraud et al., "Application to a cartilage targeting strategy: Synthesis and in vivo biodistribution of $^{14}$C-labelled quaternary ammonium-glucosamine conjugates," *Bioconjug. Chem.*, 11:212-218, 2000.

Goh et al., "Growth hormone promotion of tubulin polymerization stabilizes the microtubule network and protects against colchicine-induced apoptosis," *Endrocrinology*, 139:4364-4372, 1998.

Goldenberg et al., "Imaging of human tumor xenografts with and indim-111-labeled anti-epidermal growth factor receptor monoclonal antibody," *J. National Cancer Institute*, 81:1616-1625, 1989.

Goldenberg, "Monoclonal antibodies in cancer detection and therapy," *Am. J. Med.*, 94:297-312, 1993.

Goldsmith et al., "Somatostatin receptor imaging in lymphoma," *Sem Nucl Med*, 25:262-271, 1995.

Goldsmith, "Receptor imaging: Competitive or complementary to antibody imaging,"*Sem Nucl Med.*, 27:85-93, 1997.

Goldspeil, "Pharmaceutical issues: preparation, administration, stability, and compatibility owth other medications,"*Ann. Pharocother.*, 28:S23-S26, 1994.

Gonda, "Aerosols for delivery of therapeutic and diagnostic agents to the respiratory tract," *Critical Reviews in Therapeutic Drug Carrier Systems*, 6(4):273-313, 1990.

Green and Evan, "A matter of life and death," *Cancer Cell*, 1:19-30, 2002.

Greenfield et al., "In vitro evaluation of immunoconjugates prepared by linking mitomycin C to monoclonal antibodies via polyglutamic acid carriers," *Antibody, Immunoconjugates, and Radiopharmaceuticals*, 2(3):201-216, 1989.

Greenwald et al., "Drug delivery systems: water soluble tazol 2'-poly(ethylene glycol) ester prodrugs-design and in vivo effectiveness," *J. Med. Chem.*, 39:424-431, 1996.

Guo and Gallo, "Selective protection of 2', 2'-difluorodeoxcytidine (Gemcitabine)," *J Org Chem*, 64:8319-8322, 1999.

Guozheng and Boli, "A new potential renal imaging agent 99mtcn-ec," *J. Labelled compounds and Radiopharmaceuticals*, XXXVII:797-798, 1995.

Hadley et al,"Magnetic resonance imaging in acute head injury," *Clin. Rad.*, 39:131-139, 1988.

Halpern et al., "Stability, characterization, and kinetics of In-labeled monoclonal antitumor antibodies in normal animals and nude mouse human tumor models," *Cancer Research*, 43:5347-5355, 1983.

Harada et al., "Insulin-induced egr-1 expression in chinese hamster ovary cells in insulin receptor an dinsulin receptor substrate-1 phosphorylation-independent," *J. Biol Chem.*, 270:26632-26638, 1995.

Hay et al., "Hypoxia-selective antitumor agents. Bis(nitroimidazolyl)alkanecarboxamides: a new class of hypoxia-selective cytotoxins and hypoxic cell radiosensitizers," *J Med. Chem.*, 37:381-391, 1994.

Hermann and Patel, "Adaptive recognition by nucleic acid aptamers," *Science*, 287:820-825, 2000.

Hermanson, "Amine detection reagents," *Bioconjugate Techniques*, San Diego, Academic Press, 112-114, 1996.

Hermanson, "Ellman's assay for the determination of sulfhydryls," *Bioconjugate Techniques*, Sand Diego, Academic Press, 88-90, 1996.

Hibi et al., "PGP9.5 as a candidate tumor marker for non-small-cell lung gancer,"*American Journal of Pathology*, 155(3):711-715, 1999.

Hirsch et al., "PK11195, a ligand of the mitochondrial benzodiazepine receptor, facilitates the induction of apoptosis and reverses Bcl-2-mediated cytoprotection," *Experimental Cell Research*, 241:426-434, 1998.

Hjarnaa et al., "CHS 828, a novel pyridyl cyanoguanidine with potent antitumor activity in vitro and in vivo," *Cancer Res.*, 59:5751-5757, 1999.

Hnatowich et al., "Radioactive labeling of antibody: a simple and efficient method," *Science*, 220:613-615, 1983.

Hoes et al., "Optimization of macromolecular prodrugs of the antitumor antibiotic adriamycin," *J. Controlled Release*, 2;205-213, 1985.

Holm et al., "Folate receptor of human mammary adenocarcinoma," *APMIS*, 102:413-419, 1994.

Holmes et al., "Current status oc clinical trials with paclitaxel and docetael, taxane anticancer agents: basic science and current status," *American Chemical Society*, Washington, DC, 31-57, 1995.

Hsueh and Dolnick, "Altered folate-binding protein mRNA stability in KB cells grown in folate-deficient medium," *Biochem Pharmacol*, 45:2537-2545, 1993.

Hudecz et al., "Influence of carrier on biodistibution and in vitro cytotoxicity of methotexate-branched polypeptide conjugates," *Bioconjugate Chemistry*, American Chemical Society, 4(1):25-33,1993.

Ilgan et al., "$^{99m}$Tc-ethylenedicysteine-folate: a new tumor imaging agent, synthesis, labeling and evaluation in animals," *Cancer Biotherapy & Radiopharmaceuticals*, 13:427-435, 1998.

Inoue et al., "Evaluation of In-111 DTPA-paclitaxel scintigraphy to predict response on murine tumors to paclitaxel," *Annals of Nuclear Medicine*, 13(3):169-174, 1999.

Inoue et al., "Paclitaxel enhances the effects of the anti-epidermal growth factor receptor monoclona antibody ImClone C225 in mice with metastatic human bladder transitional cell carcinoma," *Clinical Cancer Res.*, 6:4874, 4884, 2000.

Inoue et al., "The prognostic value of angiogenesis factor expression for predicting recurrence and metastasis of bladder cancer after neoadjuvant chemotherapy and radical cystectomy," *Clin. Cancer Res.*, 6:4866-4873, 2000.

Ionov et al., "Mutational inactivation of the proapoptotic gene BAX confers selective advantage during tumor clonal evolution," *Proc. Natl. Acad. Sci.*, USA, 97(20):10872-10877, 2000.

Irie et al., "Regression of cutaneous metastic melanoma by inralesional injection with human monoclonal antibody to ganglioside GD2," *Proc. Natl. Acad. Sci.*, USA, 83:8694-8698, 1986.

Itoh et al., "Graphic (patlak) method in tc-99m-mag3 renal scintigraphy: noninvasive calculation of extraction fraction (ef) and renal plasma flow (RPF)," *J. Nuclear Med.*, 37:291P, Abstract No. 1300, 1996.

Iyer et al., "8-[18F]Fluoropenciclovir: an improved reporter probe for imaging HSV1-tk reporter gene expression in vivo using PET," *J. Nucl. Med.*, 42(1):96-105, 2001.

Jamar et al., "Clearance of the new tubular agent Tc-*99m* L,L-ethylenedicysteine: Estimation by a simplified method," *J Nucl Med*, 34:129P, 1993.

Jamar et al., "Clinical evaluation of Tc-*99m* L,L-ethylenedicysteine, a new renal tracer, in transplanted patients," *J Nucl Med*, 34:129P, 1993a.

Jeppesen et al., Impact of polymer tether length on multiple ligand-recepotor bond formation, *Science*, 293:465-468, 2001.

Jiang et al., "3-(Iodoacetamido)-benzoylurea: a novel cancericidal tubulin ligand that inhibits microtubule polymerization, phosphorylates bc1-2, and induces apoptosis in tumor cells," *Cancer Res.*, 58:5389-5395, 1998.

Jiang et al., "Antitumor activity of didemnin B in the human tumor stem cell assay," *Cancer Chemother Pharmacol*, 11:1-4, 1983.

John et al., "Tc-99m labeled ethylenediamines: quest for sigma receptor chelates," *J. Nuclear Med.*, 38:186P, Abstract No. 798, 1997.

Jones and Mayer, "Glucose metabolism in the rat small intestine: the effect of glucose analogues on hexokinase activity," *Biochem. J*, 132:125-128, 1973.

Jurisson et al., "Potential technitium small molecule radiopharmaceuticals," *Chem. Rev.*, 99:2205-2218, 1999.

Kabasakal et al., "Clinical comparison of technetium-$^{99m}$ -ec, technetium-$^{99m}$ -MAG3 and iodine-131-OIH in renal disorders," *J. Nucl. Med.*, 36(2):224-228, 1995.

Kabasakal et al., "Evaluation of technetium-99m-ethylenedicysteine in renal disorders and determination of extraction ratio," *J. Nucl. Med.*, 36(8):1398-1403, 1995.

Kabasakal et al., "Prospective validation of single plasma sample $^{99m}$Tc-ethylenedicysteine clearance in adults," *J. Nucl. Med.*, 40:429-431, 1999.

Kabasakal et al., Simplified technetium-$^{99m}$-EC clearance in adults from a single plasma sample, *J. Nuclear Med.*, 38:1784-1786,1997.

Kabasakal. "Technetium-99m ethylene dicysteine: a new renal tubular function agent," *Eur. J Nucl. Med.* 27:351-357, 2000.

Kanazawa et al., "19F NMR of 2-deoxy-2-fluro-D-glucos for tumor diagnosis in mice. An NDP-bound hexose analog as a new NMR target for imaging," *NMR in Biomed.*, 10:35-41, 1997.

Kanvinde et al., "Technetium-99m-γ-pyrones: a new class of tc-99m cationic complexes," *J. Nuclear Medicine*, 31:908, Abstract, 1990.

Kao et al., "Detection of esophageal carcinoma susing Tc-99m MIBI SPECT imaging," *Clin. Nucl. Med.*, 19(12):1069-1074, 1994.

Kao et al., "Relationship of alveolar permeability and lung inflammation in patients with active diffuse infiltrative lung disease detected by 99Tcm-DTPA radioaerosol inhalation lung scintigraphy and quantitative 67Ga lung scans," *Nucl. Med. Commun.*, 15(10):850-854, 1994.

Kao et al., "Role of radioisotope penile plethysmigraphy in the evaluation of penile hemodynamic of impotent patients," *J. Nuclear Med.*, 37:292P, Abstract No. 1304, 1996.

Kao et al., "Tc-99m MIBI uptake in breast carcinoma and axillary lymph node metastases," *Clin. Nuc. Med.*, 19(10):898-900, 1994.

Kato and Sugiyama, "Targeted delivery of peptides, proteins, and genes by receptor-mediated endocytosis," *Critical Reviews in Therapeutic Drug Carrier Systems*, 14(3):287-331, 1997.

Kato et al., "A novel method of conjugation of daunomycin with antibody with a poly-L-glutamic acid-a-fetoprotein antibody-daynomycin conjugate," *J. Med. Chem.*, 27:1602-1607, 1984.

Kengen, "Good results of tc-99m-mag3 clearance measurements with a dual headed gamma camera without plasma sampler," *J. Nuclear Med.*, 37:91P, Abstract No. 353, 1996.

Kikukawa et al., "Early and delayed Tc-99m ECD brain SPECT in SLE patients with CNS involvement," *Ann Nucl Med.* 14:25-32, 2000.

Kim et al., "Synthesis, biodistribution and imaging of mammary tumors using 99mtc-ec-polyglutamate; a glutamate receptor peptide," *J. Nuclear Medicine*, 41:231P Abstract, 2000.

Kitamura et al., "Chemical engineering of the monoclonal antibody A7 by polyethylene clycol for targeting cancer chemotherapy," *Cancer Research*, 51:4310-4315, 1991.

Klok et al., "Star-shaped fluorescent polypeptides," *Journal of Polymer Science*, 39(10):1572-1582, 2001.

Knight et al,"Thrombus imaging with technetium—99m synthetic peptides based upon the binding domain of a monoclonal antibody to activated platelets," *J. Nucl. Med.*, 35:282-288, 1991.

Koh et al., "Imaging of hypoxia in human tumors with [F-18]fluoromisonidazole,"*Int J Radiat Oncol Biol Phys*, 22:199-212, 1992.

Kopecek et al. "Targetable polymeric prodrugs," *J. Control. Release*, 6;315-327, 1987.

Kopecek et al., "Targetable water-soluble polymeric antcancer drugs: achievements and unsolved problems," *Proc. Intern. Symp. Conol. Rel. Bioact. Mater.*, 20:190-191, 1993.

Kopecek, "The potential of water-soluble polymeric carriers in targeted and site-specific drug delivery," *Journal of Controlled Release*, 11:279-290, 1990.

Kranz et al., "Conjugates of folate and anti-T-cell-receptor antibodies specifically target folate-receptor-positive tumor cells for lysis," *Proc Natl Acad Sci*, 92:9057-9061, 1995.

Kung et al., "Synthesis of new bis(aminoethanethiol) (BAT) derivatives: possible ligands for 99mTc brain imaging agents," *J. Med. Chem.*, 28:1280-1284, 1985.

Lamberts et al., "Somatostatin receptor imaging in vivo localization of tumors with a radiolabeled somatostatin analog," *J. Steoid Biochem Mol Biol*, 37:1079-1082, 1990.

Lamki, "Radioimmunoscintigraphy of cancer: problems, pitfalls, and prospects," *Nuclear Medicine Annual 1990*, New York, Raven Press Ltd., 113-150, 1990.

Larson et al., "Overview of clinical radioimmunodetection of human tumors," *Cancer*, 73(supp):832-835, 1994.

Leamon and Low, "Cytotoxicity of momordin-folate conjugates in cultured human cells," *J Biol Chem*, 267:24966-24971, 1992.

Leamon and Low, "Delivery of macromolecules into living cells: a method that exploits folate receptor endocytosis," *Proc Natl Acad Sci*, 88:5572-5576, 1991.

Leamon et al., "Cytotoxicity of folate-pseudomonas exotoxin conjugates toward tumor cells," *J Biol Chem*, 268:24847-24854, 1993.

LeClerc and Cedergren, "Modeling RNA-ligand interactions: the rev-binding element RNA-aminoglycoside complex," *J Med Chem*, 41:175-182, 1998.

Lee and Low, "Delivery of liposomes into cultured KB cells via folate receptor-mediated endocytosis," *J Biol Chem*, 269:3198-3204, 1994.

Lees et al, "Prognostic value of single-photon emission tomography in acute ischaemic strike," *Eur. Journ. Nuc. Med.*, 24:21-26, 1989.

Li et al., "Antitumor activity of poly (L-glutamic acid)-paclitaxel on syngeneic and xenografter tumors," *Clinical Cancer Res.*, 5:891-897, 1999.

Li et al., "Complete regression of well-established tumors using a novel water-soluble poly(L-glutamic acid)-paclitaxel conjugate," *Cancer Res.*, 58:2404-2409, 1998.

Li et al., "Poly(L-glutamic acid)-anticancer drug conjugates," *Advanced Drug Delivery Rev.*, 54:695-713, 2002.

Li et al., "Synthesis and evaluation of water-soluble polyethylene glycol paclitaxel conjugate as a paclitaxel prodrug," *Anticancer Drugs*, 7(5):642-648, 1996.

Li et al., "Synthesis, metal chelate stability studies, and enzyme digestion of a peptide-linked Dota derivative and its corresponding radiolabeled immunoconjugates," *Bioconjugate Chem.*, 4:275-283, 1993.

Liang et al., "The use of diaminodithiol for labeling small molecules with technetium-99m," *Nucl. Med. Biol.*, 14:63-67, 1987.

Lin et al., "The role of Tc-99m MDP and Ga-67 imaging in the clinical evaluation of malignant fibrous histiocytoma," *Clin. Nucl. Med.*, 19(11):996-1000, 1994.

Liu et al., "99mTc-labeled small peptides as diagnostic radiopharmaceuticals," *Chem. Rev.*, 99:2235-2268, 1999.

Liu et al., "Apoptotic signals delivered through the T-cell receptor of a T-cell hybrid require the immediate-early gene nur77," *Nature*, 367(6460):281-284, 1994.

Liu et al., "Bifunctional chelators for therapeutic lanthanide radiopharmaceuticals," *Bioconjugate Chemistry*, 12:7-34, 2001.

Liu et al., "Detection of anaerobic odontogenic infections by fluorine-18 fluoromisonidazole," *Eur. J. Nucl. Med.*, 23(10):1384-1387, 1996.

Liu et al., "Induction of apoptosis and activation of the capase cascade by anti-EFG receptor monoclonal antibodies in DiFI human colon cancer cells do not involve the C-jun N-terminal kinase activity," *British Journal of Cancer*, 82(12):1991-1999, 2000.

Lu et al., "Polymerizable fab' antibody fragments for targeting of anticancer drugs," *Nat. Biotech.*, 17:1101-1104, 1999.

Lu, "Antimitotic agents," In: Foye, WO. Ed., "Cancer chemotherapeutic agents," Washington, DC: American Chemical Society, 345-368, 1995.

Lundberg et al., "Conjugation of an anti-B-cell lymphoma monoclonal antibody, LL2, to long-circulating drug-carrier lipid emulsions," *J Pharm Pharmacol*, 51:1099-1105, 1999.

Macapinlac et al., "Callium-67-citrate imaging in nuclear oncology," Nucl. Med. Biol., 21(5):731-738, 1994.

Maeda et al., "Tumoritropic and lymphotropic principles of macromolecular drugs," *Crit. Rev. Ther. Drug Carrier Syst.*, 6(3)193-210, 1989.

Maeda, "SMANCS and polymer-conjugated macromolecular drugs: advantages in cancer chemotherapy," *Adv. Drug Delivery Rev.*, 6(2):181-202, 1991.

Makin and Hickman, "Apoptosis and cancer chemotherapy," *Cell Tissue Res.*, 301:143-152, 2000.

Mang'era and Verbruggen, "Synthesis and evaluation of beta-homocysteine derivatives of 99mtc-1,1-ec and 99mtc-1,1-ecd," *J. of Labelled Compounds and Radiopharmaceuticals*, 42:683-699, 1999.

Mann et al., "Molecular amplifiers: synthesis and functionalization of a poly(aminopropyl dextran bearing a uniquely reactive terminus for univalent attachment to biomolecules," *Bioconjugate Chemistry*, 3:154-159, 1992.

Maraganore et al, "Structure of the hirugen and hirulog 1 complexes of α-thrombin," *J. Mol. Biol.*, 221:1379-1393, 1991.

Marti and Risau, "Systematic hypoxia changes the organ-specific distribution of vascular endothelial growth factor and its receptors," *Proc. Natl. Acad. Sci.*, USA, 95:15809-15814, 1998.

Martin et al., "Enhanced binding of the hypoxic cell marker [$^3$H]fluoromisonidazole in ischemic myocardium," *J Nucl Med*, 30:194-201, 1989.

Martin et al., "Noninvasive detection of hypoxic myocardium using fluorine-18 fluoromisonidazole and positron emission tomography," *J. Nucl. Med.*, 33(12):2202-2208, 1992.

Mason et al., "99mtc-desferoxamine: production, stability and solute clearance measurements after aerosolization," *J. Nuclear Med.*, 31:908, Abstract No. 865, 1990.

Masui et al., "Growth inhibition of human tumor cells in athymic mice by anti-epidermal growth factor receptor monoclonal antibodies," *Cancer Research*, 44:1002-1007, 1984.

Mather et al., "Tumour cell uptake of technetium dithiocarbamate complexes," *J. Nuclear Med.*, 38:186P, Abstract No. 797, 1997.

Mathew et al., "Synthesis and evaluation of some water-soluble prodrugs and derivatives of taxol with antitumor activity," *J. Med. Chem.*, 35:145-151, 1992.

Mathias et al., "Tumor-selective radiopharmaceudcal targeting via receptor-mediated endocytosis of Gallium 67 deferoxamine-folate," *J Nucl Med*, 37:1003-1008, 1996.

Mathias et al., "Indium-111-DTPA-folate as a radiopharmaceutical for targeting tumor-associated folate binding protein," *J Nucl Med*, (Supplement) 38:133P, 1997.

Mathias et al., "Synthesis of Tc-*99m*-DTPA-folate and preliminary evaluation as a folate-receptor-targeted radiopharmaceutical,"*J Nucl Med*, (Supplement); 38:87P, 1997.

McGahon et al., "Chemotherapeutic drug-induced apoptosis in human leukaemic cells is intependent of the Fas (APO-1/CD95) receptor/ligand system," *British Journal of Haematology*, 101:539-547, 1998.

Meares et al., "Macrocyclic chelates of radiometals for diagnosis and therapy," *British J. Cancer*, 62:21-26, 1990.

Mease et al., "Comparison of renal agents for detecting unilateral acute ischemic/reperfusion renal injury in rats," *J. Nuclear Med.*, 36:231P, Abstract No. 1033, 1995.

Mendelsohn et al., "Anti-epidermal growth factor recepotr monoclonal antibodies may inhibit A431 tumor cell proliferation by blocking autocrine pathway," *Trans. Assoc. Am. Phys.*, 100:173-178, 1987.

Mendelsohn, "Epidermal growth factor receptor inhibition by a monoclonal antibody as anticancer therapy," *Clinical Cancer Research*, 3:2703-2707, 1997.

Meredith et al., "Treatment of metastatic prostate carcinoma with radiolabeled antibody CC49," J. Nucl. Med., 35(6):1017-1022, 1994.

Meyer et al., "Tryptophan hydrolase antibodies used in the diagnosis of carcinoid," *Hepato-Gastroenterology*, 45:1522-1526, 1998.

Michiels et al., "Simultaneous estimation of effective renal plasma flow and glomerular filtration rate using tc-99m-ec.," *J. Nuclear Med.*, 37:91P, Abstract No. 355, 1996.

Miltross et al., "Relationship of mitotic arrest and apoptosis to antitumor effect of paclitaxel," *J. National Cancer Institute*, 88(18):1308-1314, 1996.

Mitchell et al., "Active-specific immunotherapy for melanoma," *J. Clin. Oncol.*, 8(5):856-869, 1990.

Mochizuki et al., "Synthesis of poly-L-glutamates containing 5-substituted uracil moieties," *Nucleic Acids Symp. Ser.*, 16:121-124, 1985.

Modjahedi et al., "The receptor for EGF and its ligands: expression, prognostic value and target for therapy in cancer (review)," *Int. J. Oncology*, 4(2):277-296, 1994.

Moller et al., "Biologic activities of naturally occurring human insulin receptor mutations," *J. Biol. Chem.*, 266:10995-11001, 1991.

Moran, "Technetium-$^{99m}$-EC and other potential new agents in renal nuclear medicine," *Seminars in Nucl. Med.*, 29: 91-101, 1999.

Morton et al., "Comparison of 2-point postural drainage with diuresis renography in the assessment hydronephrosis," *J. Nuclear Med.*, 37:46P, Abstract No. 174, 1996.

Morton et al., "Prolongation of survival in metastatic melanoma after active specific immunotherapy with a new polyvalent melanoma vaccine," *Ann. Surg.*, 216(4):463-482, 1992.

Mosmann, "Rapid colorimetic assay for cellular growth and survival: application to proliferation ans cytotoxicity assay,"*J. Immunol. Methods*, 65:55-63, 1983.

Mrhac et al., "Abnormal first-pass flow through the azygos vein from valsalva maneuver," *Clinical Nucl. Med.*, 21:331-332, 1996.

Murray et al., "Matrix metalloproteinase-1 is associated with poor prognosis in oesophageal cancer," *Journal of Pathology*, 185:256-261, 1998.

Namavari et al., "Synthesis of 8-[18F]Fluoroguanin derivatives: in vivo probes for imaging gene expression with positron emission tomography," *Nucl. Med. Biol.*, 27:157-162, 2000.

Nicolaou et al., "Design, synthesis, and biological activity of protaxols," *Nature*, 364:464-466, 1993.

Nordsmark et al., "Pretreatment oxygenation predicts radiation response in advanced squamous cell carcinoma of the head and neck," *Radiother Oncol*, 41:31-39, 1996.

Nosco et al., "Development of a kit formulation for 99mtcmag3 of very high purity and very high stability," *J. Nuclear Med.*, 31:908, Abstract No. 863, 1990.

Offield et al., "PDX-1 is required for pancreatic outgrowth and differentiation of the rostral duodenum," *Development*, 122:983-995, 1996.

Oldham et al., "Comparison of action of paclitaxel and poly (L-glutamic acid)-paclitaxel conjugate in human breast cacner cells," *Int. J. Oncol.*, 16(1):125-132, 2000.

Olexa et al.,"Radiolabeling of fibrinogen using the Iodogen technique," *Throm. Res. Cen. Dept. Biochem.*, pp. 593-596, 1982.

Omelyanenko et al., "HPMA copolymer-anticancer drug-OV-TL16 antibody conjugates: influence of synthesis on the binding affinity to OVCAR-3 ovarian carcinoma cells in vitro," *J. Drug Targeting*, 3:357-373, 1996.

Omelyanenko et al., "HPMA copolymer-anticancer drug-OV-TL16 antibody conjugates II. Processing in epithelial ovarian carcinoma cells in vitro," *International Journal of Cancer*, 75(4):600-608, 1998.

Orr et al., "Similarity of folate receptor expression in UMSCC 38 cells to squamous cell carcinoma differentiation markers," *J Natl Cancer Inst*, 87:299-303, 1995.

Ozanne et al., "Over-expression of the EGF receptor is a hallmark of squamous cell carcinomas," *J. Pathol.*, 149:9-14, 1986.

Ozker et al., "Technetium-$^{99m}$-N,N-ethylenedicysteine-a comparative study of renal scintigraphy with technetium-$^{99m}$-MAG3 and iodine-131-OIH in patients with obstructive renal disease," *J. Nucl. Med.*, 35:840-845, 1994.

Palyi et al., "Effects of methylacetylenic putrescine, and ornithine decarboxylase inhibitor and potential novel anticancer agent, on human and mouse cancer cell lines," *Anti-Cancer Drugs*, 10:103-111, 1999.

Pavicevic et al., "Serum tumor marker CYFRA 21-1 in the diagnostics of NSCLC lung cancer," *Coll Antropol*, 22(2):629-635, 1998.

Pavlik et al., "Properties of anticancer agents relevant to in vitro determinations of human tumor cell sensitivity," *Cancer Chemother Pharmacol*,11:8-15, 1983.

Pedley et al., "The potential for enhanced tumour localisation by poly(ethylene glycol) modification of anti-CEA antibody," *British J. Cancer*, 70:1126-1130, 1994.

Petrak et al., "Transport of macromolecules across the capillary walls," *Adv. Drug Deliv. Review*, 3:191-214, 1989.

Phillips-Hughes et al., "Restenosis: pathophysiology and preventive strategies," *JVIR*, 7:321-333, 1996.

Pietersz et al., "Specific in vitro anti-tumor activity of methotrexate-monoclonal antibody conjugates prepared using human serum albumin as an intermediary," *Immunol. Cell Biol.*, 66:43-49, 1988.

Pimm et al., "Differences in tumor and normal tissue concentrations of iodine and indium labeled monoclonal antibody II: biodistribution studies in mice with human tumor xenografts," *Dur. J. Nucl. Med.*, 11:300-304, 1985.

Pimm et al., "Strategies for labelling branched polypeptides with a poly (L-Lysine) backbone with radioiodines 123I, 125I, 131I) and radiometals (lllIn, 51Cr) for biodistribution studies wnad radiopharmaceutical development," *Journal of Labelled Compunds and Radiopharmaceuticals*, 36(2):157-172, 1995.

Piper et al.,"A synthetic approach to poly(γ-glutamyl) conjugates of methotrexate," *J. Med. Chem.*, 26:291-294, 1983.

Pirmettis et al., "Synthesis and characterization of the tcd(ec) complex, a renal imaging agent," *J. Nuclear Med.*, 35:263P, Abstract No. 1079, 1994.

Popovici et al., "The influence of some antibiotics on hexokinase and pyruvate-kinase activity in the rat liver and kidney," *Arch. int. Pharmacodyn*,193:80-86, 1971.

Potamianos et al., "Radioimmunoscintigraphy and radioimmunotherapy in cancer: principles and application," *Anticancer Research*, 20(2A):925-948, 2000.

Prvulovich et al., "Clinical evaluation of technetium-$^{99m}$-L,L-ethylenedicysteine in patients with chronic renal failure," *J. Nucl. Med.*, 38:809-814, 1997.

Putnam et al., "Polymer conjugates with anticancer activity," *Polymer Science*, 122:55-123, 1995.

Quadri et al., "Effects of linker chemistry on the pharmacokinetics of radioimmunoconjugates," *Quart. J. Nucl., Med.*, 42:250-261, 1998.

Raffauf et al., "Colchicine. Derivatives of trimethylcolchicinic acid," *J. Am Chem Soc*, 75:5292-5294, 1953.

Rasey et al., "Characterization of the binding of labeled fluoromisonidazole in cells in vitro," *Radiat Res*, 122:301-308, 1990.

Rasey et al, "Radiolabeled fluoromisonidazole as an imaging agent for tumor hypoxia," *Int J Radiation Oncology Biol Phys*, 17:985-991, 1989.

Ratner and Clarke, "The action of formaldehyde upon cysteine," *J. Am Chem. Soc.*, 59:200-206, 1937.

Ravindranath et al., "Quantitation of the density of cell surface carbohydrate antigens on cancer cells with a sensitive cell-suspension ELISA," *J. Immunol. Methods*, 16(197):51-67, 1996.

Reed, "Apoptosis-targeted therapies for cancer," *Cancer Cell*, 3:17-22, 2003.

Reilly et al., "A comparison of EGF and Mab 528 labeled within for imaging human breast cancer," *J. Nucl. Med.*, 41:903-911, 2000.

Remington's Pharmaceutical Sciences, $19_{th}$ Ed., Mach Printing Company, 1990, Smith and Rutlage, 1975.

Reutelingsperger and van Heerde, "Annexin V, the regulator of phosphatidylserine-catalyzed inflammation and coagulation during apoptosis," Cell Mol Life Sci, 53:527-532, 1997.

Rihova et al., "Antiproliferative effect of a lectin- and anti-thy-1.2 antibody-targeted HPMA copolymer-bound doxorubicin on primary and metastatic human colorectal carcinoma and on human colorectal carcinoma transfected with the mouse thy-1.2 gene," *Bioconjugate Chemistry*, 11(5):664-673, 2000.

Rihova, "Receptor-mediated targeted drug or toxin delivery," *Adv. Drug Deliv. Rev.*, 29:273-289, 1998.

Rogers et al., "Neomycin effects on glucose transport by rat small intestine," *Digestion*, 1:159-164, 1968.

Rosenberg et al., "Experience with the use of high-dose interleukin-2 in the treatment of 652 cancer patients," *Ann. Surg.*, 210(4):474-548, 1989.

Ross et al., "Differential regulation of folate receptor isoforms in normal and malignant tissue in vivo and in established cell lines," *Cancer*, 73:2432-2443, 1994.

Roth et al., "Gene therapy for cancer: what have the inventors done and where are the inventors going?" *J. Natl. Can. Inst.*, 89(1):21-39, 1997.

Rowinsky et al., "Paclitaxel (taxol)," *New England Journal of Medicine*, 332:1004-1014, 1995.

Rowinsky et al., "Phase I and pharmacologic study of paclitaxel and cisplatin with granulocyte colony-stimulating factor: neuromuscular toxicity is dose-limiting," *J. Clin. Oncol.*, 11(10):2010-2020, 1993.

Rowland et al., "Suppression of tumor growth in mice by drug-antibody conjugate using a novel approach to linkage," *Nature*, 255:487-488, 1975.

Sabbantini et al., "Early findings in a phase I study of PG-Paclitaxel (CT2103 in recurrent ovarian or primary peritoneal cancer," *Proc. AACR-NCI-EORTC Int. Conference on Molecule Targets and Cancer Therapeutics*, Abs, 470:96, 2001.

Sasaki et al., "Assessment of antioxidative ability in brain: imaging of glutathione localization with technetium-99m meso-hexamethyl propyleneamine," *J. Nuclear Med.*, 35:263P, Abstract No. 1083, 1994.

Sato et al., "Simple estimation of fractional renal uptake of tc-99m mag3 using graphical analysis without syringe counting and renal depth correction," *J. Nuclear Med.*, 37:292P, Abstract No. 1303, 1996.

Seabold et al., "Comparison of $^{99m}$Tc-Methoxyisobutyl Isonitrile and $^{201}$Tl Scintigraphy for Detection of Residual Thyroid Cancer After $^{131}$I Ablative Therapy," *J. Nucl. Med.*, 40(9):1434-1440, 1999.

Semenza, "Regulation of mammalian O2 homeostasis by hypoxia-inducible factor 1," *Ann. Rev. Cell Dev. Biol.*, 15:551-578, 1999.

Serruys et al., "A comparison of balloon-expandable-stent implantation with balloon angioplasty in patients with cornonary artery disease," *New England J. Medicine*, 331(8):489-495, 1994.

Seymour et al., "Synthetic polymers conjugated to monoclonal antibodies: vehicles for tumor-targeted drug delivery," *Select. Cancer Therapeut.*, 7(2):59-73, 1991.

Shankar et al., "Glucosamine infusion in rats mimics the beta-cell dysfunction of non-insulin-dependent diabetes mellitus," *Metabolism*, 47:573-577, 1998.

Shattuck et al., "Validation of the two sample technique for measuring gfr in renal transplant patients," *J. Nuclear Med.*, 36:231P, Abstract No. 1036, 1995.

Shih et al., "Anthracycline immunoconjugates prepared by a site-specific linkage via an amino-dextran intermediate carrier," *Cancer Res.*, 54:4192-4198, 1991.

Shimada et al., "Biodistribution of liposomes containing synthetic galactose-terminated diacylglyceryl-poly(ethylen glycol)s," *Biochimica et Biophysica Acta*, 1326:329-341, 1997.

Shuke et al., "Modified renal counting method for estimation of tc-99m mag3 renal clearance," *J. Nuclear Med.*, 37:291P, Abstract No. 1301, 1996.

Smalley et al., "Localization of fluorescent compounds in the firefly light organ," *J. Histochem. Cytochem.*, 28(4):323-329, 1980.

Smith et al., "Prognostic significance of vascular endothelial growth factor protein levels in oral and oropharyngeal squamous cell carcinoma," *J. Clin. Oncol.*, 18(10):2046-2052, 2000.

Sobel et al.,"Noninvasive estimation of regional myocardial oxygen consumption by positron emission tomography with carbon-11 acetate in patients with myocardial infaction," *J. Nucl. Med.*, 30:1798-1808, 1989.

Stoffel et al., Evaluation of technetium-99m-L,1-ec in renal transplant recipients: a comparative study with technetium-$^{99m}$-MAG3 and iodine-125-OIH, *J. Nucl. Med.*, 35:1951-1958, 1994.

Stuttle et al.,"Imaging of bone infection with labelled white blood cells: role of contemporaneous bone marrow imaging," *Dept. Dia. Rad.*, pp. 148-151, 1990.

Subramanian et al., "Transchelation reactions in labeling ecd with tc-99m," *J. Nuclear Med.*, 31:908, Abstract No. 867, 1990.

Sudimack et al., "Targeted delivery via folate receptor," *Adv. Drug Deliv. Rev.*, 41:147-162, 2000.

Sun et al., "Idium(III) and Gallium(III) Complexes of Bis(aminoethanethiol) Ligands with Different Denticities: Stabilities, Molecular Modeling, and in Vivo Behavior," *Journal of Medicinal Chemistry*, 39(2):458, 1996.

Surma et al., "Usefulness of Tc-*99m*-N,N'-ethylene-1-dicysteine complex for dynamic kidney investigations," *Nucl Med Comm*, 15:628-635, 1994.

Surwit et al., "Clinical assessmento f In-CYT-103 immunoscintigraphy in ovarian cancer," *Gynecol. Oncol.*, 48:285-292, 1993.

Suzuki et al., "A modified graphic method for estimation of glomerular filtration index using dynamic renal images with tc-99m dtpa," *J. Nuclear Med.*, 36:231P, Abstract No. 1035, 1995.

Taggart et al., "Novel mutations associated with carnitine palmitoyltransferase II deficiency," *Human Mutation*, 13(3):210-220, 1999.

Tait and Smith, "Site-specific mutagenesis of annexin V: role of residues from Arg-200 to Lys-207 in phospholipid binding," *Arch Biochem Biophys*, 288:141-144, 1991.

Takamizawa et al., "Differential apoptosis gene expression in pediatric tumors of the kidney," *J. Ped. Surg.*, 35(2):390-395, 2000.

Takashina et al., "Comparative pharmacokinetic properties of murine monoclonal antibody A7 modified with neocarzinostatin, dextran and polyethylene glycol," *Jpn. J. Cancer Res.*, 82:1145-1150, 1991.

Tam, "Synthetic peptide vaccine design: synthesis and properties of a high-density multiple antigenic peptide system," *Proc. Natl. Acad. Sci.*, USA, 85:5409-5413, 1988.

Taylor et al., "Comparison of tc-99m0(n,n1-ethylenedicysteine isomers in rats and in normal volunteers," *J. Nuclear Med.*, 37:46P-47P, Abstract No. 177, 1996.

Taylor et al., "Comparison of technetium-$^{99m}$-LL-Ec isomers in rats and humans," *J. Nucl. Med.*, 38:821-826, 1997.

Thompson, "Apoptosis in the pathogenesis and treatment of disease," *Science*, 267:1456-1462, 1995.

Tolomeo et al., "The CD95/CD95 ligand system is not the major effector in anticancer drug-mediated apoptosis," *Cell Death and Differentiation*, 5:735-742, 1998.

Tomalia et al., "Starburst dendrimers: molecular-level control of size, shape, surface chemistry, topology and flexibility from atoms to macroscopic matter," *Agnew. Chem. Int. Ed. Engl.*, 29:138-175, 1990.

Torchilin et al., "Chelating polymer modified monoclonal antibodies for radioimmunodiagnostics and radioimmunotherapy," *J. Controlled Release*, 24:111-118, 1993.

Tschopp et al., "Apoptosis: silencing the death receptors," *Curr. Biol.*, 9:R381-R384, 1999.

Tsukamoto et al., "The quantitation of absolute tc-99m-dmsa renal uptake in children from planar posterior-view method," *J. Nuclear Med.*, 37:291P, Abstract No. 1299, 1996.

Tubis et al.,"The preparation of $^{99m}$technetium-labelled cystine, methionine and synthetic polypetide and their distribution in mice," *Int;. Journ. Appl. Rad. Isotop.*, 19:835-840, 1968.

Tuli et al., "Comparison of a simplified quantitation of tc-99m mag-3 renogram to core needle biopsy in the diagnosis of renal transplant rejection," *J. Nuclear Med.*, 37:289P, Abstract No, 1290, 1996.

Ugar et al., "The diagnosis of renovascular hypertension with technetium-99m-ethylenedicysteine captopril scintigraphy," *Investigative Radiology*, 31:497-501, 1996.

Ugur et al., "Renovascular hypertension due to takayasu's arteritis demonstrated by Tc-$^{99m}$ ethylenedicysteine captopril scintigraphy," *Clinical Nuclear Medicine*, 21:714-716, 1996.

Ugur et al., "Technetium-$^{99m}$-ethylenedicysteine in the diagnosis and follow-up of renovascular hypertension," *Investigative Radiology*, 31:378-381, 1996.

Ugur et al., "Technetium-$^{99m}$-ethylenedicysteine: an alternative agent to detect renovascular hypertension," *J. of Nuclear Med.*, 38:1662-1664, 1997.

Ugur et al., "The diagnosis of renovascular hypertension with tc-99m ethylenedicysteine captopril scintigraphy," *J. Nuclear Med.*, 37:291P, Abstract No. 1302, 1996.

Ugurel et al., "Increased serum concentration of angiogenic factors in malignant melanoma patients correlates with tumor progression and survival," *J. Clin. Oncol.*, 19(2):577-583, 2001.

Valk et al., "Hypoxia in human gliomas: Demonstration by PET with [$^{18}$F]fluoromisonidazole," *J Nucl Med*, 33:2133-2137, 1992.

Van den Eijnde et al., "In situ detection of apoptosis during embryogenesis with annexin V: from whole mount to ultrastructure," *Cytometry*, 29:313-320, 1997.

Van Heeswijk et al., "The synthesis and characterization of polypeptide-adriamycin conjugates and its complexes with adiramycin Part 1," *J. Controlled Release*, 1:301-315, 1985.

Van Nerom et al., "Comparative evaluation of Tc-*99m* L,L-ethylenedicysteine and Tc-*99m* MAG3 in volunteers," *Eur J Nucl Med*, 16:417, 1990.

Van Nerom et al., "Comparison of renal excretion ocharacteristics of isomers 1,1 and d,d of tc-99m ethylenedicysteine," *J. Nuclear Med.*, 31:806, Abstract No. 412, 1990.

Van Nerom et al., "Optimalization of the labelling of ethylenedicysteine (ec) with technetium-99m," *J. Labelled Compounds and Radiopharmaceuticals*, XXX:37-39, 1991.

Van Nerom et al., "First experience in healthy volunteers with Tc-*99m*-L,L-ethylenedicysteine, a new renal imaging agent," *Eur J Nucl Med*, 20:738-746, 1993.

Van Schepdael et al., "Capillary electrophoretic analysis of ethylene dicysteine, a precursor of the radiopharmaceutical $^{99m}$Tc ethylene dicysteine," *J. Chromatography B*, 697:251-254, 1997.

Vega et al., "Targeting adriamycin to EGF receptors by site-specific conjugation of monoclonal antibody to poly(L-glutamic acid)," Division of Deagnostic Imaging and Departmetn of Experimental Therapeutics, U.T. M.D. Anderson Cancer Center, 1515 Holcombe Blvd., Houston, TX, USA.

Verbruggen et al., "Evaluation of Tc-*99m*-L,L-ethylenedicysteine as a potential alternative to Tc-*99m* MAG3," *Eur J Nucl Med*, 16:429, 1990.

Verbruggen et al., "Is syn or anti orientation of the oxotechnetium and carboxyl group in tc-99m renal function agents affecting the renal excretion rate?" *J. Labelled Compounds and Radiopharmaceuticals*, XXX:86-88, 1991.

Verbruggen et al., "Tc-99m 1,1-ethylenedicysteine, a potential alternative to tc-99m mag3," *J. Nuclear Med.*, 31:908, Abstract No. 864, 1990.

Verbruggen et al., "Tc-*99m*-L,L-ethylenedicysteine: A renal imaging agent. I. Labelling and evaluation in animals," *J Nucl Med*, 33:551-557, 1992.

Villevalois-Cam et al., "Insulin-induced redistribution of the insulin-like growth factor II/mannose 6-phosphate receptor in intact rat liver," *J. Cell. Biochem.*, 77:310-322, 2000.

Vyas et al., "Phosphatase-activated prodrugs of paclitaxel," Taxane Anticancer Agents: Basic Science and Current Status, *American Chemical Society*, Washington, DC, 124-137, 1995.

Wahl et al., "Loss of normal p53 function conferes sensation to taxol by increasing g2/m arrest and apoptosis," *Nat. Med.*, 2(1):72-79, 1996.

Wahl, "Monoclonal antibodies in nucear medicine," *Nuclear Medicine Annual 1992*, New York, Raven Press Ltd., 91-103, 1992.

Wang et al., "Design and synthesis of [$^{111}$In]DTPA-folate for use as a tumor-targeted radiopharmaceutical," *Bioconjugate Chem*, 8:673-679, 1997.

Wang et al., "Microtubule-interfering agents activate c-Jun N-terminal kinasae/stress-activated protein kinase through both Ras and apoptosis signal-regulating kinase pathways," *J. Biol. Chem.*, 273:4928-4936, 1998.

Wang et al., "Synthesis, purification, and tumor cell uptake of Ga-67 deferoxamine-folate, a potential radiopharmaceutical for tumor imaging," *Bioconjugate Chem*, 7:56-62, 1996.

Washburn et al., "Reliable kit preparation of tc99m pentavalent dimercaptosuccinic acid [tc-99m (v) dmsa]," *J. Nuclear Med.*, 35:263P, Abstract No. 1080, 1994.

Weiss et al., "Hypersensitivity reaction from taxol," *J. Clin. Oncol.*, 8(7):1263-1268, 1990.

Weitman et al., "Cellular localization of the folate receptor: potential role in drug toxicity and folate homeostasis," *Cancer Res*, 52:6708-6711, 1992b.

Weitman et al., "The folate receptor in central nervous system malignancies of childhood," *J Neuro-Oncology*, 21:107-112, 1994.

Weitman et al., "Distribution of the folate receptor GP38 in normal and malignant cell lines and tissues," *Cancer Research*, 52:3396-3401, 1992.

Wells et al., "Glycosylation of nucleocytoplasmic proteins: signal transduction and )-glcNAc," *Science*, 291:2376-2378, 2001.

Wen et al., "Conjugation with 111In-DTPA-poly(ethylene glycol) improves imaging of anti-EGF receptor antibody C225," *J. Nuclear Medicine*, 42(10):1530-1537, 2001.

Wen et al., "Improved radiolabeling of PEFylated protein: PEGylated annexin V for noninvasive imaging of tumor apoptosis," *Bioconjugate Chemistry*, 2002.

Wen et al., "Poly(ethylene glucol) conjugated anti-EGF receptor antibody C225 with radiometal chelator attached to the termini of polymer chains," *Bioconjugate Chem.*, 12:545-553, 2001.

Wester et al.,"Synthesis and radiopharmacology of -O(2-[$^{18}$F]fluoroethyl)-L-Tyrosine for tumor imaging," *J. Nucl. Med.*, 40:205-212, 1999.

Westerhof et al., "Membrane transport of natural folates and antifolate compounds in murine L1210 leukemia cells: Role of carrier- and receptor- mediated transport systems," *Cancer Res*, 51:5507-5513, 1991.

Wright et al., "Aminoglycoside antibiotics: structures, functions, and resistance," In: *Resolving the Antibiotic Paradox*, Rosen and Mobashery eds, Kluwer Academic/Plenum Pub NY, 1998.

Wu et al., "Apoptosis induced by and anti-epidermal growth factor receptor monoclonal antibody in a human colorectal carcinoma cell line and its delay by insulin," *J. Clin. Invest.*, 95:1897-1905, 1995.

Yaghoubi et al., "Human pharacokinetic and dosimetry studies of {18F]FHBG: a reporter probe for imaging herpes simplex virus type-1 thymidine kinase reporter gene expression," *J. Nucl. Med.*, 42:1225-1234, 2001.

Yamori et al., Potent antitumor activity of MS-247, a novel DNA minor groove binder, evaluated by an in vitro and in vivo human cancer cell line panel., *Cancer Res.*, 59:4042-4049, 1999.

Yang et al., "Development of F-18-labeled fluoroerythronitroimidazole as a PET agent for imaging tumor hypoxia," *Radiology*, 194:795-800, 1995.

Yang et al., "99mtc-ec-deoxyglucose: synthesis, cellular uptake, biodistribution an dscintigraphic imaging," *J. Labelled Cpd. Radiopharm.*, 44:S513-S514, Abstract, 2001.

Yang et al., "Imaging tumor folate receptors using 99mtc-ethylenedicysteine-folate," *Proceedings of the American Association for Cancer Research*, 40:259, Abstract #1720, 1999.

Yang et al., "Imaging tumor folate receptors using radiolabeled folate and methotrexate," *J. Labelled Cpd. Radiopharm.*, 42:S696-S697, 1999.

Yang et al., "Molecular imaging using 99m-tc-ec-nitroimidazole, and 99mtc-ec-annexin v in tumor-bearing rodents," *Proceedings of the American Association for Cancer Research Annual Meeting*, 41:766, Abstract, 2000.

Yang et al., "Noninvasive assessment of tumor hypoxia with $^{99m}$Tc labeled metronidazole," *Pharmaceutical Research*, 15:743-750, 1999.

Yasui et al., "Expression of epidermal growth factor receptor in human gastric and colonic carcinomas," *Cancer Res.*, 48:137-141, 1995.

Ye et al., TRAF family proteins interact with the common neurotrophin receptor and modulate apoptosis induction, *J. Biol. Chem.*, 274(42):30202-30208, 1999.

Yeh et al., "Fluorine-18 fluoromisonidazole tumour to muscle retention ratio for the detection of hypoxia in nasopharyngeal carcinoma," *Eur. J. Nucl. Med.*, 23(10):1378-1383, 1996.

Yen et al., "A comparative study of evaluating renal scars by 99mTc-DSMA planar and SPECT renal scans, intravenous urography, and ultrasonography," *Ann. Nucl. Med.*, 8(2):147-152, 1994.

Yen et al., "Technetium-99m-DMSA renal SPECT in diagnosing and monitoring pediatric acute pyelonephritis," *J. Nucl. Med.*, 37(8):1349-1353, 1996.

Yen et al., "The role of technetium-99m sestamibi whole-body scans in diagnosing metastatic Hurthle cell carcinoma of the thyroid gland after total thyroidectomy: a comparison with iodine-131 and thallium-201 whole-body scans," *Eur. J. Nucl. Med.*, 21(9):980-983, 1994.

Yokoyama et al., "Polymer micelles as novel drug carrier: adriamycin-conjugated poly(ethylen glycol)-poly(aspartic acid) block copolymer," *J. Controlled Release*, 11:269-278, 1990.

Yokoyama et al., "Preparation of micelle-formin polymer-drug conjugates," *Bioconjugate Chem.*, 3:295-301, 1992.

Yoshinari et al., "Mode of action of a new indolocarbazole anticancer agent, J-107088, targeting topoisomerase I," *Cancer Res.*, 59:4271-4275, 1999.

Yoshino et al.,"Differential effects of troglitazone and D-chiroinositol on glucosamine-induced insulin resistance in vivo in rats," *Metabolism.* 48:1418-23, 1999.

Young et al., "Influence of immunoglobulin heavy and light-chain expression on B-cell differentiation," *Genes Develop.*, 8:1043-1057, 1994.

Zakko et al., "Biliary excretion of Tc-$^{99m}$ec in renal studies," *Clinical Nuclear Medicine*, 23:417-419, 1998.

Zareneyrizi et al., "Synthesis of [$^{99m}$Tc] ethylenedicysteine-colchicine for evaluation of antiangiogenic effect," *Anti-Cancer Drugs*, 10:685-692, 1999.

Verbeke et al., "Development of a conjugate of 99mtc-ec with aminomethylenediphosphonate in the search for a bone tracer with fast clearance from soft tissue," *Bioconjugate Chemistry*, 13:16-22, 2002.

Verbeke et al., "Preparation and preliminary evaluation of <99m>Tc-EC-for-MLFK," *Nuclear Medicine and Biology*, 29:585-592, 2002.

\* cited by examiner

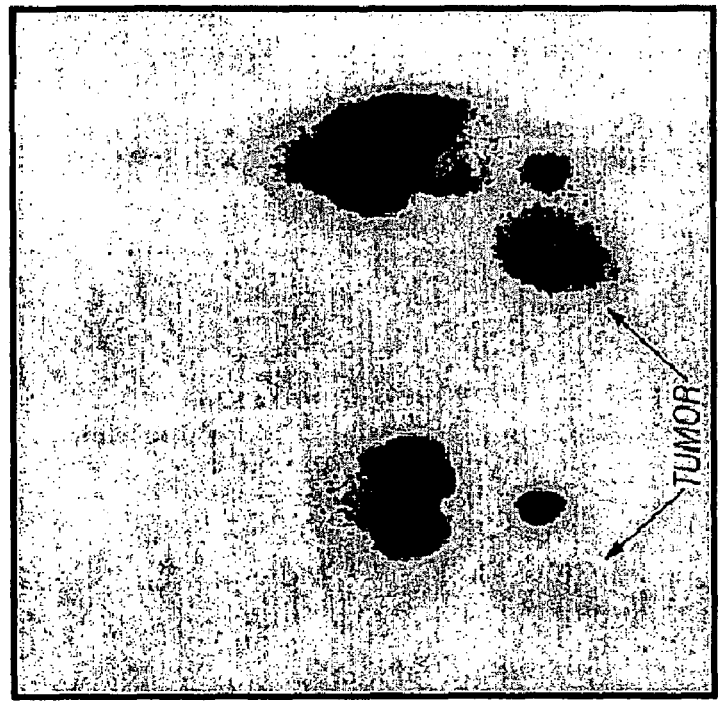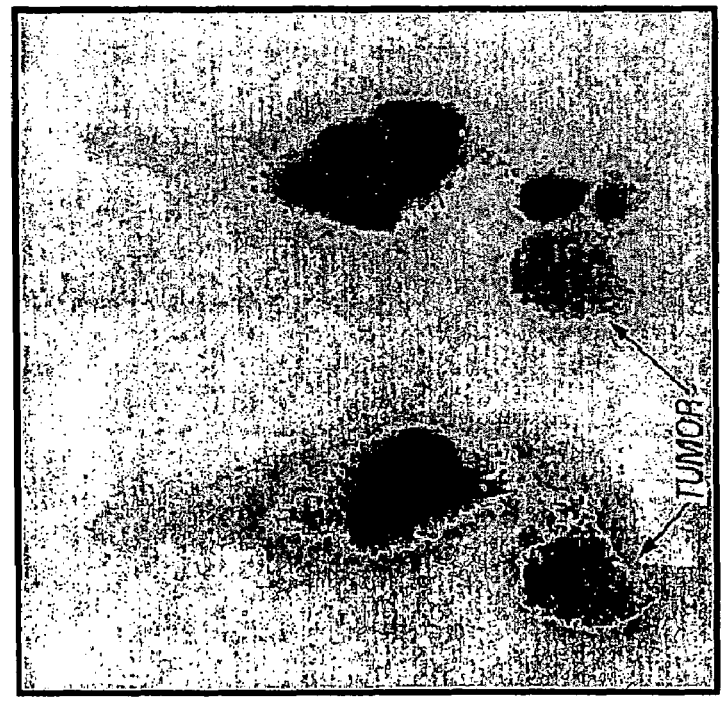
FIG. 14A

Synthesis of EC-GAP

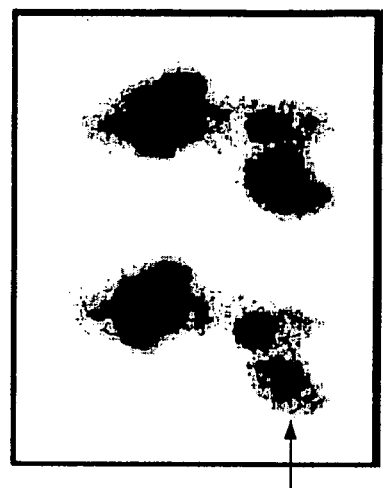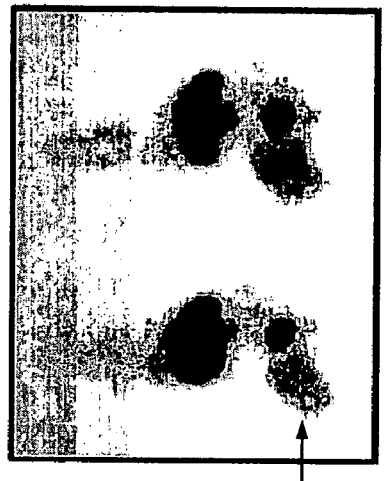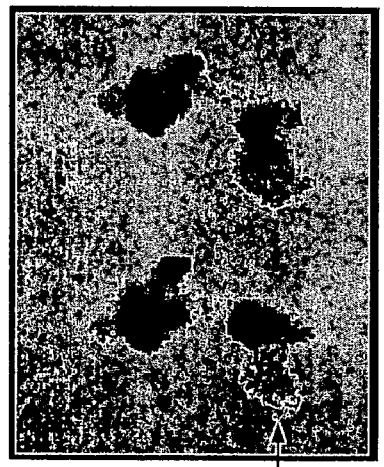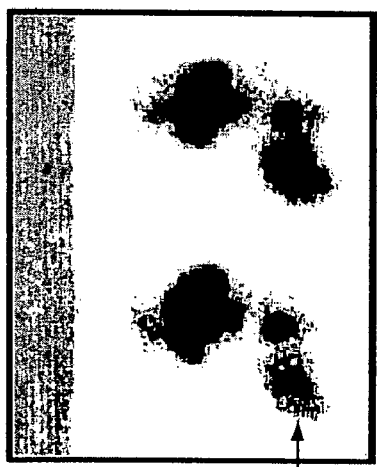
FIG. 18

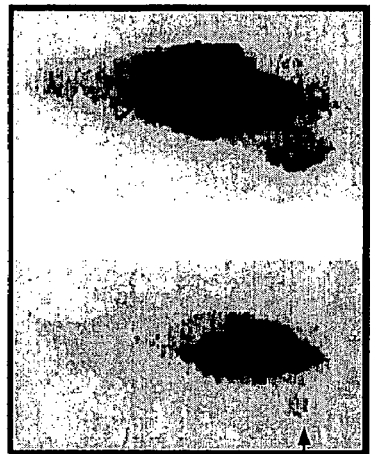 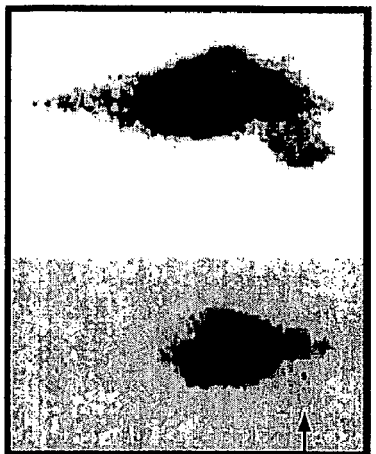 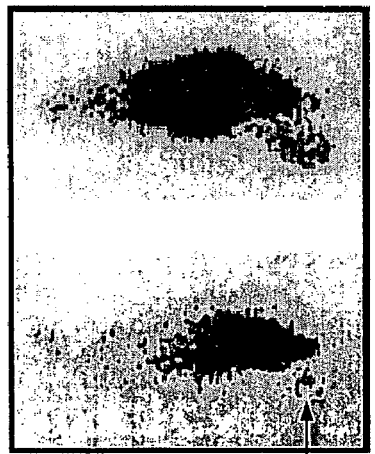 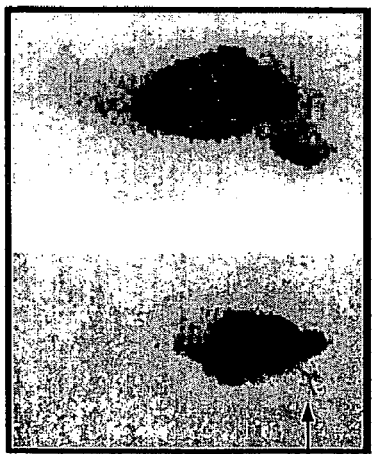
FIG. 19A

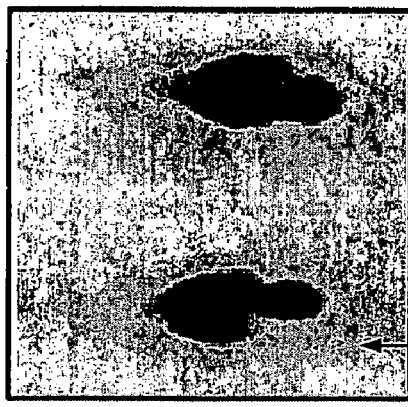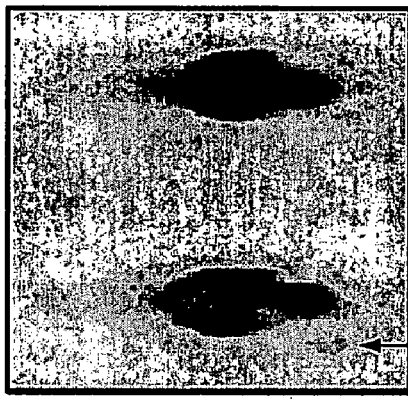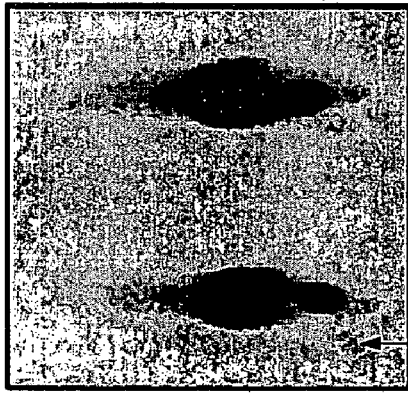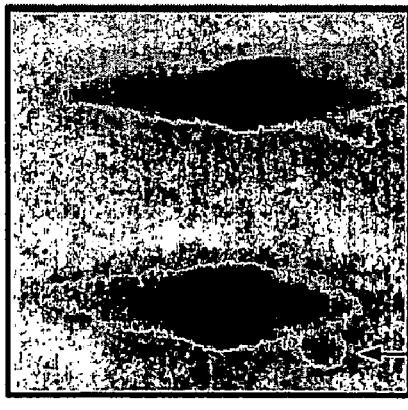
FIG. 19B

¹H-NMR of EC.

$^1$H-NMR of neomycin

1H-NMR of EC-neomycin

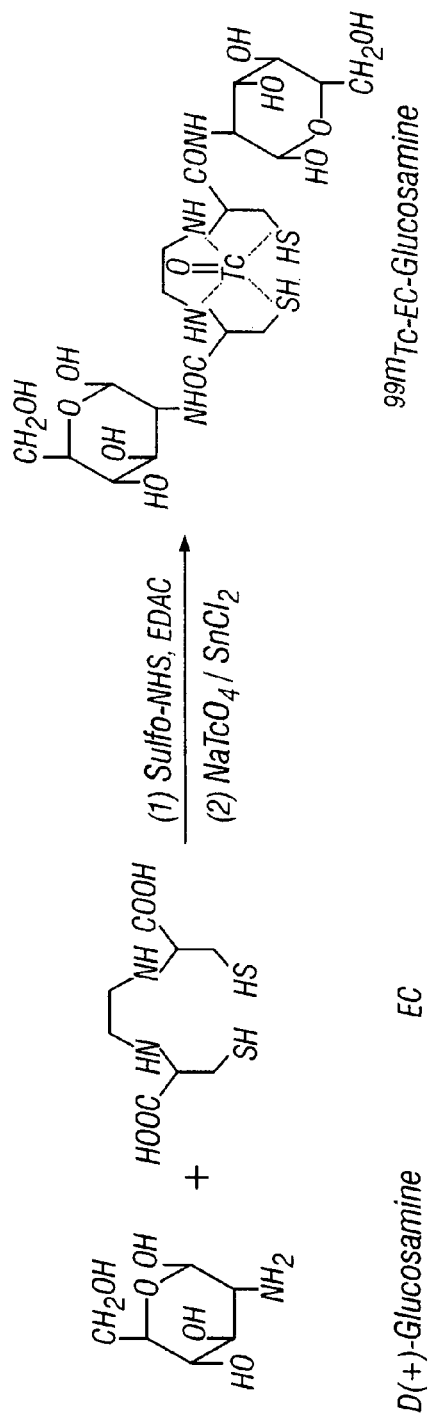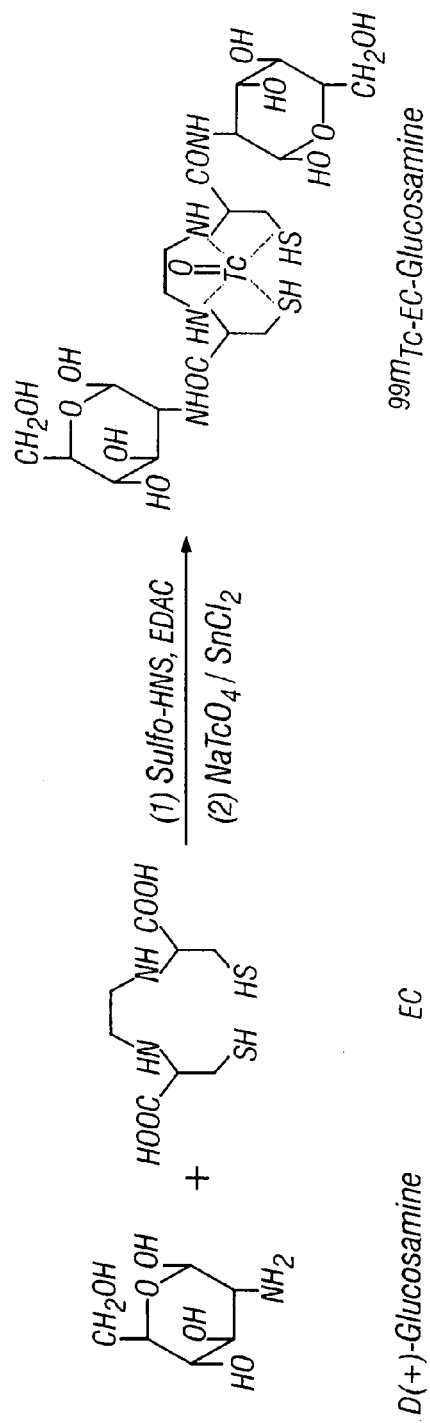

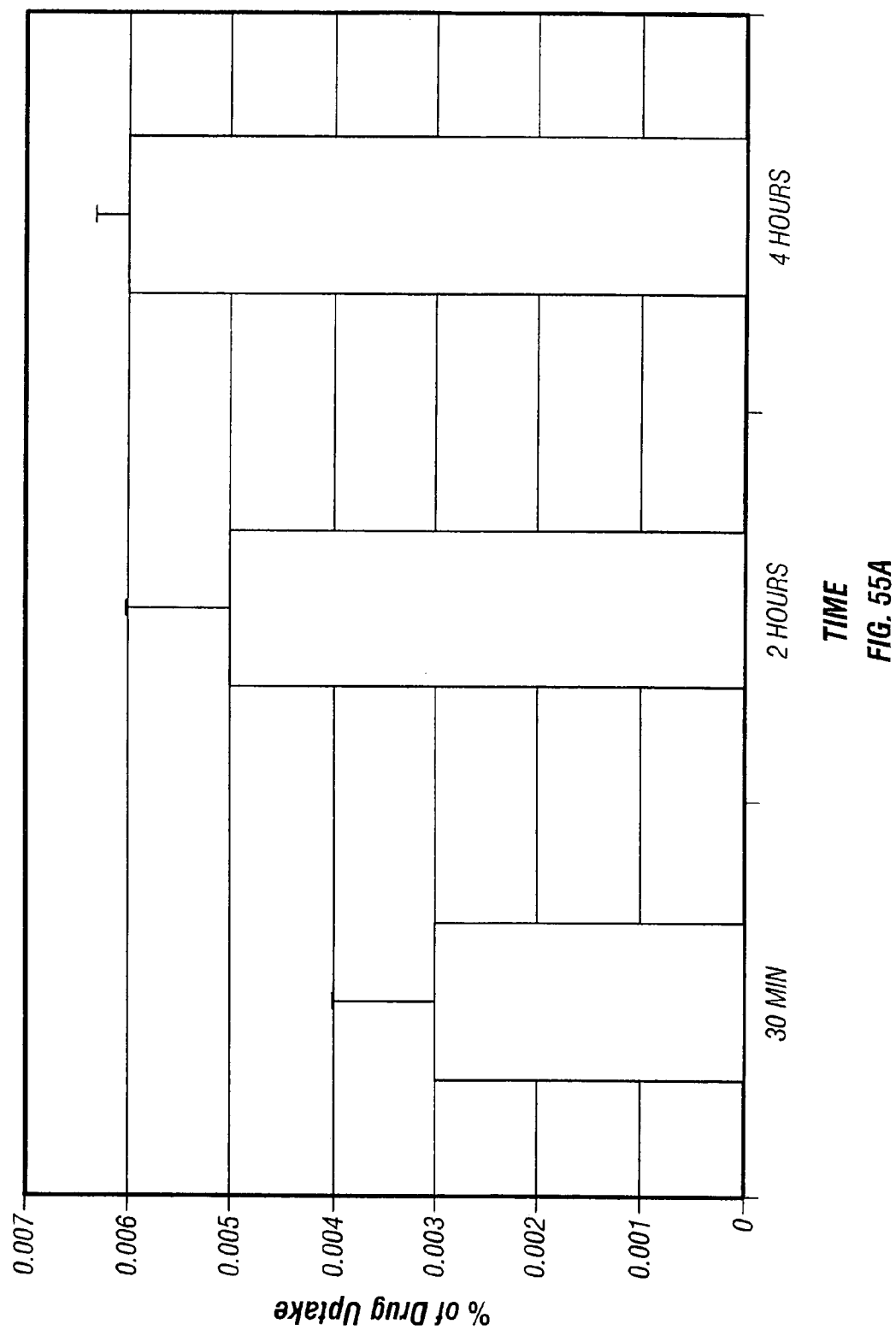

GLUCOSE DOSAGE

T=Tumor

POST OP
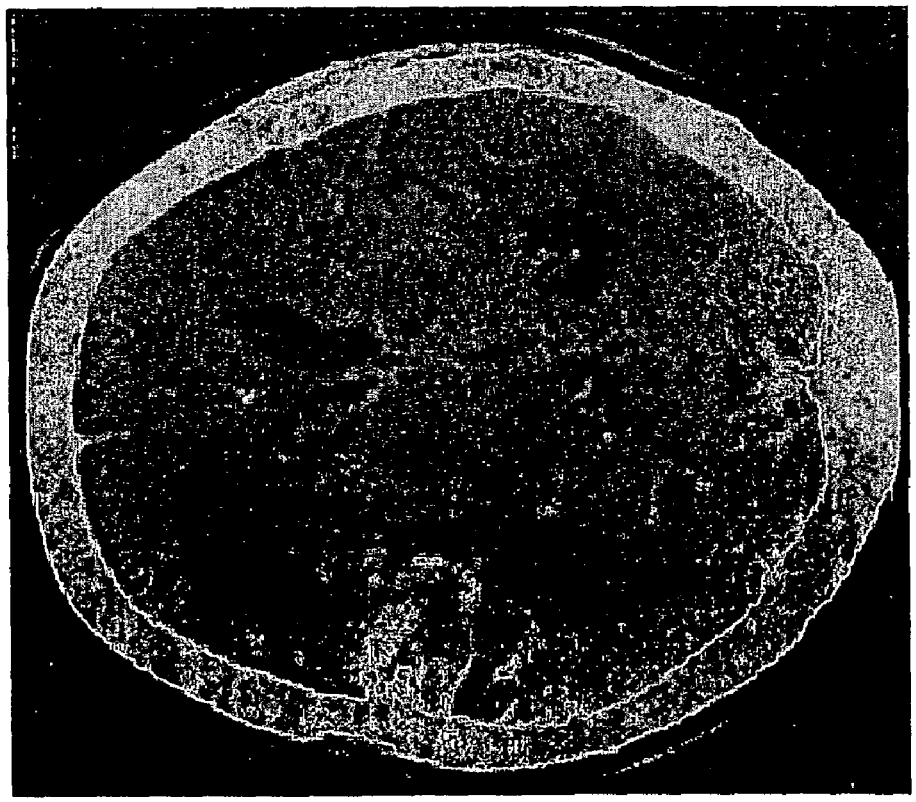
PRE OP
FIG. 82A

ETHYLENEDICYSTEINE (EC)-DRUG CONJUGATES, COMPOSITIONS AND METHODS FOR TISSUE SPECIFIC DISEASE IMAGING

This application is a divisional of application Ser. No. 09/599,152, filed Jun. 21, 2000, (now U.S. Pat. No. 7,067,111) which is a continuation-in-part of application Ser. No. 09/587,583, filed Jun. 2, 2000 (now abandoned), which is a continuation-in-part of application Ser. No. 09/434,313, filed Oct. 25, 1999 (now U.S. Pat. No. 6,692,724).

The entire text of each of the above-referenced disclosures is specifically incorporated herein by reference without disclaimer. The government does not own rights in the present invention.

BACKGROUND OF THE INVENTION

The government does not own rights in the present invention.

1. Field of the Invention

The present invention relates generally to the fields of labeling, radioimaging and chemical synthesis. More particularly, it concerns a strategy for radiolabeling target ligands. It further concerns methods of using those radiolabeled ligands in tumor imaging and tissue-specific disease imaging.

2. Description of Related Art

Improvement of scintigraphic tumor imaging is extensively determined by development of more tumor specific radiopharmaceuticals. Due to greater tumor specificity, radiolabeled ligands as well as radiolabeled antibodies have opened a new era in scintigraphic detection of tumors and undergone extensive preclinical development and evaluation. (Mathias et al., 1996, 1997a, 1997b). Radionuclide imaging modalities (positron emission tomography, PET; single photon emission computed tomography, SPECT) are diagnostic cross-sectional imaging techniques that map the location and concentration of radionuclide-labeled radiotracers. Although CT and MRI provide considerable anatomic information about the location and the extent of tumors, these imaging modalities cannot adequately differentiate invasive lesions from edema, radiation necrosis, grading or gliosis. PET and SPECT can be used to localize and characterize tumors by measuring metabolic activity.

The development of new tumor hypoxia agents is clinically desirable for detecting primary and metastatic lesions as well as predicting radioresponsiveness and time to recurrence. None of the contemporary imaging modalities accurately measures hypoxia since the diagnosis of tumor hypoxia requires pathologic examination. It is often difficult to predict the outcome of a therapy for hypoxic tumor without knowing at least the baseline of hypoxia in each tumor treated. Although the Eppendorf polarographic oxygen microelectrode can measure the oxygen tension in a tumor, this technique is invasive and needs a skillful operator. Additionally, this technique can only be used on accessible tumors (e.g., head and neck, cervical) and multiple readings are needed. Therefore, an accurate and easy method of measuring tumor hypoxia will be useful for patient selection. However, tumor to normal tissue uptake ratios vary depending upon the radiopharmaceuticals used. Therefore, it would be rational to correlate tumor to normal tissue uptake ratio with the gold standard Eppendorf electrode measures of hypoxia when new radiopharmaceuticals are introduced to clinical practice.

[$^{18}$F]FMISO has been used to diagnose head and neck tumors, myocardial infarction, inflammation, and brain ischemia (Martin et al. 1992; Yeh et al. 1994; Yeh et al. 1996; Liu et al. 1994). Tumor to normal tissue uptake ratio was used as a baseline to assess tumor hypoxia (Yet et al. 1996). Although tumor hypoxia using [$^{18}$F]FMISO was clearly demonstrated, introducing new imaging agents into clinical practice depends on some other factors such as easy availability and isotope cost. Although tumor metabolic imaging using [$^{18}$F]FDG was clearly demonstrated, introducing molecular imaging agents into clinical practice depends on some other factors such as easy availability and isotope cost. [$^{18}$F]fluorodeoxyglucose (FDG) has been used to diagnose tumors, myocardial infarction, and neurological disease. In addition, PET radiosynthesis must be rapid because of short half-life of the positron isotopes. $^{18}$F chemistry is also complex. The $^{18}$F chemistry is not reproducible in different molecules. Thus, it would be ideal to develop a chelator which could conjugate to various drugs. The preferred isotope would be $^{99m}$Tc due to low cost ($0.21/mCi vs. $50/mCi for $^{18}$F) and low energy (140 Kev vs. 571 Kev for $^{18}$F). $^{99m}$Tc is easily obtained from a $^{99}$Mo generator. Due to favorable physical characteristics as well as extremely low price, $^{99m}$Tc has been preferred to label radiopharmaceuticals.

Several compounds have been labeled with $^{99m}$Tc using nitrogen and sulfur chelates (Blondeau et al., 1967; Davison et al., 1980). Bis-aminoethanethiol tetradentate ligands, also called diaminodithol compounds, are known to form very stable Tc(V)O complexes on the basis of efficient binding of the oxotechnetium group to two thiolsulfur and two amine nitrogen atoms. $^{99m}$Tc-L,L-ethylenedicysteine ($^{99m}$Tc-EC) is a recent and successful example of N$_2$S$_2$ chelates. EC can be labeled with $^{99m}$Tc easily and efficiently with high radiochemical purity and stability, and is excreted through the kidney by active tubular transport (Surma et al., 1994; Van Nerom et al., 1990, 1993; Verbruggen et al., 1990, 1992). Other applications of EC would be chelated with galium-68 (a positron emitter, t½=68 min) for PET and gadolinium, iron or manganese for magnetic resonance imaging (MRI). $^{99m}$Tc-EC-neomycin and $^{99m}$Tc-EC-deoxyglucose were developed and their potential use in tumor characterization was evaluated.

SUMMARY OF THE INVENTION

The present invention overcomes these and other drawbacks of the prior art by providing a new radiolabeling strategy to target tissues for imaging. The invention provides radiolabeled tissue-specific ligands, as well as methods for making the radiolabeled ligands and for using them to image tissue-specific diseases.

The present invention provides compositions for tissue specific disease imaging. The imaging compositions of the invention generally include a radionuclide label chelated with ethylenedicysteine and a tissue specific ligand conjugated to the ethylenedicysteine on one or both of its acid arms. The ethylenedicysteine forms an N$_2$S$_2$ chelate with the radionuclide label. Of course, the chelated compound will include an ionic bond between the ranionuclide and the chelating compound. The terms "EC-tissue specific ligand conjugate," "EC-derivative" and "EC-drug conjugate" are used interchangeably herein to refer to the unlabeled ethylenedicysteine-tissue specific ligand compound. As used herein, the term "conjugate" refers to a covalently bonded compound.

Ethylenedicysteine is a bis-aminoethanethiol (BAT) tetradentate ligand, also known as diaminodithiol (DADT) compounds. Such compounds are known to form very stable Tc(V)O-complexes on the basis of efficient binding of the oxotechnetium group to two thiol-sulphur and two amine-nitrogen atoms. The $^{99m}$Tc labeled diethylester ($^{99m}$Tc-L,L-

ECD) is known as a brain agent. $^{99m}$Tc-L,L-ethylenedicysteine ($^{99m}$Tc-L,L-EC) is its most polar metabolite and was discovered to be excreted rapidly and efficiently in the urine. Thus, $^{99m}$Tc-L,L-EC has been used as a renal function agent. (Verbruggen et al. 1992).

A tissue specific ligand is a compound that, when introduced into the body of a mammal or patient, will specifically bind to a specific type of tissue. It is envisioned that the compositions of the invention may include virtually any known tissue specific compound. Preferably, the tissue specific ligand used in conjunction with the present invention will be an anticancer agent, DNA topoisomerase inhibitor, antimetabolite, tumor marker, folate receptor targeting ligand, tumor apoptotic cell targeting ligand, tumor hypoxia targeting ligand, DNA intercalator, receptor marker, peptide, nucleotide, organ specific ligand, antimicrobial agent, such as an antibiotic or an antifungal, glutamate pentapeptide or an agent that mimics glucose. The agents that mimic glucose may also be referred to as "sugars."

Preferred anticancer agents include methotrexate, doxorubicin, tamoxifen, paclitaxel, topotecan, LHRH, mitomycin C, etoposide, tomudex, podophyllotoxin, mitoxantrone, captothecin, colchicine, endostatin, fludarabin and gemcitabine. Preferred tumor markers include PSA, ER, PR, AFP, CA-125, CA-199, CEA, interferons, BRCA1, cytoxan, p53, VEGF, integrins, endostatin, HER-2/neu, antisense markers or a monoclonal antibody. It is envisioned that any other known tumor marker or any monoclonal antibody will be effective for use in conjunction with the invention. Preferred folate receptor targeting ligands include folate, methotrexate and tomudex. Preferred tumor apoptotic cell or tumor hypoxia targeting ligands include annexin V, colchicine, nitroimidazole, mitomycin or metronidazole. Preferred antimicrobials include ampicillin, amoxicillin, penicillin, cephalosporin, clidamycin, gentamycin, kanamycin, neomycin, natamycin, nafcillin, rifampin, tetracyclin, vancomycin, bleomycin, and doxycyclin for gram positive and negative bacteria and amphotericin B, amantadine, nystatin, ketoconazole, polymycin, acyclovir, and ganciclovir for fungi. Preferred agents that mimic glucose, or sugars, include neomycin, kanamycin, gentamycin, paromycin, amikacin, tobramycin, netilmicin, ribostamycin, sisomicin, micromicin, lividomycin, dibekacin, isepamicin, astromicin, aminoglycosides, glucose or glucosamine.

In certain embodiments, it will be necessary to include a linker between the ethylenedicysteine and the tissue specific ligand. A linker is typically used to increase drug solubility in aqueous solutions as well as to minimize alteration in the affinity of drugs. While virtually any linker which will increase the aqueous solubility of the composition is envisioned for use in conjunction with the present invention, the linkers will generally be either a poly-amino acid, a water soluble peptide, or a single amino acid. For example, when the functional group on the tissue specific ligand, or drug, is aliphatic or phenolic-OH, such as for estradiol, topotecan, paclitaxel, or raloxifen etoposide, the linker may be poly-glutamic acid (MW about 750 to about 15,000), poly-aspartic acid (MW about 2,000 to about 15,000), bromo ethylacetate, glutamic acid or aspartic acid. When the drug functional group is aliphatic or aromatic-$NH_2$ or peptide, such as in doxorubicin, mitomycin C, endostatin, annexin V, LHRH, octreotide, and VIP, the linker may be poly-glutamic acid (MW about 750 to about 15,000), poly-aspartic acid (MW about 2,000 to about 15,000), glutamic acid or aspartic acid. When the drug functional group is carboxylic acid or peptide, such as in methotrexate or folic acid, the linker may be ethylenediamine, or lysine.

While the preferred radionuclide for imaging is $^{99m}$Tc, it is envisioned that other radionuclides may be chelated to the EC-tissue specific ligand conjugates, or EC-drug conjugates of the invention, especially for use as therapeutics. For example, other useful radionuclides are $^{188}$Re, $^{186}$Re, $^{153}$Sm, $^{166}$Ho, $^{90}$Y, $^{89}$Sr, $^{67}$Ga, $^{68}$Ga, $^{111}$In, $^{153}$Gd, and $^{59}$Fe. These compositions are useful to deliver the therapeutic radionuclides to a specific lesion in the body, such as breast cancer, ovarian cancer, prostate cancer (using for example, $^{186/188}$Re-EC-folate) and head and neck cancer (using for example, $^{186/188}$Re-EC-nitroimidazole).

Specific embodiments of the present invention include $^{99m}$Tc-EC-annexin V, $^{99m}$Tc-EC-colchicine, $^{99m}$Tc-EC-nitroimidazole, $^{99m}$Tc-EC-glutamate pentapeptide, $^{99m}$Tc-EC-metronidazole, $^{99m}$Tc-EC-folate, $^{99m}$Tc-EC-methotrexate, $^{99m}$Tc-EC-tomudex, $^{99m}$Tc-EC-neomycin, $^{99m}$Tc-EC-kanamycin, $^{99m}$Tc-EC-aminoglycosides, (glucosamine, EC-deoxyglucose), $^{99m}$Tc-EC-gentamycin, and $^{99m}$Tc-EC-tobramycin.

The present invention further provides a method of synthesizing a radiolabeled ethylenedicysteine drug conjugate or derivative for imaging or therapeutic use. The method includes obtaining a tissue specific ligand, admixing the ligand with ethylenedicysteine (EC) to obtain an EC-tissue specific ligand derivative, and admixing the EC-tissue specific ligand derivative with a radionuclide and a reducing agent to obtain a radionuclide labeled EC-tissue specific ligand derivative. The radionuclide is chelated to the EC via an $N_2S_2$ chelate. The tissue specific ligand is conjugated to one or both acid arms of the EC either directly or through a linker as described above. The reducing agent is preferably a dithionite ion, a stannous ion or a ferrous ion.

The present invention further provides a method for labeling a tissue specific ligand for imaging, therapeutic use or for diagnostic or prognostic use. The labeling method includes the steps of obtaining a tissue specific ligand, admixing the tissue specific ligand with ethylenedicysteine (EC) to obtain an EC-ligand drug conjugate, and reacting the drug conjugate with $^{99m}$Tc in the presence of a reducing agent to form an $N_2S_2$ chelate between the ethylenedicysteine and the $^{99m}$Tc.

For purposes of this embodiment, the tissue specific ligand may be any of the ligands described above or discussed herein. The reducing agent may be any known reducing agent, but will preferably be a dithionite ion, a stannous ion or a ferrous ion.

In another embodiment, the present invention provides a method of imaging a site within a mammalian body. The imaging method includes the steps of administering an effective diagnostic amount of a composition comprising a $^{99m}$Tc labeled ethylenedicysteine-tissue specific ligand conjugate and detecting a radioactive signal from the $^{99m}$Tc localized at the site. The detecting step will typically be performed from about 10 minutes to about 4 hours after introduction of the composition into the mammalian body. Most preferably, the detecting step will be performed about 1 hour after injection of the composition into the mammalian body.

In certain preferred embodiments, the site will be an infection, tumor, heart, lung, brain, liver, spleen, pancreas, intestine or any other organ. The tumor or infection may be located anywhere within the mammalian body but will generally be in the breast, ovary, prostate, endometrium, lung, brain, or liver. The site may also be a folate-positive cancer or estrogen-positive cancer.

The invention also provides a kit for preparing a radiopharmaceutical preparation. The kit generally includes a sealed via or bag, or any other kind of appropriate container, containing a predetermined quantity of an ethylenedicysteine-tissue specific ligand conjugate composition and a sufficient amount of reducing agent to label the conjugate with $^{99m}$Tc. In certain cases, the ethylenedicysteine-tissue specific ligand conjugate composition will also include a linker between the ethylenedicysteine and the tissue specific ligand. The tissue specific ligand may be any ligand that specifically binds to any specific tissue type, such as those discussed herein. When a linker is included in the composition, it may be any linker as described herein.

The components of the kit may be in any appropriate form, such as in liquid, frozen or dry form. In a preferred embodiment, the kit components are provided in lyophilized form. The kit may also include an antioxidant and/or a scavenger. The antioxidant may be any known antioxidant but is preferably vitamin C. Scavengers may also be present to bind leftover radionuclide. Most commercially available kits contain glucoheptonate as the scavenger. However, glucoheptonate does not completely react with typical kit components, leaving approximately 10-15% left over. This leftover glucoheptonate will go to a tumor and skew imaging results. Therefore, the inventors prefer to use EDTA as the scavenger as it is cheaper and reacts more completely.

Another aspect of the invention is a prognostic method for determining the potential usefulness of a candidate compound for treatment of specific tumors. Currently, most tumors are treated with the "usual drug of choice" in chemotherapy without any indication whether the drug is actually effective against that particular tumor until months, and many thousands of dollars, later. The imaging compositions of the invention are useful in delivering a particular drug to the site of the tumor in the form of a labeled EC-drug conjugate and then imaging the site within hours to determine whether a particular drug.

In that regard, the prognostic method of the invention includes the steps of determining the site of a tumor within a mammalian body, obtaining an imaging composition which includes a radionuclide chelated to EC which is conjugated to a tumor specific cancer chemotherapy drug candidate, administering the composition to the mammalian body and imaging the site to determine the effectiveness of the candidate drug against the tumor. Typically, the imaging step will be performed within about 10 minutes to about 4 hours after injection of the composition into the mammalian body. Preferably, the imaging step will be performed within about 1 hour after injection of the composition into the mammalian body.

The cancer chemotherapy drug candidate to be conjugated to EC in the prognostic compositions may be chosen from known cancer chemotherapy drugs. Such drugs appear in Table 2. There are many anticancer agents known to be specific for certain types of cancers. However, not every anticancer agent for a specific type of cancer is effective in every patient. Therefore, the present invention provides for the first time a method of determining possible effectiveness of a candidate drug before expending a lot of time and money on treatment.

Yet another embodiment of the present invention is a reagent for preparing a scintigraphic imaging agent. The reagent of the invention includes a tissue specific ligand, having an affinity for targeted sites in vivo sufficient to produce a scintigraphically-detectable image, covalently linked to a $^{99m}$Tc binding moiety. The $^{99m}$Tc binding moiety is either directly attached to the tissue specific ligand or is attached to the ligand through a linker as described above. The $^{99m}$Tc binding moiety is preferably an $N_2S_2$ chelate between $^{99m}$Tc in the +4 oxidation state and ethylenedicysteine (EC). The tissue specific ligand will be covalently linked to one or both acid arms of the EC, either directly or through a linker as described above. The tissue specific ligand may be any of the ligands as described above.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8A shows the synthetic scheme and FIG. 8B illustrates the $^1$H-NMR confirmation of the structure.

FIGS. 14A and 14B. Illustrates breast tumor uptake of $^{99m}$Tc-EC-NIM vs. $^{99m}$Tc-EC in rats (FIG. 14A) and in rats treated with paclitaxel compared to controls (FIG. 14B).

FIG. 15C shows tumor uptake in sarcoma bearing rats treated with paclitaxel while FIG. 15D shows tumor uptake in rats not treated with paclitaxel. There was a decreased uptake of $^{99m}$Tc-EC-NIM after treatment with paclitaxel.

FIG. 18. Scintigraphic images of breast tumors in $^{99m}$Tc-EC-ANNEX V injected group at different time intervals.

FIGS. 19A and 19B. Comparison of uptake difference of $^{99m}$Tc-EC-ANNEX V between pre-(FIG. 19A) and post-(FIG. 19B) paclitaxel treatment in ovarian tumor bearing group.

FIG. 49. Synthetic scheme of $^{99m}$Tc-EC-Glucosamine.

FIGS. 55A, 55B, 55C. In vitro cellular uptake assay of $^{99m}$Tc-EC (FIG. 56A), $^{99m}$Tc-EC-deoxyglucose-GAP (FIG. 56B), and $^{18}$F-FDG (FIG. 56C) in lung cancer cell line (A549). $^{99m}$Tc-EC-DG showed similar uptake compared to $^{18}$F-FDG.

FIG. 59. Synthetic scheme of $^{99m}$Tc-EC-deoxyglucose.

FIG. 82A. MRI of a patient with malignant astrocytoma.

DESCRIPTION OF ILLUSTRATIVE EMBODIMENTS

Figure 1:
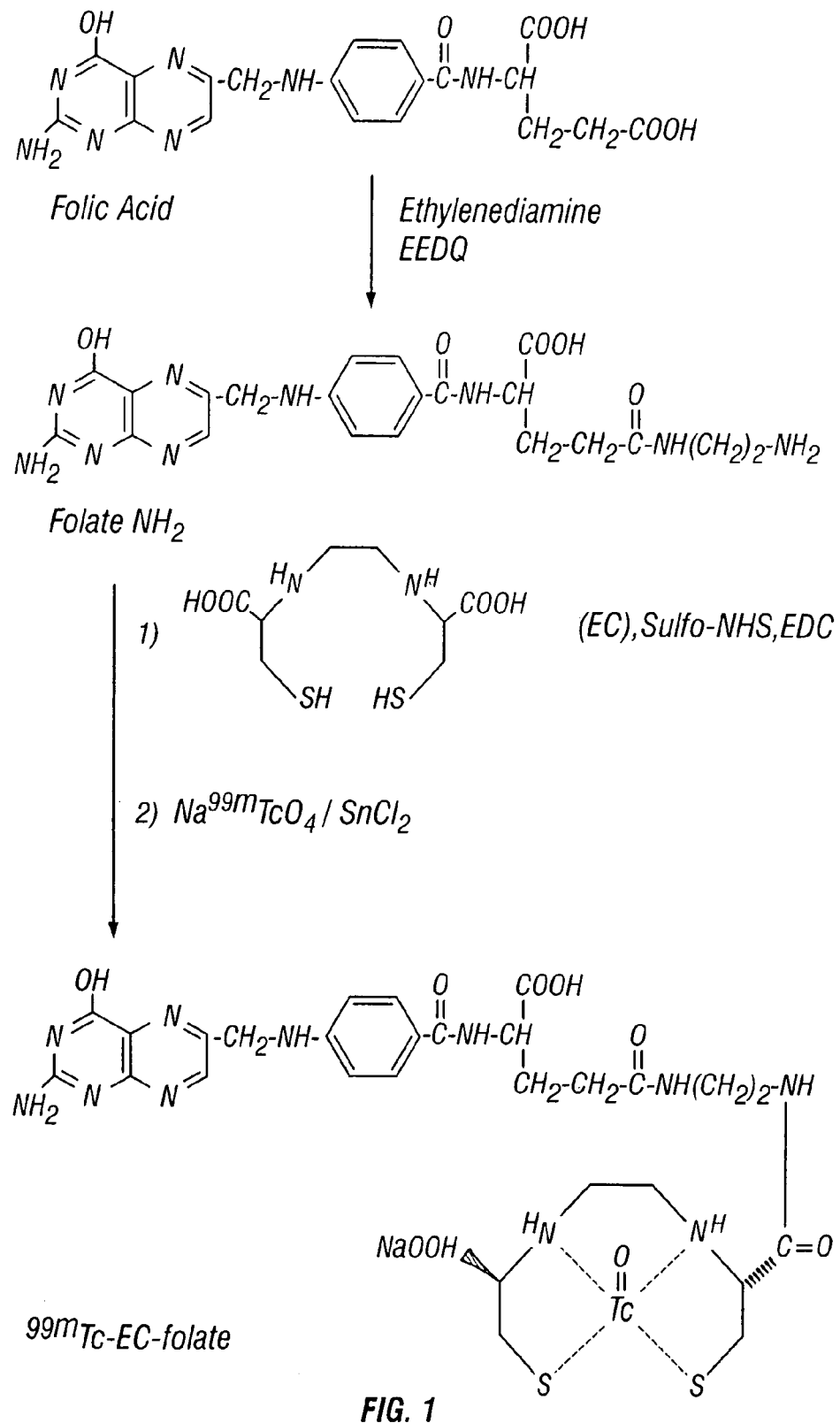
FIG. 1. Synthetic scheme of $^{99m}$Tc-EC-folate.

In the field of nuclear medicine, certain pathological conditions are localized, or their extent is assessed, by detecting the distribution of small quantities of internally-administered radioactively labeled tracer compounds (called radiotracers or radiopharmaceuticals). Methods for detecting these radiopharmaceuticals are known generally as imaging or radioimaging methods.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

A variety of radionuclides are known to be useful for radioimaging, including $^{67}$Ga, $^{99m}$Tc, $^{111}$In, $^{123}$I, $^{125}$I, $^{169}$Yb or $^{186}$Re. Due to better imaging characteristics and lower price, attempts have been made to replace the $^{123}$I, $^{131}$I, $^{67}$Ga and $^{111}$In labeled compounds with corresponding $^{99m}$Tc labeled compounds when possible. Due to favorable physical characteristics as well as extremely low price ($0.21/mCi), $^{99m}$Tc has been preferred to label radiopharmaceuticals. Although it has been reported that DTPA-drug conjugate could be labeled with $^{99m}$Tc effectively (Mathias et al., 1997), DTPA moiety does not chelate with $^{99m}$Tc as stable as with $^{111}$In. (Goldsmith, 1997).

A number of factors must be considered for optimal radioimaging in humans. To maximize the efficiency of detection, a radionuclide that emits gamma energy in the 100 to 200 keV range is preferred. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site. $^{99m}$Tc is a preferred radionuclide because it emits gamma radiation at 140 keV, it has a physical half-life of 6 hours, and it is readily available on-site using a molybdenum-99/technetium-99m generator.

Bis-aminoethanethiol tetradentate ligands, also called diaminodithiol compounds, are known to form very stable Tc(V)O-complexes on the basis of efficient binding of the oxotechnetium group to two thiolsulfur and two amine nitrogen atoms. (Davison et al., 1980; 1981; Verbruggen et al., 1992). $^{99m}$Tc-L,L-ethylenedicysteine ($^{99m}$Tc-EC) is the most recent and successful example of $N_2S_2$ chelates. (Verbruggen et al., 1992; Van Nerom et al., 1993; Surma et al., 1994). EC, a new renal imaging agent, can be labeled with $^{99m}$Tc easily and efficiently with high radiochemical purity and stability and is excreted through kidney by active tubular transport. (Verbruggen et al., 1992; Van Nerom et al., 1993; Surma et al., 1994; Verbruggen et al., 1990; Van Nerom et al., 1990; Jamar et al., 1993). Other applications of EC would be chelated with galium-68 (a positron emitter, t½=68 minutes) for PET and gadolinium, iron or manganese for magnetic resonance imaging (MRI).

The present invention utilizes $^{99m}$Tc-EC as a labeling agent to target ligands to specific tissue types for imaging. The advantage of conjugating the EC with tissue targeting ligands is that the specific binding properties of the tissue targeting ligand concentrates the radioactive signal over the area of interest. While it is envisioned that the use of $^{99m}$Tc-EC as a labeling strategy can be effective with virtually any type of compound, some suggested preferred ligands are provided herein for illustration purposes. It is contemplated that the $^{99m}$Tc-EC-drug conjugates of the invention may be useful to image not only tumors, but also other tissue-specific conditions, such as infection, hypoxic tissue (stroke), myocardial infarction, apoptotic cells, Alzheimer's disease and endometriosis.

Radiolabeled proteins and peptides have been reported in the prior art. (Ege et al., U.S. Pat. No. 4,832,940, Abrams et al., 1990; Bakker et al., 1990; Goldsmith et al., 1995, 1997; Olexa et al. 1982; Ranby et al. 1988; Hadley et al. 1988; Lees et al. 1989; Sobel et al. 1989; Stuttle, 1990; Maraganore et al. 1991; Rodwell et al. 1991; Tubis et al. 1968; Sandrehagen 1983). However, $^{99m}$Tc-EC has not been used in conjunction with any ligands, other than as the diethylester (Kabasakal, 2000), prior to the present invention. The diethylester of EC was used as a cerebral blood flow agent (Kikukawa, et al., 2000).

Although optimal for radioimaging, the chemistry of $^{99m}$Tc has not been as thoroughly studied as the chemistry of other elements and for this reason methods of radiolabeling with $^{99m}$Tc are not abundant. $^{99m}$Tc is normally obtained as $^{99m}$Tc pertechnetate (TcO4$^-$; technetium in the +7 oxidation state), usually from a molybdenum-99/technetium-99m generator. However, pertechnetate does not bind well with other compounds. Therefore, in order to radiolabel a compound, $^{99m}$Tc pertechnetate must be converted to another form. Since technetium does not form a stable ion in aqueous solution, it must be held in such solutions in the form of a coordination complex that has sufficient kinetic and thermodynamic stability to prevent decomposition and resulting conversion of $^{99m}$Tc either to insoluble technetium dioxide or back to pertechnetate.

For the purpose of radiolabeling, it is particularly advantageous for the $^{99m}$Tc complex to be formed as a chelate in which all of the donor groups surrounding the technetium ion are provided by a single chelating ligand—in this case, ethylenedicysteine. This allows the chelated $^{99m}$Tc to be covalently bound to a tissue specific ligand either directly or through a single linker between the ethylenedicysteine and the ligand.

Technetium has a number of oxidation states: +1, +2, +4, +5, +6 and +7. When it is in the +1 oxidation state, it is called Tc MIBI. Tc MIBI must be produced with a heat reaction. (Seabold et al. 1999). For purposes of the present invention, it is important that the Tc be in the +4 oxidation state. This oxidation state is ideal for forming the $N_2S_2$ chelate with EC. Thus, in forming a complex of radioactive technetium with the drug conjugates of the invention, the technetium complex, preferably a salt of $^{99m}$Tc pertechnetate, is reacted with the drug conjugates of the invention in the presence of a reducing agent.

The preferred reducing agent for use in the present invention is stannous ion in the form of stannous chloride ($SnCl_2$) to reduce the Tc to its +4 oxidation state. However, it is contemplated that other reducing agents, such as dithionate ion or ferrous ion may be useful in conjunction with the present invention. It is also contemplated that the reducing agent may be a solid phase reducing agent. The amount of reducing agent can be important as it is necessary to avoid the formation of a colloid. It is preferable, for example, to use from about 10 to about 100 μg SnCl$_2$ per about 100 to about 300 mCi of Tc pertechnetate. The most preferred amount is about 0.1 mg SnCl$_2$ per about 200 mCi of Tc pertechnetate and about 2 ml saline. This typically produces enough Tc-EC-tissue specific ligand conjugate for use in 5 patients.

It is often also important to include an antioxidant in the composition to prevent oxidation of the ethylenedicysteine. The preferred antioxidant for use in conjunction with the present invention is vitamin C (ascorbic acid). However, it is contemplated that other antioxidants, such as tocopherol, pyridoxine, thiamine or rutin, may also be useful.

In general, the ligands for use in conjunction with the present invention will possess either amino or hydroxy groups that are able to conjugate to EC on either one or both acid arms. If amino or hydroxy groups are not available (e.g., acid functional group), a desired ligand may still be conjugated to EC and labeled with $^{99m}$Tc using the methods of the invention by adding a linker, such as ethylenediamine, amino propanol, diethylenetriamine, aspartic acid, polyaspartic acid, glutamic acid, polyglutamic acid, or lysine. Ligands contemplated for use in the present invention include, but are not limited to, angiogenesis/antiangiogenesis ligands, DNA topoisomerase inhibitors, glycolysis markers, antimetabolite ligands, apoptosis/hypoxia ligands, DNA intercalators, receptor markers, peptides, nucleotides, antimicrobials such as antibiotics or antifungals, organ specific ligands and sugars or agents that mimic glucose.

EC itself is water soluble. It is necessary that the EC-drug conjugate of the invention also be water soluble. Many of the ligands used in conjunction with the present invention will be water soluble, or will form a water soluble compound when conjugated to EC. If the tissue specific ligand is not water soluble, however, a linker which will increase the solubility of the ligand may be used. Linkers may attach to an aliphatic or aromatic alcohol, amine or peptide or to a carboxylic and or peptide. Linkers may be either poly amino acid (peptide) or amino acid such as glutamic acid, aspartic acid or lysine. Table I illustrates desired linkers for specific drug functional groups.

TABLE 1

| Drug Functional Group | Linker | Example |
|---|---|---|
| Aliphatic or phenolio-OH | EC-Poly (glutamic acid) (MW. 750-15,000) or EC. poly(aspertic acid) (MW. 2000-15,000) or bromo ethylacetate or EC-glutamic acid or EC-aspertic acid. | A |
| Aliphatic or aromatic-NH$_2$ or peptide | EC-poly(glutamic acid) (MW. 750-15,000) or EC-poly(aspertic acid) (MW. 2000-15,000) or EC-glutamic acid (mono- or diester) or EC-aspartic acid. | B |
| Carboxylic acid or peptide | Ethylene diamine, lysine | C |

Examples:
A. estradiol, topotecan, paclitaxel, raloxlfen etoposide
B. doxorubicin, mitomycin C, endostatin, annexin V. LHRH, octreotide, VIP
C. methotrexate, folic acid It is also envisioned that the EC-tissue specific ligand drug conjugates of the invention may be chelated to other radionuclides and used for radionuclide therapy. Generally, it is believed that virtually any α, β-emitter, γ-emitter, or β, γ-emitter can be used in conjunction with the invention. Preferred β, γ-emitters include $^{166}$Ho, $^{188}$Re, $^{186}$Re, $^{153}$Sm, and $^{89}$Sr. Preferred β-emitters include $^{90}$Y and $^{225}$Ac. Preferred γ-emitters include $^{67}$Ga, $^{68}$Ga, $^{64}$Cu, $^{62}$Cu and $^{111}$In. Preferred α-emitters include $^{211}$At and $^{212}$Bi. It is also envisioned that para-magnetic substances, such as Gd, Mn and Fe can be chelated with EC for use in conjunction with the present invention.

Complexes and means for preparing such complexes are conveniently provided in a kit form including a sealed vial containing a predetermined quantity of an EC-tissue specific ligand conjugate of the invention to be labeled and a sufficient amount of reducing agent to label the conjugate with $^{99m}$Tc. $^{99m}$Tc labeled scintigraphic imaging agents according to the present invention can be prepared by the addition of an appropriate amount of $^{99m}$Tc or $^{99m}$Tc complex into a vial containing the EC-tissue specific ligand conjugate and reducing agent and reaction under conditions described in Example 1 hereinbelow. The kit may also contain conventional pharmaceutical adjunct materials such as, for example, pharmaceutically acceptable salts to adjust the osmotic pressure, buffers, preservatives, antioxidants, and the like. The components of the kit may be in liquid, frozen or dry form. In a preferred embodiment, kit components are provided in lyophilized form.

Radioactively labeled reagents or conjugates provided by the present invention are provided having a suitable amount of radioactivity. In forming $^{99m}$Tc radioactive complexes, it is generally preferred to form radioactive complexes in solutions containing radioactivity at concentrations of from about 0.01 millicurie (mCi) to about 300 mCi per mL.

$^{99m}$Tc labeled scintigraphic imaging agents provided by the present invention can be used for visualizing sites in a mammalian body. In accordance with this invention, the $^{99m}$Tc labeled scintigraphic imaging agents are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 300 mCi, preferably 10 mCi to about 200 mCi. The solution to be injected at unit dosage is from about 0.01 mL to about 10 mL. After intravenous administration, imaging of the organ or tumor in vivo can take place, if desired, in hours or even longer, after the radiolabeled reagent is introduced into a patient. In most instances, a sufficient amount of the administered dose will accumulate in the area to be imaged within about 0.1 of an hour to permit the taking of scintiphotos. Any conventional method of scintigraphic imaging for diagnostic or prognostic purposes can be utilized in accordance with this invention.

The $^{99m}$Tc-EC labeling strategy of the invention may also be used for prognostic purposes. It is envisioned that EC may be conjugated to known drugs of choice for cancer chemotherapy, such as those listed in Table 2. These EC-drug conjugates may then be radio labeled with $^{99m}$Tc and administered to a patent having a tumor. The labeled EC-drug conjugates will specifically bind to the tumor. Imaging may be performed to determine the effectiveness of the cancer chemotherapy drug against that particular patient's particular tumor. In this way, physicians can quickly determine which mode of treatment to pursue, which chemotherapy drug will be most effective. This represents a dramatic improvement over current methods which include choosing a drug and administering a round of chemotherapy. This involves months of the patient's time and many thousands of dollars before the effectiveness of the drug can be determined.

The $^{99m}$Tc labeled EC-tissue specific ligand conjugates and complexes provided by the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmostic pressure, buffers, preservatives, antioxidants and the like. Among the preferred media are normal saline and plasma.

Specific, preferred targeting strategies are discussed in more detail below.

Tumor Folate Receptor Targeting

The radiolabeled ligands, such as pentetreotide and vasoactive intestinal peptide, bind to cell receptors, some of which are overexpressed on tumor cells (Britton and Granowska, 1996; Krenning et al., 1995; Reubi et al., 1992; Goldsmith et al., 1995; Virgolini et al., 1994). Since these ligands are not immunogenic and are cleared quickly from the plasma, receptor imaging would seem to be more promising compared to antibody imaging.

Folic acid as well as antifolates such as methotrexate enter into cells via high affinity folate receptors (glycosylphosphatidylinositol-linked membrane folate-binding protein) in addition to classical reduced-folate carrier system (Westerhof et al., 1991; Orr et al., 1995; Hsuch and Dolnick, 1993). Folate receptors (FRs) are overexposed on many neoplastic cell types (e.g., lung, breast, ovarian, cervical, colorectal, nasopharyngeal, renal adenocarcinomas, malign melanoma and ependymomas), but primarily expressed only several normal differentiated tissues (e.g., choroid plexus, placenta, thyroid and kidney) (Orr et al., 1995; Weitman et al., 1992a; Campbell et al., 1991; Weitman et al., 1992b; Holm et al., 1994; Ross et al., 1994; Franklin et al., 1994; Weitman et al., 1994). FRs have been used to deliver folate-conjugated protein toxins, drug/antisense oligonucleotides and liposomes into tumor cells overexpressing the folate receptors (Ginobbi et al., 1997; Leamon and Low, 1991; Leamon and Low, 1992; Leamon et al., 1993; Lee and Low, 1994). Furthermore, bispecific antibodies that contain anti-FR antibodies linked to anti-T cell receptor antibodies have been used to target T cells to FR-positive tumor cells and are currently in clinical trials for ovarian carcinomas (Canevari et al., 1993; Bolhuis et al., 1992; Patrick et al., 1997; Coney et al., 1994; Kranz et al., 1995). Similarly, this property has been inspired to develop radiolabeled folate-conjugates, such as $^{67}$Ga-deferoxamine-folate and $^{111}$In-DTPA-folate for imaging of folate receptor positive tumors (Mathias et al., 1996; Wang et al., 1997; Wang et al., 1996; Mathias et al., 1997b). Results of limited in vitro and in vivo studies with these agents suggest that folate receptors could be a potential target for tumor imaging. In this invention, the inventors developed a series of new folate receptor ligands. These ligands are $^{99m}$Tc-EC-folate, $^{99m}$Tc-EC-methotrexate ($^{99m}$Tc-EC-MTX), $^{99m}$Tc-EC-tomudex ($^{99m}$Tc-EC-TDX).

Tumor Hypoxia Targeting

Tumor cells are more sensitive to conventional radiation in the presence of oxygen than in its absence; even a small percentage of hypoxic cells within a tumor could limit the response to radiation (Hall, 1988; Bush et al., 1978; Gray et al., 1953). Hypoxic radioresistance has been demonstrated in many animal tumors but only in few tumor types in humans (Dische, 1991; Gatenby et al., 1988; Nordsmark et al., 1996). The occurrence of hypoxia in human tumors, in most cases, has been inferred from histology findings and from animal tumor studies. In vivo demonstration of hypoxia requires tissue measurements with oxygen electrodes and the invasiveness of these techniques has limited their clinical application.

Misonidazole (MISO) is a hypoxic cell sensitizer, and labeling MISO with different radioisotopes (e.g., $^{18}$F, $^{123}$I, $^{99m}$Tc) may be useful for differentiating a hypoxic but metabolically active tumor from a well-oxygenated active tumor by PET or planar scintigraphy. [$^{18}$F]Fluoromisonidazole (FMISO) has been used with PET to evaluate tumors hypoxia. Recent studies have shown that PET, with its ability to monitor cell oxygen content through [$^{18}$F]FMISO, has a high potential to predict tumor response to radiation (Koh et al., 1992; Valk et al., 1992; Martin et al., 1989; Rasey et al., 1989; Rasey et al., 1990; Yang et al., 1995). PET gives higher resolution without collimation, however, the cost of using PET isotopes in a clinical setting is prohibitive. Although labeling MISO with iodine was the choice, high uptake in thyroid tissue was observed. Therefore, it is desirable to develop compounds for planar scintigraphy that the isotope is less expensive and easily available in most major medical facilities. In this invention, the inventors present the synthesis of $^{99m}$Tc-EC-2-nitroimidazole and $^{99m}$Tc-EC-metronidazole and demonstrate their potential use as tumor hypoxia markers.

Peptide Imaging of Cancer

Peptides and amino acids have been successfully used in imaging of various types of tumors (Wester et al., 1999; Coenen and Stocklin, 1988; Raderer et al., 1996; Lambert et al., 1990; Bakker et al., 1990; Stella and Mathew, 1990; Butterfield et al., 1998; Piper et al., 1983; Mochizuki et al., Dickinson and Hiltner, 1981). Glutamic acid based peptide has been used as a drug carrier for cancer treatment (Stella and Mathew, 1990; Butterfield et al., 1998; Piper et al., 1983; Mochizuki et al., 1985; Dickinson and Hiltner, 1981). It is known that glutamate moiety of folate degraded and formed polyglutamate in vivo. The polyglutamate is then re-conjugated to folate to form folyl polyglutamate, which is involved in glucose metabolism. Labeling glutamic acid peptide may be useful in differentiating the malignancy of the tumors. In this invention, the inventors report the synthesis of EC-glutamic acid pentapeptide and evaluate its potential use in imaging tumors.

Imaging Tumor Apoptotic Cells

Apoptosis occurs during the treatment of cancer with chemotherapy and radiation (Lennon et al., 1991; Abrams et al., 1990; Blakenberg et al., 1998; Blakenberg et al., 1999; Tait and Smith, 1991) Annexin V is known to bind to phosphotidylserin, which is overexpressed by tumor apoptotic cells (Blakenberg et al., 1999; Tait and Smith, 1991). Assessment of apoptosis by annexin V would be useful to evaluate the efficacy of therapy such as disease progression or regression. In this invention, the inventors synthesize $^{99m}$Tc-EC-annexin V (EC-ANNEX) and evaluate its potential use in imaging tumors.

Imaging Tumor Angiogenesis

Angiogenesis is in part responsible for tumor growth and the development of metastasis. Antimitotic compounds are antiangiogenic and are known for their potential use as anticancer drugs. These compounds inhibit cell division during the mitotic phase of the cell cycle. During the biochemical process of cellular functions, such as cell division, cell motility, secretion, ciliary and flagellar movement, intracellular transport and the maintenance of cell shape, microtubules are involved. It is known that antimitotic compounds bind with high affinity to microtubule proteins (tubulin), disrupting microtubule assembly and causing mitotic arrest of the proliferating cells. Thus, antimitotic compounds are considered as microtubule inhibitors or as spindle poisons (Lu, 1995).

Many classes of antimitotic compounds control microtubule assembly-disassembly by binding to tubulin (Lu, 1995; Goh et al., 1998; Wang et al., 1998; Rowinsky et al., 1990; Imbert, 1998). Compounds such as colchicinoids interact with tubulin on the colchicine-binding sites and inhibit microtubule assembly (Lu, 1995; Goh et al., 1998; Wang et al., 1998). Among colchicinoids, colchicine is an effective anti-inflammatory drug used to treat prophylaxis of acute gout. Colchicine also is used in chronic myelocytic leukemia. Although colchicinoids are potent against certain types of tumor growth, the clinical therapeutic potential is limited due to inability to separate the therapeutic and toxic effects (Lu, 1995). However, colchicine may be useful as a biochemical tool to assess cellular functions. In this invention, the inventors developed $^{99m}$Tc-EC-colchicine (EC-COL) for the assessment of biochemical process on tubulin functions.

Imaging Tumor Apoptotic Cells

Apoptosis occurs during the treatment of cancer with chemotherapy and radiation. Annexin V is known to bind to phosphotidylserin, which is overexpressed by tumor apoptotic cells. Assessment of apoptosis by annexin V would be useful to evaluate the efficacy of therapy such as disease progression or regression. Thus, $^{99m}$Tc-EC-annexin V (EC-ANNEX) was developed.

Imaging Tumor Hypoxia

The assessment of tumor hypoxia by an imaging modality prior to radiation therapy would provide rational means of selecting patients for treatment with radiosensitizers or bioreductive drugs (e.g., tirapazamine, mitomycin C). Such selection of patients would permit more accurate treatment patients with hypoxic tumors. In addition, tumor suppressor gene (P53) is associated with multiple drug resistance. To correlate the imaging findings with the overexpression of P53 by histopathology before and after chemotherapy would be useful in following-up tumor treatment response. $^{99m}$Tc-EC-2-nitroimidazole and $^{99m}$Tc-EC-metronidazole were developed.

Imaging Tumor Angiogenesis

Angiogenesis is in part responsible for tumor growth and the development of metastasis. Antimitotic compounds are antiangiogenic and are known for their potential use as anticancer drugs. These compounds inhibit cell division during the mitotic phase of the cell cycle. During the biochemical process of cellular functions, such as cell division, cell motility, secretion, ciliary and flagellar movement, intracellular transport and the maintenance of cell shape, microtubules are involved. It is known that antimitotic compounds bind with high affinity to microtubule proteins (tubulin), disrupting microtubule assembly and causing mitotic arrest of the proliferating cells. Thus, antimitotic compounds are considered as microtubule inhibitors or as spindle poisons. Colchicine, a potent antiangiogenic agent, is known to inhibit microtubule polymerization and cell arrest at metaphase. Colchicine (COL) may be useful as a biochemical tool to assess cellular functions. $^{99m}$Tc-EC-COL was then developed.

Imaging Hypoxia Due to Stroke

Although tumor cells are more or less hypoxic, it requires an oxygen probe to measure the tensions. In order to mimic hypoxic conditions, the inventors imaged 11 patients who had experienced stroke using $^{99m}$Tc-EC-metronidazole ($^{99m}$Tc-EC-MN). Metronidazole is a tumor hypoxia marker. Tissue in the area of a stroke becomes hypoxic due to lack of oxygen. The SPECT images were conducted at 1 and 3 hours post injection with $^{99m}$Tc-EC-MN. All of these imaging studies positively localized the lesions. CT does not show the lesions very well or accurately. MRI and CT in some cases exaggerate the lesion size. The following are selected cases from three patients.

Figure 28:
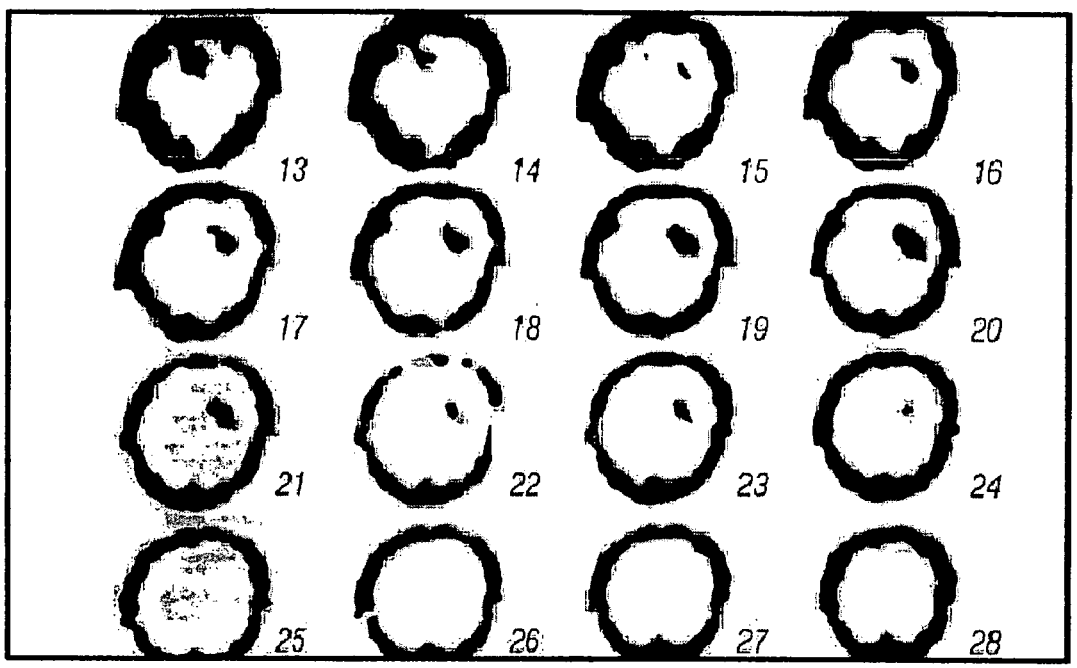
FIG. 28. SPECT with $^{99m}$Tc-EC-MN of 59 year old male patient who suffered stroke. Images taken one hour post-injection.
Figure 29:
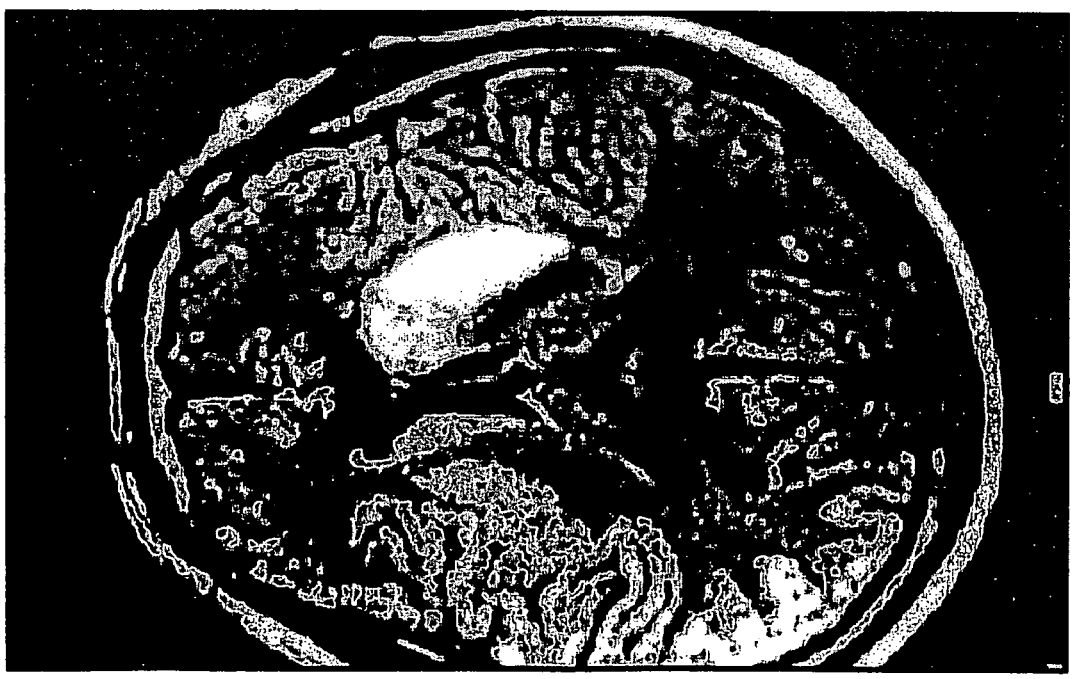
FIG. 29. MRI T1 weighted image of same patient as FIG. 28.

Case 1. A 59 year old male patient suffered a stroke in the left basal ganglia. SPECT $^{99m}$Tc-EC-MN identified the lesions at one hour post-injection (FIG. 28), which corresponds to MRI T1 weighted image (FIG. 29).

Figure 30:
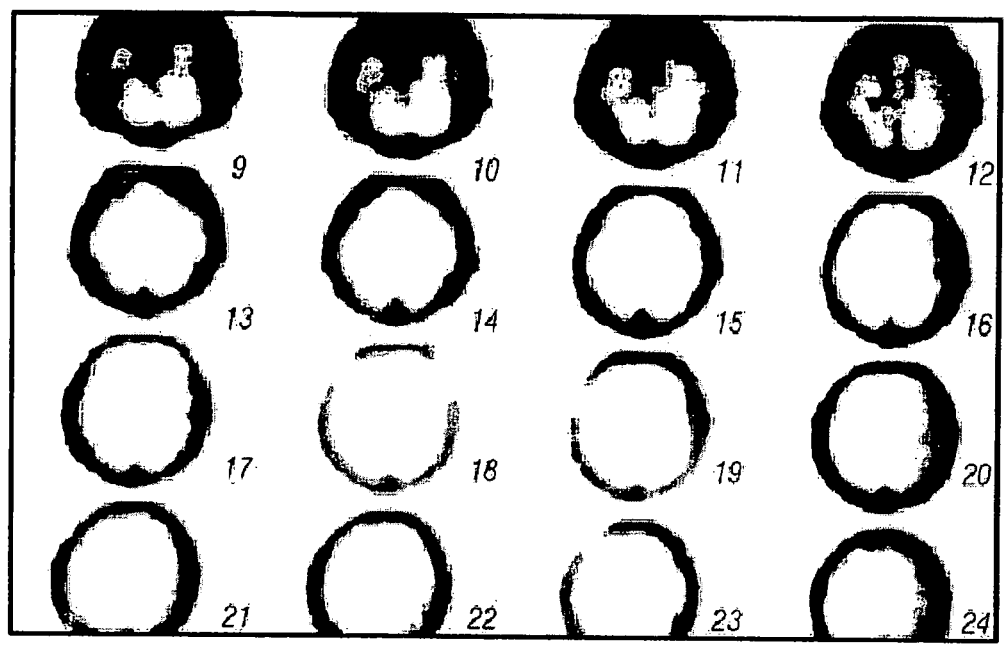
FIG. 30. SPECT with $^{99m}$Tc-EC-MN of 73 year old male patient one day after stroke at one hour post-injection.
Figure 31:
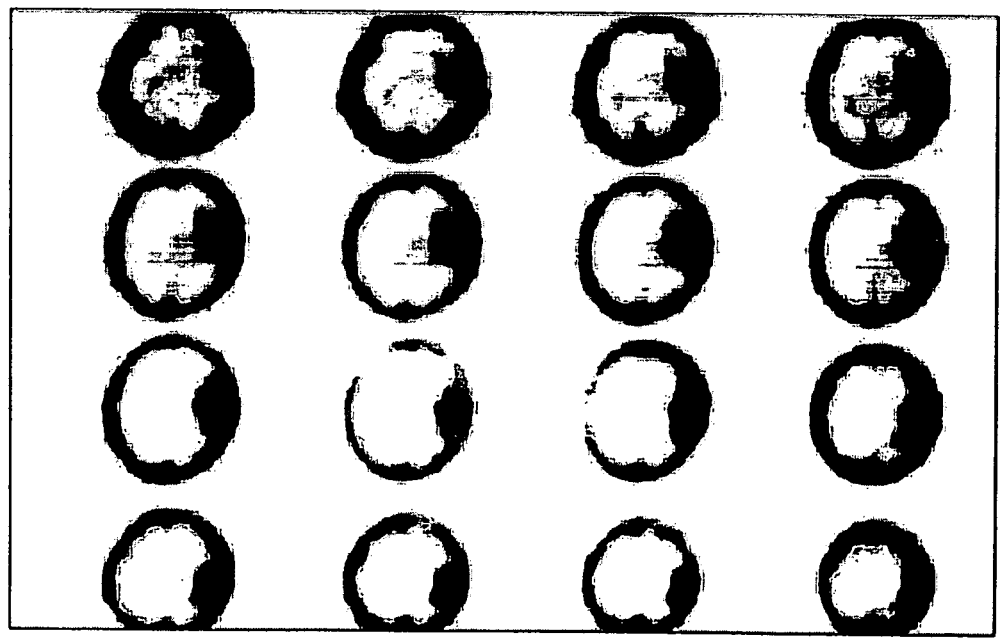
FIG. 31. SPECT with $^{99m}$Tc-EC-MN of same 73 year old patient as imaged in FIG. 30 twelve days after stroke at one hour post-injection.
Figure 33:
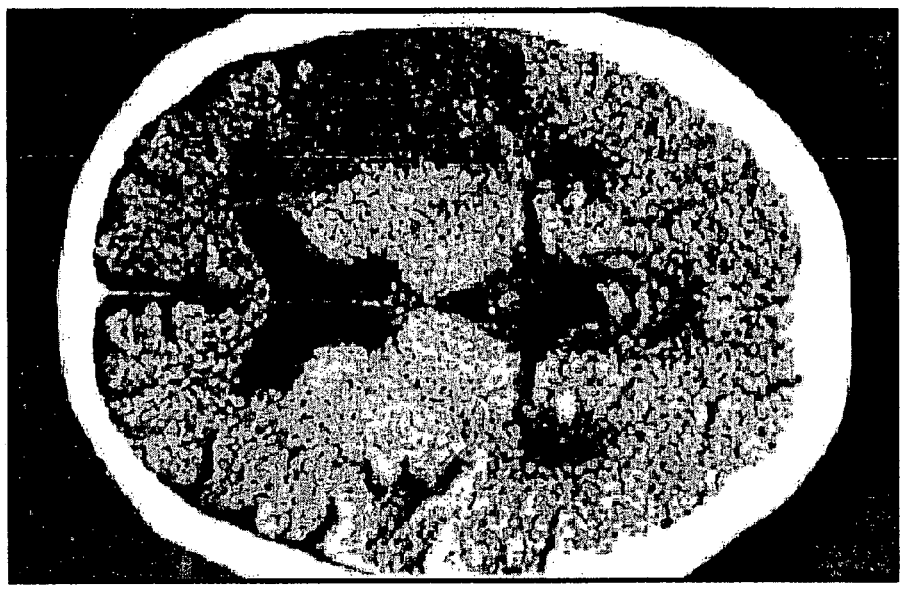
FIG. 33. CT of same 73 year old male stroke patient as imaged in FIG. 32, twelve days after stroke. Note, no marked difference between days one and twelve using CT for imaging.
Figure 32:
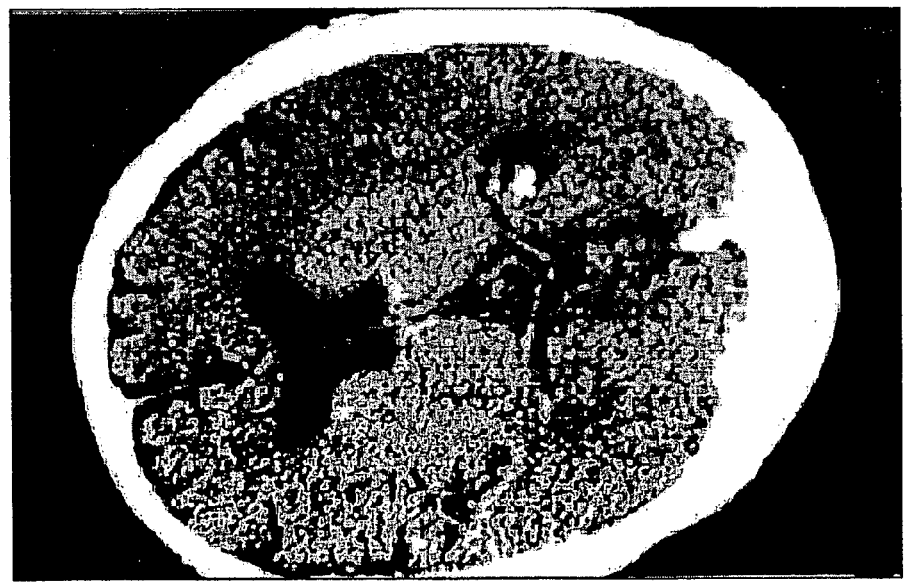
FIG. 32. CT of same 73 year old male stroke patient as imaged in FIG. 30, one day after stroke.

Case 2. A 73 year old male patient suffered a stroke in the left medium cerebral artery (MCA) territory. SPECT $^{99m}$Tc-EC-MN was obtained at day 1 and day 12 (FIGS. 30 and 31) at one hour post-injection. The lesions showed significant increased uptake at day 12. CT showed extensive cerebral hemorrhage in the lesions. No marked difference was observed between days 1 and 12 (FIGS. 32 and 33). The findings indicate that the patient symptoms improved due to the tissue viability (from anoxia to hypoxia). SPECT $^{99m}$Tc-EC-MN provides functional information which is better than CT images.

Figure 34:
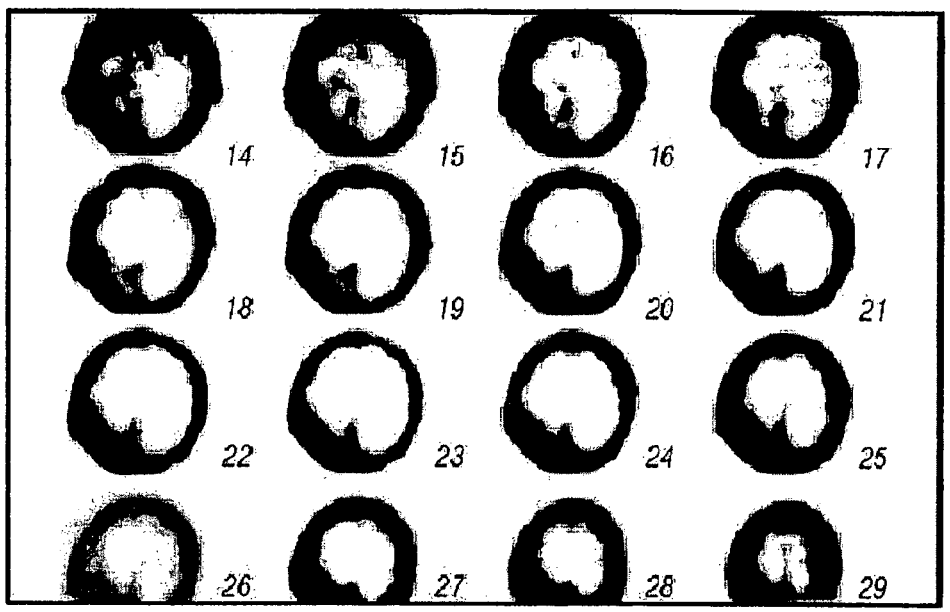
FIG. 34. SPECT with 99mTc-EC-MN of 72 year old male patient who suffered a stroke at one hour post-injection.
Figure 35:
FIG. 35. CT of same 72 year old stroke patient as imaged in FIG. 34. Note how CT image exaggerates the lesion size.

Case 3. A 72 year old male patient suffered a stroke in the right MCA and PCA area. SPECT $^{99m}$Tc-EC-MN identified the lesions at one hour post-injection (FIG. 34). CT exaggerates the lesion size. (FIG. 35).

Tumor Glycolysis Targeting

The radiolabeled ligands, such as polysaccharide (neomycin, kanamycin, tobramycin) and monosaccharide (glucosamine) bind to cell glucose transporter, followed by phosphorylation which are overexpressed on tumor cells (Rogers et al., 1968; Fanciulli et al., 1994; Popovici et al., 1971; Jones et al., 1973; Hermann et al., 2000). Polysaccharide (neomycin, kanamycin, tobramycin) and monosaccharide (glucosamine) induced glucose level could be suppressed by insulin (Harada et al., 1995; Moller et al., 1991; Offield et al., 1996; Shankar et al., 1998; Yoshino et al., 1999; Villevalois-Cam et al., 2000) Since these ligands are not immunogenic and are cleared quickly from the plasma, metabolic imaging would seem to be more promising compared to antibody imaging.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Tumor Folate Receptor Targeting

Synthesis of EC

EC was prepared in a two-step synthesis according to the previously described methods (Ratner and Clarke, 1937; Blondeau et al., 1967; each incorporated herein by reference). The precursor, L-thiazolidine-4-carboxylic acid, was synthesized (m.p. 195°, reported 196-197°). EC was then prepared (m.p. 237°, reported 251-253°). The structure was confirmed by $^1$H-NMR and fast-atom bombardment mass spectroscopy (FAB-MS).

Synthesis of Aminoethylamido Analogue of Methotrexate (MTX-NH$_2$)

MIX (227 ma, 0.5 mmol) was dissolved in 1 ml of HCI solution (2N). The pH value was <3. To this stirred solution, 2 ml of water and 4 ml of N-ethoxycarbonyl-2-ethoxy-1,2-dihydroquinoline (EEDQ, 6.609% in methanol, 1 mmol) were added at room temperature. Ethylenediamine (EDA, 0.6 ml, 10 mmol) was added slowly. The reaction mixture was stirred overnight and the solvent was evaporated in vacuo. The raw solid material was washed with diethyl ether (10 ml), acetonitrile (10 ml) and 95% ethyl alcohol (50 ml) to remove the unreacted EEDQ and EDA. The product was then dried by lyophilization and used without further purification. The product weighed 210 mg (84.7%) as a yellow powder. m.p. of product: 195-198° C. (dec, MIX); $^1$H-NMR (D$_2$O) δ 2.98-3.04 (d, 8H, —(CH$_2$)$_2$CONH(CH$_0$)$_2$NH$_2$), 4.16-4.71 (m, 6H, —CH$_2$. pteridinyl, aromatic-NCH$_3$, NH—CH—COOH glutamate), 6.63-6.64 (d, 2H, aromatic-CO), 7.51-753 (d, 2H. aromatic-N), 8.36 (s, 1H, pteridinyl). FAB MS m/z calcd for C$_{22}$H$_{28}$, N$_{10}$, O$_4$(M)$^+$496.515, found 496.835.

Synthesis of Aminoethylamido Analogue of Folate (Folate-NH$_2$)

Folic acid dihydrate (1 g, 2.0 mmol) was added in 10 ml of water. The pH value was adjusted to 2 using HCI (2 N). To this stirred solution, N-ethoxycarbonyl-2-ethoxy-1,2-dihydroquinoline (EEDQ, 1 g in 10 ml methanol, 4.0 mmol) and ethylenediamine (EDA, 1.3 ml, 18 mmol) were added slowly. The reaction mixture was stirred overnight at room temperature. The solvent was evaporated in vacuo. The product was precipitated in methanol (50 ml) and further washed with acetone (100 ml) to remove the unreacted EEDQ and EDIT. The product was then freeze-dried and used without further purification. Ninhydrin (2% in methanol) spray indicated the positivity of amino group. The product weighed 0.6 g (yield 60%) as a yellow powder. m.p. of product: 250° (dec). $^1$H-NMR (D$_2$O) δ1.97-2.27 (m, 2H, —CH$_2$ glutamate of folate), 3.05-3.40 (d, 6H, —CH$_2$CONH(CH$_2$)$_2$NH$_2$), 4.27-4.84 (m, 3H, —CH$_2$-pteridinyl, NH—CH—COOH glutamate), 6.68-6.70 (d, 2H, aromatic-CO), 7.60-7.62 (d, 2H, aromatic-N), 8.44 (s, 1H, pteridinyl). FAB MS m/z calcd for C$_{21}$H$_{25}$N$_9$, O$_5$(M)$^+$ 483, found 483.21.

Synthesis of Ethylenedicysteine-Folate (EC-Folate)

To dissolve EC, NaOH (2N, 0.1 ml) was added to a stirred solution of EC (114 ma, 0.425 mmol) in water (1.5 ml). To this colorless solution, sulfo-NHS (92.3 mg, 0.425 mmol) and EDC (81.5 mg, 0.425 mmol) were added. Folate-NH$_2$ (205 mg, 0.425 mmol) was then added. The mixture was stirred at room temperature for 24 hours. The mixture was dialyzed for 48 hours using Spectra/POR molecular porous membrane with molecule cut-off at 500 (Spectrum Medical Industries Inc., Houston, Tex.). After dialysis, the product was freeze dried. The product weighed 116 mg (yield 35%). m.p. 195° (dec); $^1$H-NMR (D$_2$O) δ1.98-2.28 (m, 2H, —CH2 glutamate of folate), 2.60-2.95 (m, 4H and —CH$_2$—SH of EC). 3.24-3.34 (m, 10H, —CH$_2$—CO, ethylenediamine of folate and ethylenediamine of EC), 4.27-4.77 (m, 5H, —CH-pteridinyl, NH—CH—COOH glutamate of folate and NH—CH—COOH of EC), 6.60-6.62 (d, 2H, aromatic-CO), 7.58-7.59 (d, 2H. aromatic-N), 8.59 (s, 1H, pteridinyl). Anal. calcd for C29H37N$_{11}$S$_2$O$_8$ Na$_2$(8H$_2$O), FAB MS m/z (M)$^+$ 777.3 (free of water). C, 37.79; H. 5.75; N, 16.72; S, 6.95. Found: m/z (M)$^+$ 777.7 (20), 489.4 (100). C, 37.40; H, 5.42; N. 15.43; S, 7.58.

Radiolabeling of EC-Folate and EC with $^{99m}$Tc

Radiosynthesis of $^{99m}$Tc-EC-folate was achieved by adding required amount of $^{99m}$Tc-pertechnetate into home-made kit containing the lyophilized residue of EC-folate (3 mg), SnCl$_2$ (100 μg), Na$_2$ $_{HPO4}$(13.5 mg), ascorbic acid (0.5 mg) and NaEDTA (0.5 mg). Final pH of preparation was 7.4. $^{99m}$Tc-EC was also obtained by using home-made kit containing the lyophilized residue of EC (3 mg), SnCl$_2$ (100 μg), Na$_2$, IPO$_4$ (13.5 mg), ascorbic acid (0.5 mg) and NaEDTA (0.5 mg) at pH 10. Final pH of preparation was then adjusted to 7.4. Radiochemical purity was determined by TLC (ITLC SG, Gelman Sciences, Ann Arbor, Mich.) eluted with, respectively, acetone (system A) and ammonium acetate (1M in water):methanol (4:1) (system B). From radio-TLC (Bioscan, Washington, D.C.) analysis, the radiochemical purity was >95% for both radiopharmaceuticals. Radio-TLC data are summarized in Table 2. Synthesis of $^{99m}$Tc-EC-folate is shown in FIG. 1.

TABLE 2

DRUGS OF CHOICE FOR CANCER CHEMOTHERAPY
The tables that follow list drugs used for treatment of cancer in the USA and Canada and their major adverse effects. The Drugs of Choice listing based on the opinions of Medical Letter consultants. Some drugs are listed for indications for which they have not been approved by the US Food and Drug Administration. Anticancer drugs and their adverse effects follow. For purposes of the present invention, these lists are meant to be exemplary and not exhaustive.

| Cancer | Drugs of Choice | Some alternatives |
|---|---|---|
| Adrenocortical** | Mitotane | Doxorubicin, streptozocin, |
|  | Cisplatin | etoposide |
| Bladder* | Local: Instillation of BCG | Instillation of mitomycin, |
|  | Systemic: Methotrexate + vinblastine + doxorubicin + claplatin (MVAC) | doxorubicin or thiotape Pecitaxel, substitution of |
|  | Claplatin + Methotrexate + vinblastine (CMV) | carboplatin for claplatin in combinations |
| Brain |  |  |
| Anaplastic astrocytoma* | Procarbazine + lamutine + vincristine | Carmustine, Claplatin |
| Anaplastic oligodendro-Giloma* | Procarbazine + lamustine + vincristine | Carmustine, Claplatin |
| Gilabiastome** | Carmustine or lamustine | Procarbazine, claplatin |
| Medulloblastoma | Vincristine + carmustine ± mechiorethamine ± methotrexate | Etoposide |

TABLE 2-continued

DRUGS OF CHOICE FOR CANCER CHEMOTHERAPY

The tables that follow list drugs used for treatment of cancer in the USA and Canada and their major adverse effects. The Drugs of Choice listing based on the opinions of Medical Letter consultants. Some drugs are listed for indications for which they have not been approved by the US Food and Drug Administration. Anticancer drugs and their adverse effects follow. For purposes of the present invention, these lists are meant to be exemplary and not exhaustive.

| | | |
|---|---|---|
| | Mechlorethamine + vincristine + procarbazine + prednisone (MOPP) | |
| | Vincristine + claplatin ± cyclophosphamide | |
| Primary central nervous system lymphoma | Methotrexate (high dose Intravenous and/or Intrathecal) ± cytarabine (Intravenous and/or Intrathecal) | |
| | Cyclophosphamide + Doxorubicin + vincristine + prednisone (CHOP) | |
| Breast | Adjuvant[1]: Cyclophosphamide + methotrexate + fluorouracil (CMF); | |
| | Cyclophosphamide + Doxorubicin ± fluorouracil (AC or CAF); Tamoxifen | |
| | Metastatic: Cyclophosphamide + methotrexate + fluorouracil (CMF) or | Paclitaxel; thiotepa + Doxorubicin + vin-blastine; mitomycin + vinblastine; |
| | Cyclophosphamide + duxorubicin ± fluorouracil (AC or CAF) for receptor-negative and/or hormone-refractory; | mitomycin + methotrexate + mitoxantrone; fluorouracil by continuous infusion; Bone |
| | Tamoxifen for receptor-positive and/or hormone-sensitive[2] | marrow transplant[3] |
| Cervix** | Claplatin | Chlorambucil, vincristine, |
| | Ifosfamide with means | fluorouracil, Doxorubicin, |
| | Bleomycin + ifosfamide with means + claplatin | methotrexate, altretamine |
| Chorlocarcinoma | Methotrexate ± leucovorin | Methotrexate + dactinomycin + cyclophosphamide |
| | Dactinomycin | (MAC) |
| | | Etoposide + methotrexate + dactinomycin + cyclophosphamide + vincristine |
| Colorectal* | Adjuvant colon[4]: Fluorouracil + levam-isole; | Hepatic metastases: |
| | fluorouracil + leucovorin | Intrahepatic-arterial floxuridine |
| | Metastatic: fluorouracil + leucovorin | Mitomycin |
| Embryonal rhabdomyosar-coma[5] | Vincristine + dectinomycin ± cyclophasphamide | Same + Doxorubicin |
| | Vincristine + ifosfamide with means + etoposide | |
| Endometrial** | Megastrol or another progestin | fluorouracil, tamoxifen, |
| | Doxorubicin + claplatin ± cyclophosphamide | altretamine |
| Esophageal* | Claplatin + fluorouracil | Doxorubicin, methotraxate, mitomycin |
| Ewing's sarcoma[5] | Cyclophosphamide (or ifosfamide with means) + Doxorubicin + vincristine (CAV) ± dactinomycin | CAV + etoposide |
| Gastric** | Fluorouracil ± leucavorin | Claplatin Doxorubicin, etoposide, methotrexate + leucovorin, mitomycin |
| Head and neck squambus cell*[6] | Claplatin + fluorouracil | Blomycin, carboplatin, paclitaxel |
| | Methotrexate | |
| Islet cell** | Streptozocin + Doxorubicin | Streptozocin + fluorouracil; chlorozotocin†; octreotide |
| Kaposi's sarcoma* (Aids-related) | Etoposide or interferon alfa or vinblastine | Vincristine, Doxorubicin, |
| | Doxorubicin + bleomycin + vincristine or vinblastine (ABV) | bleomycin |
| Leukemia | | |
| Acute lymphocytic leukemia (ALL)[7] | Induction: Vincristine + prednisone + asparaginase ± daunorubicin | Induction: same ± high-dose methotrexate ± cyterabine; |
| | CNS prophylaxis: Intrathecal methotrexate ± systemic high-dose methotrexate with leutovorin ± Intrathecal cytarabine ± Intrathecal hydrocortisone | pegaspargase instead of asparaginese Teniposide or etoposide High-dose cytarabine |
| | Maintenance: Methotrexate + mercaptopurine | Maintenance: same + periodic |
| | Bone marrow transplant.[3][8] | vincristine + prednisone |
| Acute myeloid leukemia (AML)[9] | Induction: Cytsrabine + either daunorubicin or idarubicin | Cytarabine + mitoxentrone High-dose cyterabine |
| | Post Induction: High-dose cytarabine ± other drugs such as etoposide | |
| | Bone marrow transplant[3]. | |
| Chronic lymphocytic leukemia (CLL) | Chlorambucil ± prednisone | Cladribine, cyclophosphamide, |
| | Fludarabin | pentostatin, vincristine, Doxorubicin |

TABLE 2-continued

DRUGS OF CHOICE FOR CANCER CHEMOTHERAPY
The tables that follow list drugs used for treatment of cancer in the USA and
Canada and their major adverse effects. The Drugs of Choice listing based on the
opinions of Medical Letter consultants. Some drugs are listed for indications for which
they have not been approved by the US Food and Drug Administration. Anticancer drugs
and their adverse effects follow. For purposes of the present invention, these lists are
meant to be exemplary and not exhaustive.

| | | |
|---|---|---|
| Chronic myeloid leukemia (CML)[10] | | |
| Chronic phase | Bone marrow transplant[3]<br>Interferon alfa<br>Hydroxyures | Busulfan |
| Accelerated[11] | Bone marrow transplant[3] | Hydroxyures, busulfen |
| Blast crisis[11] | Lymphoid: Vincristine + prednisone + L-separaginess + intrathecal methotrexate (± maintenance with methotrexate + 8-marcaptopurine) | Tretinoln[†]<br>Amsecrine, [†]azacitidine<br>Vincristine ± plicamycin |
| Hairy cell Leukemia | Pentostatin or cladribine | Interferon alfa, chlorambucil, fludarabin |
| Liver** | Doxorubicin<br>Fluorouracil | Intrahepatic-arterial floxuridine or claplatin |
| Lung, small cell (cat cell) | Claplatin + etoposide (PE)<br>Cyclophosphamide + doxorubicin + vincristine (CAV)<br>PE alternated with CAV<br>Cyclophosphamide + etoposide + claplatin (CEP)<br>Duxorubicin + cyclophosphamide + etoposide (ACE) | Ifosfamide with means + carboplatin + etoposide (ICE)<br>Daily oral etoposide<br>Etoposide + ifosfamide with means + claplatin (VIP<br>Paclitaxel |
| Lung (non-small cell)** | Claplatin + etoposide<br>Claplatin + Vinblastine ± mitomycin<br>Claplatin + vincrisine | Claplatin + fluorouracil + leucovorin<br>Carboplatin + paclitaxel |
| Lymphomas | | |
| Hodgkin's[12] | Doxorubicin + bleomycin + vinblastine + dacarbazine (ABVD)<br>ABVD alternated with MOPP<br>Mechlorethamine + vincristine + procarbazine (± prednisone) + doxorubicin + bleomycin + vinblastine (MOP[P]-ABV) | Mechlorethamine + vincristine + procarbazine + prednisone (MOPP)<br>Chlorambusil + vinblastine + procarbazine + prednisone ± carmustine<br>Etoposide + vinblastine + doxorubicin<br>Bone marrow transplant[3] |
| Non-Hodgkin's | | |
| Burkitt's lymphoma | Cyclophosphamide + vincristine + methotrexate<br>Cyclophosphamide + high-dose cytarabine ± methotrexate with leutovorin<br>Intrathecal methotrexate or cytarabine | Ifosfamide with means<br>Cyclophosphamide + doxorubicin + vincrletine + prednisone (CHOP) |
| Difuse large-cell lymphoma | Cyclophosphamide + doxorubicin + vincristine + prednisone (CHOP) | Dexamethasone sometimes substituted for prednisone<br>Other combination regimens, which may include methotrexate, etoposide, cytarabine, bleomycin, procarbazine, ifosfamide and mitoxantrone<br>Bone marrow transplant[3] |
| Follicular lymphoma | Cyclophosphamide or chlorambusil | Same ± vincristine and prednisone, ± etoposide<br>Interferon alfa, cladribine, fludarabin<br>Bone marrow transplant[3]<br>Cyclophosphamide + doxorubicin + vincristine + prednisone (CHOP) |
| Melanoma** | Interferon Alfa<br>Dacarbazine | Carmustine, lomustine, cisplatin<br>Dacarbazine + claplatin + carmustine + tamoxifen<br>Aldesleukin |
| Mycosis fungoides* | PUVA (psoralen + ultraviolet A)<br>Mechlorethamine (topical)<br>Interferon alfa<br>Electron beam radiotherapy<br>Methotrexate | Isotretinoin, topical carmustine, pentosistin, fludarabin, cladribine, photopheresis (extra-corporeal photochemitherapy), chemotherapy as in non-Hodgkin's lymphoma |
| Mysloma* | Melphelan (or cyclophosphamide) + prednisons<br>Melphalan ± carmustine + cyclophosphamide + prednisons + vincristine<br>Dexamethasone + doxorubicin + vincristine (VAD) | Interferon alfa<br>Bone marrow transplant[3]<br>High-dose dexamethasons |

TABLE 2-continued

DRUGS OF CHOICE FOR CANCER CHEMOTHERAPY
The tables that follow list drugs used for treatment of cancer in the USA and
Canada and their major adverse effects. The Drugs of Choice listing based on the
opinions of Medical Letter consultants. Some drugs are listed for indications for which
they have not been approved by the US Food and Drug Administration. Anticancer drugs
and their adverse effects follow. For purposes of the present invention, these lists are
meant to be exemplary and not exhaustive.

| | | |
|---|---|---|
| | Vincristine + carmustine + doxorubicin + prednisons (VBAP) | |
| Neuroblestoma* | Doxorubicin + cyclophosphamide + claplatin + teniposide or etoposide | Carboplatin, etoposide Bone marrow transplant[3] |
| | doxorubicin + cyclophosphamide | |
| | Claplatin + cyclophosphamide | |
| Osteogenic sarcoma[5] | Doxorubicin + claplatin ± etopside ± ifosfamide | Ifosfamide with means, etoposide, carboplatin, high-dose methotrexate with leucovorin |
| | | Cyclophosphamide + etoposide |
| Ovary | Claplatin (or carboplatin) + paclitaxel | Ifosfamide with means, |
| | Claplatin (or carboplatin) + cyclophosphamide | paclitaxel, tamoxifen, |
| | (CP) ± doxorubicin | melphalan, altretamine |
| | (CAP) | |
| Pancreatic** | Fluoroutacil ± leucovorin | Gemoltabinet |
| Prostate | Leuprolide (or goserelln) ± flutamide | Estramustine ± vinblastine, aminoglutethimide + hydrocortleone, estramustine + etoposide, diethylstllbestrol, nilutamide |
| Renal** | Aldesleukin | Vinblastine, floxuridine |
| | Inteferon alfa | |
| Retinoblestoma[5*] | Doxorubicin + cyclophosphamide ± claplatin ± etoposide ± vincristina | Carboplatin, etoposide, Ifosfamide with means |
| Sarcomas, soft tissue, adult* | Doxorubicin ± decarbazine ± cyclophosphamide ± Ifosfamide with means | Mitornyeln + doxorubicin + claplatin Vincristina, etoposide |
| Testicular | Claplatin + etoposide ± bleomycin (PEB) | Vinblestine (or etoposide) + Ifosfamide with means + claplatin (VIP) Bone marrow transplant[3] |
| Wilms' tumor[5] | Dectinomycln + vincriatine ± doxorubicin ± cyclophosphamide | Ifosfamide with means, etoposide, carboplatin |

*Chemotherapy has only moderate activity.
**Chemotherapy has only minor activity.
[1]Tamoxifen with or without chemotherapy is generally recommended for postmenopausal estrogen-receptor-positive, mode-positive patients and chemotherapy with or without tamoxlfen for premenopausal mode-positive patients. Adjuvant treatment with chemotherapy and/or tamoxifen is recommended for mode-negative patients with larger tumors or other adverse prognostic indicators.
[2]Megastrol and other hormonal agents may be effective in some patients with tamoxifen fails.
[3]After high-dose chemotherapy (Medical Letter, 34: 79, 1982).
[4]For rectal cancer, postoperative adjuvant treatment with fluoroutacil plus radiation, preceded and followed by treatment with fluorouracil alone.
[5]Drugs have major activity only when combined with surgical resection, radiotherapy or both.
[6]The vitamin A analog lactratinoln (Acgutana) can control pre-neoplastic lesions (leukoplakla) and decreases the rate of second primary tumors (SE Banner et al, J Natl Cancer Inst, 88: 140 1994).
†Available in the USA only for investigational use.
[7]High-risk patients (e.g., high counts, cytogenetic abnormalities, adults) may require additional drugs for induction, maintenance and "Intensificiation" (use of additional drugs after achievement of remission). Additional drugs include cyclophosphamida, mitoxantrone and thloguanine. The results of one large controlled trial in the United Kingdom suggest that Intensificiation may improve survival in all children with ALL (JM Chasselle et al, Lancet, 34B: 143, Jan. 21, 1995).
[8]Patients with a poor prognosis initially or those who relapse after remission.
[9]Some patients with acute promyelocytic leukemia have had complete responses to tratinoin. Such treatment can cause a toxic syndrome characterized primarily by fever and respiratory distress (RP Warrell, Jr et al, N Engl J Med. 328: 177, 1993).
[10]Allogeheic HLA-identical sibling bone marrow transplantation can cure 40% to 70% of patients with CML in chronic phase, 18% to 28% of patients with accelerated phase CML, and <15% patients in blast crisis. Disease-free survival after bone marrow transplantations adversely influenced by age >50 years, duration of disease >3 years from diagnosis, and use of one-antigen-mismatched or matched-unrelated donor marrow. Interferon also may be curative in patients with chronic phase CML who achieve a complete cytogenetic response (about 10%); it is the treatment of choice for patents >80 years old with newly diagnosed chronic phase CML and for all patients who are not candidates for an allgensic bone marrow transplant. Chemotherapy alone is palliative.
[11]If a second chronic phase is achieved with any of these combinations, allogeneic bone marrow transplant should be considered. Bone marrow transplant in second chronic phase may be curative for 30% to 35% of patients with CML.
[12]Limited-stage Hodgkin's disease (stages 1 and 2) is curable by radiotherapy. Disseminated disease (stages 3 b and 4) require chemotherapy. Some intermediate stages and selected clinical situations may benefit from both.
+ Available in the USA only for investigational use.

TABLE 2-continued

DRUGS OF CHOICE FOR CANCER CHEMOTHERAPY
The tables that follow list drugs used for treatment of cancer in the USA and
Canada and their major adverse effects. The Drugs of Choice listing based on the
opinions of Medical Letter consultants. Some drugs are listed for indications for which
they have not been approved by the US Food and Drug Administration. Anticancer drugs
and their adverse effects follow. For purposes of the present invention, these lists are
meant to be exemplary and not exhaustive.

ANTICANCER DRUGS AND HORMONES

| Drug | Acute Toxicity‡ | Delayed toxicity‡ |
| --- | --- | --- |
| Aldesleukin (Interleukin-2; Proleukin - Cetus Oncology) | Fever; fluid retention; hypertension; respiratory distress; rash; anemia; thrombocytophenia; nausea and vomiting; diarrhea; capillary leak syndrome; naphrotoxlolty; myocardialtoxicity; hepatotoxicity; erythernanodosum; neutrophil chemotactic defects | Neuropsychiatric disorders; hypothyrldiam; nephrotic syndrome; possibly acute leukoencaphalopathy; brachial plexopathy; bowel perforation |
| Altretamine (hexamethyl-melamine; Hexalen - U Bioscience) | Nausea and vomiting | Bone marrow depression; CNS depression; peripheral neuropathy; visual hallucinations; stexis; tremors, alopecia; rash |
| Aminogiutethimide (Cytadren - Ciba) | Drowsiness; nausea; dizziness; rash | Hypothryroidism (rare); bone marrow depression; fever; hypotension; mascullinization |
| †Amsacrine (m-AMSA; amaidine; AMSP P-D-Parke-Davis, Amsidyl-Warner-Lambert) | Nausea and vomiting; diarrhea; pain or phlebitis on infuelon; anaphylaxia | Bone marrow depression; hepatic injury; convulsions; stomatite; ventricular fibrillation; alopecia; congestive heart failure; renal dysfunction |
| Asparaginase (Elspar-merck; Kidrolase in Canada) | Nausea and vomiting; fever; chills; headache; hypersensitivity, anaphylexia; abdominal pain; hyperglycemia leading to coma | CNS depression or hyperexcitability; acute hemorrhagic pancreatitis; coagulation defects; thromboals; renal damage; hepactic damage |
| Cervix** | Claplatin Ifosfamide with means Bleomycin patin Ifosfamide with means | Chlorambucil, vincristine, fluoroutacil, doxorubicin, methotrexete, altretamine |
| Chorlocarcinoma | Methotrexete ± leucovorin Dactinomyclin | Methotrexete + dectinomycin + cyclophosphamide (MAC) Etoposide + methotrexate + dactinomycin + cyclophosphamide + vincrlatine |
| Colorectal* | Adjuvant colon⁴: Fluoroutacil + lavamleole; fluoroutacil + leucovarin Metastatic: Fluoroutacil + leucvarin | Hepatic metastases: Intrahepactic-arterial floxuridine Mitomyclin |
| Embryonal rhebdomyosarcoma⁶ | Vincriatine + dectinomycin ± cyclophosphamide Vincristine + Ifosfamide with means + etoposide | Same + doxorubicin |
| Endometrial** Cancer | Megastrol or another progeetin Doxorubicin + claplatin ± cyclophosphamide Drugs of Choice | Fluoroutacil, tamoxifen, altretamine Some alternatives |
| Esophageal* | Claplatin + Fluoroutacil | Doxorubicin, methotrexete, mitomycin |
| Ewing's sarcoma⁵ | Cyclophosphamide (or ifosfamide with means) + doxorubicin + vincrietine (CAV) ± dectinomycin | CAV + etoposide |
| Gastric** | Fluoroutacil ± leucovoin | Claplatin, doxorubicin, etoposide, methotrexete + leucovorin, mitomycin |
| Head and neck squamous cell*⁵ | Claplatin + fluoroutacil Methotrexete | Blaonycin, carboplatin, paciltaxel |
| Islet call** | Streptozocin + doxorubicin | Streptozocln + fluoroutacil; chlorozotocin; actreatide |
| Kaposal's sercoma* (AIDS-related) | Etoposide or Interferon alfa or vinbleomycin stine Doxorubicin + bleomycin + vincristine or vinbleomycin stine (ABV) | Vincristine, doxorubicin, bleomycln |
| Leukemias Acute lymphocytic leukemia (ALL)⁷ | Induction: Vincristine + prednisone + asparaginase ± daunorubieln CNS prophylaxia; Intrathecal methotrexete ± systemic high-dose methotrexete with leucovorin ± Intrethecal cytarabine ± Intrathecal hydrocortisone Maintenance: methotrexete ± mercaptopurine Bone marrow transplant³ | Industion: same ± high-dose methotrexete ± cyterabine; pegaspargase instead of aspareginese Teniposide or etoposide High-dose cytarabine Maintenance: same + periodic vincristine + prednisone |

TABLE 2-continued

DRUGS OF CHOICE FOR CANCER CHEMOTHERAPY
The tables that follow list drugs used for treatment of cancer in the USA and
Canada and their major adverse effects. The Drugs of Choice listing based on the
opinions of Medical Letter consultants. Some drugs are listed for indications for which
they have not been approved by the US Food and Drug Administration. Anticancer drugs
and their adverse effects follow. For purposes of the present invention, these lists are
meant to be exemplary and not exhaustive.

| | | |
|---|---|---|
| Acute myeloid leukemia (AML)[9] | Induction: Cytarabine + either daunbrublein or idarubieln<br>Post Induction: High-dose cytarabine ± other drugs such as etoposide<br>Bone marrow transplant[3] | Cytarabine + mitoxantrone<br>High-dose cytarabine |
| Chronic lymophocytic leukemia (CLL) | Chlorambuell ± prednisone<br>Fludarabin | Claplatin, cyclophosphamide, pentostatin, vinorlstine, doxorubicin |

†Available in the USA only for investigational use.
‡Dose-limiting effects are in bold type. Cutaneous reactions (sometimes severe), hyperpigmentation, and ocular toxicity have been reported with virtually all nonhormonal anticancer drugs. For adverse interactions with other drugs, see the Medical Letter Handbook of Adverse Drug Interactions, 1995.
[1]Available in the USA only for investigational use.
[2]Megestrol and other hormonal agents may be effective in some pateients when tamoxifen fails.
[3]After high-dose chemotherapy (Medical Letter, 34: 78, 1992).
[4]For rectal cancer, postoperative adjuvant treatment with fluoroutacil plus radiation, preceded and followed by treatment with fluoroutacil alone.
[5]Drugs have major activity only when combined with surgical resection, radiotherapy or both.
[6]The vitamin A analog isotretinoin (Accutane) can control pre-neoplastic isions (leukoplaka) and decreases the rats of second primary tumors (SE Senner et al., J Natl Cancer Inst. 88: 140, 1994).
[7]High-risk patients (e.g., high counts, cytogenetic abnormalities, adults) may require additionaldrugs for Induction, maintenance and "Intensification" (use of additional drugs after achievement of remission). Additional drugs include cyclophosphamide, mitoxantrone and thioguamine. The results of one large controlled trial in the United Kingdom suggest that intensilibation may improve survival in all children with ALL (jm Chassella et al., Lancet, 348: 143, Jan. 21. 1998).
[8]Patients with a poor prognosis initially or those who relapse after remission
[9]Some patients with acute promyclocytic leukemia have had complete responses to tretinoin. Such treatment can cuase a toxic syndrome characterized primarily by fever and respiratory distress (RP Warrell, Jr et al. N Eng J. Med, 329: 177, 1993).
[10]Allogenaic HLA Identical sibling bone marrow transplantation can cure 40% to 70% of patients with CML in chroni phase, 15% to 25% of patients with accelerated phase CML, and <15% patients in blast crisis. Disease-free survival after bone marrow transplantation is adversely influenced by age >50 years, duration of disease >3 years from diagnosis, and use of one antigen mismatched or matched-unrelated donor marrow. Inteferon alfa may be curative in patients with chronic phase CML who achieve a complete cytogenetic resonse (about 10%); It is the treatment of choices for patients >50 years old with newly diagnosed chronic phase CML and for all patients who are not candidates for an allogenic bone marrow transplant. Chemotherapy alone is palliative.

Radiolabeling of EC-MTX and EC-TDX with $^{99m}$Tc

Figure 2:
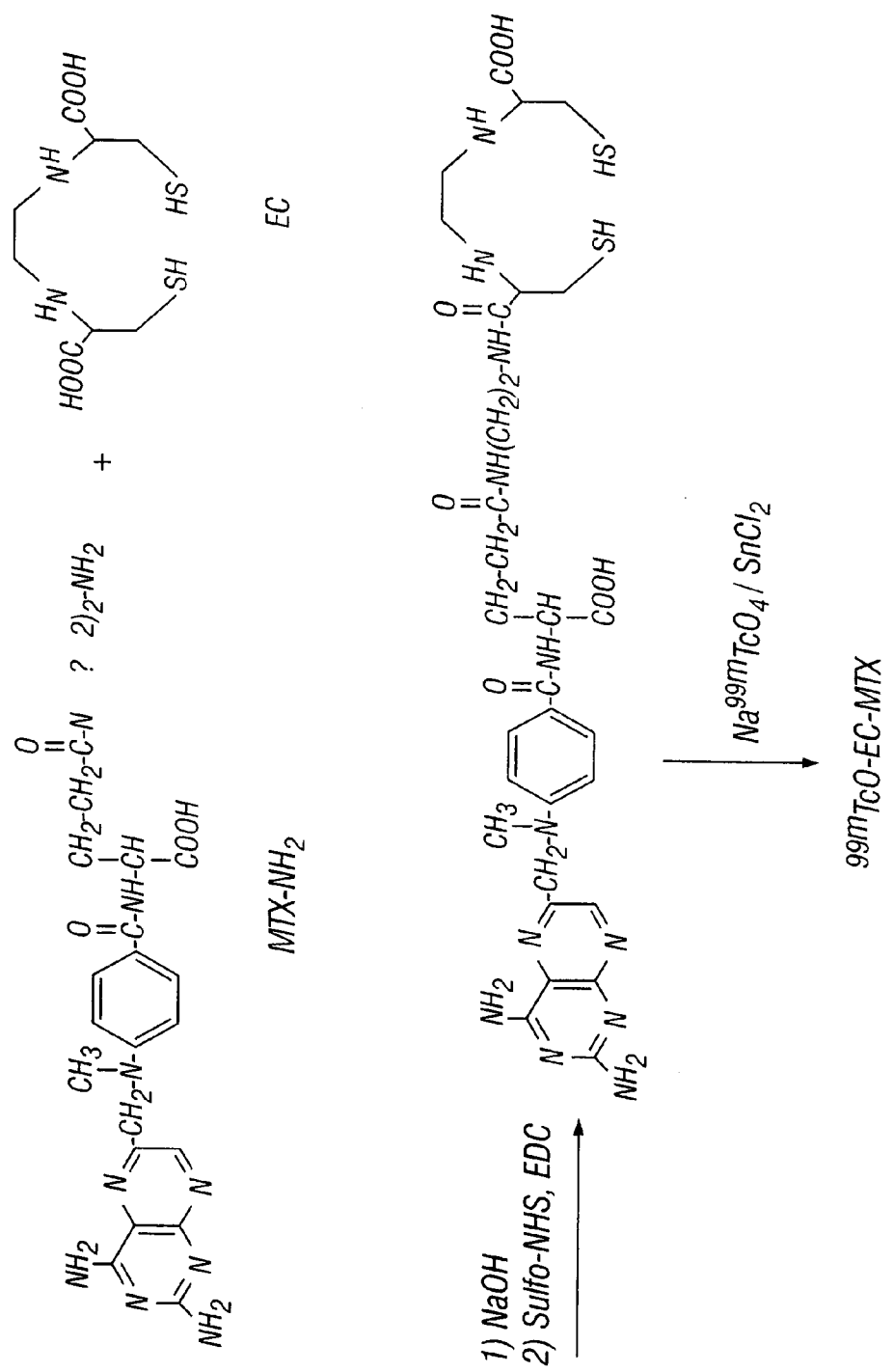
FIG. 2. Synthetic scheme of $^{99m}$Tc-EC-MTX (methotrexate).
Figure 3:
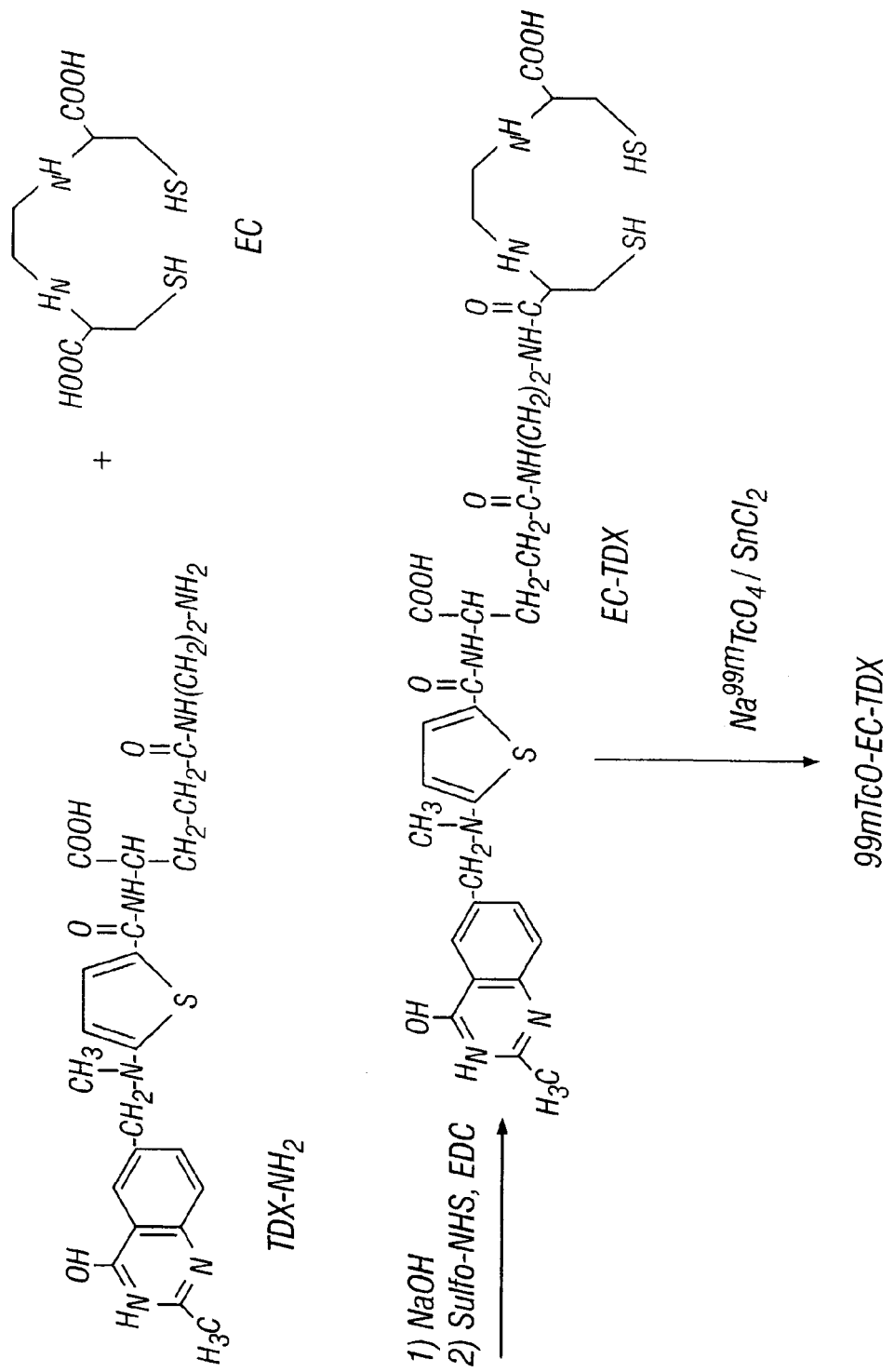
FIG. 3. Synthetic scheme of $^{99m}$Tc-EC-TDX (tomudex).

Use the same method described for the synthesis of EC-folate, EC-MTX and EC-TDX were prepared. The labeling procedure is the same as described for the preparation of $^{99m}$Tc-EC-folate except EC-MTX and EC-TDX were used. Synthesis of $^{99m}$Tc-EC-MTX and $^{99m}$Tc-EC-TDX is shown in FIG. 2 and FIG. 3.

Stability Assay of $^{99m}$Tc-EC-Folate, $^{99m}$Tc-EC-MTX and $^{99m}$Tc-EC-TDX Stability of $^{99m}$Tc-EC-Folate, $^{99m}$Tc-EC-MTX and $^{99m}$Tc-EC-TDX was tested in serum samples. Briefly, 740 KBq of 1 mg $^{99m}$Tc-EC-Folate, $^{99m}$Tc-EC-MIX and $^{99m}$Tc-EC-TDX was incubated in dog serum (200 µl) at 37° C. for 4 hours. The serum samples was diluted with 50% methanol in water and radio-TLC repeated at 0.5, 2 and 4 hours as described above.

Tissue Distribution Studies

Female Fischer 344 rats (150±25 g) (Harlan Sprague-Dawley, Indianapolis, Ind.) were inoculated subcutaneously with 0.1 ml of mammary tumor cells from the 13762 tumor cell line suspension ($10^6$ cells/rat, a tumor cell line specific to Fischer rats) into the hind legs using 25-gauge needles. Studies performed 14 to 17 days after implantation when tumors reached approximately 1 cm diameter. Animals were anesthetized with ketamine (10-15 mg/rat, intraperitoneally) before each procedure.

In tissue distribution studies, each animal injected intravenously with 370-550 KBq of $^{99m}$Tc-EC-folate or $^{99m}$Tc-EC (n=3/time point). The injected mass of each ligand was 10 µg per rat. At 20 min, 1, 2 and 4 h following administration of the radiopharmaceuticals, the anesthetized animals were sacrificed and the tumor and selected tissues were excised, weighed and counted for radioactivity by a gamma counter (Packard Instruments, Downers Grove, Ill.). The biodistribution of tracer in each sample was calculated as percentage of the injected dose per gram of tissue wet weight (% ID/g). Counts from a diluted sample of the original injectate were used for reference. Tumor/nontarget tissue count density ratios were calculated from the corresponding % ID/g values. Student-t test was used to assess the significance of differences between two groups.

In a separate study, blocking studies were performed to determine receptor-mediated process. In blocking studies, for $^{99m}$Tc-EC-folate was co-administered (i.v.) with 50 and 150 µmol/kg folic acid to tumor bearing rats (n=3/group). Animals were killed 1 h post-injection and data was collected.

Scintigraphic Imaging and Autoradiography Studies

Scintigraphic images, using a gamma camera (Siemens Medical Systems, Inc., Hoffman Estates, Ill.) equipped with low-energy, parallel-hole collimator, were obtained 0.5, 2 and 4 hrs after i.v. injection of 18.5 MBq of $^{99m}$Tc-labeled radiotracer.

Whole-body autoradiogram were obtained by a quantitative image analyzer (Cyclone Storage Phosphor System, Packard, Meridian, Conn.). Following i.v. injection of 37

MBq of $^{99m}$Tc-EC-folate, animal killed at 1 h and body was fixed in carboxymethyl cellulose (4%). The frozen body was mounted onto a cryostat (LKB 2250 cryomicrotome) and cut into 100 μm coronal sections. Each section was thawed and mounted on a slide. The slide was then placed in contact with multipurpose phosphor storage screen (MP, 7001480) and exposed for 15 h $^{99m}$Tc-labeled). The phosphor screen was excited by a red laser and resulting blue light that is proportional with previously absorbed energy was recorded.

Results

Chemistry and Stability of $^{99m}$Tc-EC-Folate

A simple, fast and high yield aminoethylamido and EC analogues of folate, MTX and TDX were developed. The structures of these analogues were confirmed by NMR and mass spectroscopic analysis. Radiosynthesis of EC-folate with $^{99m}$Tc was achieved with high (>95%) radiochemical purity. $^{99m}$Tc-EC-folate was found to be stable at 20 min. 1, 2 and 4 hours in dog serum samples.

Biodistribution of $^{99m}$Tc-EC-Folate

Figure 4:
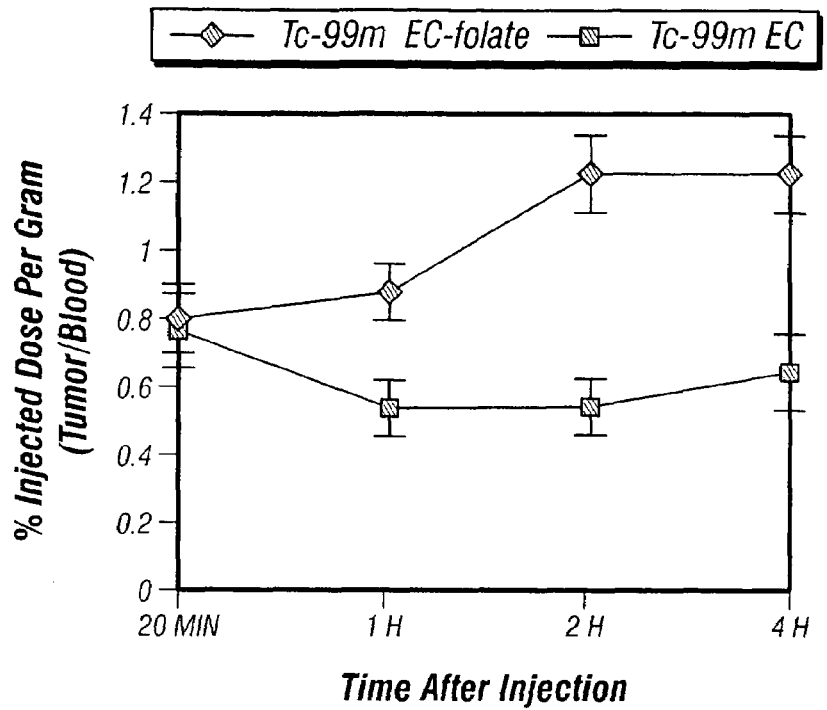
FIG. 4. Biodistribution studies for $^{99m}$Tc-EC and $^{99m}$Tc-EC-folate.

Biodistribution studies showed that tumor/blood count density ratios at 20 min-4 h gradually increased for $^{99m}$Tc-EC-folate, whereas these values decreased for $^{99m}$Tc-EC in the same time period (FIG. 4). % ID/g uptake values, tumor/blood and tumor/muscle ratios for $^{99m}$Tc-EC-folate and $^{99m}$Tc-EC were given in Tables 3 and 4, respectively.

ethyl acetate, Rf=0.45), yielded 75%. Mesylated metronidazole was then reacted with sodium azide to afford azido analogue (TLC:ethyl acetate, Rf=0.52), yielded 80%. The azido analogue was reduced by triphenyl phosphine and yielded (60%) the desired amino analogue (m.p. 190-192° C., reported 194-195° C., TLC:ethyl acetate, Rf=0.15). Ninhydrin (2% in methanol) spray indicated the positivity of amino group of MN—NH$_2$. The structure was confirmed by $^1$H-NMR and mass spectroscopy (FAB-MS) m/z 171(M$^+$H, 100).

Synthesis of Ethylenedicysteine-Metronidazole (EC-MN)

Sodium hydroxide (2N, O.2 ml) was added to a stirred solution of EC (134 ma, 0.50 mmol) in water (5 ml). To this colorless solution, sulfo-NHS (217 mg, 1.0 mmol) and 1~)C (192 ma. 1.0 mmol) were added. MN-NH: dihydrochloride salt (340 mg, 2.0 mmol) was then added. The mature was stirred at room temperature for 24 hours. The mixture was dialyzed for 48 hrs using Spectra/POR molecular porous membrane with cut-off at 500 (Spectrum Medical Industries Inc., Houston, Tex.). After dialysis, the product was frozen dried using lyophilizer (Labconco, Kansas City, Mo.). The product weighed 315 mg (yield 55%). $^1$H-NMR (D$_2$O) δ 2.93 (s, 6H, nitroimidazole-CH$_3$), 2.60-2.95 (m, 4H and —CH$_2$—SH of EC), 3.30-3.66 (m, 8H, ethylenediamine of EC and nitromidazole-CH$_2$—CH$_2$—NH$_2$), 3.70-3.99 (t, 2H,

TABLE 3

Biodistribution of $^{99m}$Tc-EC-folate in Breast Tumor-Bearing Rats

| | % of injected $^{99m}$Tc-EC-folate dose per organ or tissue | | | |
|---|---|---|---|---|
| | 20 min | 1 h | 2 h | 4 h |
| Blood | 0.370 ± 0.049 | 0.165 ± 0.028 | 0.086 ± 0.005 | 0.058 ± 0.002 |
| Lung | 0.294 ± 0.017 | 0.164 ± 0.024 | 0.092 ± 0.002 | 0.063 ± 0.003 |
| Liver | 0.274 ± 0.027 | 0.185 ± 0.037 | 0.148 ± 0.042 | 0.105 ± 0.002 |
| Stomach | 0.130 ± 0.002 | 0.557 ± 0.389 | 0.118 ± 0.093 | 0.073 ± 0.065 |
| Kidney | 4.328 ± 0.896 | 4.052 ± 0.488 | 5.102 ± 0.276 | 4.673 ± 0.399 |
| Thyroid | 0.311 ± 0.030 | 0.149 ± 0.033 | 0.095 ± 0.011 | 0.066 ± 0.011 |
| Muscle | 0.058 ± 0.004 | 0.0257 ± 0.005 | 0.016 ± 0.007 | 0.008 ± 0.0005 |
| Intestine | 0.131 ± 0.013 | 0.101 ± 0.071 | 0.031 ± 0.006 | 0.108 ± 0.072 |
| Urine | 12.637 ± 2.271 | 10.473 ± 3.083 | 8.543 ± 2.763 | 2.447 ± 0.376 |
| Tumor | 0.298 ± 0.033 | 0.147 ± 0.026 | 0.106 ± 0.029 | 0.071 ± 0.006 |
| Tumor/Blood | 0.812 ± 0.098 | 0.894 ± 0.069 | 1.229 ± 0.325 | 1.227 ± 0.129 |
| Tumor/Muscle | 5.157 ± 0.690 | 5.739 ± 0.347 | 6.876 ± 2.277 | 8.515 ± 0.307 |

Values shown represent the mean ± standard deviation of data from 3 animals

Scintigraphic Imaging and Autoradiography Studies

Figures 6A, 6B:
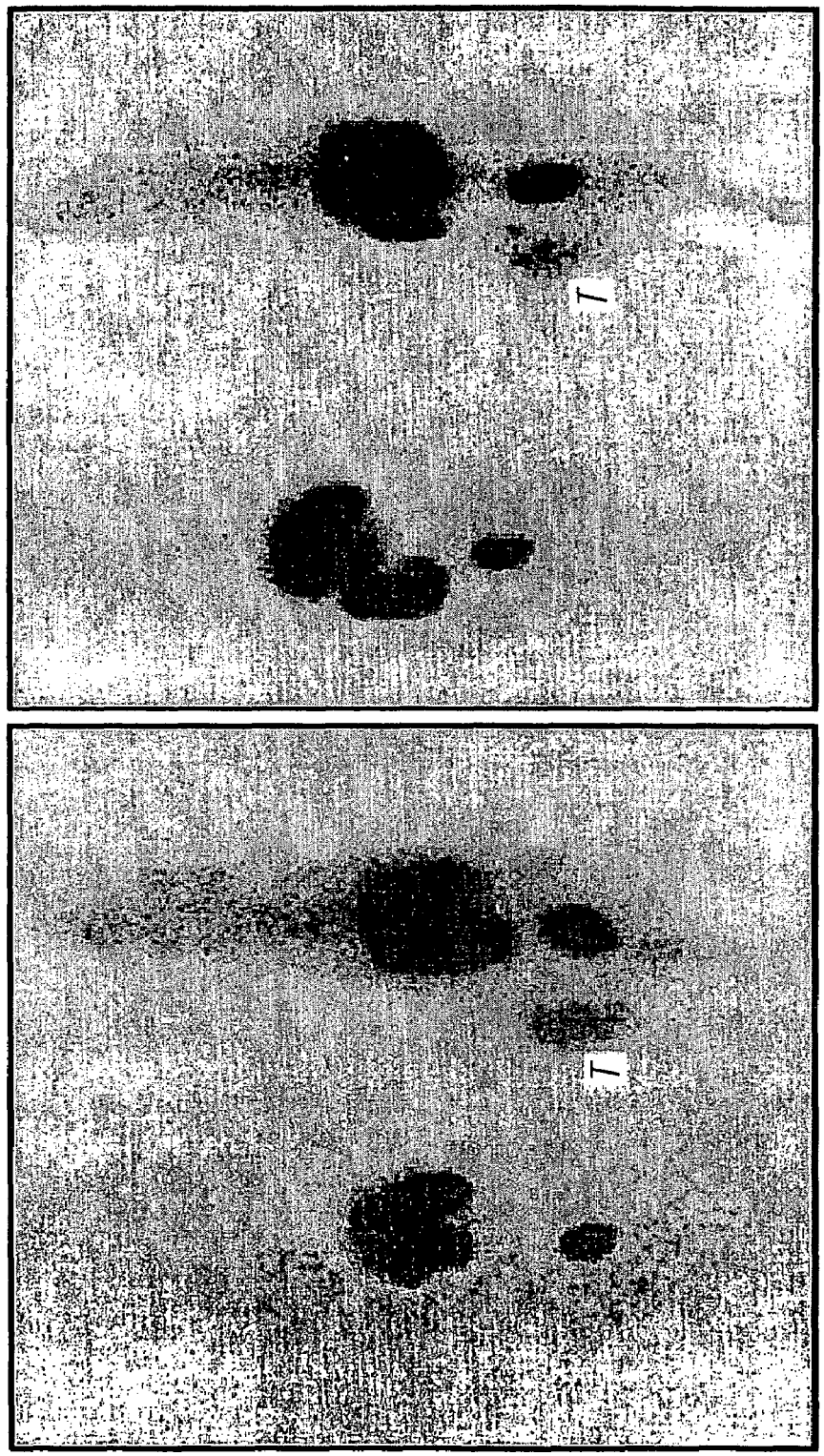
FIGS. 6A and 6B. Scintigraphic images of tumor in $^{99m}$Tc-EC-folate injected group as compared to $^{99m}$Tc-EC injected group.

Scintigraphic images obtained at different time points showed visualization of tumor in $^{99m}$Tc-EC-folate injected group. Contrary, there was no apparent tumor uptake in $^{99m}$Tc-EC injected group (FIG. 6). Both radiotracer showed evident kidney uptake in all images. Autoradiograms performed at 1 h after injection of $^{99m}$Tc-EC-folate clearly demonstrated tumor activity.

EXAMPLE 2

Tumor Hypoxia Targeting

Synthesis of 2-(2-methyl-5-nitro-$^1$H imidazolyl)ethylamine(amino analogue of metronidazole, MN-NH$_2$)

Figure 7:
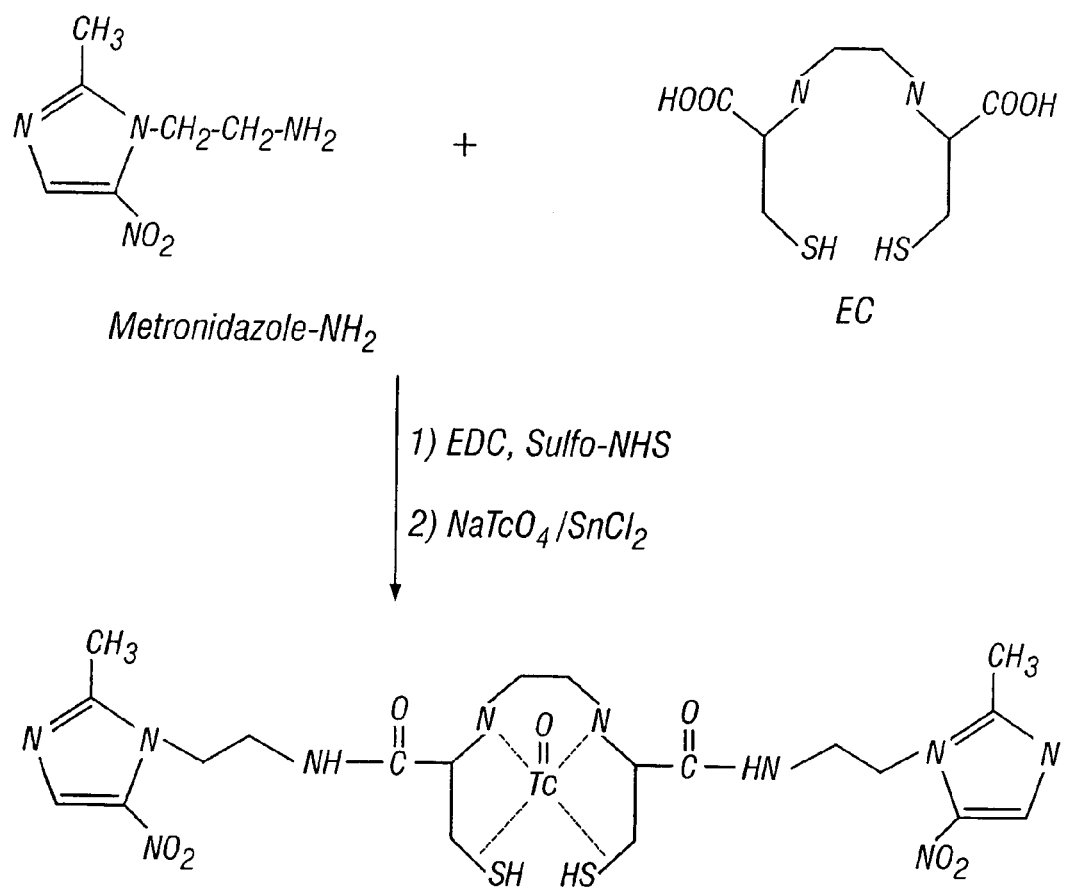
FIG. 7. Synthetic scheme of EC-MN (metronidazole)

Amino analogue of metronidazole was synthesized according to the previously described methods (Hay et al., 1994) Briefly, metronidazole was converted to a mesylated analogue (m.p. 149-150° C., reported 153-154° C., TLC:

NH—CH—CO of EC), 5.05 (t, 4H, metronidazole-CH$_2$—CH$_2$—NH$_2$) (s, 2H, nitroimidazole C=CH). FAB MS m/z 572 (M$^+$, 20). The synthetic scheme of EC-MN is shown in FIG. 7.

Synthesis of 3-(2-nitro-$^1$H-imidazolyl)propylamine (amino analogue of nitroimidazole, NIM-NH$_2$)

To a stirred mixture containing 2-nitloimidazole (1 g, 8.34 mmol) and Cs$_2$, CO$_3$ (2.9 g, 8.90 mmol) in dimethylformaide (DMF, 50 ml), 1,3-ditosylpropane (3.84 g, 9.99 mmol) was added. The reaction was heated at 80° C. for 3 hours. The solvent was evaporated under vacuum and the residue was suspended in ethylacetate. The solid was filtered, the solvent was concentrated, loaded on a silica gel-packed column and eluted with hexane:ethylacetate (1:1). The product, 3-tosylpropyl-(2-nitroimidazole), was isolated (1.67 g, 57.5%) with m.p. 108-111° C. $^1$H-NMR (CDCl$_3$) δ 2.23 (m, 2H), 2.48 (S. 3H), 4.06 (t, 2H, J=5.7 Hz), 4.52 (t, 2H, J=6.8 Hz), 7.09 (S. 1H), 7.24 (S. 1H), 7.40 (d, 2H, J=8.2 Hz). 7.77 (d, 2H, J=8.2 Hz).

Tosylated 2-nitroimidazole (1.33 g, 4.08 mmol) was then reacted with sodium azide (Q29 g, 4.49 mmol) in DMF (10 ml) at 100° C. for 3 hours. After cooling, water (20 ml) was added and the product was extracted from ethylacetate (3×20 ml). The solvent was dried over $MgSO_4$ and evaporated to dryness to afford azido analogue (0.6 g, 75%, TLC: hexane: ethyl acetate; 1:1, Rf=0.42). $^1$H-NMR ($CDCl_3$) δ 2.14 (m, 2H), 3.41 (t, 2H, J=6.2 Hz), 4.54 (t, 2H, J=6.9 Hz), 7.17 (S. 2H).

The azido analogue (0.57 g, 2.90 mmol) was reduced by taphenyl phosphine (1.14 g, 4.35 mmol) in tetrahydrofuran (PHI;) at room temperature for 4 hours. Concentrate HCI (12 ml) was added and heated for additional 5 hours. The product was extracted from ethylacetate and water mixture. The ethylacetate was dried over $MgSO_4$ and evaporated to dryness to afford amine hydrochloride analogue (360 ma, 60%). Ninhydrin (2% in methanol) spray indicated the positivity of amino group of NIM-NH. $^1$H-NMR ($D_2O$) δ 2.29 (m, 2H), 3.13 (t, 2H, J=7.8 Hz), 3.60 (br, 2H), 4.35 (t, 2H, J=7.4 Hz), 7.50 (d, 1H, J=2.1 Hz), 7.63 (d, 1H, J=2.1 Hz).

Synthesis of Ethylenedicysteine-Nitroimidazole (EC-NIM)

Figure 8A:
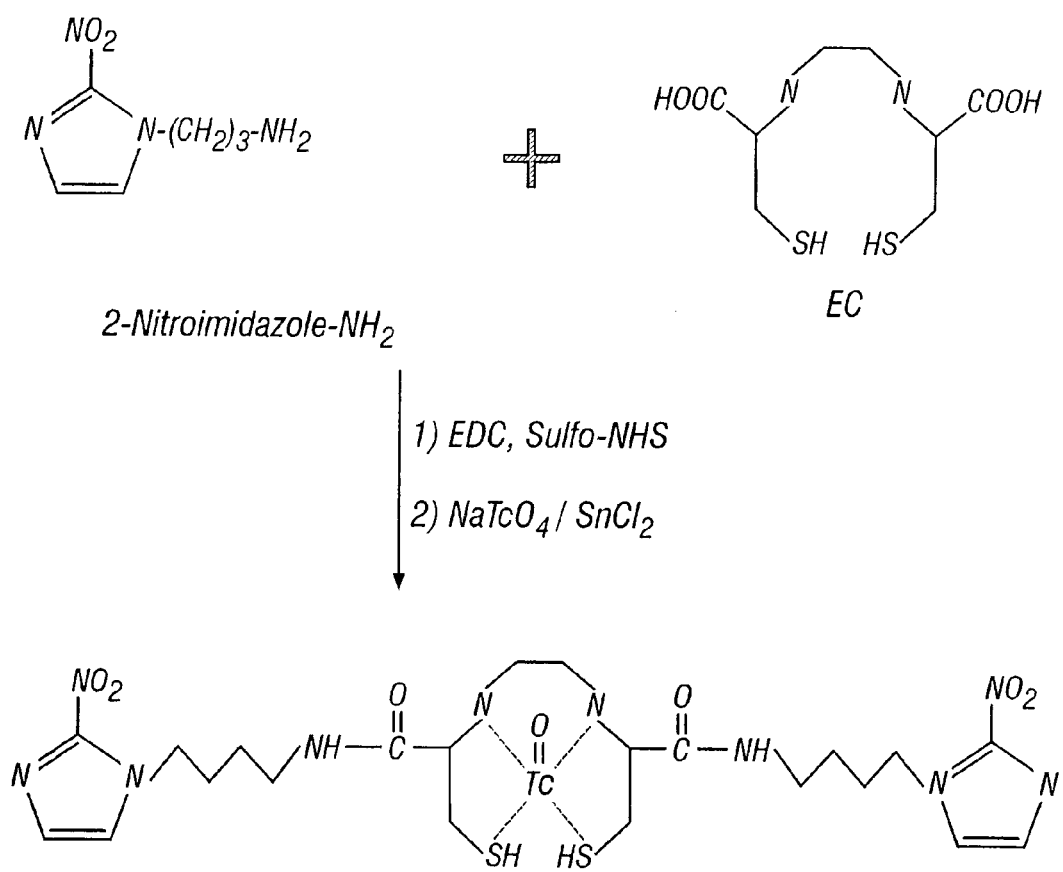
FIGS. 8A and 8B. For EC-NIM.
Figure 8B:
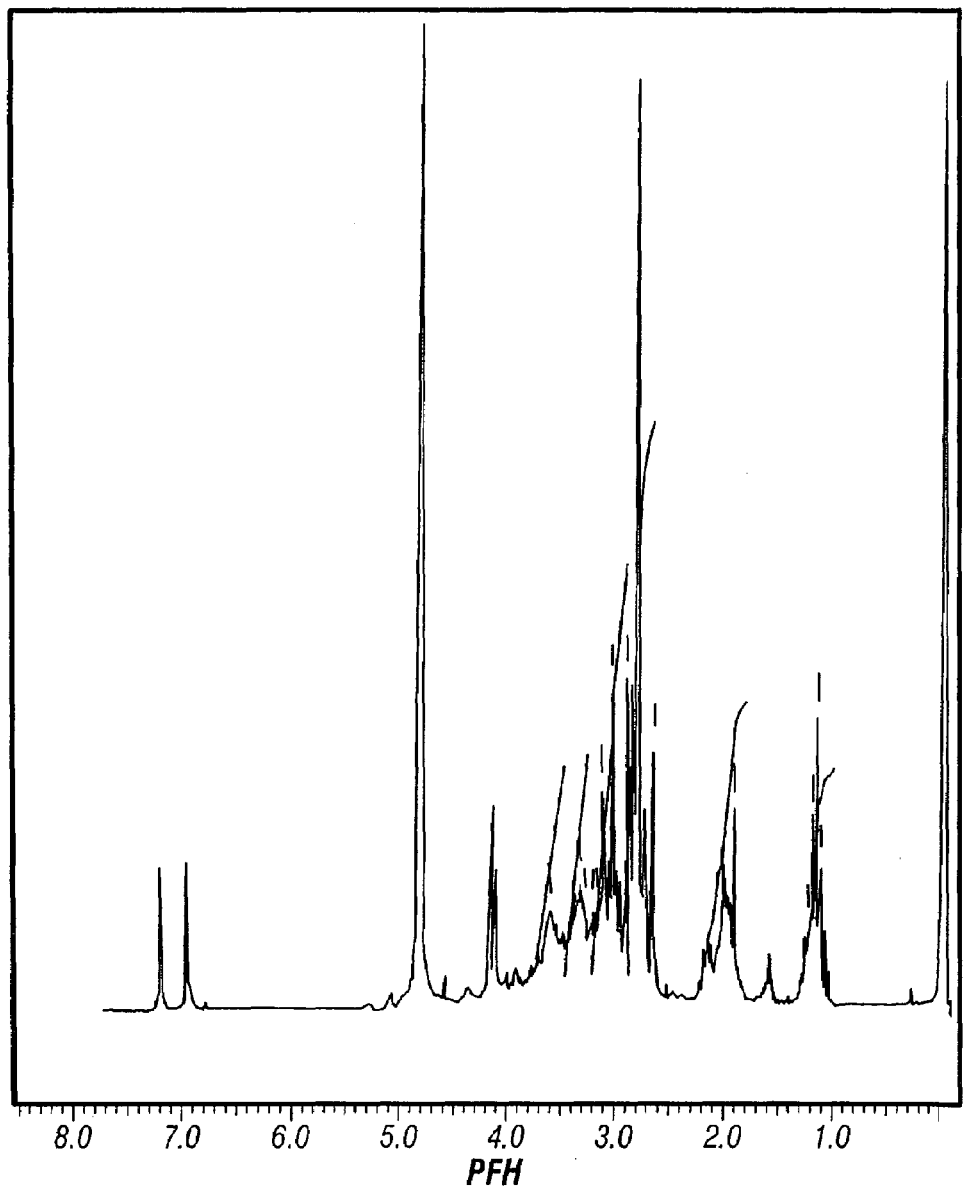

Sodium hydroxide (2N, 0.6 ml) was added to a stirred solution of EC (134 ma, 0.50 mmol) in water (2 ml). To this colorless solution, sulfo-NHS (260.6 mg, 1.2 mmol), EDC (230 ma, 1.2 mmol) and sodium hydroxide (2N, 1 ml) were added. $NIM-NH_2$ hydrochloride salt (206.6 mg, 1.0 mmol) was then added. The mixture was stirred at room temperature for 24 hours. The mixture was dialyzed for 48 hrs using Spectra/POR molecular porous membrane with cut-off at 500 (Spectrum Medical Industries Inc., Houston, Tex.). After dialysis, the product was frozen dried using lyophilizer (Labconco, Kansas City, Mo.). The product weighed 594.8 mg (yield 98%). The synthetic scheme of EC-NIM is shown in FIG. 8A. The structure is confirmed by $^1$H-NMR ($D_2O$) (FIG. 8B).

Radiolabeling of EC-MN and EC-NIM with $^{99m}Tc$

Radiosynthesis of $^{99m}Tc$-EC-MN and $^{99m}Tc$-EC-NIM were achieved by adding required amount of pertechnetate into home-made kit containing the lyophilized residue of EC-MN or EC-NIM (3 mg), $SnCl_2$, (100 μg), $Na_{2\ HPO4}$ (13.5 mg), ascorbic acid (0.5 mg) and NaEDTA (0.5 mg). Final pH of preparation was 7.4. Radiochemical purity was determined by TLC (ITLAC SG, Gelman Sciences, Ann Arbor, Mich.) eluted with acetone (system A) and ammonium acetate (1M in water):methanol (4:1) (system B), respectively. From radio-TLC (Bioscan, Washington, D.C.) analysis, the radiochemical purity was >96% for both radiotracers.

Synthesis of [$^{18}$F]FMISO and [$^{131}$I]IMISO

[Should this be $^{18}$?][Fl]uoride was produced by the cyclotron using proton irradiation of enriched $^{18}$O-water in a small-volume silver target. The tosyl MIS0 (Hay et al., 1994) (20 mg) was dissolved in acetonitrile (1.5 ml), added to the kryptofix-fluoride complex. After heating, hydrolysis and column purification, A yield of 25-40% (decay corrected) of pure product was isolated with the end of bombardment (EOB) at 60 min. HPLC was performed on a C-18 ODS-20 T column, 4.6×25 mm (Waters Corp., Milford, Mass.), with water/acetonitrile, (80/20), using a flow rate of 1 ml/min. The no-carrier-added product corresponded to the retention time (6.12 min) of the unlabeled FMISO under similar conditions. The radiochemical purity was greater than 99%. Under the UV detector (310 nm), there were no other impurities. The specific activity of [$^{18}$F]FMISO determined was 1 Ci/μmol based upon UV and radioactivity detection of a sample of known mass and radioactivity.

[$^{131}$I]IMISO was prepared using the same precursor (Cherif et al., 1994), briefly, 5 mg of tosyl MISO was dissolved in acetonitrile (1 ml), and $Na^{131}I$ (1 mCi in 0.1 ml 1N NaOH) (Dupont New England Nuclear, Boston. Mass.) was added. After heating and purification, the product (60-70% yield) was obtained. Radio-TLC indicated the Rf values of 0.01 for the final product using chloroform methanol (7:3) as an eluant.

Stability Assay of $^{99m}Tc$-EC-MN and $^{99m}Tc$-EC-NIM

Stability of labeled $^{99m}Tc$-EC-MN and $^{99m}Tc$-EC-NIM were tested in serum samples. Briefly, 740 KBq of 1 mg $^{99m}Tc$-EC-MN and $^{99m}Tc$-EC-NIM were incubated in dog serum (200 μl) at 37° C. for 4 hours. The serum samples were diluted with 50% methanol in water and radio-TLC repeated at 0.5, 2 and 4 hours as described above.

Tissue Distribution Studies of $^{99m}Tc$-EC-MN

Female Fischer 344 rats (150±25 g) (Harlan Sprague-Dawley, Indianapolis, Ind.) were inoculated subcutaneously with 0.1 ml of mammary tumor cells from the 13762 tumor cell line suspension ($10^6$ cells/rat, a tumor cell line specific to Fischer rats) into the hind legs using 25-gauge needles. Studies performed 14 to 17 days after implantation when tumors reached approximately 1 cm diameter. Rats were anesthetized with ketamine (10-15 mg/rat, intraperitoneally) before each procedure.

In tissue distribution studies, each animal was injected intravenously with 370-550 KBq of $^{99m}Tc$-EC-MN or $^{99m}Tc$-EC (n=3/time point). The injected mass of $^{99m}Tc$-EC-MN was 10 μg per rat. At 0.5, 2 and 4 hrs following administration of the radiotracers, the rats were sacrificed and the selected tissues were excised, weighed and counted for radioactivity. The biodistribution of tracer in each sample was calculated as percentage of the injected dose per gram of tissue wet weight (% ID/g). Tumor/nontarget tissue count density radios were calculated from the corresponding % ID/g values. The data was compared to [$^{18}$F]FMISO and [$^{131}$I]IMISO using the same animal model. Student t-test was used to assess the significance of differences between groups.

Scintigraphic Imaging and Autoradiography Studies

Scintigraphic images, using a gamma camera (Siemens Medical Systems, Inc., Hoffman Estates, Ill.) equipped with low-energy, parallel-hole collimator, were obtained 0.5, 2 and 4 hrs after i.v. injection of 18.5 MBq of each radiotracer.

Whole-body autoradiogram was obtained by a quantitative image analyzer (Cyclone Storage Phosphor System, Packard, Meridian, Conn.). Following i.v. injection of 37 MBq of $^{99m}Tc$-EC-MN, the animals were killed at 1 h and the body were fixed in carboxymethyl cellulose (4%) as previously described (Yang et al., 1995). The frozen body was mounted onto a cryostat (LKB 2250 cryomicrotome) and cut into 100 μm coronal sections. Each section was thawed and mounted on a slide. The slide was then placed in contact with multipurpose phosphor storage screen (MP, 7001480) and exposed for 15 hrs.

To ascertain whether $^{99m}Tc$-EC-NIM could monitor tumor response to chemotherapy, a group of rats with tumor volume 1.5 cm and ovarian tumor-bearing mice were treated with paclitaxel (40 mg/kg/rat, 80 mg/kg/mouse, i.v.) at one single dose. The image was taken on day 4 after paclitaxel treatment. Percent of injected dose per gram of tumor weight with or without treatment was determined.

Polarographic Oxygen Microelectrode $pO_2$ Measurements

To confirm tumor hypoxia, intratumoral $pO_2$ measurements were performed using the Eppendorf computerized histographic system. Twenty to twenty-five $pO_2$ measurements along each of two to three linear tracks were performed at 0.4 mm intervals on each tumor (40-75 measurements total). Tumor pO measurements were made on three tumor-bearing rats. Using an on-line computer system, the pot measurements of each track were expressed as absolute values relative to the location of the measuring point along the track, and as the relative frequencies within a $pO_2$ histogram between 0 and 100 mmHg with a class width of 2.5 mm.

Results

Radiosynthesis and Stability of $^{99m}$Tc-EC-MN and $^{99m}$Tc-EC-NIM

Figure 13:
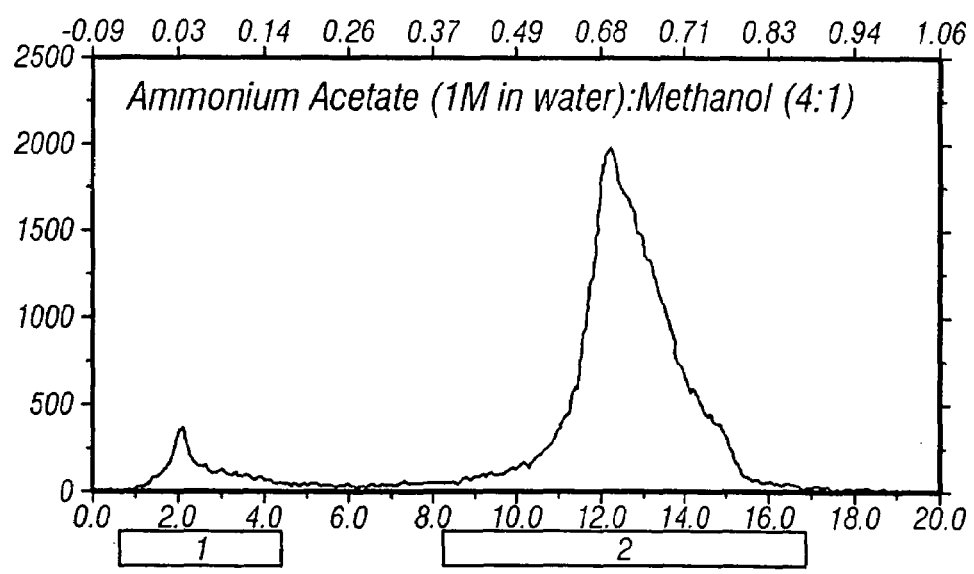
FIG. 13. Illustrates stability of $^{99m}$Tc-EC-NIM in dog serum samples.

Radiosynthesis of EC-MN and EC-NIM with $^{99m}$Tc were achieved with high (>95%) radiochemical purity Radiochemical yield was 100%. $^{99m}$Tc-EC-MN and $^{99m}$Tc-EC-NIM (FIG. 13) were found to be stable at 0.5, 2 and 4 hrs in dog serum samples. There was no degradation products observed. Radiofluorination and radioiodination of MISO were achieved easily using the same precursor. In both labeled MISO analogues, the radiochemical purity was greater than 99%.

In Vivo Tissue Distribution Studies

Figure 9:
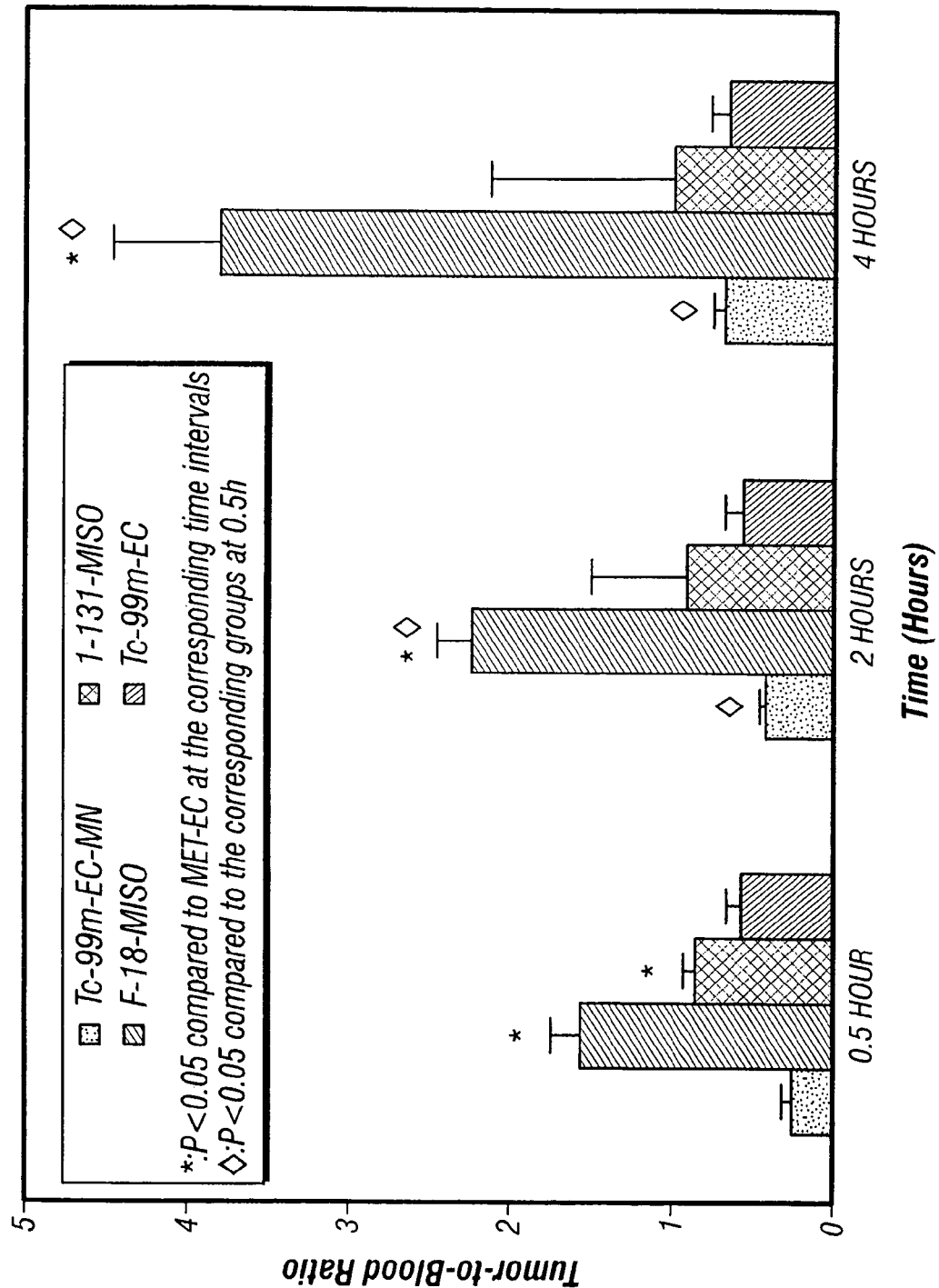
FIG. 9. Biodistribution studies (tumor/blood ratios) for $^{99m}$Tc-EC-MN, [$^{18}$F]FMISO and [$^{131}$I]IMISO.
Figure 10:
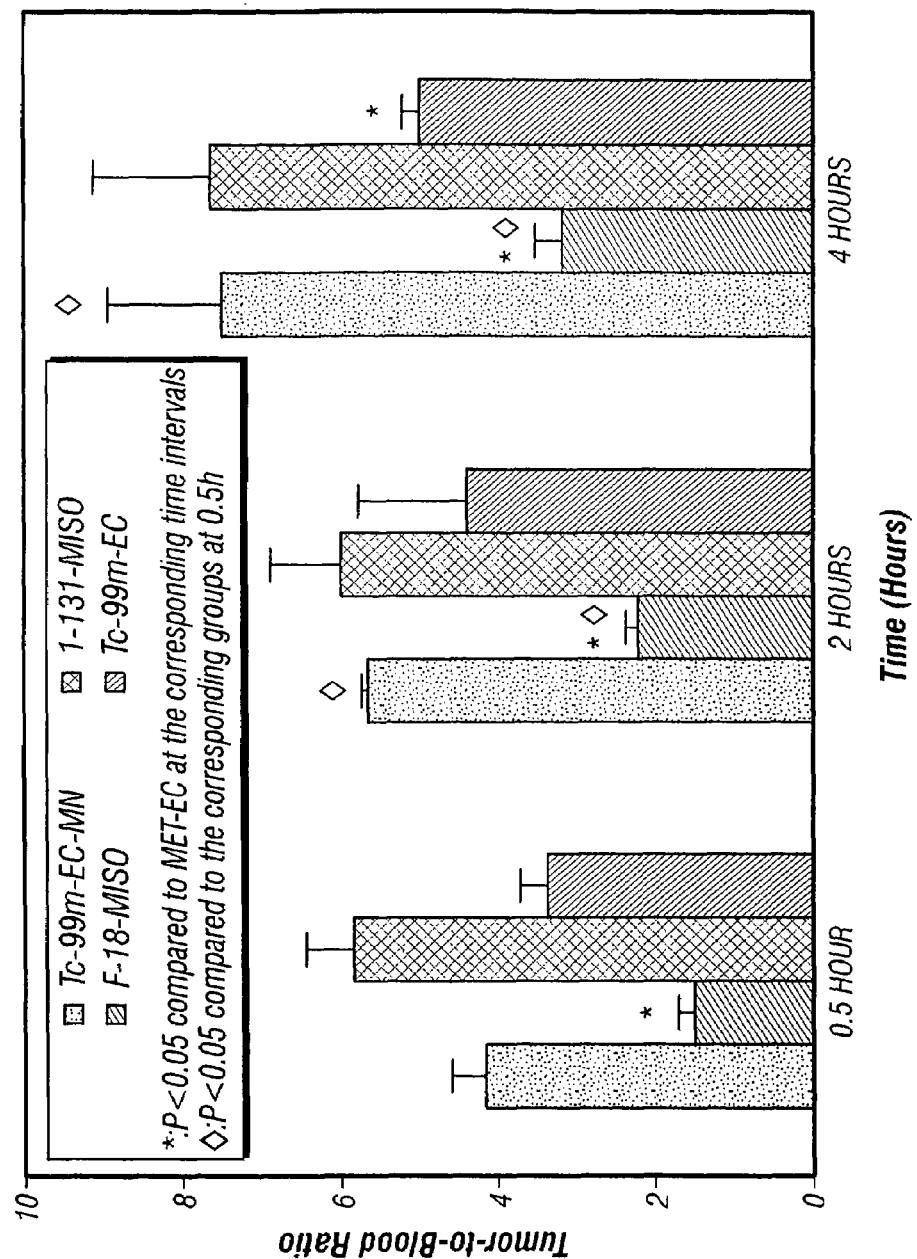
FIG. 10. Biodistribution studies (tumor/muscle ratios) for $^{99m}$Tc-EC, [$^{18}$F]FMISO and [$^{131}$I]IMISO.

The tissue distribution of $^{99m}$Tc-EC-MN and $^{99m}$Tc-EC in the tumor-bearing rats is shown in Tables 4 and 5. Due to high affinity for ionic $^{99m}$Tc, there was no significant and consistent thyroid uptake, suggesting the in vivo stability of $^{99m}$Tc-EC-MN (Table 5).

time period (FIG. 9 and FIG. 10). [$^{18}$F]FMISO showed the highest tumor-to-blood uptake ratio than those with [$^{131}$I] IMISO and $^{99m}$Tc-EC-MN at 30 min, 2 and 4 hrs post-injection. Tumor/blood and tumor/muscle ratios for $^{99m}$Tc-EC-MN and [$^{131}$I]IMISO at 2 and 4 hrs postinjection were not significantly different (p<0.05).

Scintigraphic Imaging and Autoradiographic Studies

Figure 11A:
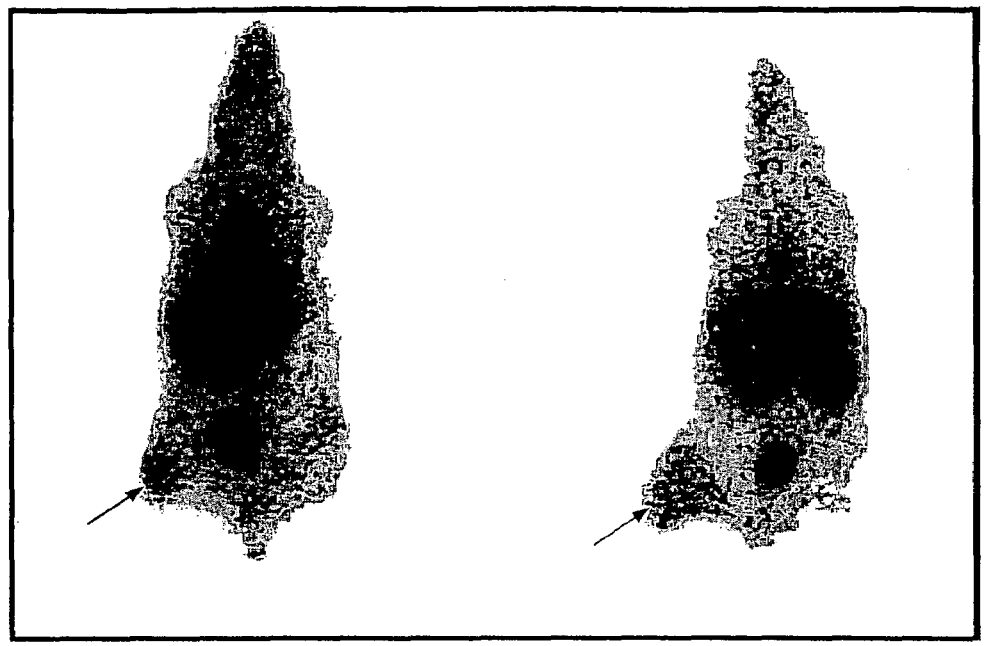
FIGS. 11A and 11B. Scintigraphic images of tumor in $^{99m}$Tc-EC-MN (FIG. 11A) and $^{99m}$Tc-EC (FIG. 11B) injected groups.
Figure 11B:
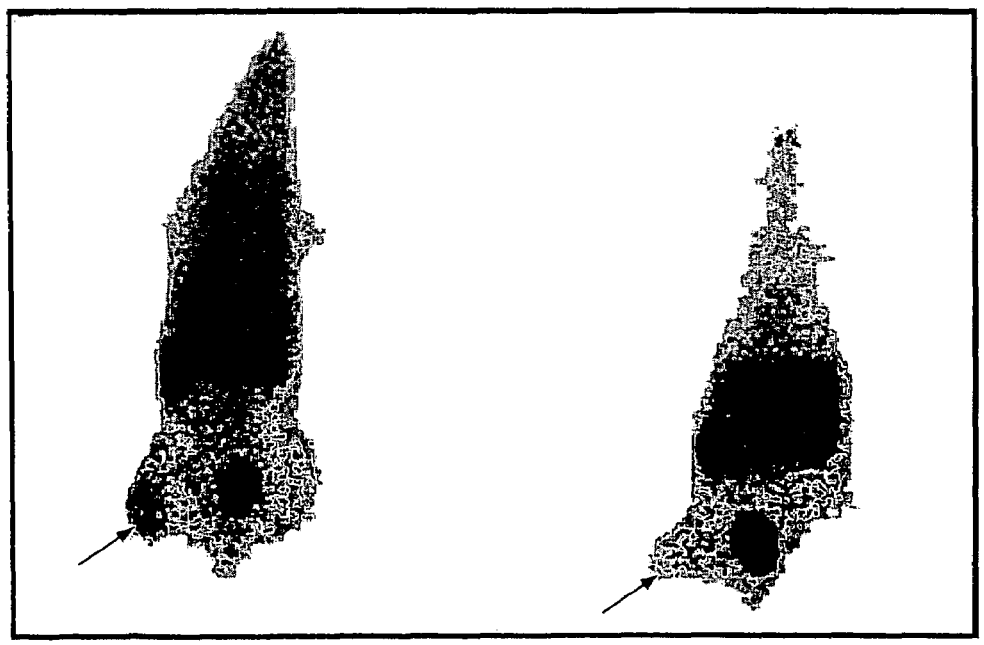
Figure 12:
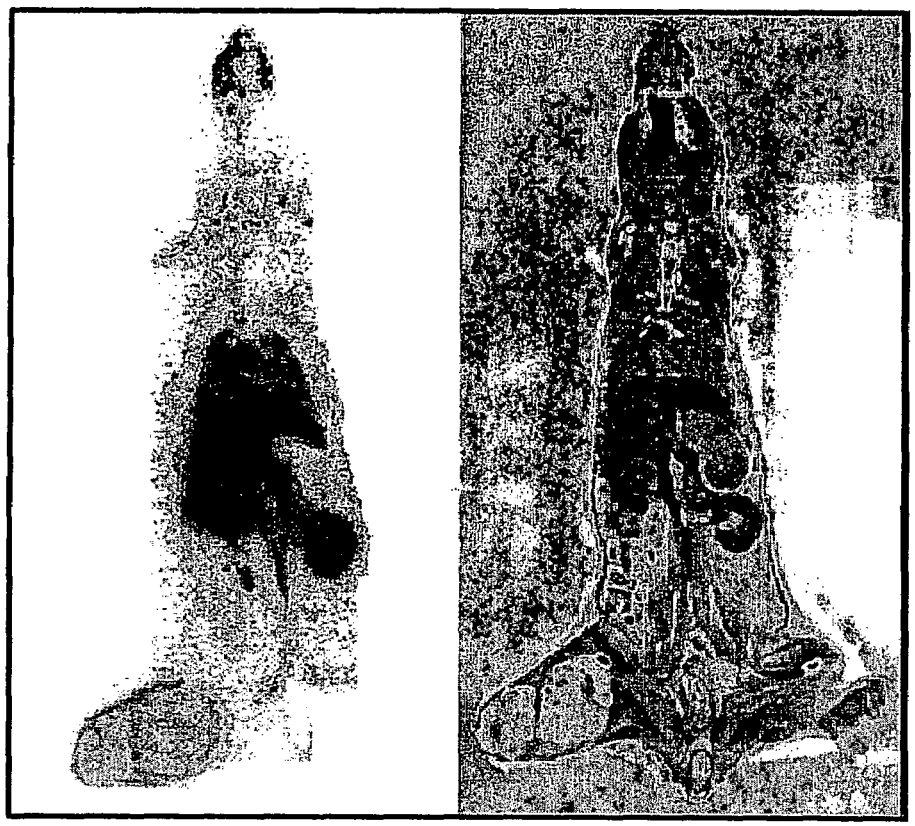
FIG. 12. Autoradiograms performed at 1 hour after injection with $^{99m}$Tc-EC-MN.

Scintigraphic images obtained at different time points showed visualization of tumor in $^{99m}$Tc-EC-MN and $^{99m}$Tc-EC-NIM groups. Contrary, there was no apparent tumor uptake in $^{99m}$Tc-EC injected group (FIG. 11). Autoradiograms performed at 1 hr after injection of $^{99m}$Tc-EC-MN clearly demonstrated tumor activity (FIG. 12). Compare to $^{99m}$Tc-EC-NM, $^{99m}$Tc-EC-NIM appeared to provide better scintigraphic images due to higher tumor-to-background ratios. In breast tumor-bearing rats, tumor uptake was markedly higher in $^{99m}$Tc-EC-NIM group compared to $^{99m}$Tc-EC (FIG. 14A). Data obtained from percent of injected dose of $^{99m}$Tc-EC-NIM per gram of tumor weight indicated that a

TABLE 4

Biodistribution of $^{99m}$Tc-EC in Breast Tumor-Bearing Rats

% of injected $^{99m}$Tc-EC dose per organ or tissue

| | 20 min | 1 h | 2 h | 4 h |
|---|---|---|---|---|
| Blood | 0.435 ± 0.029 | 0.273 ± 0.039 | 0.211 ± 0.001 | 0.149 ± 0.008 |
| Lung | 0.272 ± 0.019 | 0.187 ± 0.029 | 0.144 ± 0.002 | 0.120 ± 0.012 |
| Liver | 0.508 ± 0.062 | 0.367 ± 0.006 | 0.286 ± 0.073 | 0.234 ± 0.016 |
| Stomach | 0.136 ± 0.060 | 0.127 ± 0.106 | 0.037 ± 0.027 | 0.043 ± 0.014 |
| Kidney | 7.914 ± 0.896 | 8.991 ± 0.268 | 9.116 ± 0.053 | 7.834 ± 1.018 |
| Thyroid | 0.219 ± 0.036 | 0.229 ± 0.118 | 0.106 ± 0.003 | 0.083 ± 0.005 |
| Muscle | 0.060 ± 0.006 | 0.043 ± 0.002 | 0.028 ± 0.009 | 0.019 ± 0.001 |
| Intestine | 0.173 ± 0.029 | 0.787 ± 0.106 | 0.401 ± 0.093 | 0.103 ± 0.009 |
| Urine | 9.124 ± 0.808 | 11.045 ± 6.158 | 13.192 ± 4.505 | 8.693 ± 2.981 |
| Tumor | 0.342 ± 0.163 | 0.149 ± 0.020 | 0.115 ± 0.002 | 0.096 ± 0.005 |
| Tumor/Blood | 0.776 ± 0.322 | 0.544 ± 0.004 | 0.546 ± 0.010 | 0.649 ± 0.005 |
| Tumor/Muscle | 5.841 ± 3.253 | 3.414 ± 0.325 | 4.425 ± 1.397 | 5.093 ± 0.223 |

Values shown represent the mean ± standard deviation of data from 3 animals

Figure 5:
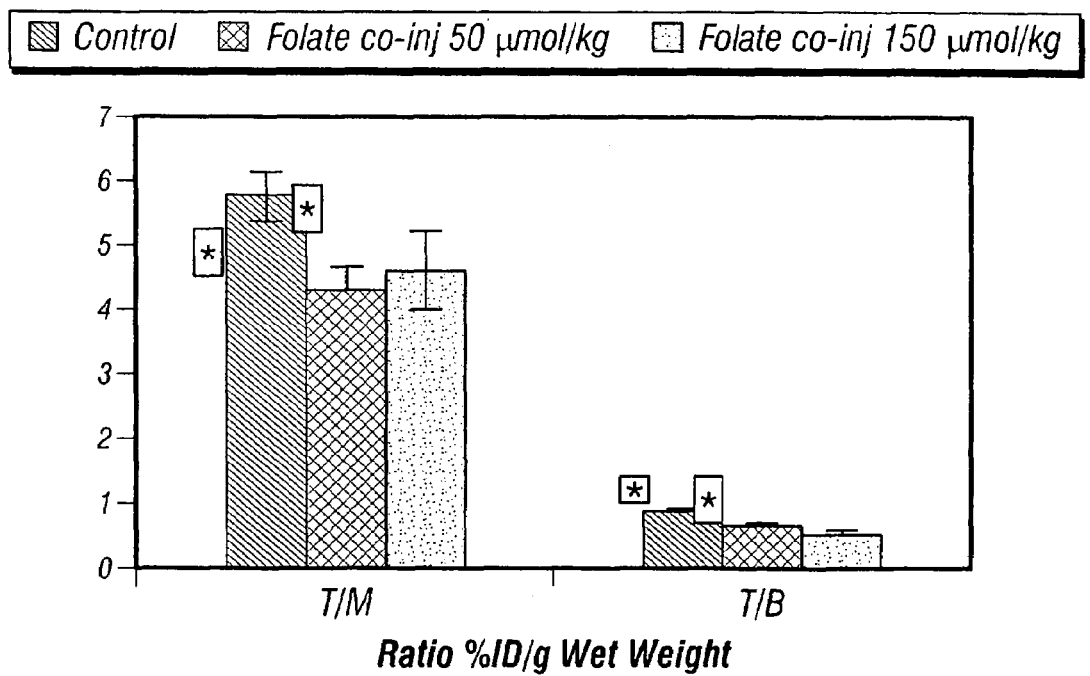
FIG. 5. Blocking studies for tumor/muscle and tumor/blood count ratios with $^{99m}$Tc-EC-folate.

In blocking studies, tumor/muscle and tumor/blood count density ratios were significantly decreased (p<0.01) with folic acid co-administrations (FIG. 5).

TABLE 5

Biodistribution of $^{99m}$Tc-EC-metronidazole conjugate in breast tumor bearing rats[1]

| | 30 Min. | 2 Hour | 4 Hour |
|---|---|---|---|
| Blood | 1.46 ± 0.73 | 1.19 ± 0.34 | 0.76 ± 0.14 |
| Lung | 0.79 ± 0.39 | 0.73 ± 0.02 | 0.52 ± 0.07 |
| Liver | 0.83 ± 0.36 | 0.91 ± 0.11 | 0.87 ± 0.09 |
| Spleen | 0.37 ± 0.17 | 0.41 ± 0.04 | 0.37 ± 0.07 |
| Kidney | 4.30 ± 1.07 | 5.84 ± 0.43 | 6.39 ± 0.48 |
| Muscle | 0.08 ± 0.03 | 0.09 ± 0.01 | 0.07 ± 0.01 |
| Intestine | 0.27 ± 0.12 | 0.39 ± 0.24 | 0.22 ± 0.05 |
| Thyroid | 0.051 ± 0.16 | 0.51 ± 0.09 | 0.41 ± 0.02 |
| Tumor | 0.034 ± 0.13 | 0.49 ± 0.02 | 0.50 ± 0.09 |

[1]Each rat received 99m Tc-EC-metronidazole (10 μCi, iv). Each value is percent of injected dose per gram weight (n = 3)/time interval. Each data represents mean of three measurements with standard deviation.

Figure 14B:
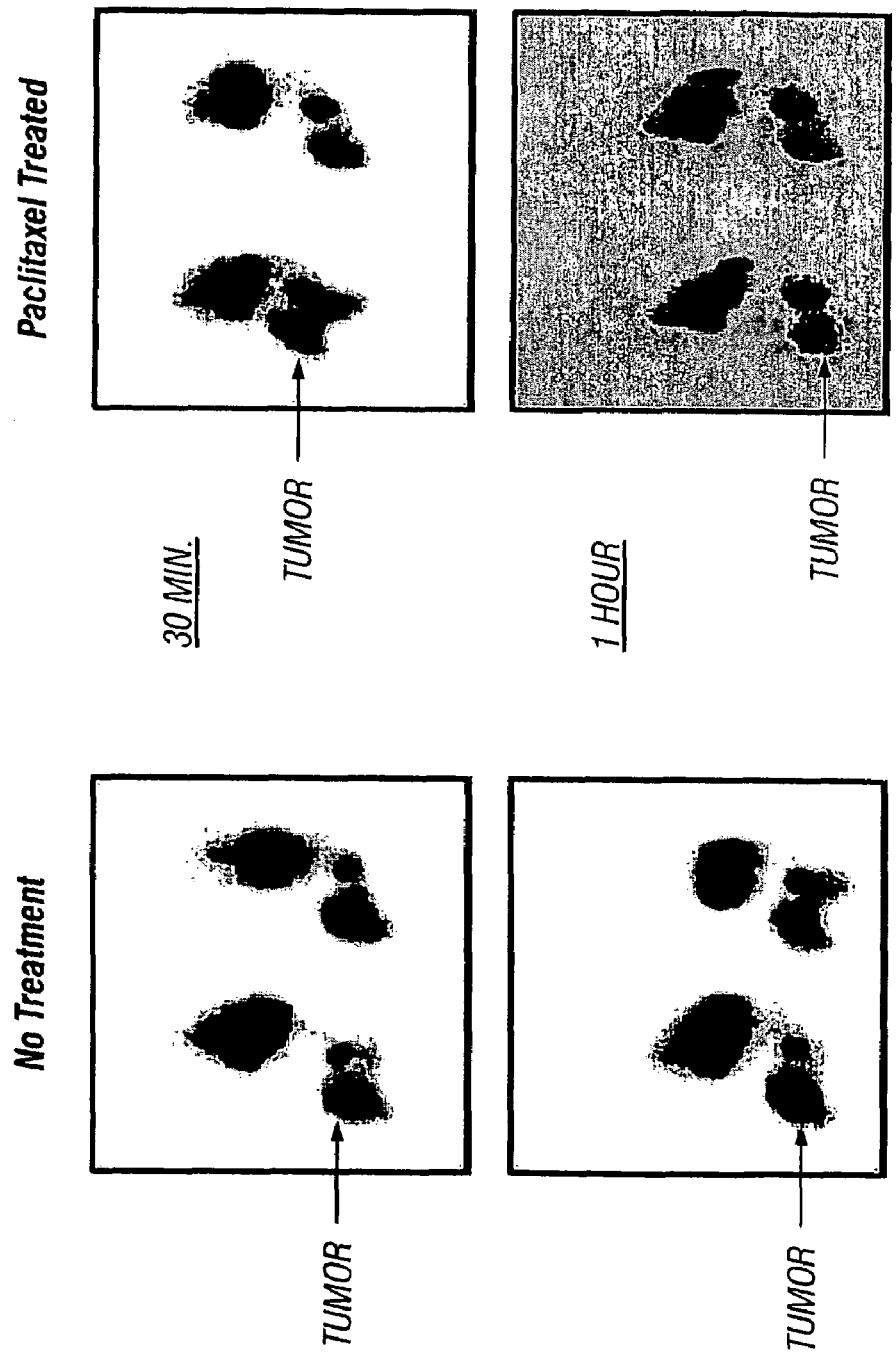

Biodistribudon studies showed that tumor/blood and tumor/muscle count density ratios at 0.54 hr gradually increased for $^{99m}$Tc-EC-MN, [$^{18}$F]FMISO and [$^{131}$I]IMISO, whereas these values did not alter for $^{99m}$Tc-EC in the same 25% decreased uptake in the rats treated with paclitaxel when compared to control group (FIG. 14B).

Figure 15A:
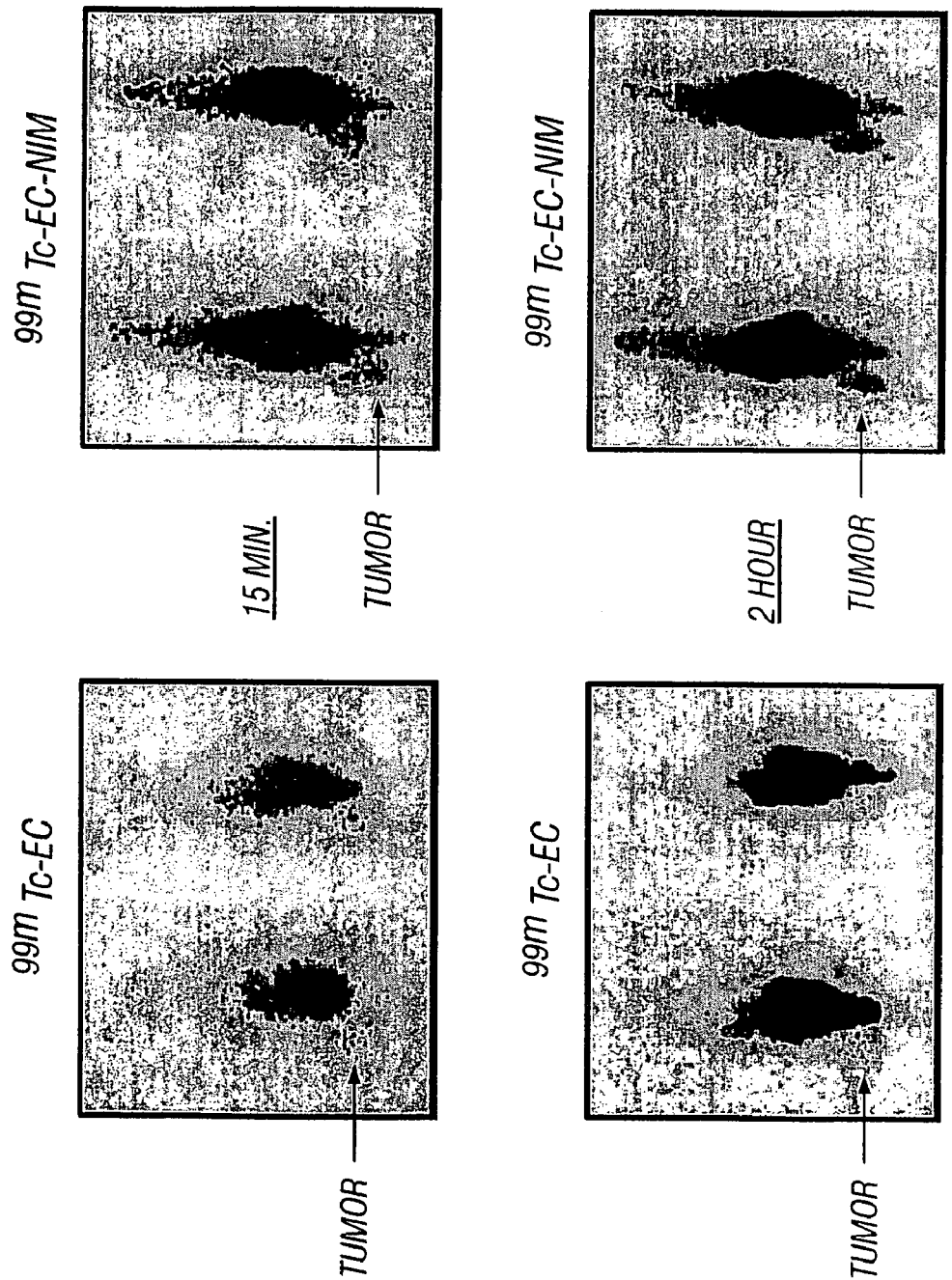
FIGS. 15A, 15B, 15C, and 15D. Illustrates ovarian tumor uptake of $^{99m}$Tc-EC-NIM vs. $^{99m}$Tc-EC in rats (FIG. 15A) The tumor uptake in rats treated with paclitaxel (FIG. 15B) was less than tumor uptake in rats not treated with paclitaxel (FIG. 15A). Also illustrated is tumor uptake of $^{99m}$Tc-EC-NIM in rats having sarcomas.
Figure 15B:
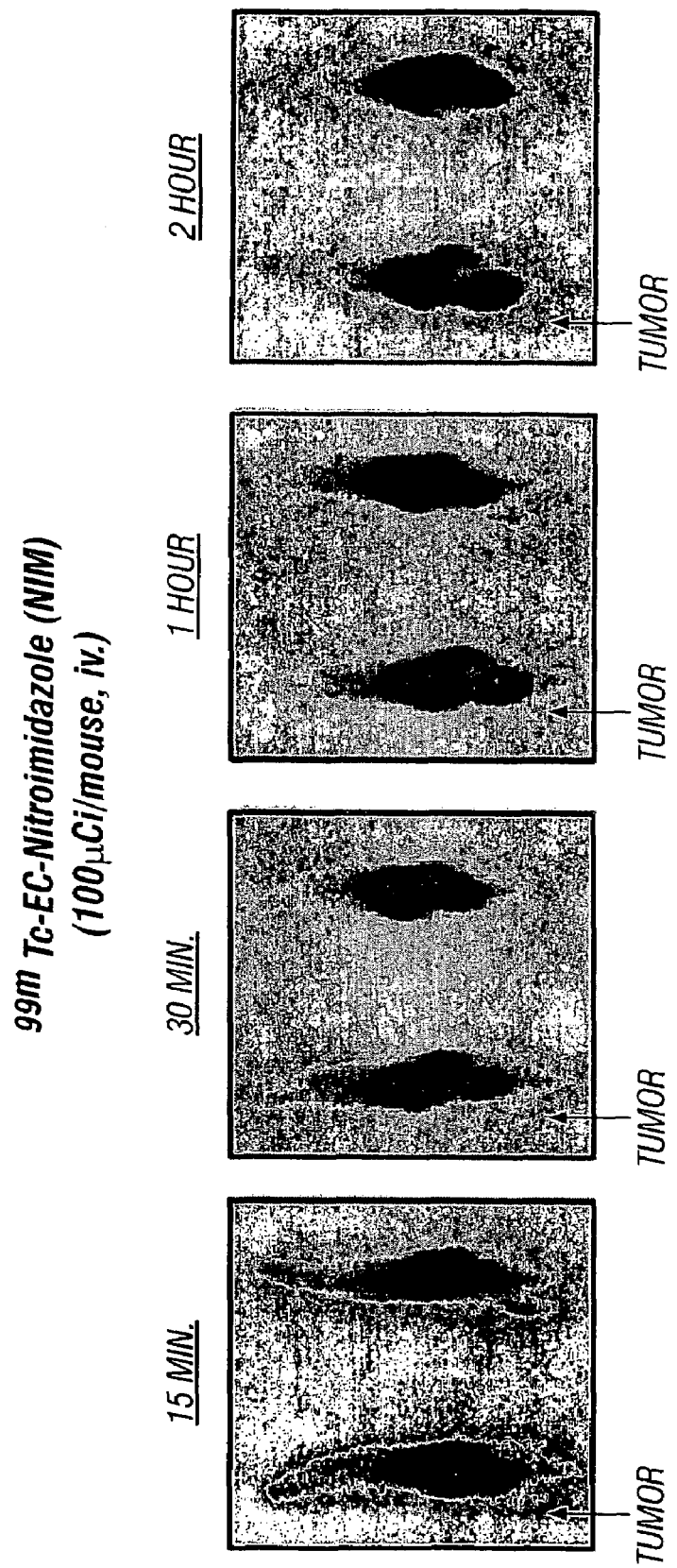
Figure 15C:
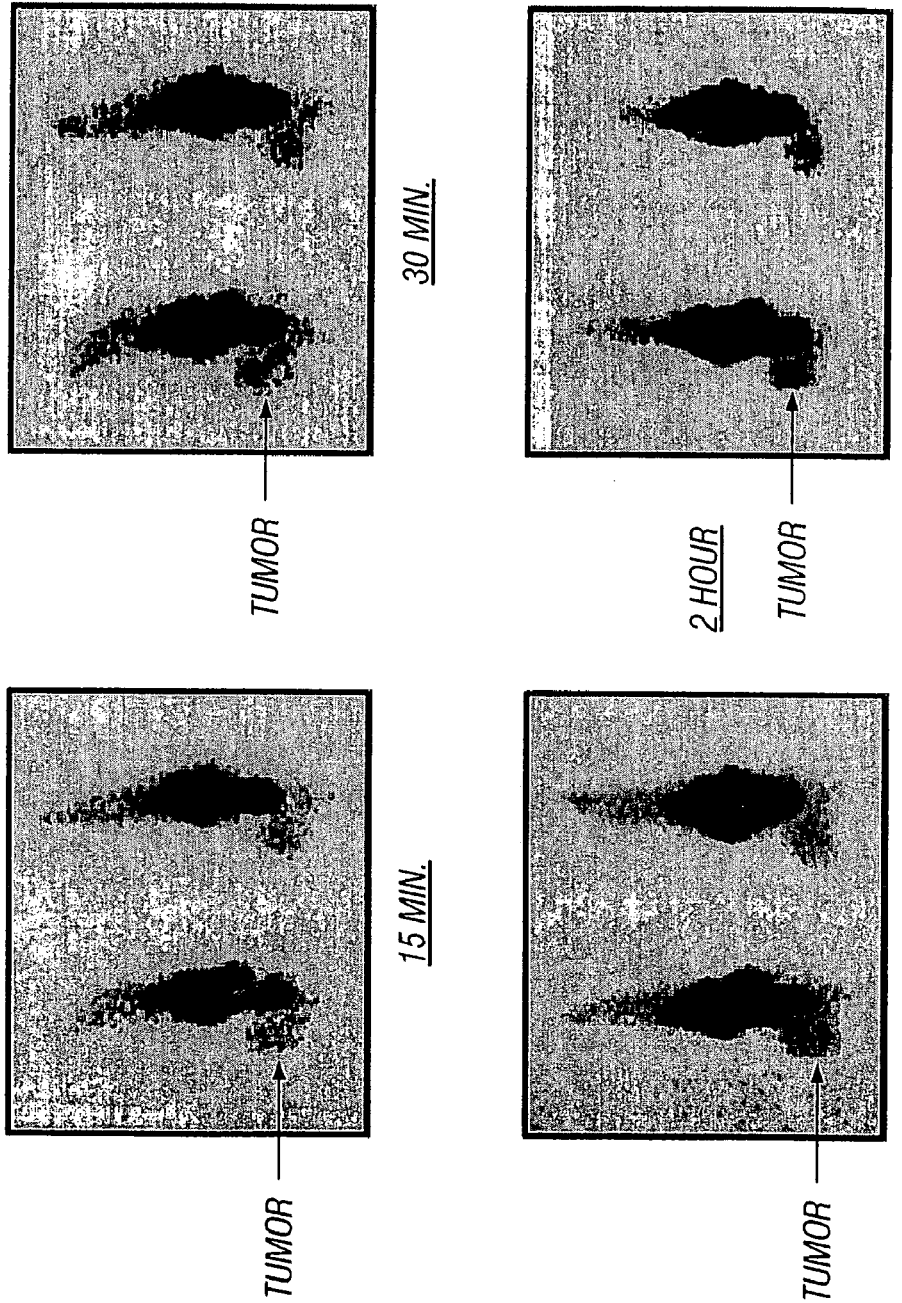
Figure 15D:
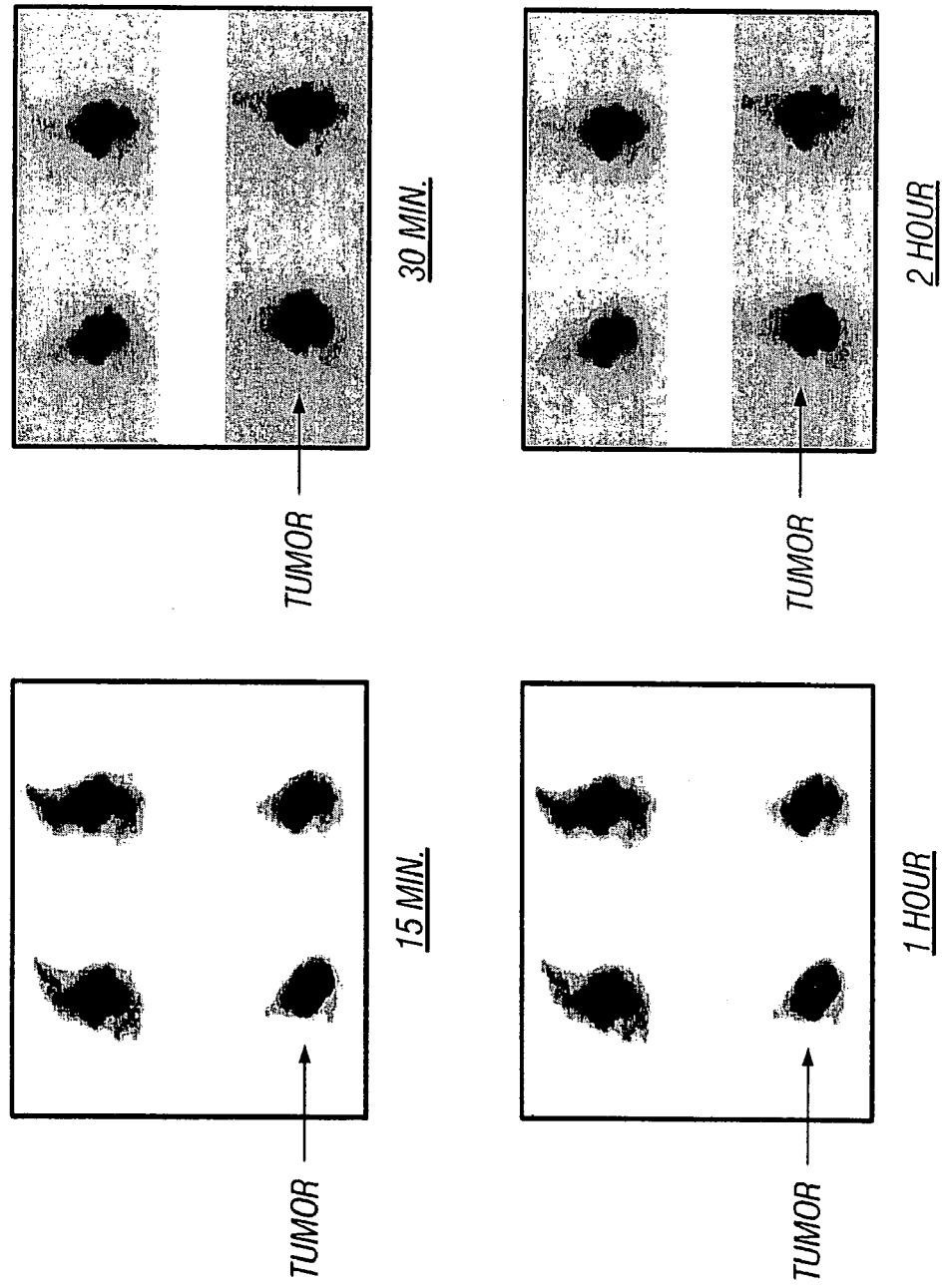

In ovarian tumor-bearing mice, there was a decreased tumor uptake in mice treated with paclitaxel (FIG. 15A and FIG. 15B). Similar results were observed in sarcoma-bearing (FIG. 15C and FIG. 15D). Thus, $^{99m}$Tc-EC-NIM could be used to assess tumor response to paclitaxel treatment.

Polarographic Oxygen Microelectrode $pO_2$ Measurements

Intratumoral $PO_2$ measurements of tumors indicated the tumor oxygen tension ranged 4.6±1.4 mmHg as compared to normal muscle of 35±10 mmHg. The data indicate that the tumors are hypoxic.

EXAMPLE 3

Peptide Imaging of Cancer

Synthesis of Ethylenedicysteine-Pentaglutamate (EC-GAP)

Figure 16:
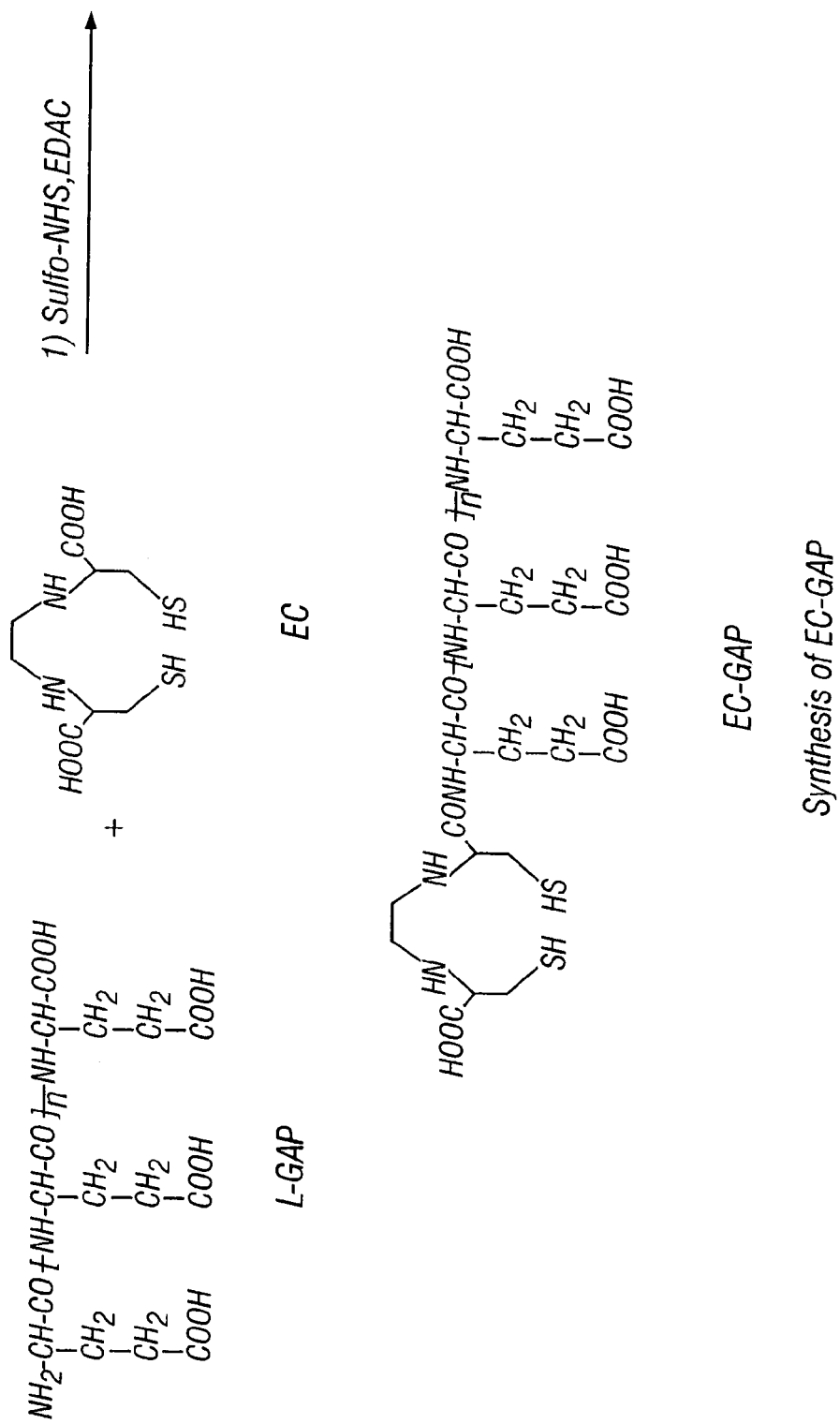
FIG. 16. Synthetic scheme of EC-GAP (pentaglutamate).

Sodium hydroxide (1N, 1 ml) was added to a stirred solution of EC (200 mg, 0.75 mmol) in water (10 ml). To this colorless solution, sulfo-NHS (162 mg, 0.75 mmol) and EDC (143 mg, 0.75 mmol) were added. Pentaglutamate sodium salt (M.W. 750-1500, Sigma Chemical Company) (500 mg, 0.67 mmol) was then added. The mixture was stirred at room temperature for 24 hours. The mixture was dialyzed for 48 hrs using Spectra/POR molecular porous membrane with cut-off at 500 (Spectrum Medical Industries Inc., Houston, Tex.). After dialysis, the product was frozen dried using lyophilizer (Labconco, Kansas City, Mo.). The product in the salt form weighed 0.95 g. The synthetic scheme of EC-GAP is shown in FIG. 16.

Stability Assay of $^{99m}$Tc-EC-GAP

Radiolabeling of EC-GAP with $^{99m}$Tc was achieved using the same procedure described previously. The radiochemical purity was 100%. Stability of labeled $^{99m}$Tc-EC-GAP was tested in serum samples. Briefly, 740 KBq of 1 mg $^{99m}$Tc-EC-GAP was incubated in dog serum (200 µl) at 37° C. for 4 hours. The serum samples were diluted with 50% methanol in water and radio-TLC repeated at 0.5, 2 and 4 hours as described above.

Scintigraphic Imaging Studies

Scintigraphic images, using a gamma camera equipped with low-energy, parallel-hole collimator, were obtained 0.5, 2 and 4 hrs after i.v. injection of 18.5 MBq of each radiotracer.

Results

Stability Assay of $^{99m}$Tc-EC-GAP $^{99m}$Tc-EC-GAP found to be stable at 0.5, 2 and 4 hrs in dog serum samples. There was no degradation products observed.

Scintigraphic Imaging Studies

Figure 17:
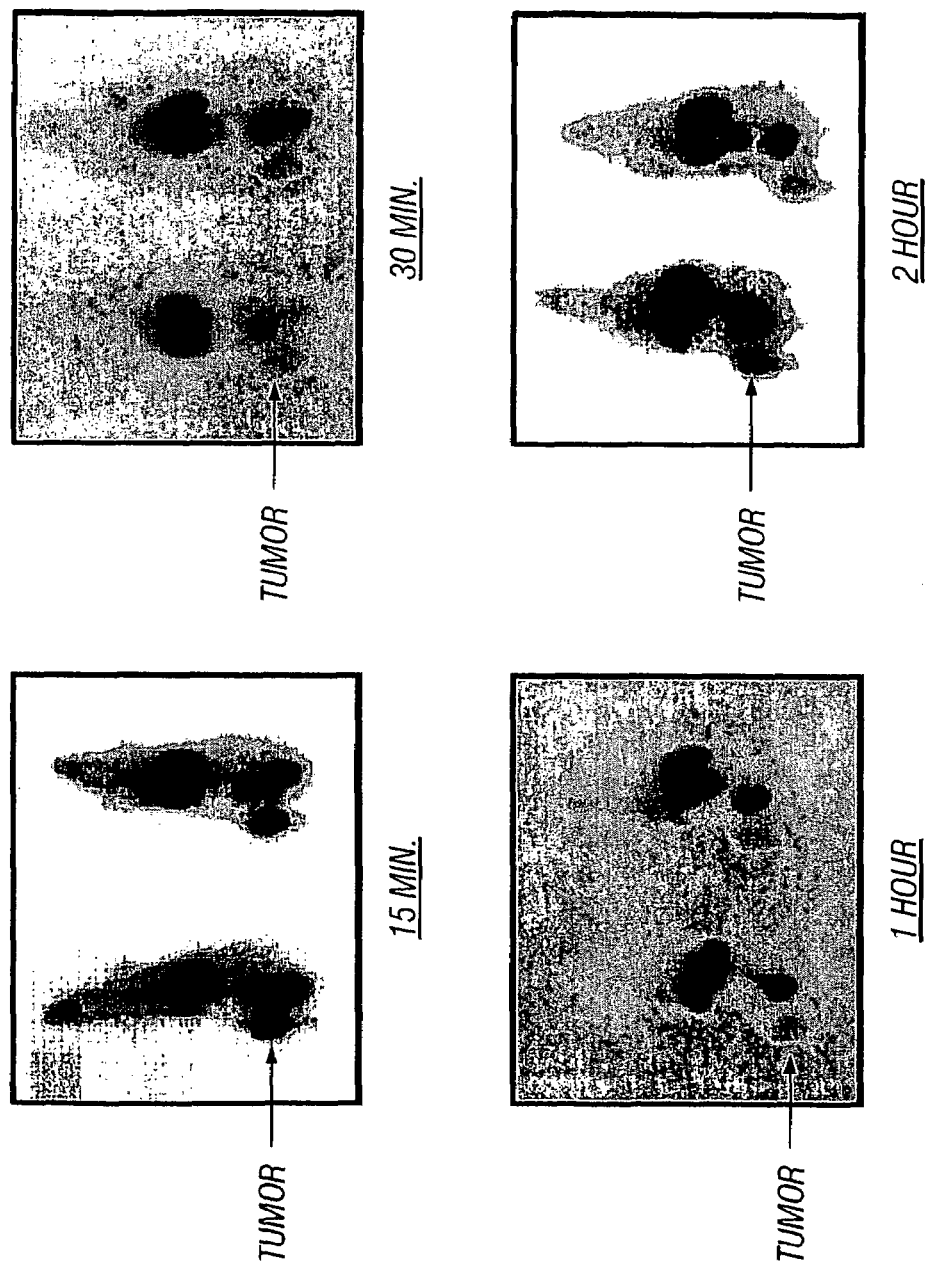
FIG. 17. Scintigraphic images of breast tumors in $^{99m}$Tc-EC-GAP injected group.

Scintigraphic images obtained at different time points showed visualization of tumor in $^{99m}$Tc-EC-GAP group. The optimum uptake is at 30 min to 1 hour post-administration (FIG. 17).

EXAMPLE 4

Imaging Tumor Apoptotic Cells

Synthesis of Ethylenedicysteine-Annexin V (EC-ANNEX)

Sodium bicarbonate (1N, 1 ml) was added to a stirred solution of EC (5 mg, 0.019 mmol). To this colorless solution, sulfo-NHS (4 mg, 0.019 mmol) and EDC (4 mg, 0.019 mmol) were added. Annexin V (M.W. 33 kD, human, Sigma Chemical Company) (0.3 mg) was then added. The mixture was stirred at room temperature for 24 hours. The mixture was dialyzed for 48 hrs using Spectra/POR molecular porous membrane with cut-off at 10,000 (Spectrum Medical Industries Inc., Houston, Tex.). After dialysis, the product was frozen dried using lyophilizer (Labconco, Kansas City, Mo.). The product in the salt form weighed 12 mg.

Stability Assay of $^{99m}$Tc-EC-ANNEX

Radiolabeling of EC-ANNEX with $^{99m}$Tc was achieved using the same procedure described in EC-GAP. The radiochemical purity was 100%. Stability of labeled $^{99m}$Tc-EC-ANNEX was tested in serum samples. Briefly, 740 KBq of 1 mg $^{99m}$Tc-EC-ANNEX was incubated in dog serum (200 µl) at 37° C. for 4 hours. The serum samples were diluted with 50% methanol in water and radio-TLC repeated at 0.5, 2 and 4 hours as described above.

Scintigraphic Imaging Studies

Scintigraphic images, using a gamma camera equipped with low-energy, parallel-hole collimator, were obtained 0.5, 2 and 4 hrs after i.v. injection of 18.5 MBq of the radiotracer. The animal models used were breast, ovarian and sarcoma. Both breast and ovarian-tumor bearing rats are known to overexpress high apoptotic cells. The imaging studies were conducted on day 14 after tumor cell inoculation. To ascertain the tumor treatment response, the pre-imaged mice were administered paclitaxel (80 mg/Kg, iv, day 14) and the images were taken on day 18.

Results

Stability Assay of $^{99m}$Tc-EC-ANNEX $^{99m}$Tc-EC-ANNEX found to be stable at 0.5, 2 and 4 hrs in dog serum samples. There was no degradation products observed.

Scintigraphic Imaging Studies

Figure 20A:
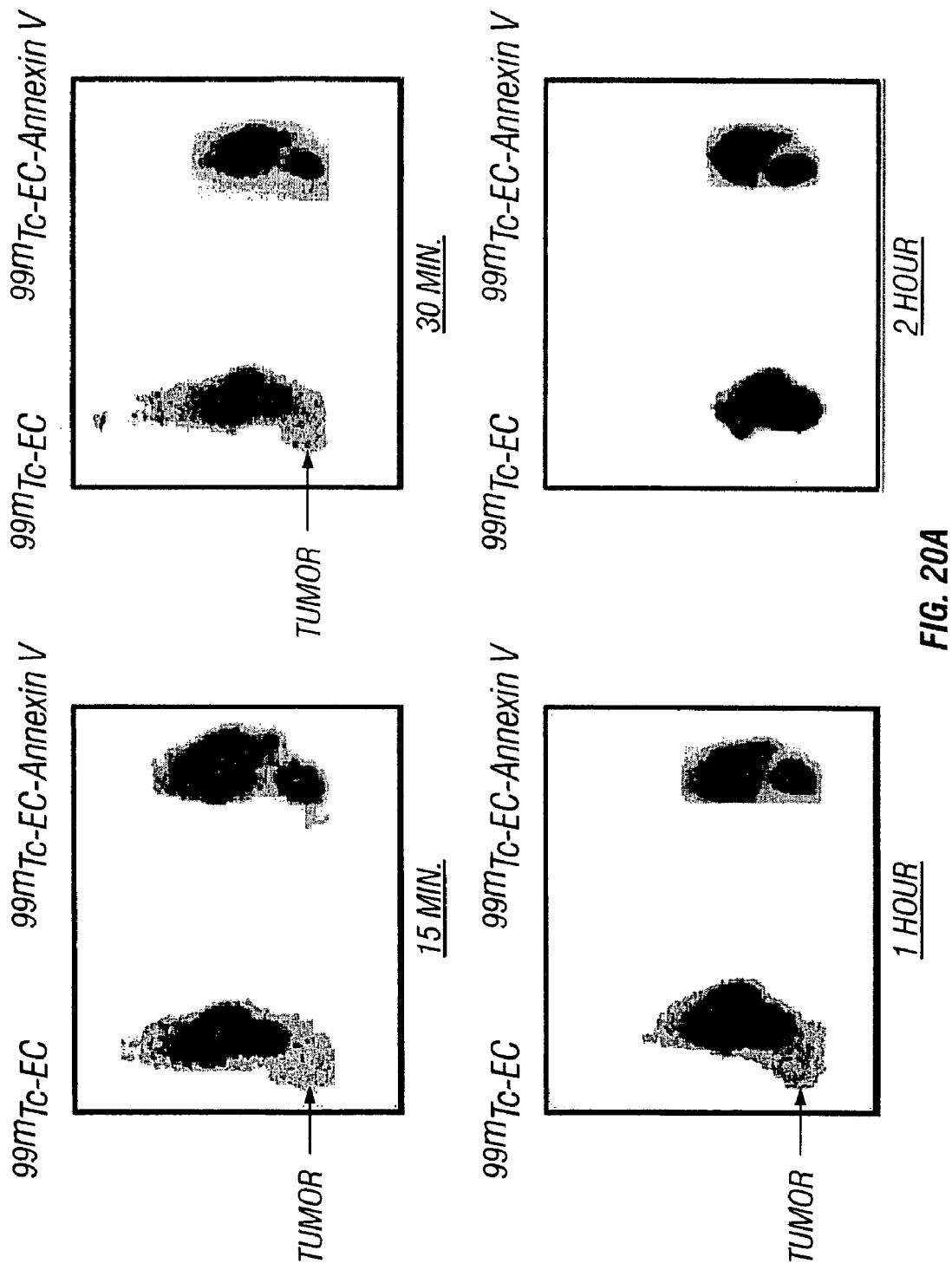
FIGS. 20A and 20B. Comparison of uptake difference of $^{99m}$Tc-EC-ANNEX V between pre-(FIG. 20A) and post-(FIG. 20B) paclitaxel treatment in sarcoma tumor bearing group.
Figure 20B:
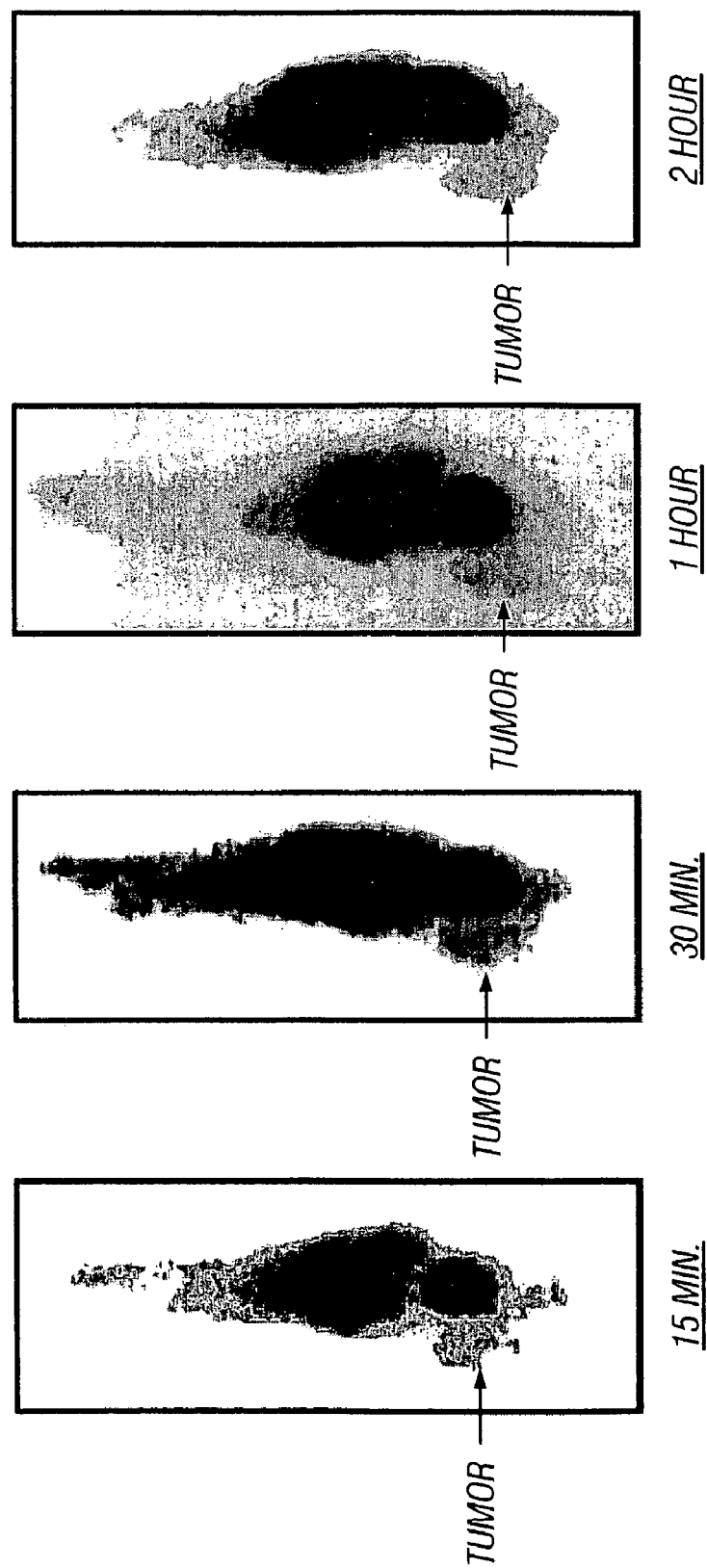

Scintigraphic images obtained at different time points showed visualization of tumor in $^{99m}$Tc-EC-ANNEX group (FIGS. 18-20). The images indicated that highly apoptotic cells have more uptake of $^{99m}$Tc-EC-ANNEX. There was no marked difference of tumor uptake between pre- and post-[aclitaxel treatment in the high apoptosis (ovarian tumor-bearing) group (FIG. 19A and FIG. 19B) and in the low apoptosis (sarcoma tumor-bearing) group (FIG. 20A and FIG. 20B).

EXAMPLE 5

Imaging Tumor Angiogenesis

Synthesis of (Amino Analogue of Colchcine, COL-NH$_2$)

Demethylated amino and hydroxy analogue of colchcine was synthesized according to the previously described methods (Orr et al., 1995). Briefly, colchicine (4 g) was dissolved in 100 ml of water containing 25% sulfuric acid. The reaction mixture was heated for 5 hours at 100° C. The mixture was neutralized with sodium carbonate. The product was filtered and dried over freeze dryer, yielded 2.4 g (70%) of the desired amino analogue (m.p. 153-155° C., reported 155-157° C.). Ninhydrin (2% in methanol) spray indicated the positivity of amino group of COL-NH$_2$. The structure was confirmed by $^1$H-NMR and mass spectroscopy (FAB-MS). $^1$H-NMR (CDCl$_3$)δ 8.09 (S, 1H), 7.51 (d, 1H, J=12 Hz), 7.30 (d, 1H, J=12 Hz), 6.56 (S, 1H), 3.91 (S, 6H), 3.85 (m, 1H), 3.67 (S, 3H), 2.25-2.52 (m, 4H). m/z 308.2(M$^+$, 20), 307.2 (100).

Synthesis of Ethylenedicysteine-Colchcine (EC-COL)

Figure 21:
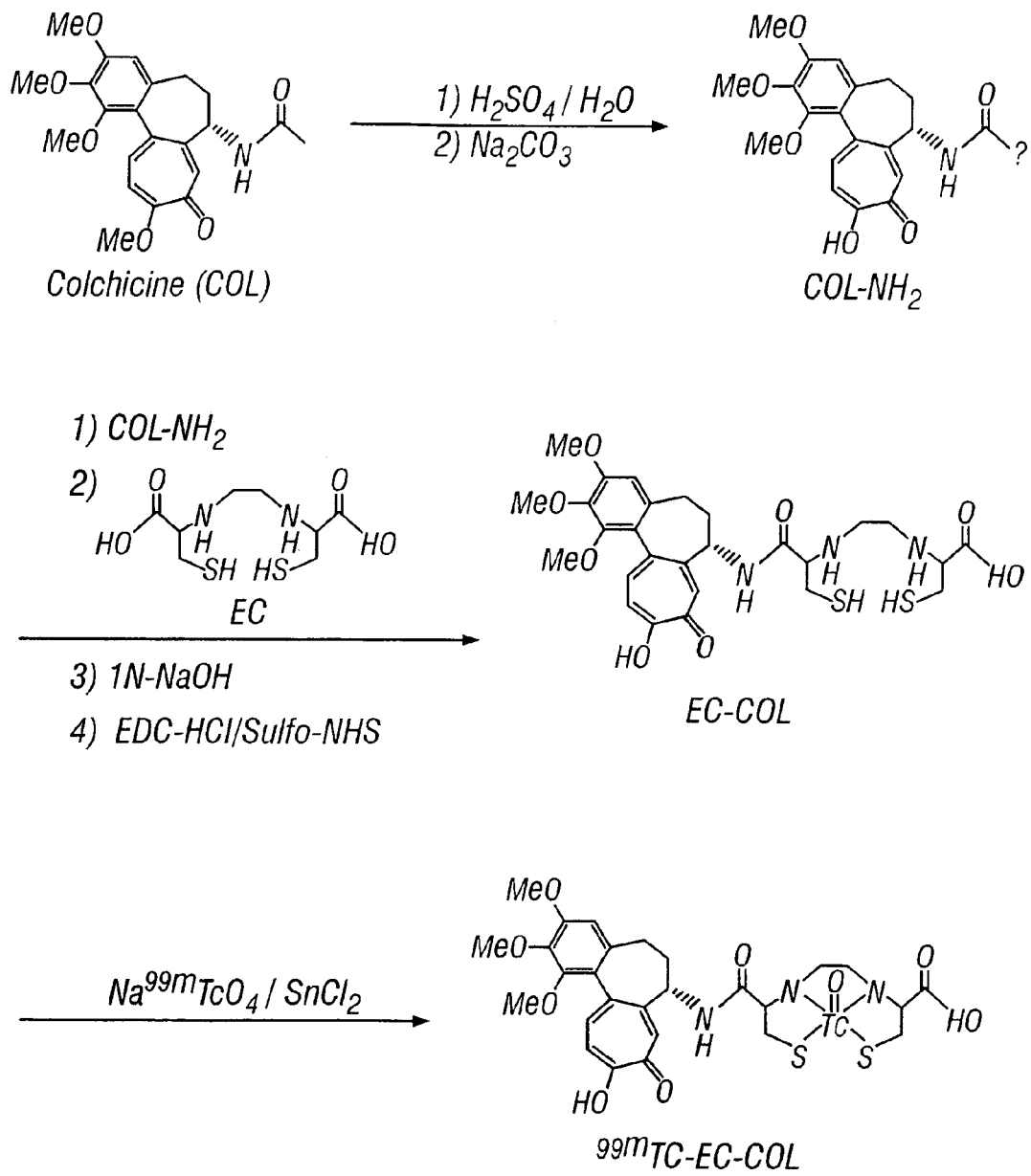
FIG. 21. Synthetic scheme of EC-COL (-colchicine).

Sodium hydroxide (2N, 0.2 ml) was added to a stirred solution of EC (134 mg, 0.50 mmol) in water (5 ml). To this colotiess solution, sulfo-NHS (217 mg, 1.0 mmol) and EDC (192 mg, 1.0 mmol) were added. COL-NH$_2$ (340 mg, 2.0 mmol) was then added. The mixture was stirred at room temperature for 24 hours. The mixture was dialyzed for 48 hrs using Spectra/POR molecular porous membrane with cut-off at 500 (Spectrum Medical Industries Inc., Houston, Tex.). After dialysis, the product was frozen dried using lyophilizer (Labconco, Kansas City, Mo.). The product weighed 315 mg (yield 55%). $^1$H-NMR (D$_2$O) δ 7.39 (S, 1H), 7.20 (d, 1H, J=12 Hz), 7.03 (d, 1H, J=12 Hz), 6.78 (S, 1H), 4.25-4.40 (m, 1H), 3.87 (S, 3H, —OCH$_3$), 3.84 (S, 3H, —OCH$_3$), 3.53 (S, 3H, —OCH$_3$), 3.42-3.52 (m, 2H), 3.05-3.26 (m, 4H), 2.63-2.82 (m, 4H), 2.19-2.25 (m, 4H). FAB MS m/z 580 (sodium salt, 20). The synthetic scheme of EC-COL is shown in FIG. 21.

Radiolabeling of EC-COL and EC with $^{99m}$Tc

Radiosynthesis of $^{99m}$Tc-EC-COL was achieved by adding required amount of $^{99m}$Tc-pertechnetate into home-made kit containing the lyophilized residue of EC-COL (5 mg), SnCl$_2$ (100 µg), Na$_2$ $_{HPO4}$ (13.5 mg), ascorbic acid (0.5 mg) and NaEDTA (0.5 mg). Final pH of preparation was 7.4. $^{99m}$Tc-EC was also obtained by using home-made kit containing the lyophilized residue of EC (5 mg), SnCl$_2$ (100 µg), Na$_2$ $_{HPO4}$ (13.5 mg), ascorbic acid (0.5 mg) and NaEDTA (0.5 mg) at pH 10. Final pH of preparation was then adjusted to 7.4. Radiochemical purity was determined by TLC (ITLC SG, Gelman Sciences, Ann Arbor, Mich.) eluted with ammonium acetate (1M in water):methanol (4:1). Radio-thin layer chromatography (TLC, Bioscan, Washington, D.C.) was used to analyze the radiochemical purity for both radiotracers.

Stability Assay of $^{99m}$Tc-EC-COL

Stability of labeled $^{99m}$Tc-EC-COL was tested in serum samples. Briefly, 740 KBq of 5 mg $^{99m}$Tc-EC-COL was incubated in the rabbinate serum (500 μl) at 37° C. for 4 hours. The serum samples was diluted with 50% methanol in water and radio-TLC repeated at 0.5, 2 and 4 hours as described above.

Tissue Distribution Studies

Female Fischer 344 rats (150±25 g) (Harlan Sprague-Dawley, Indianapolis, Ind.) were inoculated subcutaneously with 0.1 ml of mammary tumor cells from the 13762 tumor cell line suspension (10 cells/rat, a tumor cell line specific to Fischer rats) into the hind legs using 25-gauge needles. Studies performed 14 to 17 days after implantation when tumors reached approximately 1 cm diameter. Rats were anesthetized with ketamine (10-15 mg/rat, intraperitoneally) before each procedure.

In tissue distribution studies, each animal was injected intravenously with 370-550 KBq of $^{99m}$Tc-EC-COL or $^{99m}$Tc-EC (n=3/time point). The injected mass of $^{99m}$Tc-EC-COL was 10 μg per rat. At 0.5, 2 and 4 hrs following administration of the radiotracers, the rats were sacrificed and the selected tissues were excised, weighed and counted for radioactivity. The biodistribution of tracer in each sample was calculated as percentage of the injected dose per gram of tissue wet weight (% ID/g). Tumor/nontarget tissue count density ratios were calculated from the corresponding % ID/g values. Student t-test was used to assess the significance of differences between groups.

Scintigraphic Imaging Studies

Scintigraphic images, using a gamma camera (Siemens Medical Systems, Inc., Hoffman Estates, Ill.) equipped with low-energy, parallel-hole collimator, were obtained 0.5, 2 and 4 hrs after i.v. injection of 300 μCi of $^{99m}$Tc-EC-COL and $^{99m}$Tc-EC. Computer outlined region of interest (ROI) was used to quantitate (counts per pixel) the tumor uptake versus normal muscle uptake.

Results

Radiosynthesis and Stability of $^{99m}$Tc-EC-COL

Figure 22:
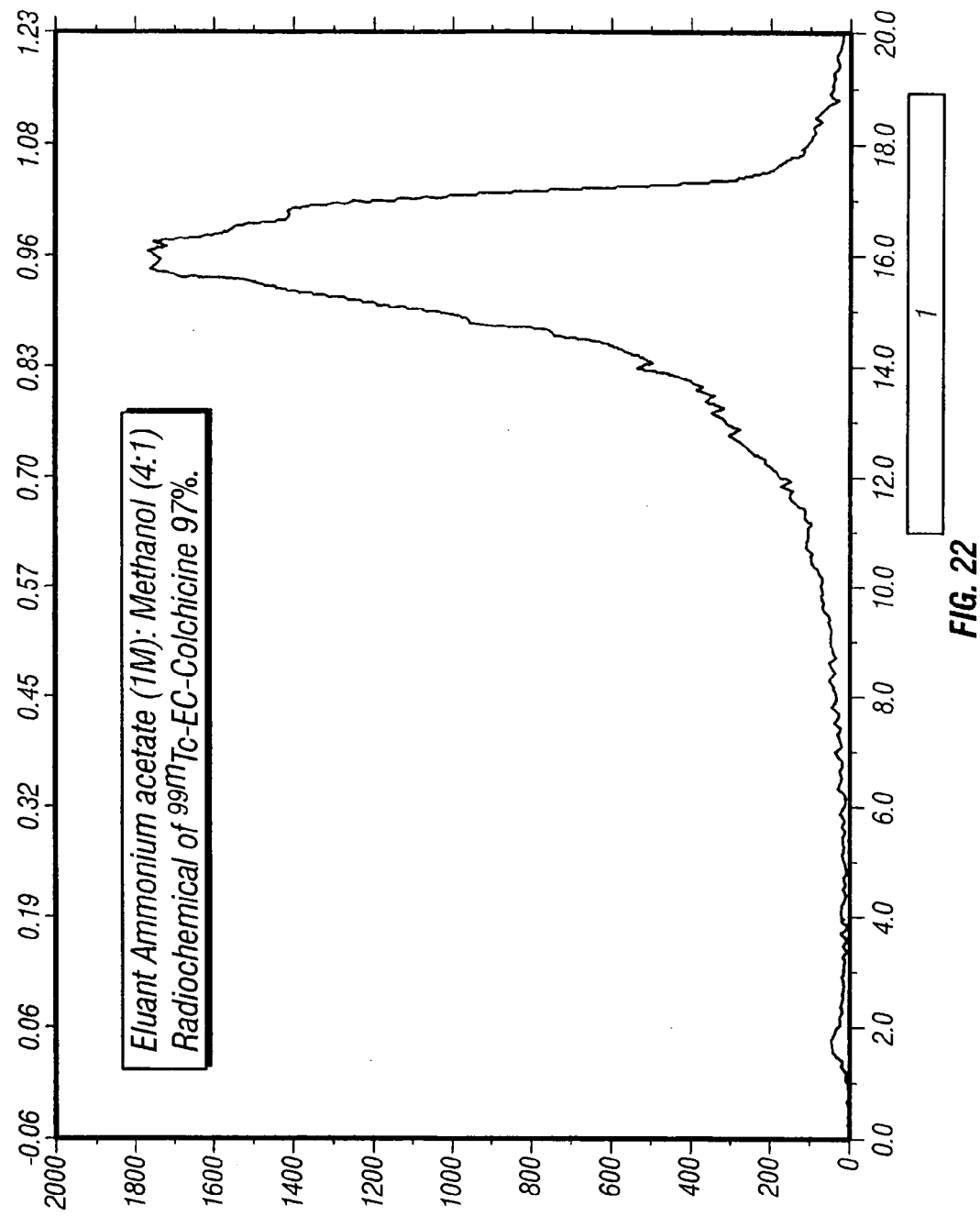
FIG. 22. Illustration that no degradation products observed in EC-COL synthesis.

Radiosynthesis of EC-COL with $^{99m}$Tc was achieved with high (>95%) radiochemical purity (FIG. 21). $^{99m}$Tc-EC-COL was found to be stable at 0.5, 2 and 4 hrs in rabbit serum samples. There was no degradation products observed (FIG. 22).

In Vivo Biodistribution

Figure 23:
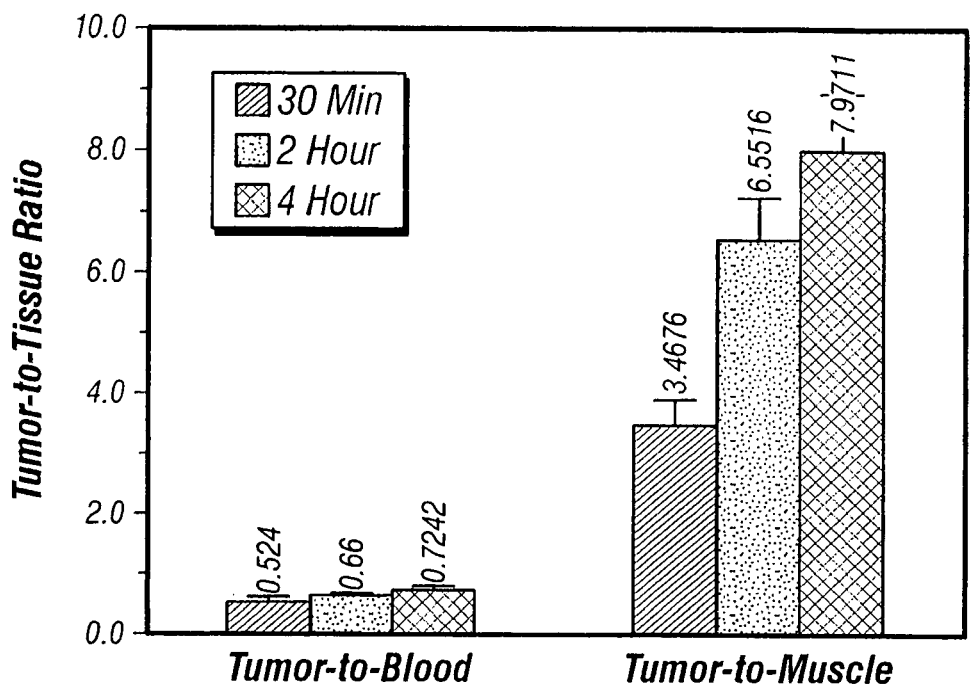
FIG. 23. Ratios of tumor to muscle and tumor to blood as function of time for $^{99m}$Tc-EC-COL.
Figure 24:
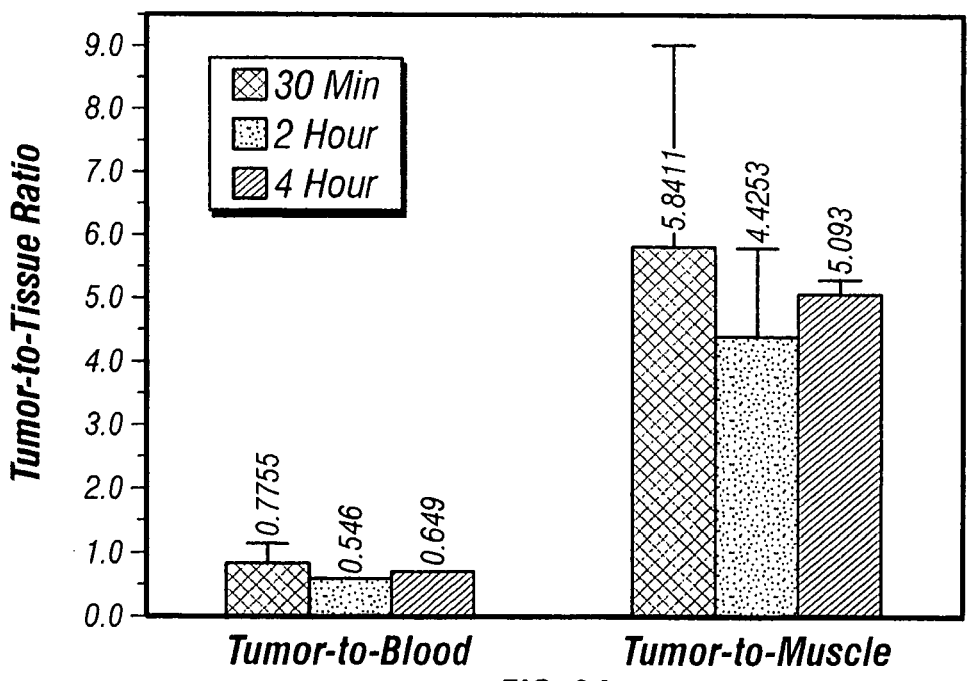
FIG. 24. Ratios of tumor to muscle and tumor to blood as function of time for $^{99m}$Tc-EC.

In vivo biodistribution of $^{99m}$Tc-EC-COL and $^{99m}$Tc-EC in breast-tumor-bearing rats are shown in Tables 4 and 6. Tumor uptake value (% ID/g) of $^{99m}$Tc-EC-COL at 0.5, 2 and 4 hours was 0.436±0.089, 0.395±0.154 and 0.221±0.006 (Table 6), whereas those for $^{99m}$Tc-EC were 0.342±0.163, 0.115±0.002 and 0.097±0.005, respectively (Table 4). Increased tumor-to-blood (0.52±0.12 to 0.72±0.07) and tumor-to-muscle (3.47±0.40 to 7.97±0.93) ratios as a function of time were observed in $^{99m}$Tc-EC-COL group (FIG. 23). Conversely, tumor-to-blood and tumor-to-muscle values showed time-dependent decrease with $^{99m}$Tc-EC when compared to $^{99m}$Tc-EC-COL group in the same time period (FIG. 24).

TABLE 6

Biodistribution of $^{99m}$Tc-EC-Colchicine in Breast Tumor Bearing Rats

|  | 30 Min. | 2 Hour | 4 Hour |
|---|---|---|---|
| Blood | 0.837 ± 0.072 | 0.606 ± 0.266 | 0.307 ± 0.022 |
| Lung | 0.636 ± 0.056 | 0.407 ± 0.151 | 0.194 ± 0.009 |
| Liver | 1.159 ± 0.095 | 1.051 ± 0.213 | 0.808 ± 0.084 |
| Spleen | 0.524 ± 0.086 | 0.559 ± 0.143 | 0.358 ± 0.032 |
| Kidney | 9.705 ± 0.608 | 14.065 ± 4.007 | 11.097 ± 0.108 |
| Muscle | 0.129 ± 0.040 | 0.071 ± 0.032 | 0.028 ± 0.004 |
| Stomach | 0.484 ± 0.386 | 0.342 ± 0.150 | 0.171 ± 0.123 |
| Uterus | 0.502 ± 0.326 | 0.343 ± 0.370 | 0.133 ± 0.014 |
| Thyroid | 3.907 ± 0.997 | 2.297 ± 0.711 | 1.709 ± 0.776 |
| Tumor | 0.436 ± 0.089 | 0.395 ± 0.154 | 0.221 ± 0.006 |

*Each rat received $^{99m}$Tc-EC-Colchicine (10 μCi, iv.). Each value is the percent of injected dose per gram tissue weight (n = 3)/time interval. Each data represents mean of three measurements with standard deviation.

TABLE 7

Rf Values Determined by Radio-TLC (ITLC-SG) Studies

|  | System A* | System B† |
|---|---|---|
| $^{99m}$Tc-EC-folate | 0 | 1(>95%) |
| $^{99m}$Tc-EC- | 0 | 1(>95%) |
| Free $^{99m}$TC | 1 | 1 |
| Reduced $^{99m}$TC | 0 | 0 |

*Acetone
†Ammonium Acetate (1M in water):Methanol (4:1)

Gamma Scintigraphic Imaging of $^{99m}$Tc-EC-COL in Breast Tumor-Bearing Rats

Figure 25:
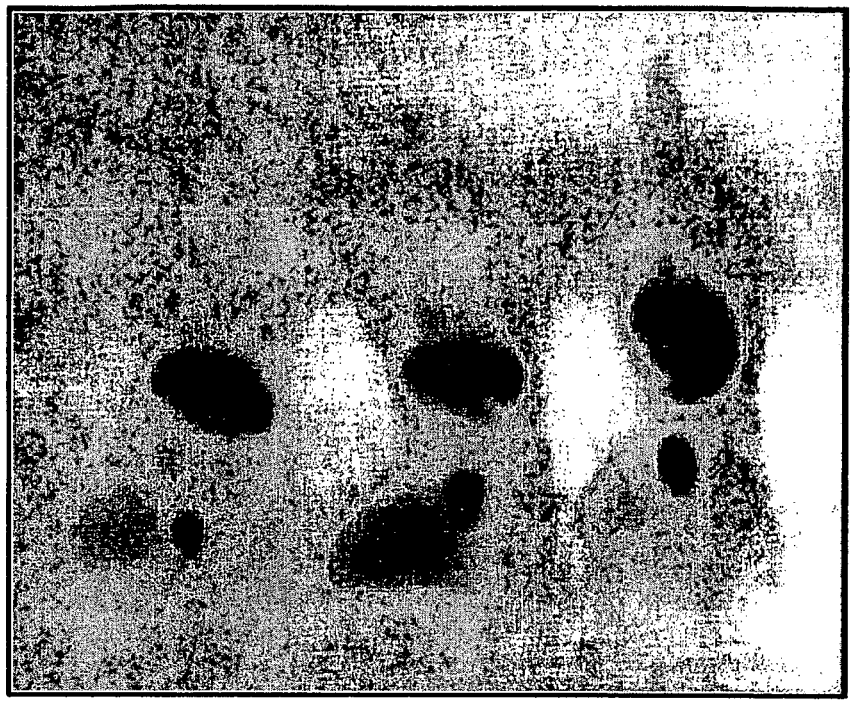
FIG. 25. In vivo imaging studies in breast tumor bearing rats with $^{99m}$Tc-EC-COL.
Figure 26:
FIG. 26. In vivo imaging studies in breast tumor bearing rats with $^{99m}$Tc-EC.
Figure 27:
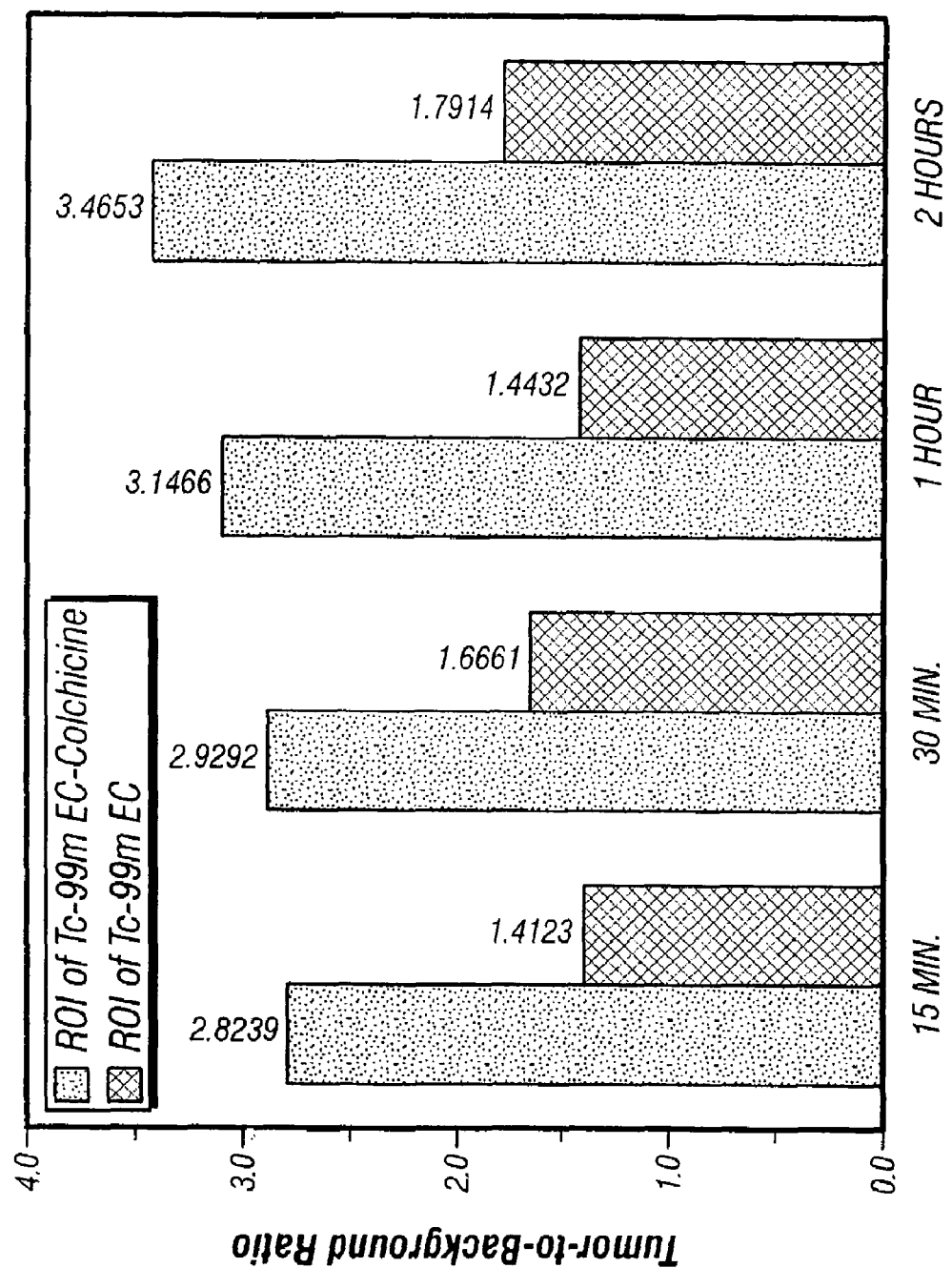
FIG. 27. Computer outlined region of interest after injection of $^{99m}$Tc-EC-COL vs. $^{99m}$Tc-EC.

In vivo imaging studies in three breast-tumor-bearing rats at 1 hour post-administration indicated that the tumor could be visualized well with $^{99m}$Tc-EC-COL group (FIG. 25), whereas, less tumor uptake in the $^{99m}$Tc-EC group was observed (FIG. 26). Computer outlined region of interest (ROI) showed that tumor/background ratios in $^{99m}$Tc-EC-COL group were significantly higher than $^{99m}$Tc-EC group) (FIG. 27).

Tumor Glycolysis Targeting

EXAMPLE 6

Development of $^{99m}$Tc-EC-Neomycin

Synthesis of EC

EC was prepared in a two-step synthesis according to the previously described methods (Ratner and Clarke, 1937; Blondeau et al., 1967). The precursor, L-thiazolidine-4-carboxylic acid, was synthesized (m.p. 195°, reported 196-197°). EC was then prepared (m.p. 237°, reported 251-253°). The structure was confirmed by $^1$H-NMR and fast-atom bombardment mass spectroscopy (FAB-MS).

Synthesis of Ethylenedicysteine-Neomycin (EC-Neomycin)

Figure 36:
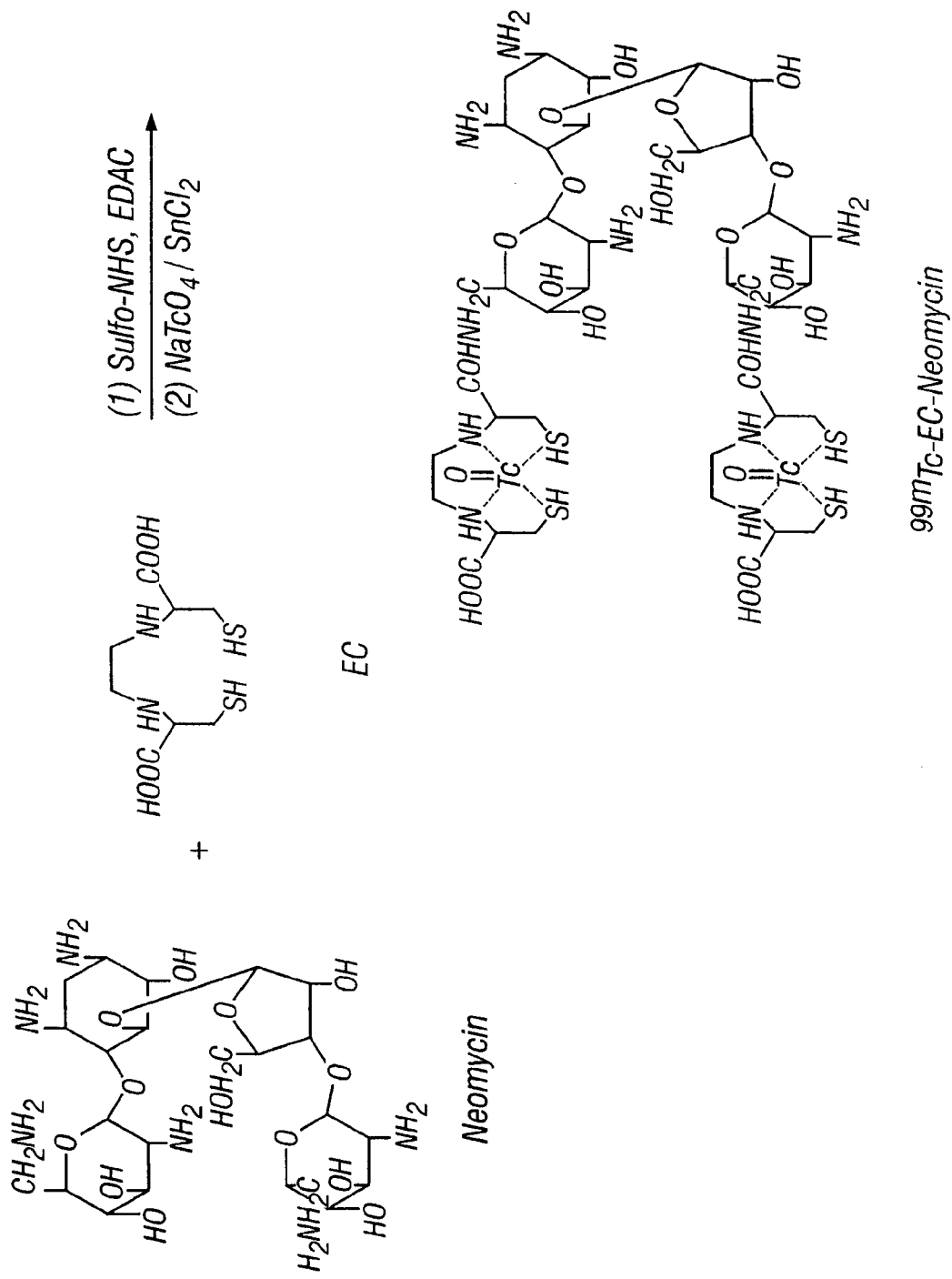
FIG. 36. Synthetic scheme of 99mTc-EC-neomycin.
Figure 38A:
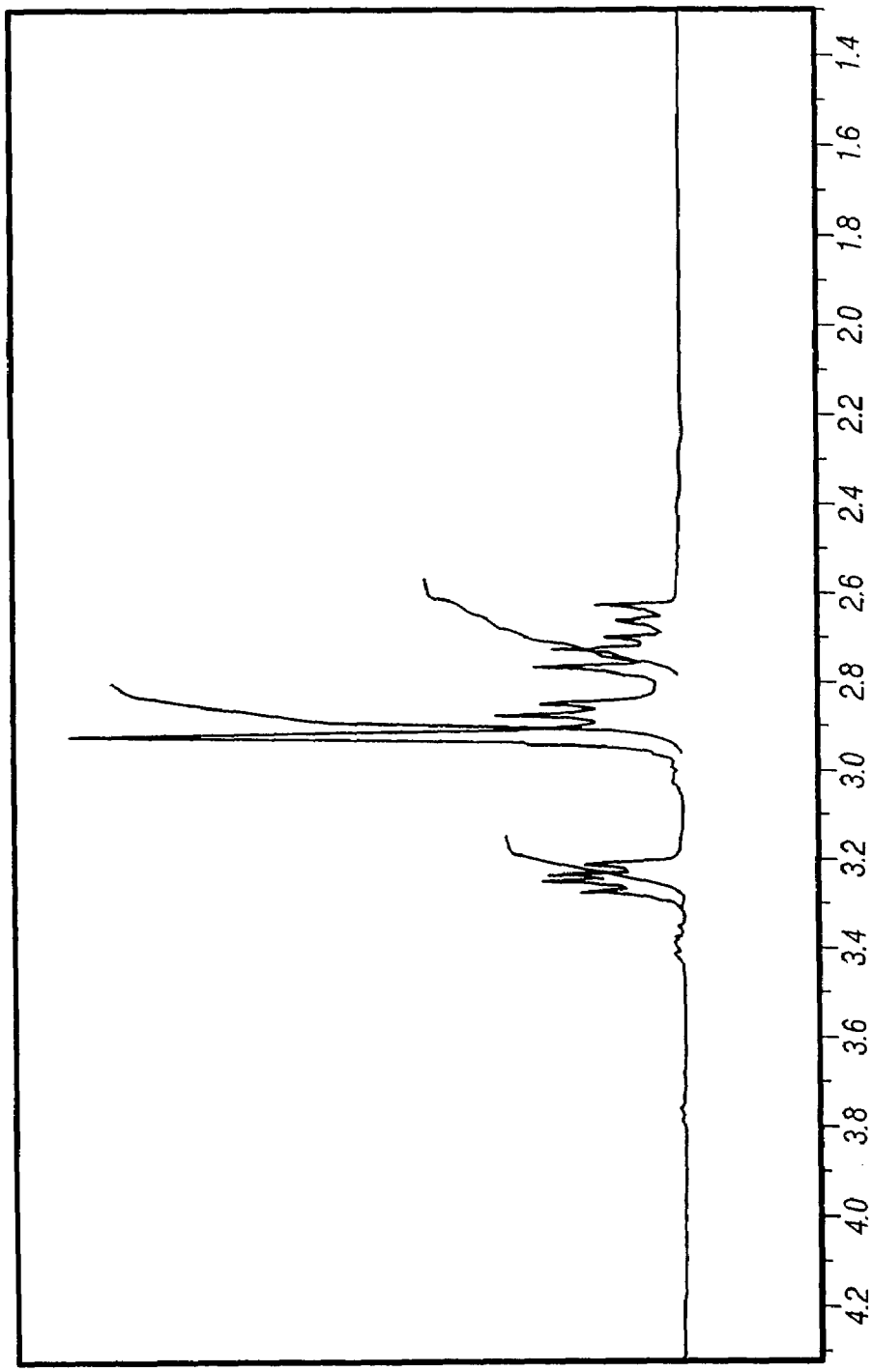
FIG. 38A. $^1$H-NMR of EC.
Figure 38B:
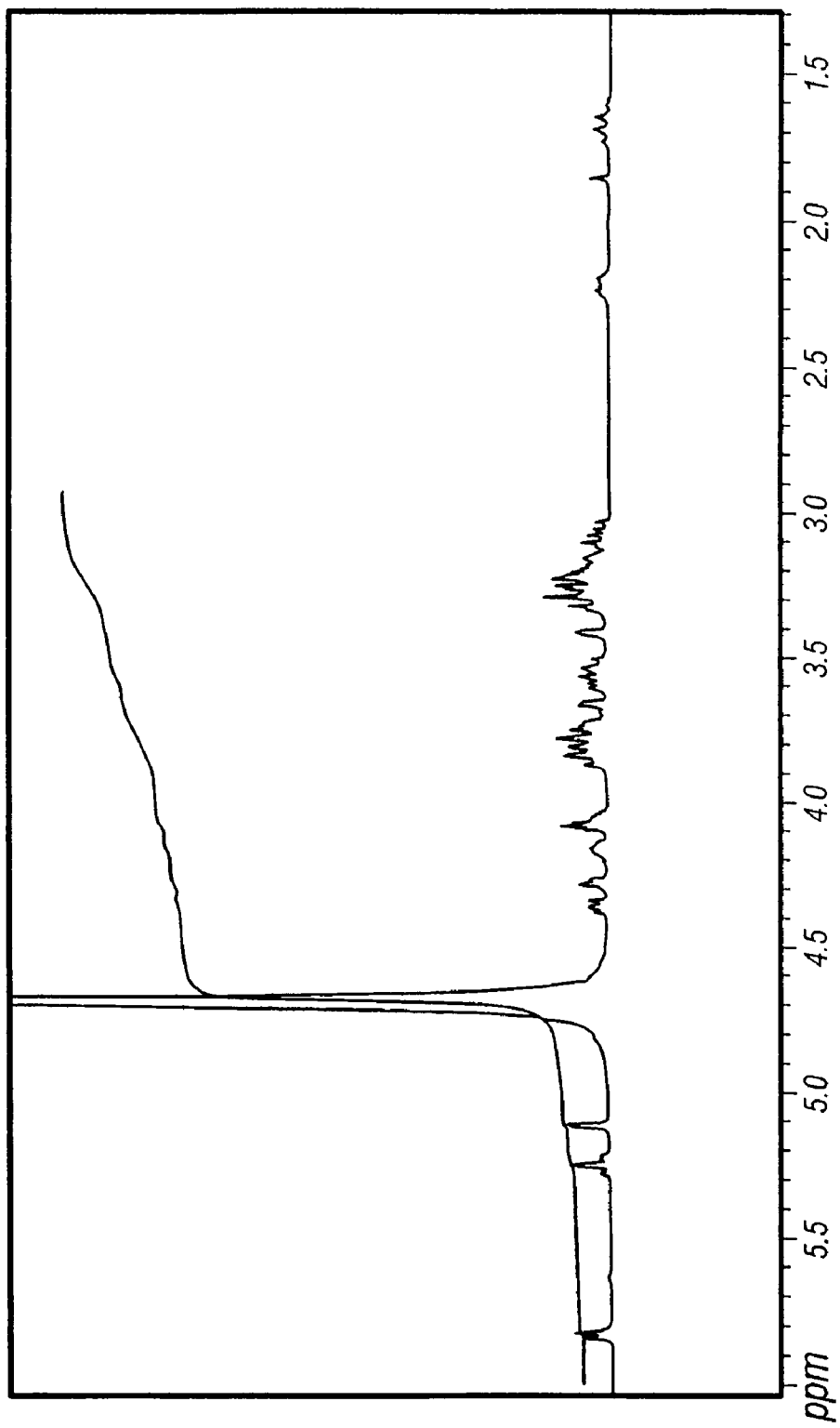
FIG. 38B. $^1$H-NMR of neomycin.
Figure 38C:
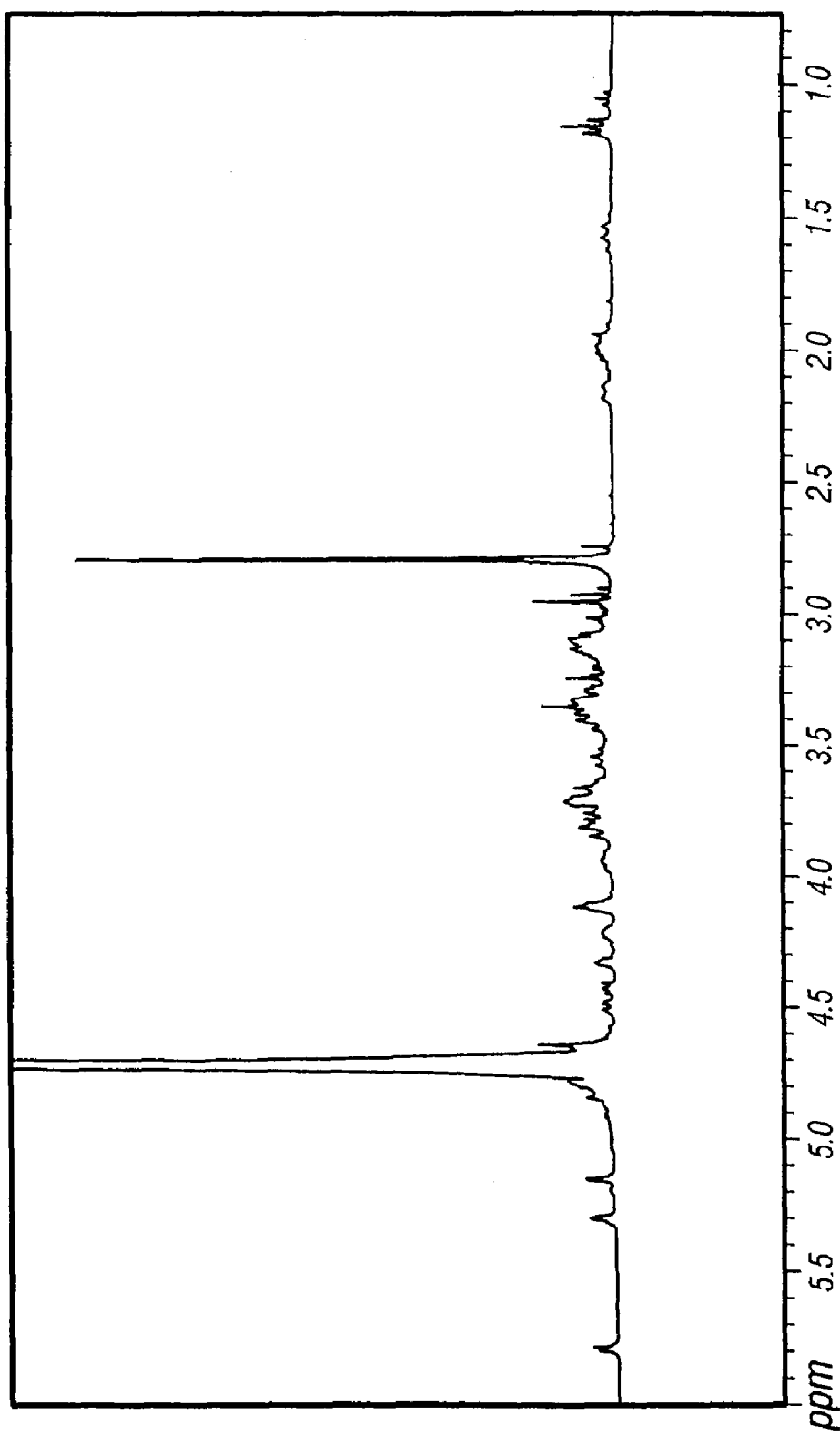
FIG. 38C. $^1$H-NMR of EC-neomycin.
Figure 39:
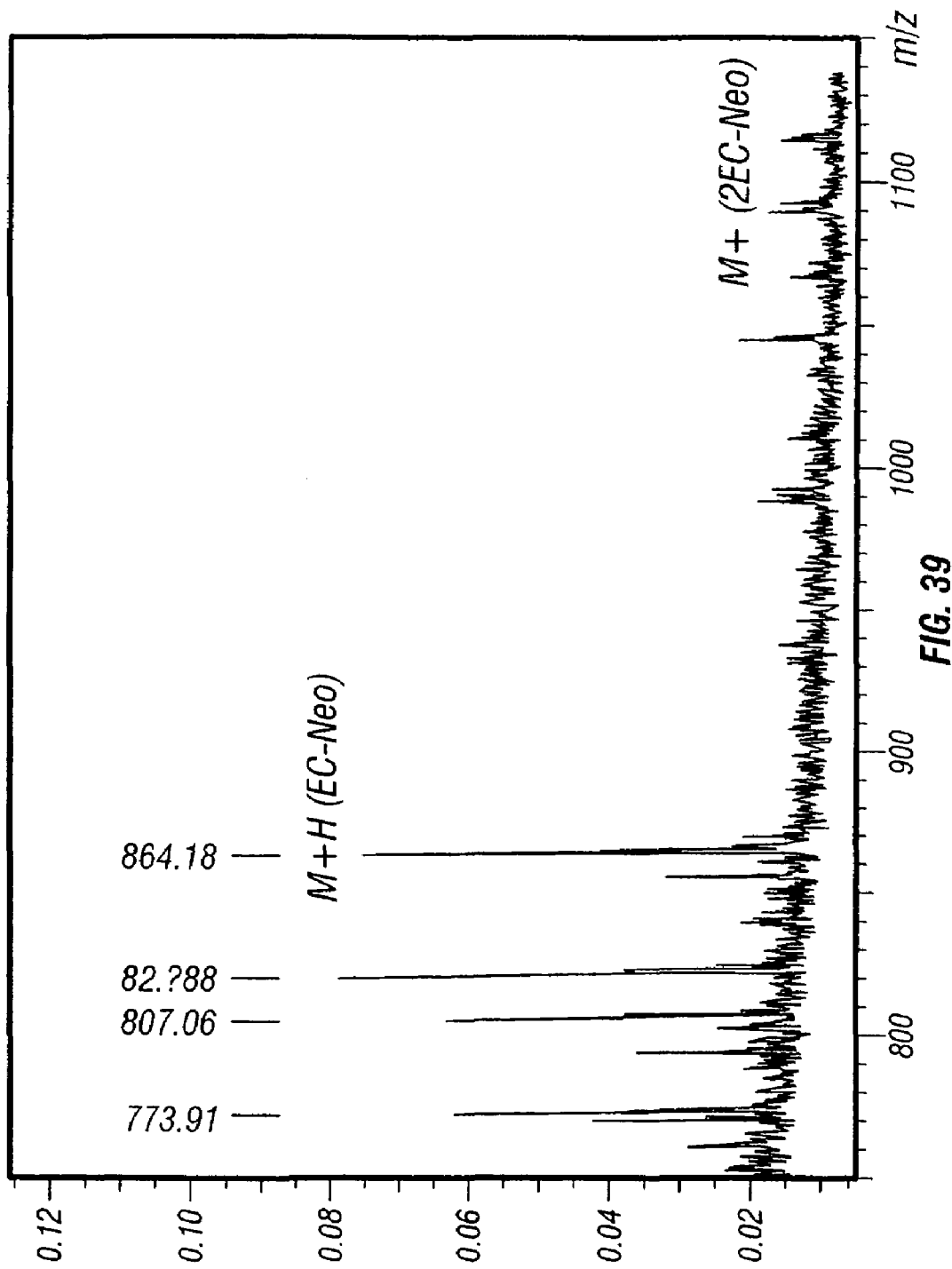
FIGS. 39A and 39B. Mass spectrometry of EC-neomycin (M+1112.55).
Figure 40A:
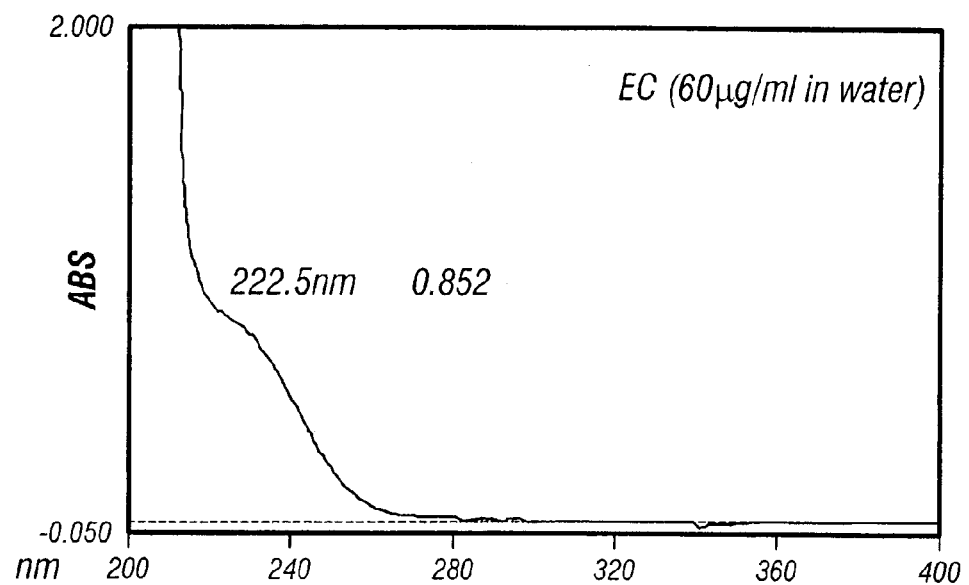
FIG. 40A. UV wavelength scan of EC.
Figure 40B:
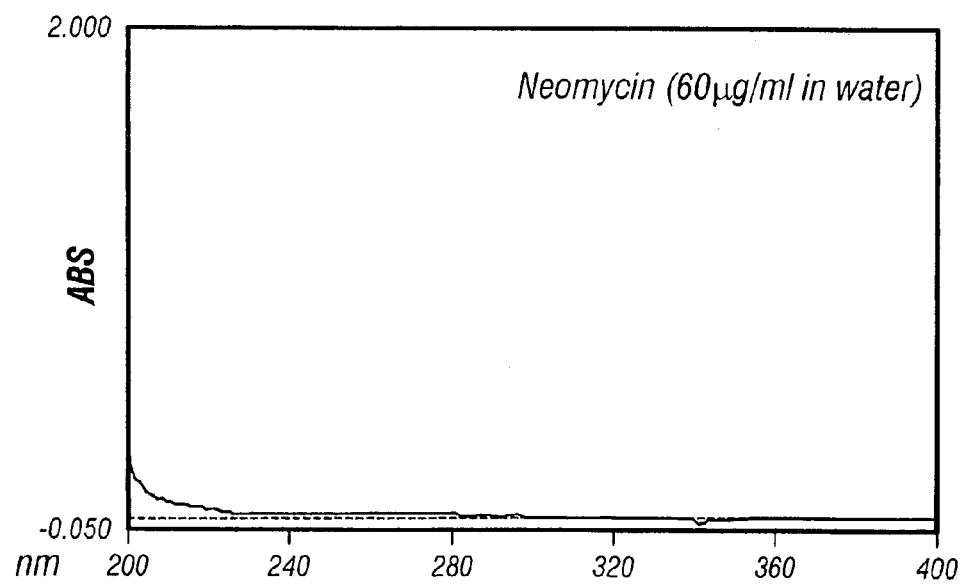
FIG. 40B. UV wavelength scan of neomycin.
Figure 40C:
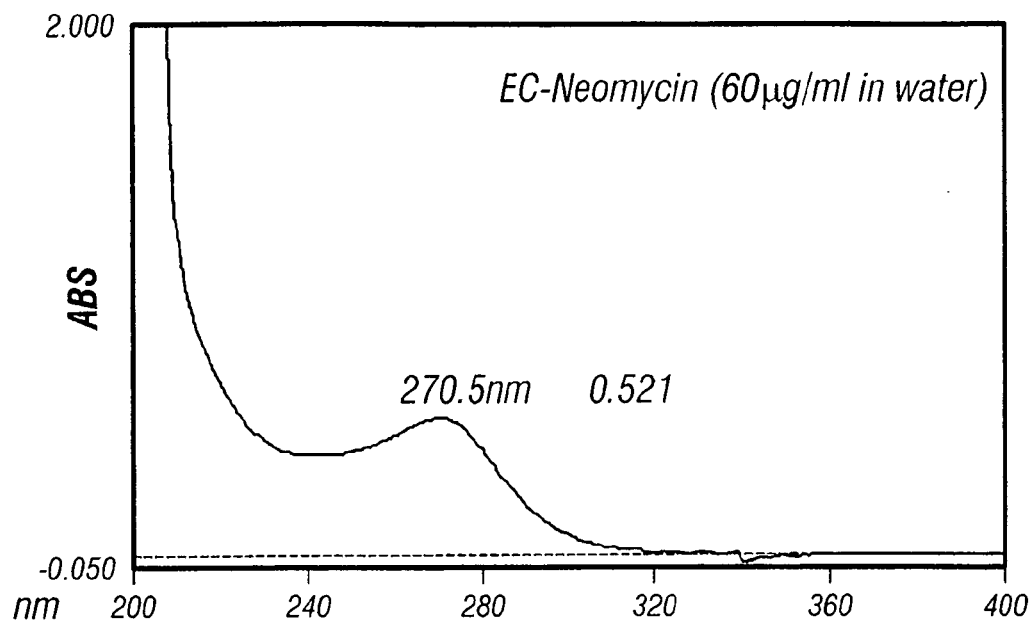
FIG. 40C. UV wavelength scan of EC-neomycin.

Sodium hydroxide (2N, 0.2 ml) was added to a stirred solution of EC (134 mg, 0.50 mmol) in water (5 ml). To this colorless solution, sulfo-NHS (217 mg, 1.0 mmol) and EDC (192 mg, 1.0 mmol) were added. Neomycin trisulfate salt (909 mg, 1.0 mmol) was then added. The mixture was stirred at room temperature for 24 hours. The mixture was dialyzed for 48 hours using Spectra/POR molecular porous membrane with cut-off at 500 (Spectrum Medical Industries Inc., Houston, Tex.). After dialysis, the product was frozen dried using lyophilizer (Labconco, Kansas City, Mo.). The product weighed 720 mg (yield 83%). The synthetic scheme of EC-neomycin is shown in FIG. 36. The structure is confirmed by $^1$H-NMR (FIGS. 38A-B), mass spectrometry (FIGS. 39A-B) and elemental analysis (Galbraith Laboratories, Inc. Knoxville, Tenn.). Elemental analysis $C_{39}H_{75}N_{10}S_4O_{19} \cdot 15H_2O$(C, H, N, S), Calc. C, 33.77; H, 7.58; N: 10.11, S: 9.23; found C, 32.44; H, 5.90; N, 10.47, S: 10.58. UV wavelength of EC-neomycin was shifted to 270.5 nm when compared to EC and neomycin (FIGS. 40A-C)

Radiolabeling of EC-MN and EC-Neomycin with $^{99m}$Tc

Figure 41:
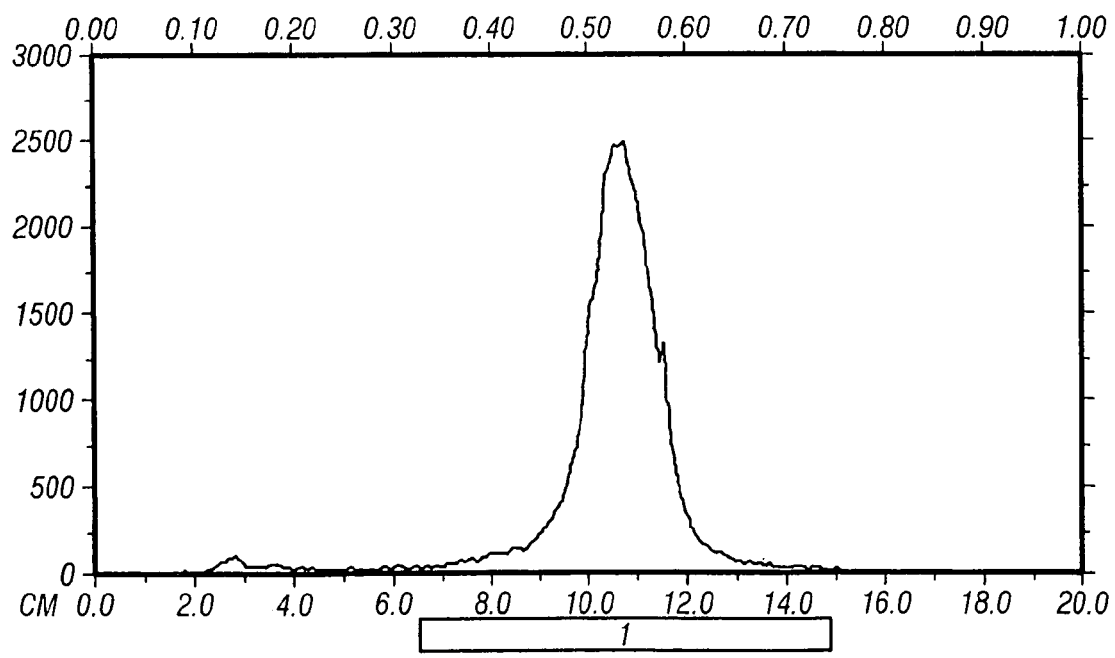
FIG. 41. Radio-TLC analysis of $^{99m}$Tc-EC-neomycin.
Figure 42:
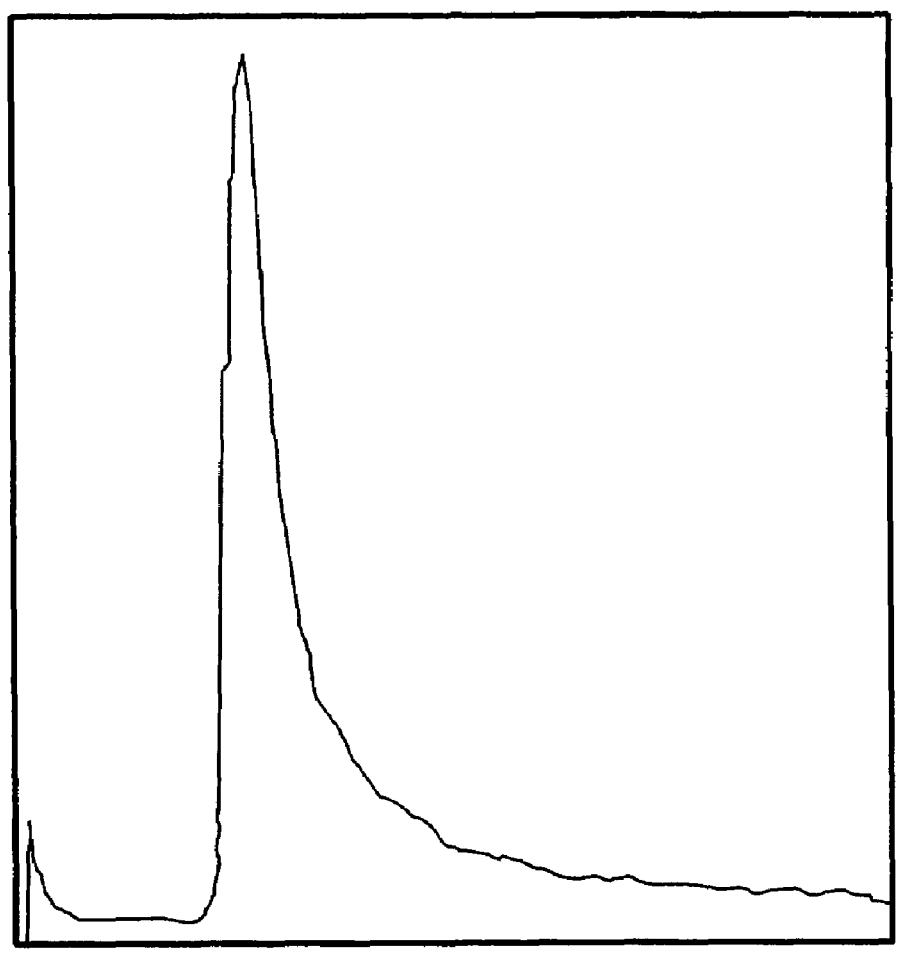
FIG. 42. HPLC analysis of $^{99m}$Tc-EC-neomycin (radioactive detector).
Figure 43:
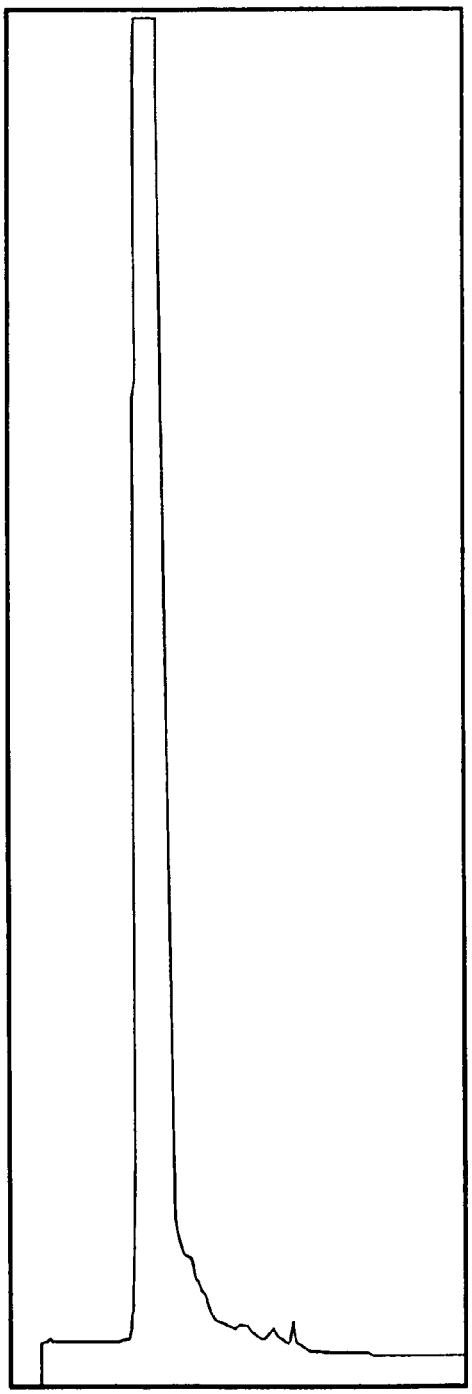
FIG. 43. HPLC analysis of $^{99m}$Tc-EC-neomycin (UV 254 nm).
Figure 44:
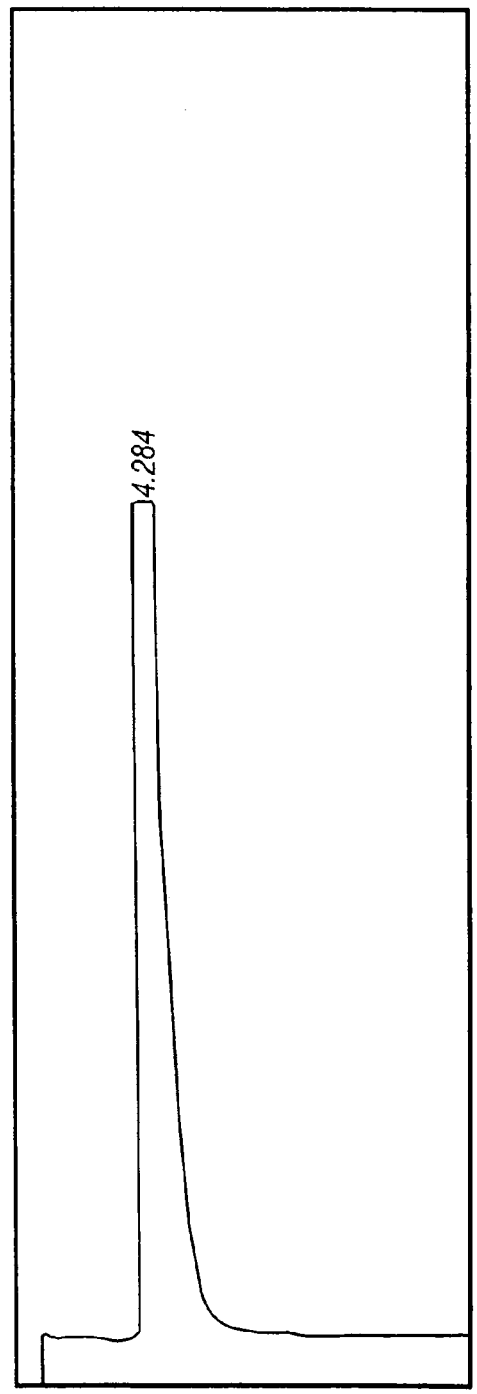
FIG. 44. HPLC analysis of $^{18}$F-FDG (radioactive detector).
Figure 45:
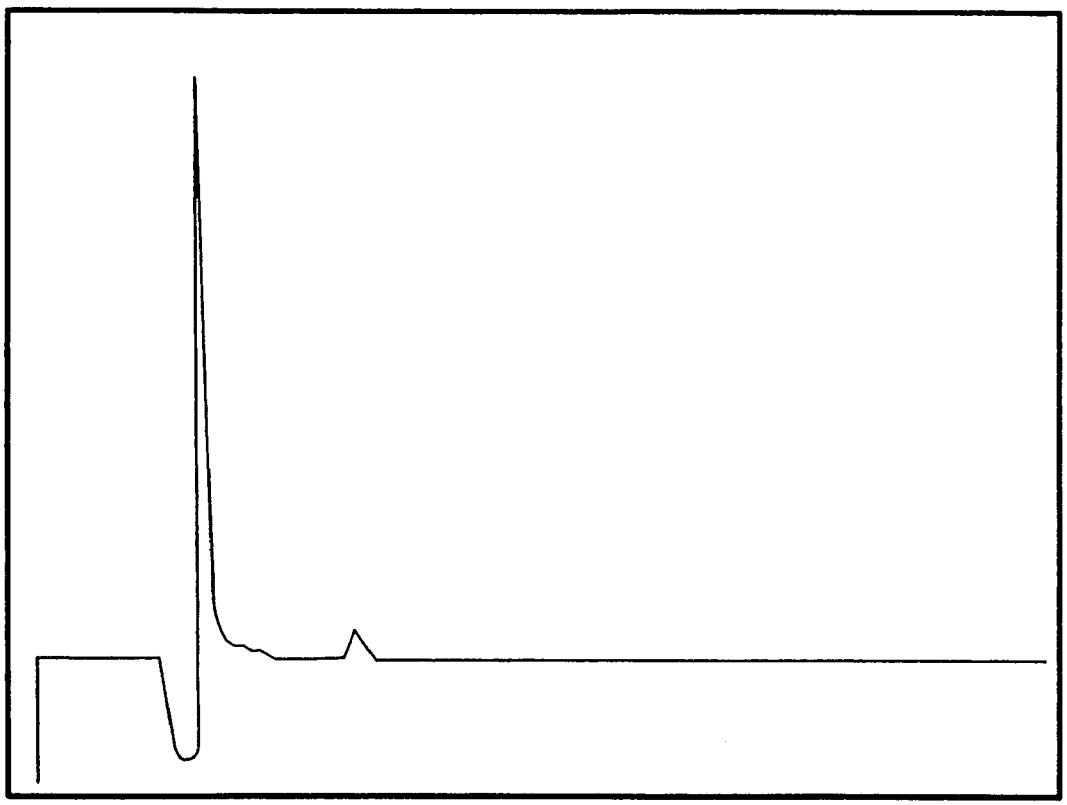
FIG. 45. HPLC analysis of $^{18}$F-FDG (UV 254 nm).

Radiosynthesis of $^{99m}$Tc-EC and $^{99m}$Tc-EC-neomycin were achieved by adding required amount of $^{99m}$Tc-pertechnetate into home-made kit containing the lyophilized residue of EC or EC-neomycin (10 mg), $SnCl_2$ (100 μg), $Na_{2\ HPO4}$ (13.5 mg) and ascorbic acid (0.5 mg). NaEDTA (0.5 mg) in 0.1 ml of water was then added. Final pH of preparation was 7.4. Radiochemical purity was determined by TLC (ITLC SG, Gelman Sciences, Ann Arbor, Mich.) eluted with ammonium acetate (1M in water):methanol (4:1). From radio-TLC (Bioscan, Washington, D.C.) analysis (FIG. 41) and HPLC analysis (FIGS. 42-45), the radiochemical purity was >95% for both radiotracers.

Stability Assay of $^{99m}$Tc-EC and $^{99m}$Tc-EC-Neomycin

Stability of labeled $^{99m}$Tc-EC and $^{99m}$Tc-EC-neomycin were tested in dog serum samples. Briefly, 740 KBq of 1 mg $^{99m}$Tc-EC and $^{99m}$Tc-EC-neomycin were incubated in dog serum (200 μl) at 37° C. for 4 hours. The serum samples were diluted with 50% methanol in water and radio-TLC repeated at 0.5, 2 and 4 hours as described above.

Tissue Distribution Studies of $^{99m}$Tc-EC-Neomycin

Female Fischer 344 rats (150±25 g) (Harlan Sprague-Dawley, Indianapolis, Ind.) were innoculated subcutaneously with 0.1 ml of mammary tumor cells from the 13762 tumor cell line suspension ($10^6$ cells/rat, a tumor cell line specific to Fischer rats) into the hind legs using 25-gauge needles. Studies performed 14 to 17 days after implantation when tumors reached approximately 1 cm diameter. Rats were anesthetized with ketamine (10-15 mg/rat, intraperitoneally) before each procedure.

In tissue distribution studies, each animal was injected intravenously with 10-20 μCi of $^{99m}$Tc-EC or $^{99m}$Tc-EC-neomycin (n=3/time point). The injected mass of $^{99m}$Tc-EC-neomycin was 200 μg per rat. At 0.5, 2 and 4 hours following administration of the radiotracers, the rats were sacrificed and the selected tissues were excised, weighed and counted for radioactivity. The biodistribution of tracer in each sample was calculated as percentage of the injected dose per gram of tissue wet weight (% ID/g). Tumor/nontarget tissue count density ratios were calculated from the corresponding % ID/g values. When compared to $^{99m}$Tc-EC (Table 4) and free technetium (Table 9), tumor-to tissue ratios increased as a function of time in $^{99m}$Tc-EC-neomycin group (Table 8).

Scintigraphic Imaging Studies

Figure 37A:
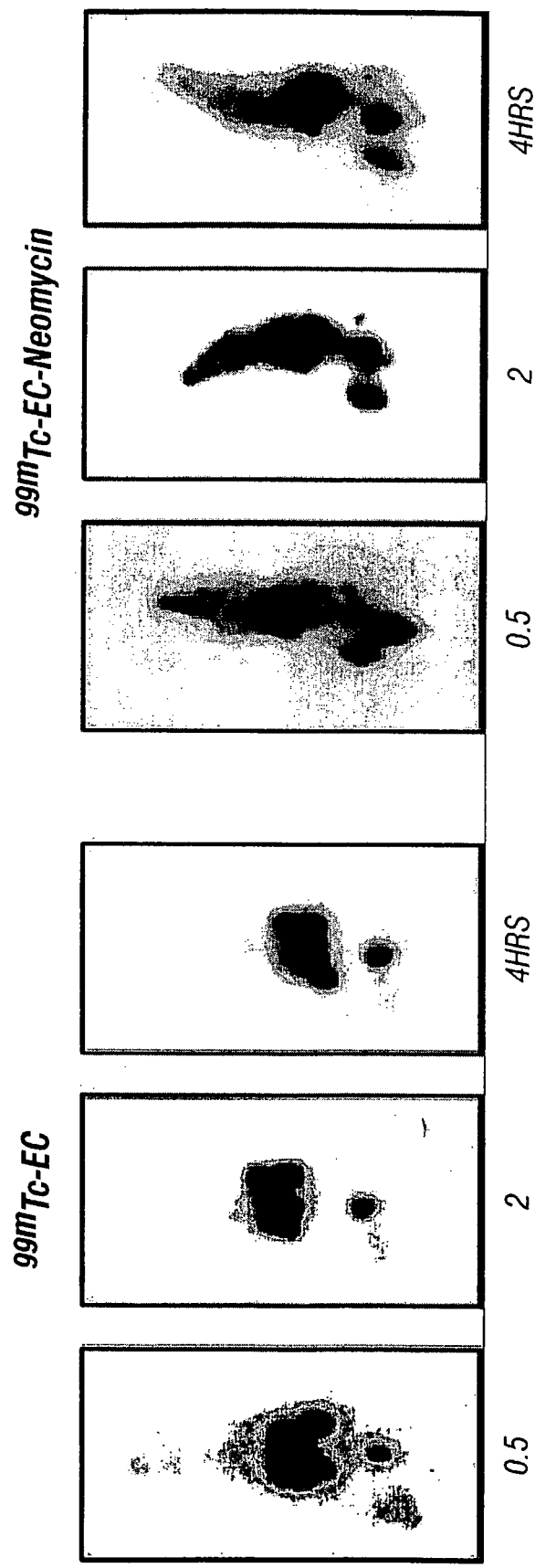
FIG. 37A. Scintigraphic image of breast tumor-bearing rats after administration of $^{99m}$Tc-EC and $^{99m}$Tc-EC-neomycin (100 µCi/rat, iv.) showed that the tumor could be well visualized from 0.5-4 hours postinjection.
Figure 37B:
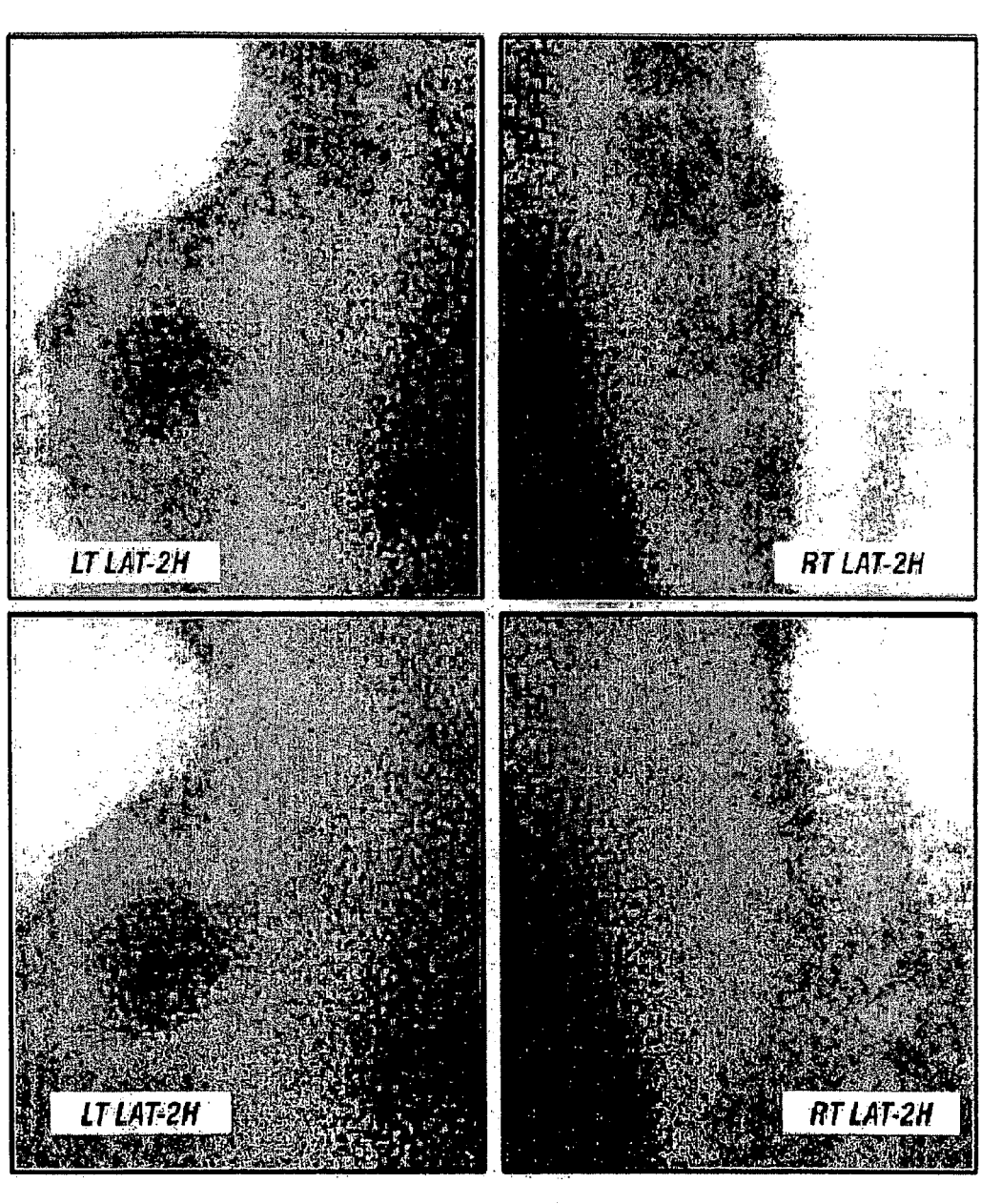
FIG. 37B. Scintimammography with $^{99m}$Tc-EC-neomycin (30 mCi, iv.) of a breast cancer patient. Images taken two hours post-injection.

Scintigraphic images, using a gamma camera (Siemens Medical Systems, Inc., Hoffman Estates, Ill.) equipped with low-energy, parallel-hole collimator, were obtained 0.5, 2 and 4 hours after i.v. injection of 100 μCi of each radiotracer. Compare to $^{99m}$Tc-EC, high uptake in the tumors was observed (FIG. 37A). Preliminary clinical imaging studies were conducted in a patient with breast cancer. The tumor was visualized well at 2 hours post-administration of $^{99m}$Tc-EC-neomycin (FIG. 37B).

TABLE 8

Biodistribution of $^{99m}$Tc-EC-neomycin in Breast Tumor Bearing Rats

|  | 30 Min. | 1 Hour | 2 Hour | 4 Hour |
|---|---|---|---|---|
| Blood | 0.463 ± 0.007 | 0.262 ± 0.040 | 0.139 ± 0.016 | 0.085 ± 0.004 |
| Lung | 0.344 ± 0.011 | 0.202 ± 0.030 | 0.114 ± 0.014 | 0.080 ± 0.003 |
| Liver | 0.337 ± 0.012 | 0.269 ± 0.013 | 0.221 ± 0.020 | 0.195 ± 0.012 |
| Stomach | 0.279 ± 0.039 | 0.147 ± 0.001 | 0.061 ± 0.008 | 0.054 ± 0.008 |
| Spleen | 0.159 ± 0.008 | 0.114 ± 0.013 | 0.095 ± 0.007 | 0.089 ± 0.003 |
| Kidney | 8.391 ± 0.395 | 8.804 ± 0.817 | 8.356 ± 0.408 | 8.638 ± 0.251 |
| Thyroid | 0.349 ± 0.008 | 0.202 ± 0.028 | 0.114 ± 0.007 | 0.086 ± 0.001 |
| Muscle | 0.093 ± 0.001 | 0.049 ± 0.010 | 0.021 ± 0.006 | 0.010 ± 0.001 |
| Intestine | 0.159 ± 0.004 | 0.093 ± 0.014 | 0.061 ± 0.004 | 0.266 ± 0.200 |
| Urine | 25.402 ± 8.621 | 21.786 ± 2.690 | 0.224 ± 0.000 | 2.609 ± 2.377 |
| Tumor | 0.419 ± 0.023 | 0.279 ± 0.042 | 0.166 ± 0.023 | 0.131 ± 0.002 |
| Brain | 0.022 ± 0.001 | 0.014 ± 0.003 | 0.010 ± 0.001 | 0.007 ± 0.001 |
| Heart | 0.147 ± 0.009 | 0.081 ± 0.012 | 0.040 ± 0.004 | 0.029 ± 0.002 |
| Tumor/Blood | 0.906 ± 0.039 | 1.070 ± 0.028 | 1.196 ± 0.061 | 1.536 ± 0.029 |
| Tumor/Muscle | 4.512 ± 0.220 | 5.855 ± 0.458 | 8.364 ± 1.469 | 12.706 ± 0.783 |
| Tumor/Brain | 19.495 ± 1.823 | 20.001 ± 0.890 | 17.515 ± 2.035 | 20.255 ± 1.693 |

Values shown represent the mean ± standard deviation of data from 3 animals.

TABLE 9

Biodistribution of $^{99m}$Tc Pertechnetate in Breast Tumor Bearing Rats

|  | 30 Min. | 2 Hour | 4 Hour |
|---|---|---|---|
| Blood | 1.218 ± 0.328 | 0.666 ± 0.066 | 0.715 ± 0.052 |
| Lung | 0.646 ± 0.291 | 0.632 ± 0.026 | 0.387 ± 0.024 |
| Liver | 0.541 ± 0.232 | 0.304 ± 0.026 | 0.501 ± 0.081 |
| Spleen | 0.331 ± 0.108 | 0.187 ± 0.014 | 0.225 ± 0.017 |
| Kidney | 0.638 ± 0.197 | 0.489 ± 0.000 | 0.932 ± 0.029 |
| Thyroid | 24.821 ± 5.181 | 11.907 ± 15.412 | 17.232 ± 5.002 |
| Muscle | 0.130 ± 0.079 | 0.076 ± 0.002 | 0.063 ± 0.003 |
| Intestine | 0.153 ± 0.068 | 0.186 ± 0.007 | 0.344 ± 0.027 |
| Tumor | 0.591 ± 0.268 | 0.328 ± 0.016 | 0.423 ± 0.091 |
| Brain | 0.038 ± 0.014 | 0.022 ± 0.002 | 0.031 ± 0.009 |
| Heart | 0.275 ± 0.089 | 0.145 ± 0.015 | 0.166 ± 0.012 |
| Tumor/Blood | 0.472 ± 0.093 | 0.497 ± 0.073 | 0.597 ± 0.144 |
| Tumor/Muscle | 4.788 ± 0.833 | 4.302 ± 0.093 | 6.689 ± 1.458 |
| Tumor/Liver | 1.084 ± 0.023 | 1.084 ± 0.115 | 0.865 ± 0.270 |

Values shown represent the mean ± standard deviation of data from 3 animals.

In Vitro Cellular Uptake of $^{99m}$Tc-EC-Drug Conjugates

Figure 46:
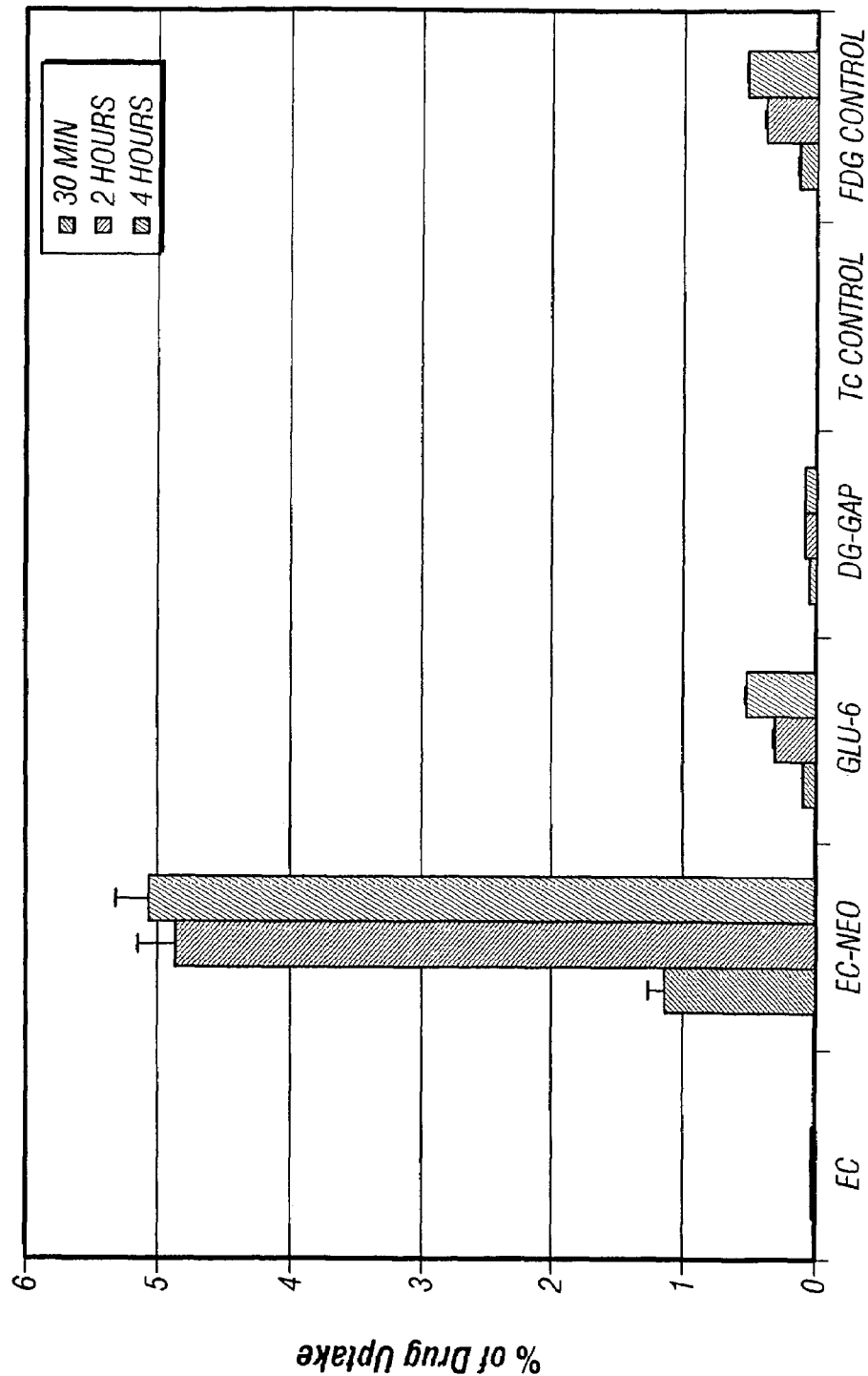
FIG. 46. In vitro cellular uptake assay of a series of $^{99m}$Tc-EC-drug conjugates in lung cancer cell line. $^{99m}$Tc-EC-neomycin showed highest uptake in the agents tested.

To evaluate the cellular uptake of $^{99m}$Tc-EC-drug conjugates, each well containing 80,000 cells (A549 lung cancer cell line) was added with 2 μCi of $^{99m}$Tc-EC-neomycin and $^{18}$F-FDG. After incubation at 0.5-4 hours, the cells were washed with phosphate buffered saline 3 times and followed by trypsin to lose the cells. The cells were then counted by a gamma counter. $^{99m}$Tc-EC-neomycin showed highest uptake among those agents tested in human lung cancer cell line (FIG. 46).

Effect of Glucose on Cellular Uptake of $^{99m}$Tc-EC-Neomycin and $^{18}$F-FDG

Neomycin is known to influence glucose absorption (Rogers et al., 1968; Fanciulli et al., 1994). Previous experiments have shown that $^{99m}$Tc-EC-neomycin has higher uptake than $^{18}$F-FDG in human lung cancer cell line (A549). To determine if uptake of $^{99m}$Tc-EC-neomycin is mediated via glucose-related mechanism, glucose (0.1 mg-2.0 mg) was added to each well containing either 50,000 (breast) cells or 80,000 cells (lung) along with 2 μCi of $^{99m}$Tc-EC-neomycin and $^{18}$F-FDG. After incubation, the cells were washed with phosphate buffered saline 3 times and followed by trypsin to lose the cells. The cells were then counted by a gamma counter.

Figure 47:
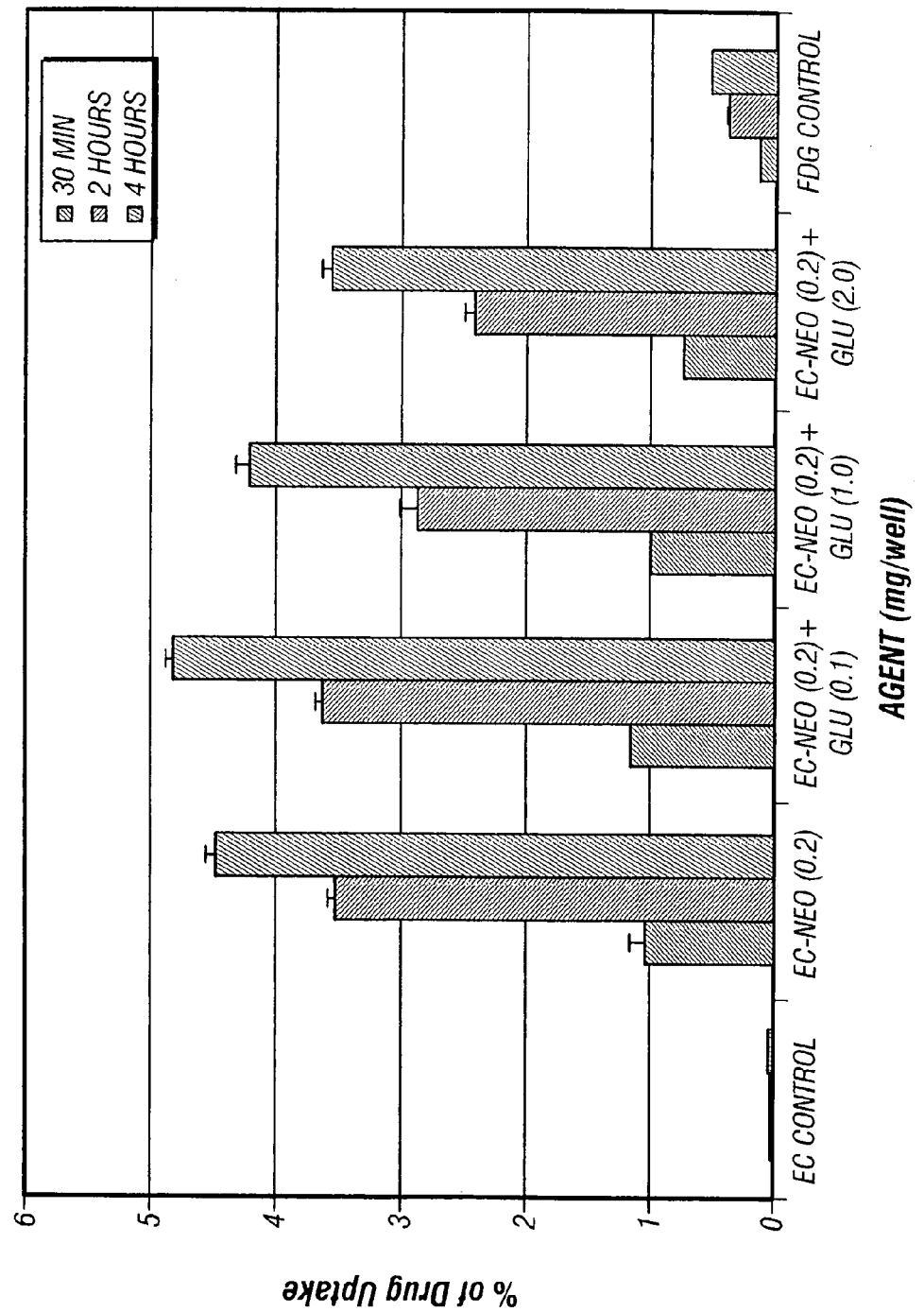
FIG. 47. Effect of glucose on cellular (A549) uptake of $^{99m}$Tc-EC-neomycin and $^{18}$F-FDG.
Figure 48A:
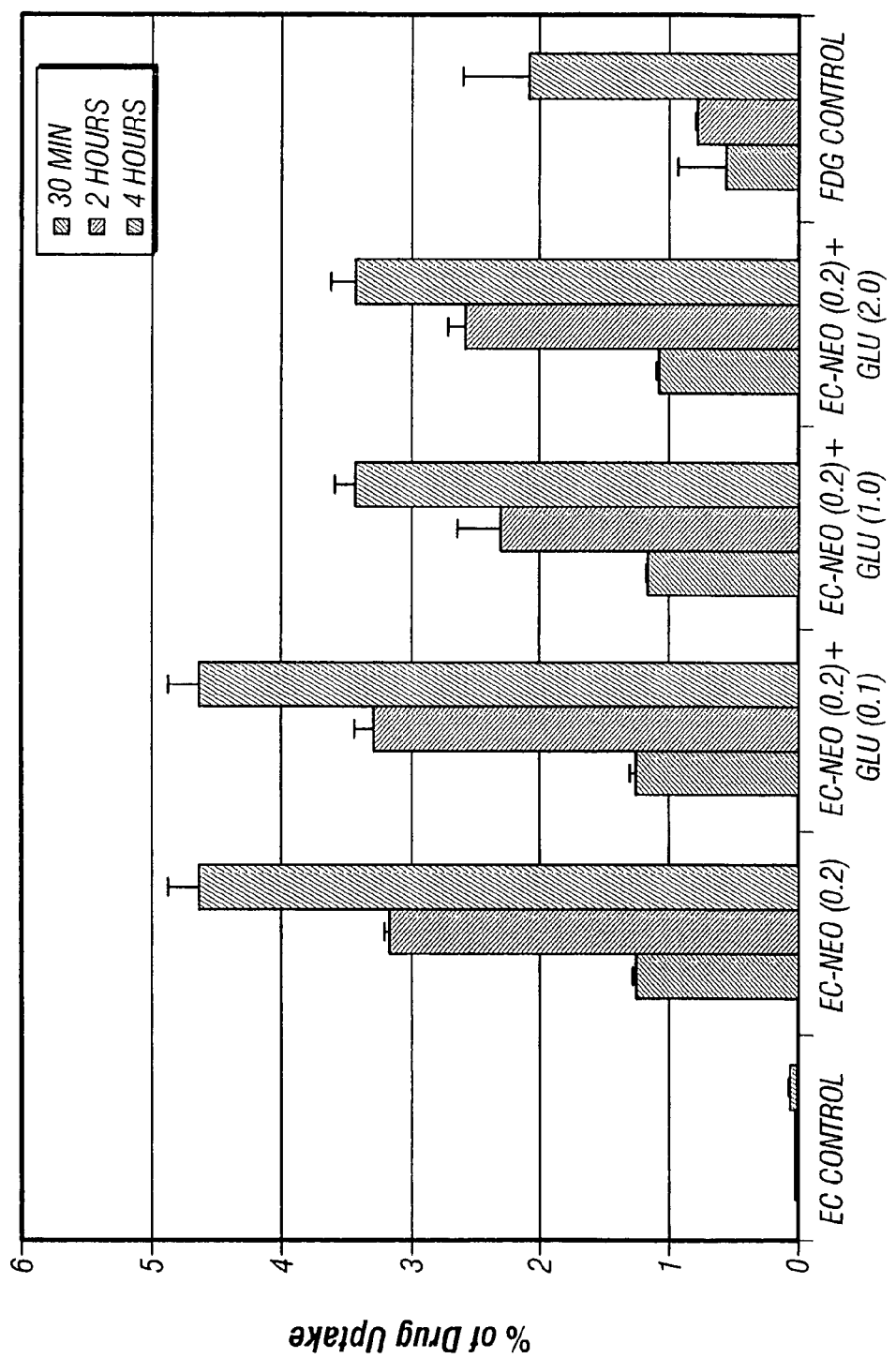
FIGS. 48A and 48B. Effect of glucose on cellular (H1299) uptake of $^{99m}$Tc-EC-neomycin and $^{18}$F-FDG illustrated as percent of drug uptake (FIG. 48A) and as percent of change with glucose loading (FIG. 48B).
Figure 48B:
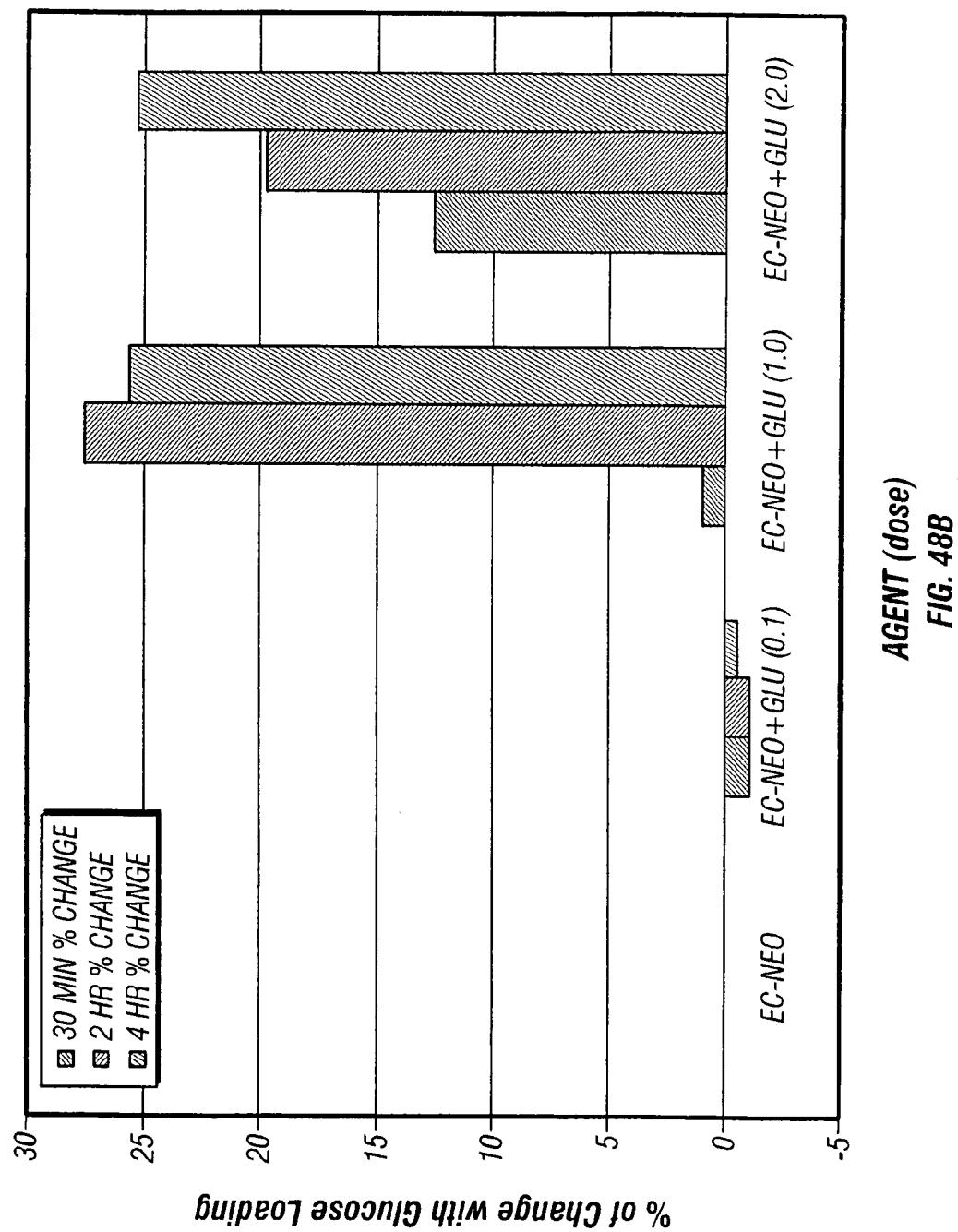
Figure 50:
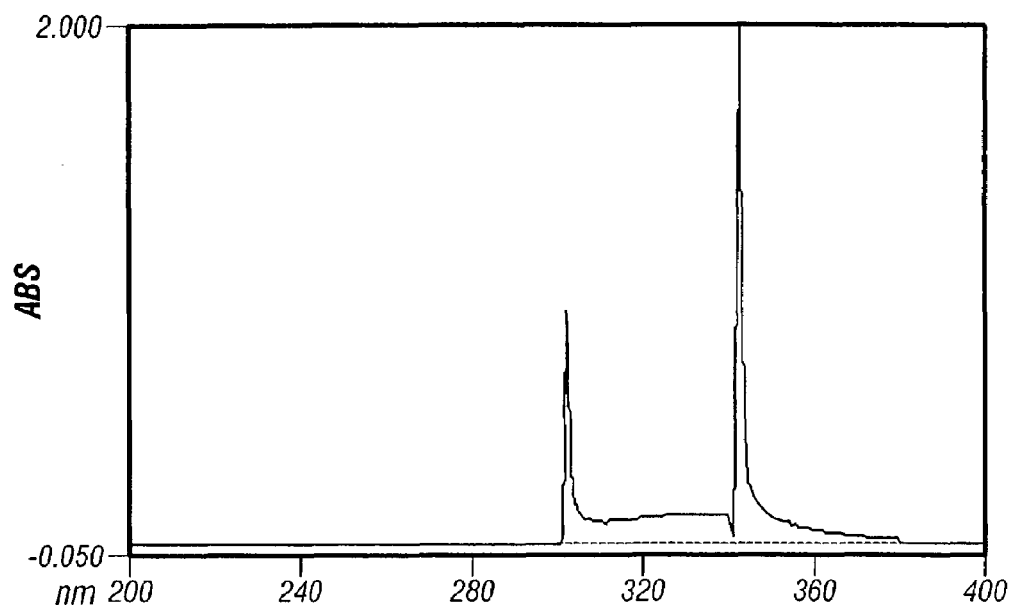
FIG. 50. Hexokinase assay of glucose.
Figure 51:
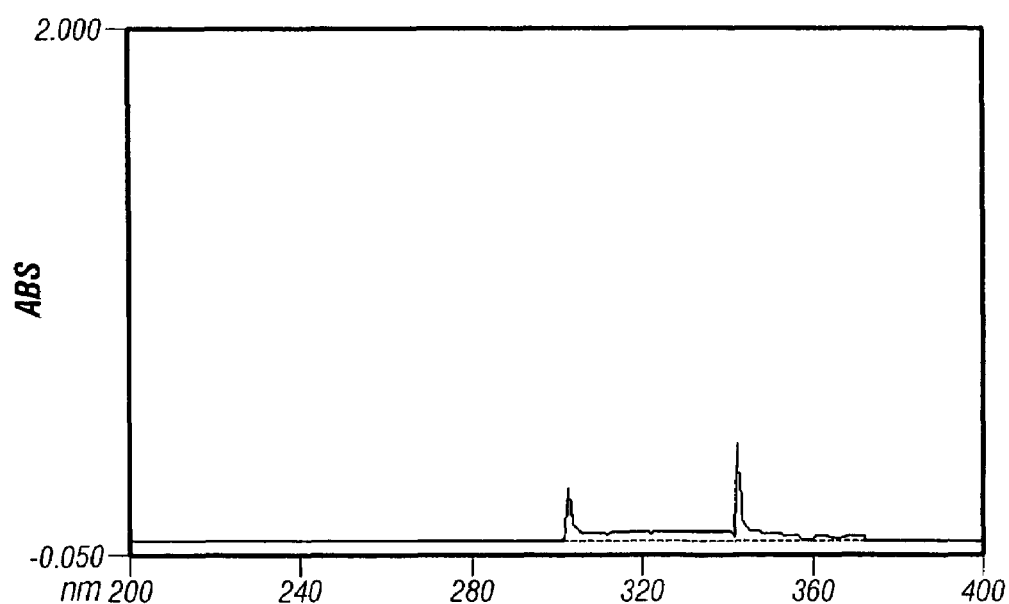
FIG. 51. Hexokinase assay of glucosamine.
Figure 52:
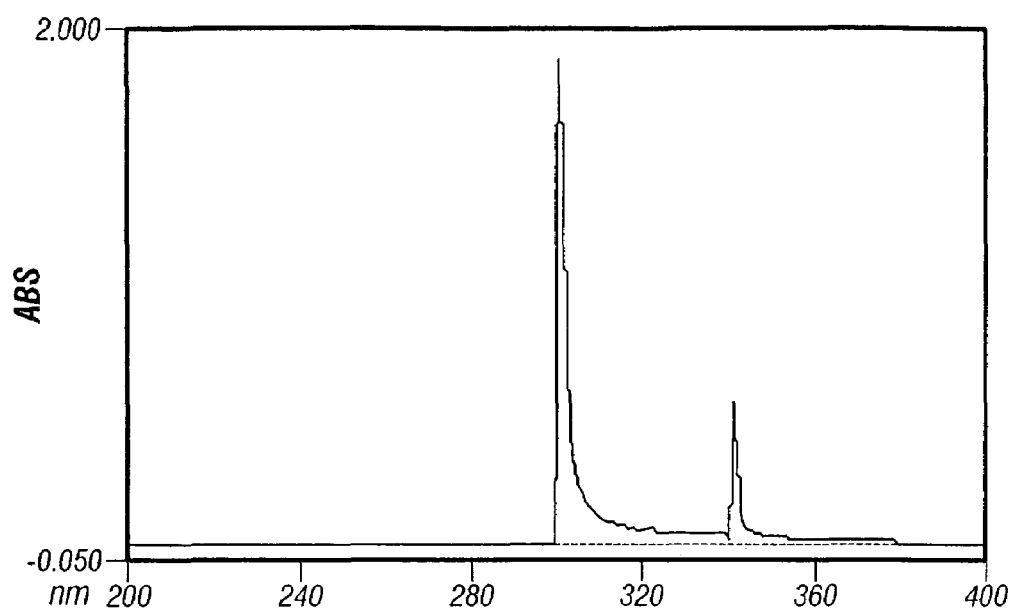
FIG. 52. Hexokinase assay of EC-glucosamine.
Figure 53:
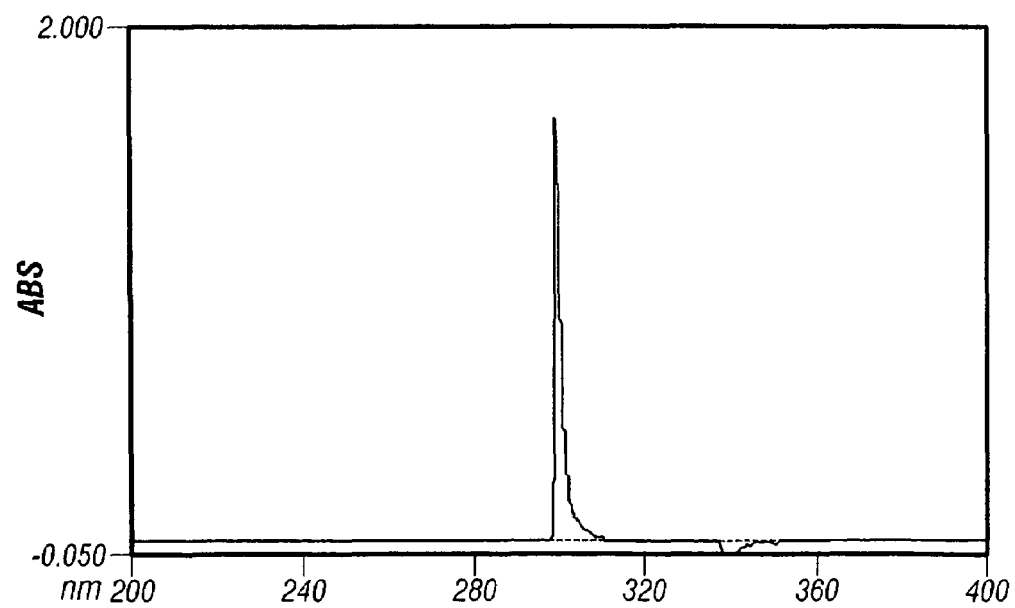
FIG. 53. Hexokinase assay of EC-GAP-glucosamine.
Figure 54:
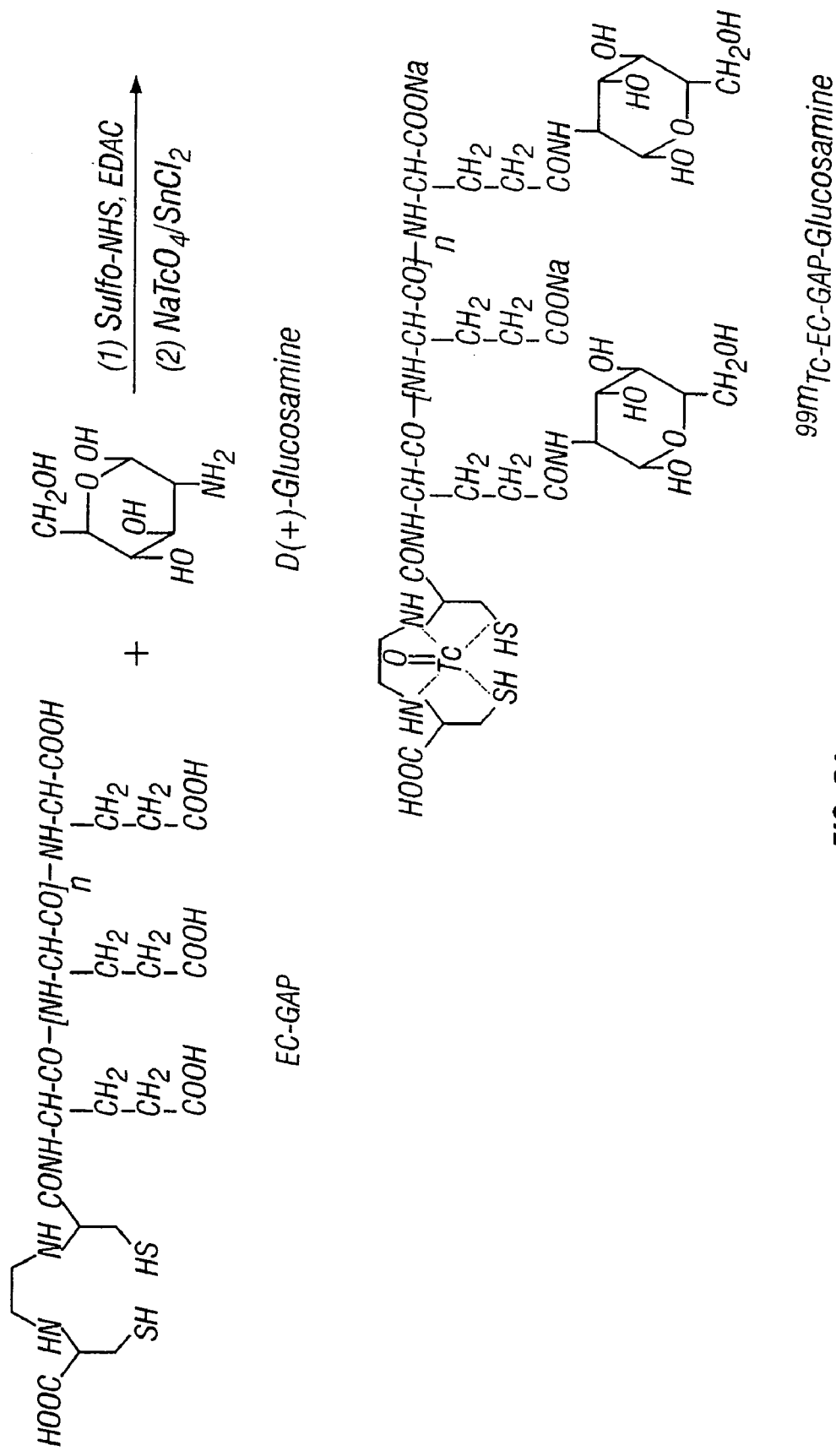
FIG. 54. Synthetic scheme of $^{99m}$Tc-EC-GAP-glucosamine.
Figure 55B:
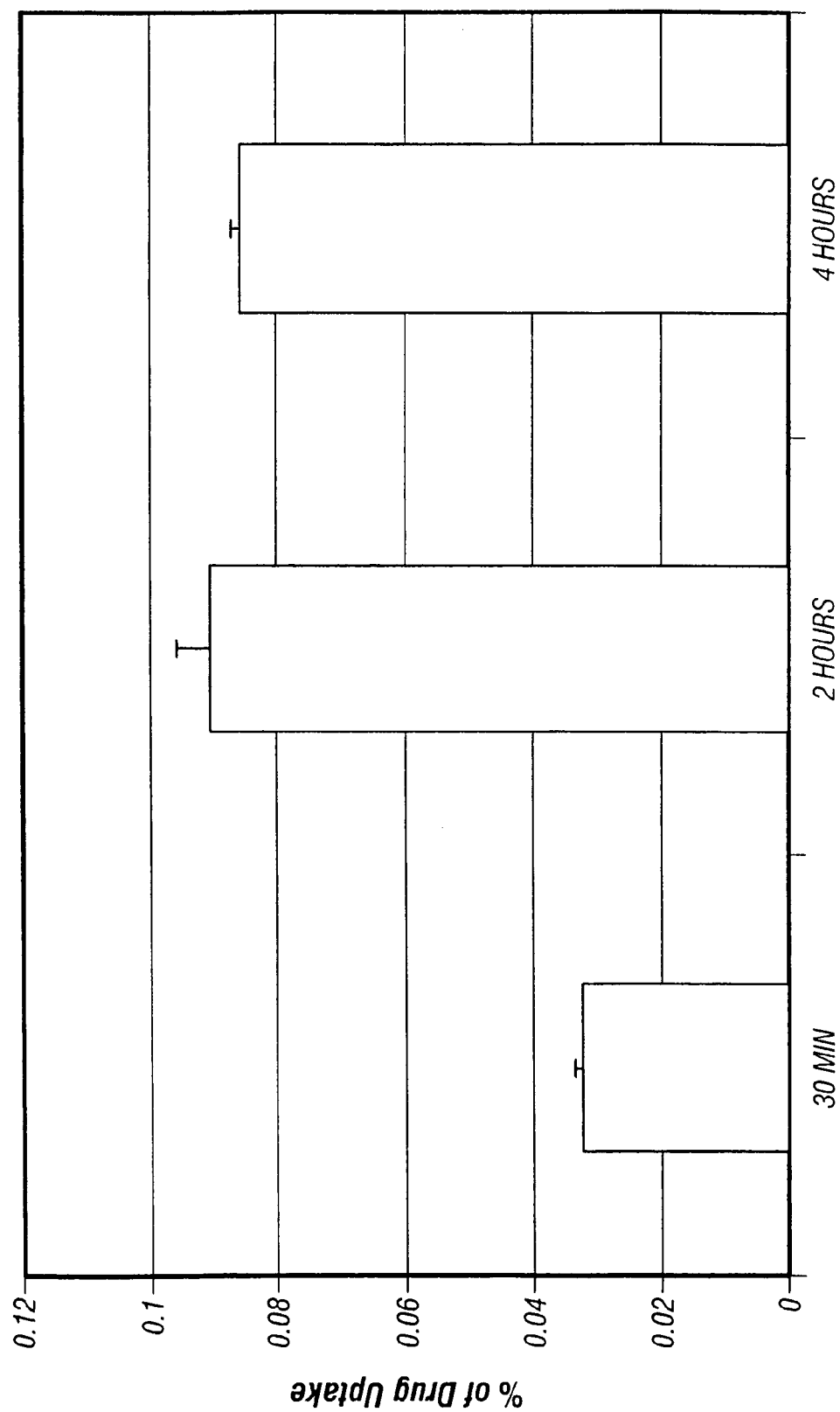
Figure 55C:
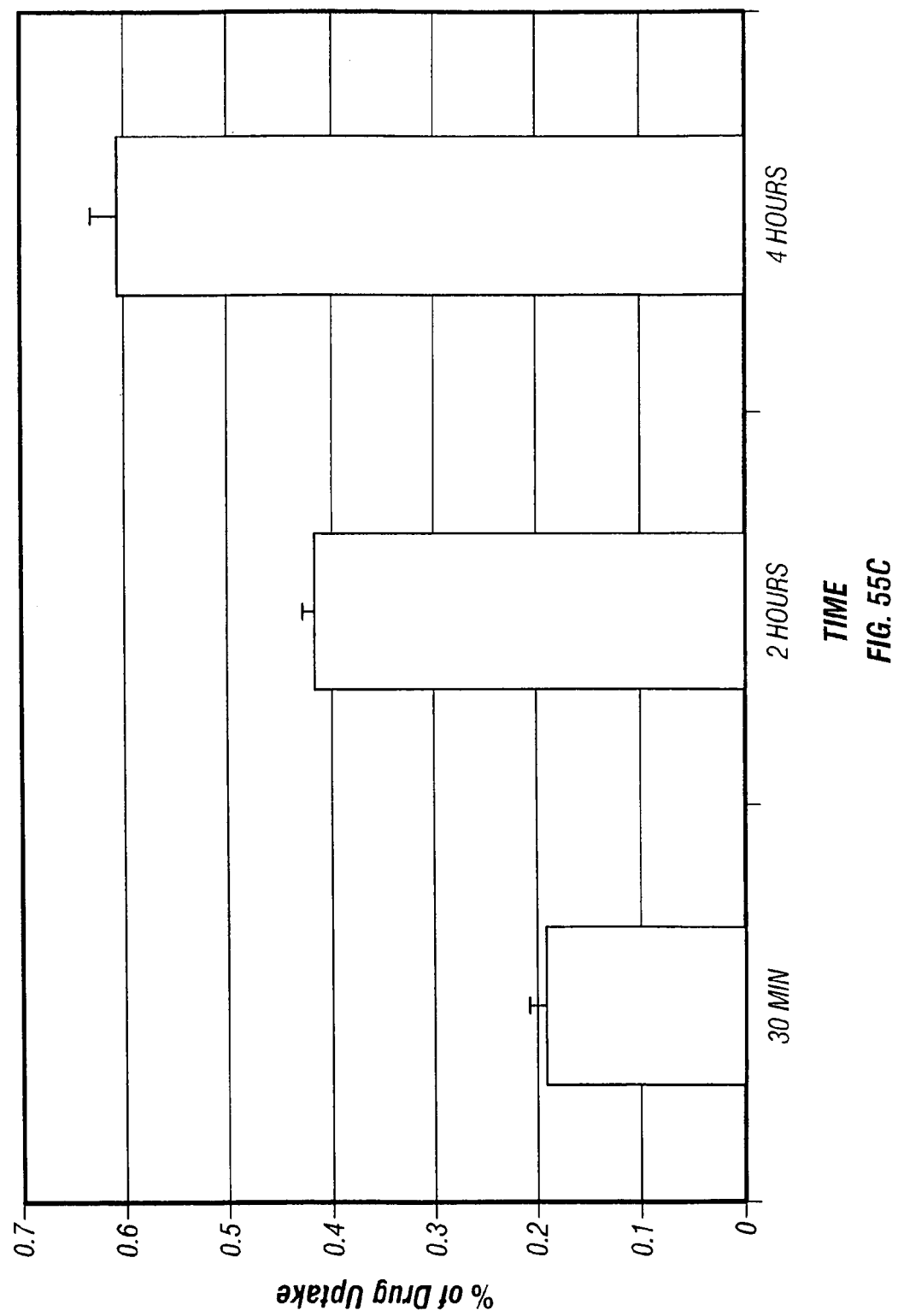
Figure 56:
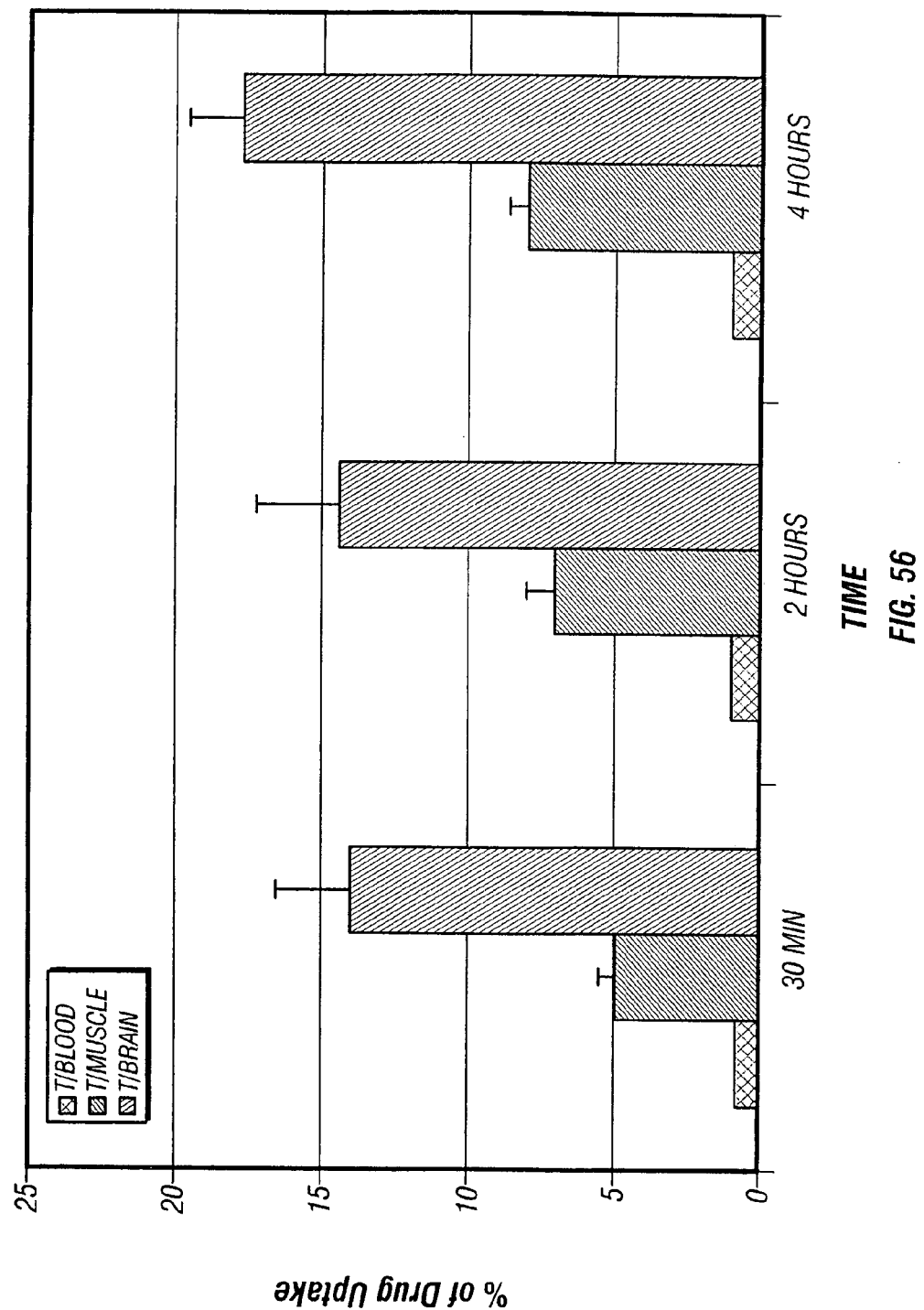
FIG. 56. Tumor-to-tissue count density ratios of $^{99m}$Tc-EC-GAP in breast tumor-bearing rats.
Figure 57:
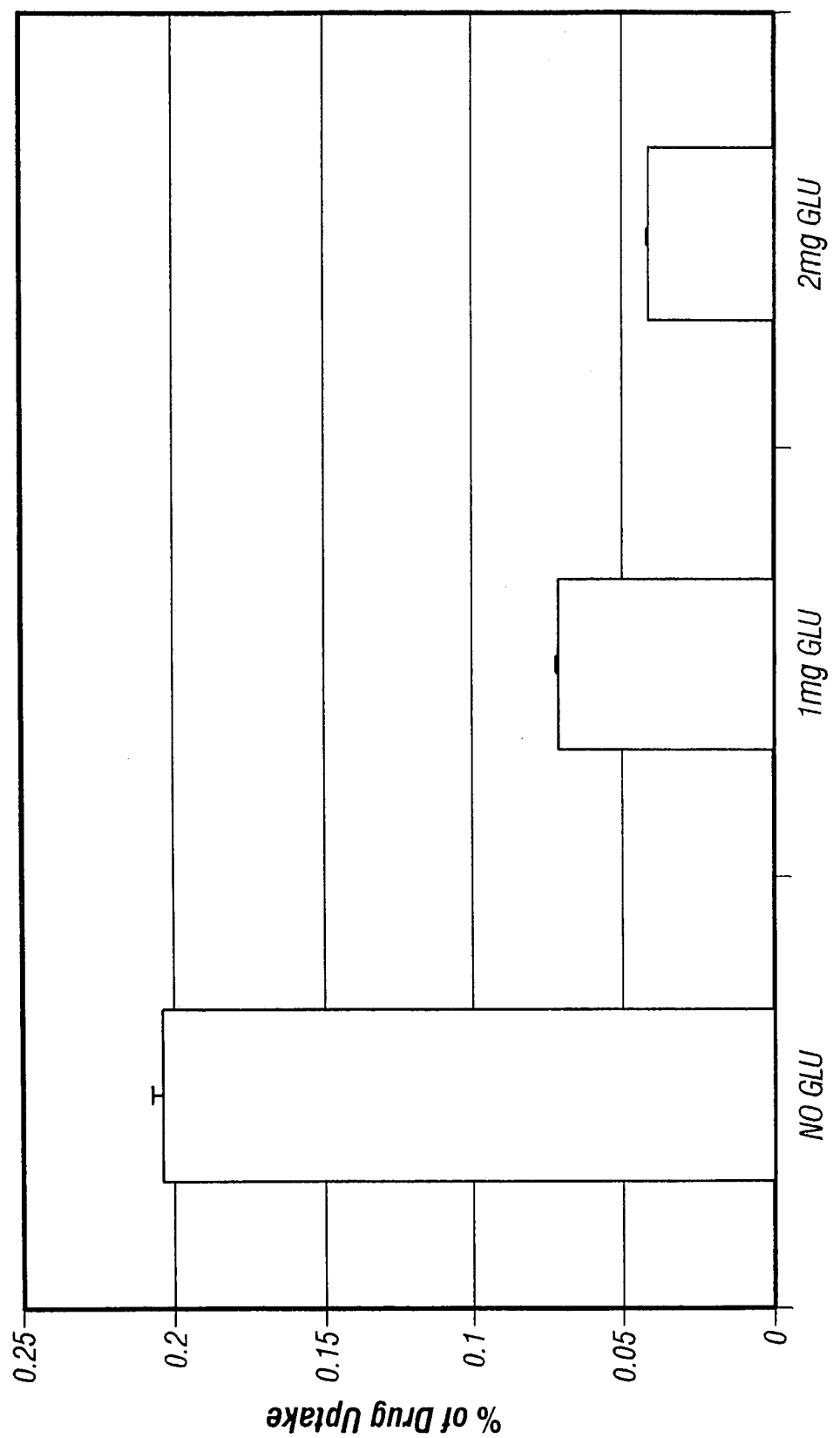
FIG. 57 In vitro cellular uptake of $^{18}$PDG with glucose loading at 2 hours post-injection in breast cancer cell line (13762).
Figure 58:
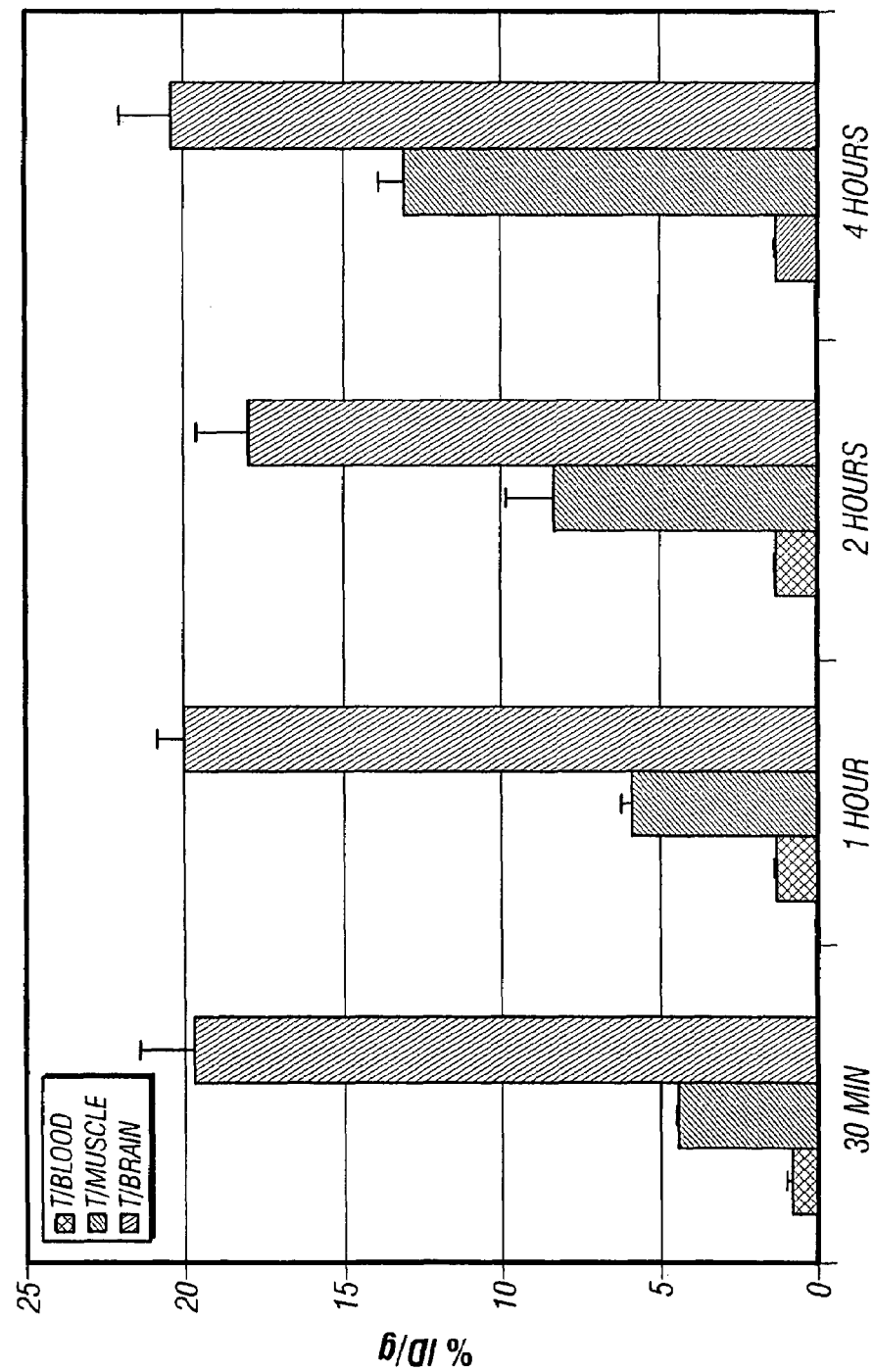
FIG. 58. In vivo tissue uptake of $^{99m}$Tc-EC-neomycin in breast tumor-bearing mice.

By adding glucose at the concentration of 0.1-2.0 mg/well, decreased uptake of $^{99m}$Tc-EC-neomycin in two lung cancer cell lines and one breast cell line was observed. Similar results were observed in $^{18}$F-FDG groups. $^{99m}$Tc-EC (control) showed no uptake. The findings suggest that the cellular uptake of $^{99m}$Tc-EC-neomycin may be mediated via glucose-related mechanism (FIGS. 47, 48A and 48B).

EXAMPLE 7

Tumor Metabolic Imaging with $^{99m}$Tc-EC-Deoxyglucose

Synthesis of EC-Deoxyglucose (EC-DG)

Figure 60:
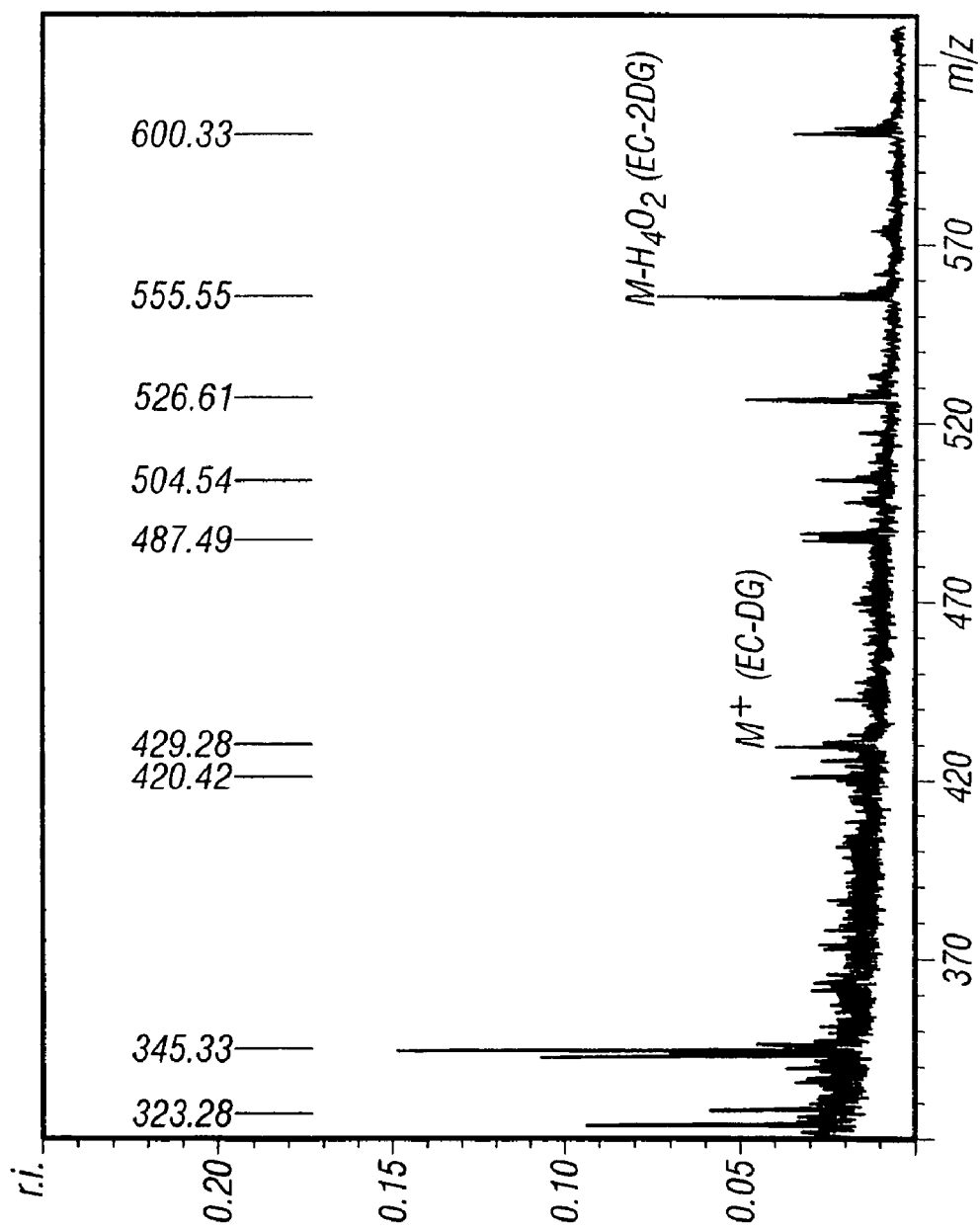
FIG. 60. Mass spectrometry of EC-deoxyglucose.
Figure 61:
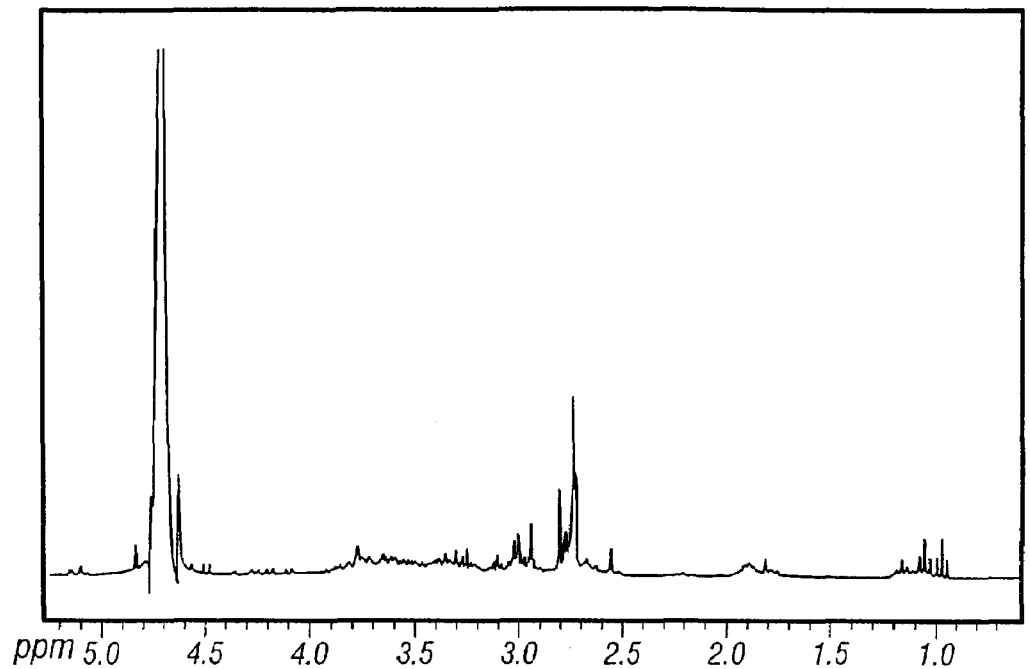
FIG. 61. $^1$H-NMR of EC-deoxyglucose (EC-DG).
Figure 62:
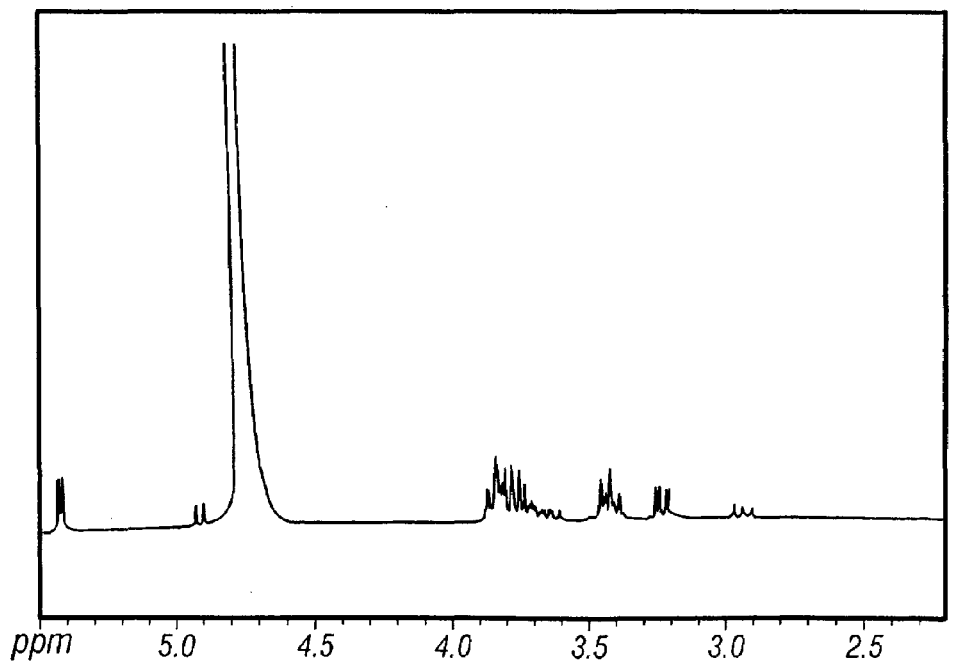
FIG. 62. $^1$H-NMR of glucosamine.
Figure 63:
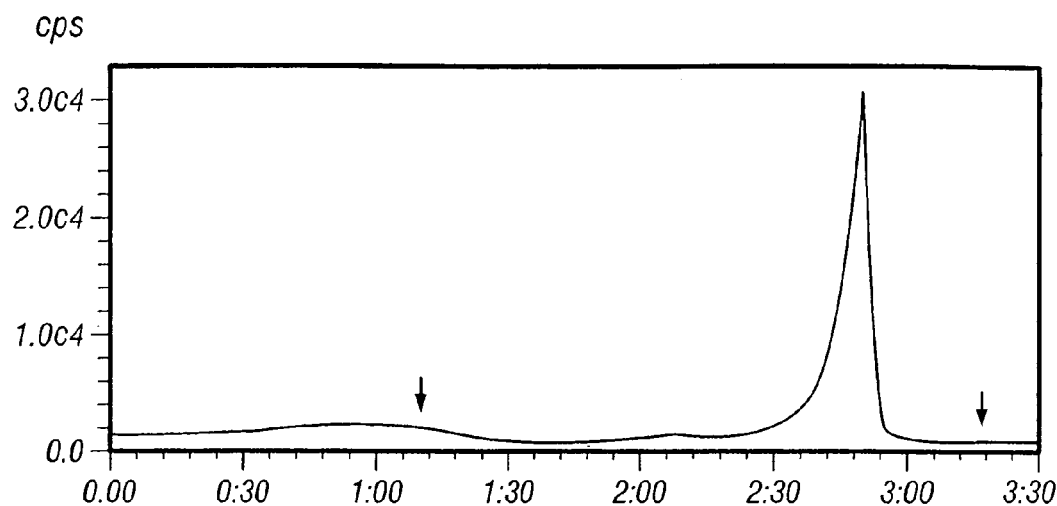
FIG. 63. Radio-TLC analysis of $^{99m}$Tc-EC-DG.
Figure 64A:
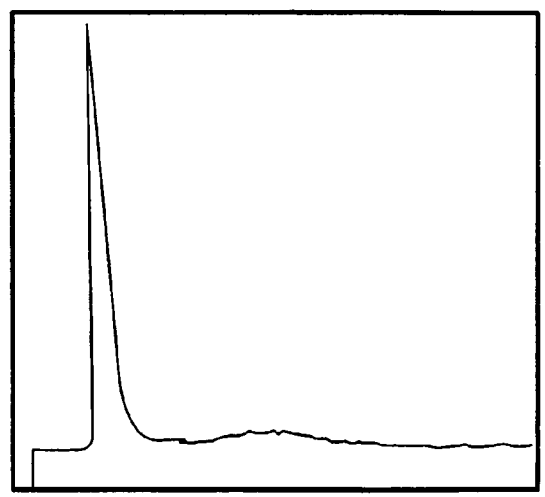
FIG. 64. HPLC analysis of $^{99m}$Tc-EC-deoxyglucose and $^{99m}$Tc-EC-(radioactive detector).
Figure 64B:
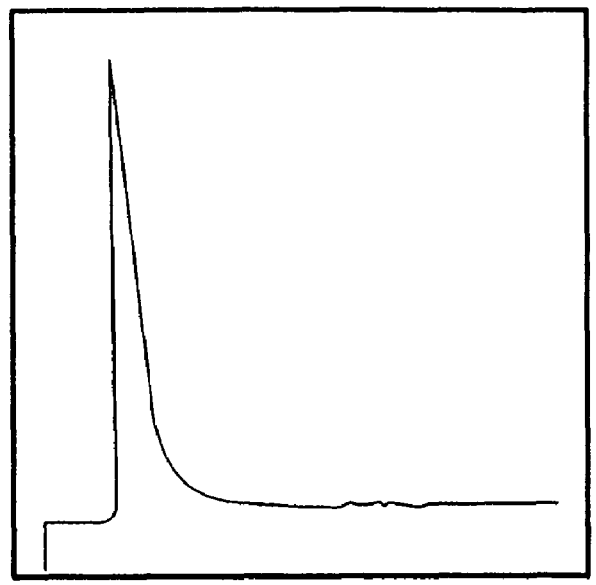
Figure 65:
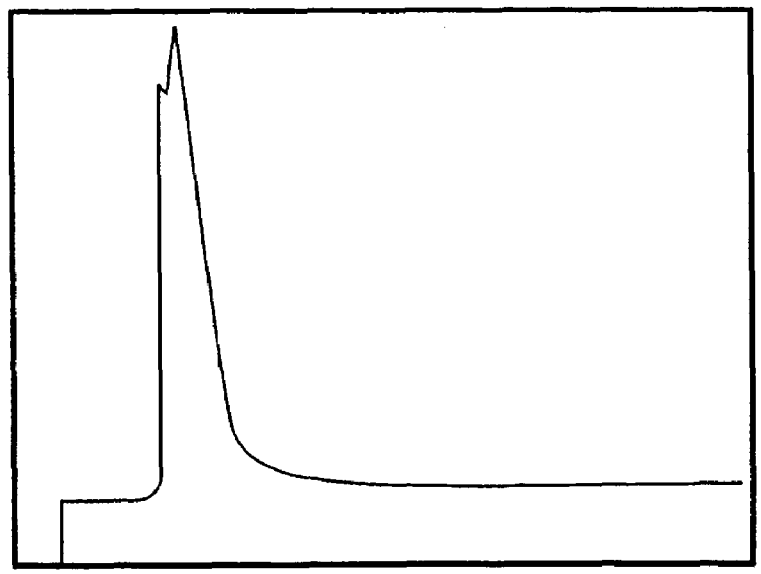
FIG. 65. HPLC analysis of $^{99m}$Tc-EC-deoxyglucose and $^{99m}$Tc-EC (radioactive detector, mixed).

Sodium hydroxide (1N, 1 ml) was added to a stirred solution of EC (110 mg, 0.41 mmol) in water (5 ml). To this colorless solution, sulfo-NHS (241.6 mg, 1.12 mmol) and EDC (218.8 mg, 1.15 mmol) were added. D-Glucosamine hydrochloride salt (356.8 mg, 1.65 mmol) was then added. The mixture was stirred at room temperature for 24 hours. The mixture was dialyzed for 48 hours using Spectra/POR molecular porous membrane with cut-off at 500 (Spectrum Medical Industries Inc., Houston, Tex.). After dialysis, the product was frozen dried using lyophilizer (Labconco, Kansas City, Mo.). The product in the salt form weighed 568.8 mg. The synthetic scheme is shown in FIG. 59. The structure was confirmed by mass spectrometry (FIG. 60) and proton NMR (FIGS. 61 and 62). Radiochemical purity of $^{99m}$Tc-EC-DG was 100% as determined by radio-TLC (FIG. 63) and HPLC (FIGS. 64 and 65) analysis.

Hexokinase Assay

Figure 66:
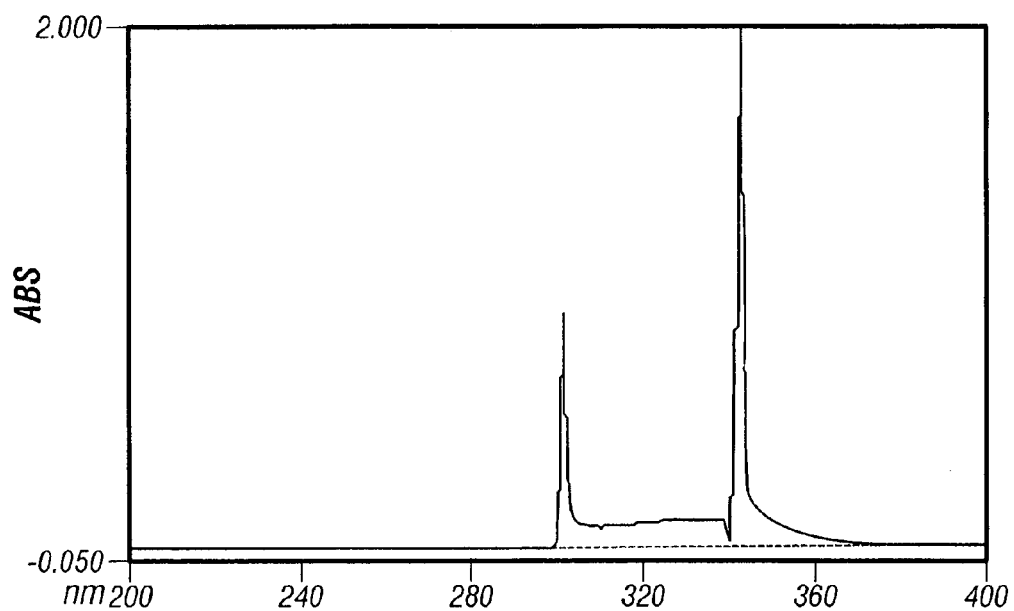
FIG. 66. Hexokinase assay of glucose.
Figure 67:
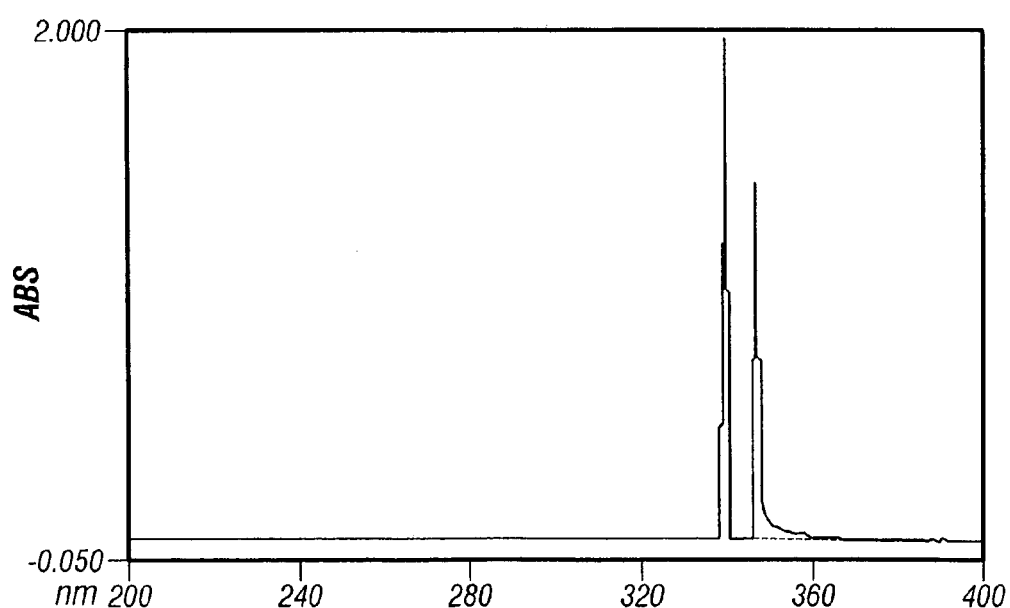
FIG. 67. Hexokinase assay of FDG.
Figure 68:
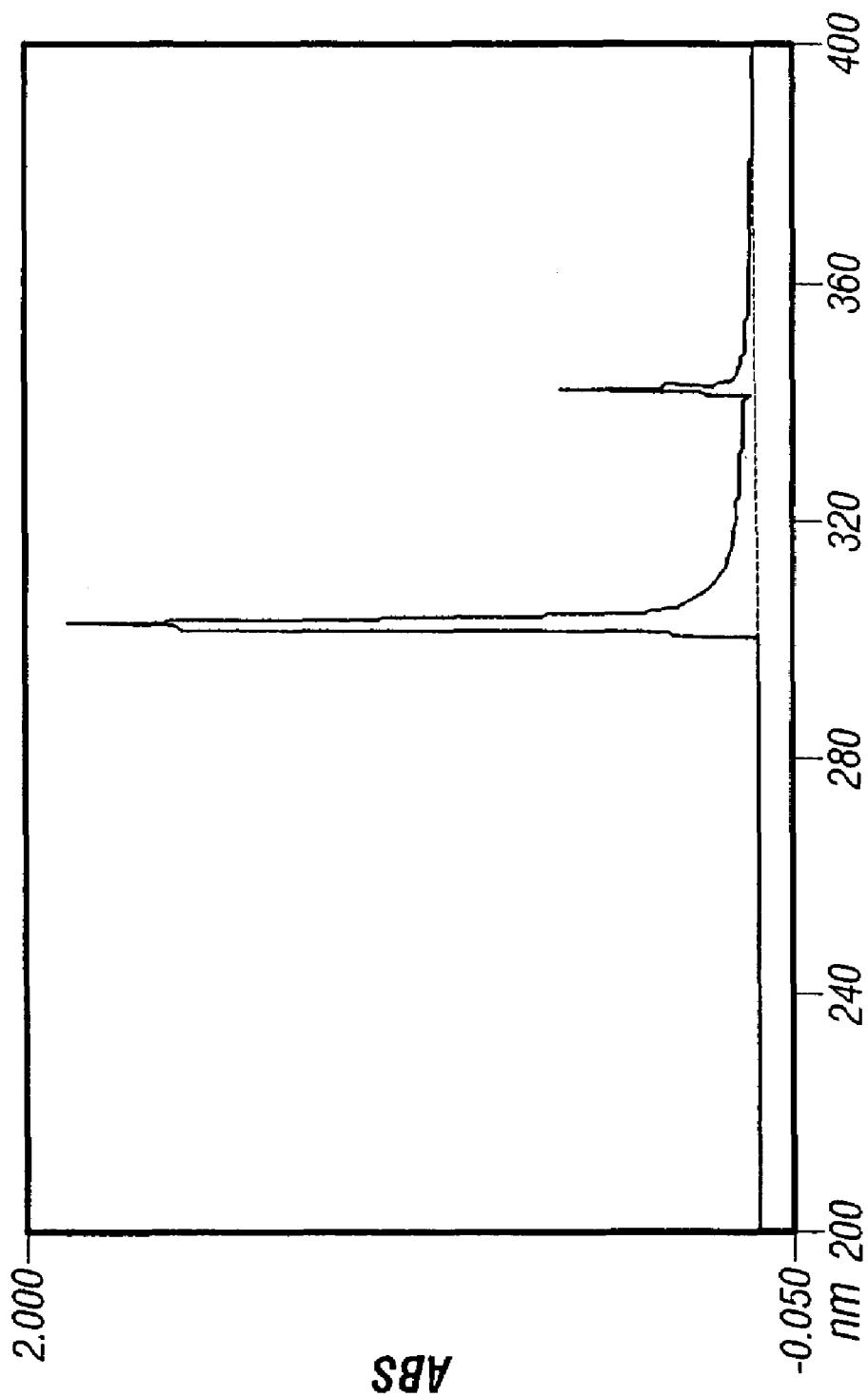
FIG. 68. Hexokinase assay of EC-DG.

To determine if EC-DG mimics glucose phosphorylation, a hexokinase assay was conducted. Using a ready made kit (Sigma Chemical Company), EC-DG, glucosamine and glucose (standard) were assayed at UV wavelength 340 nm. Glucose, EC-DG and glucosamine showed positive hexokinase assay (FIGS. 66-68).

In Vitro Cellular Uptake Assay

Figure 69:
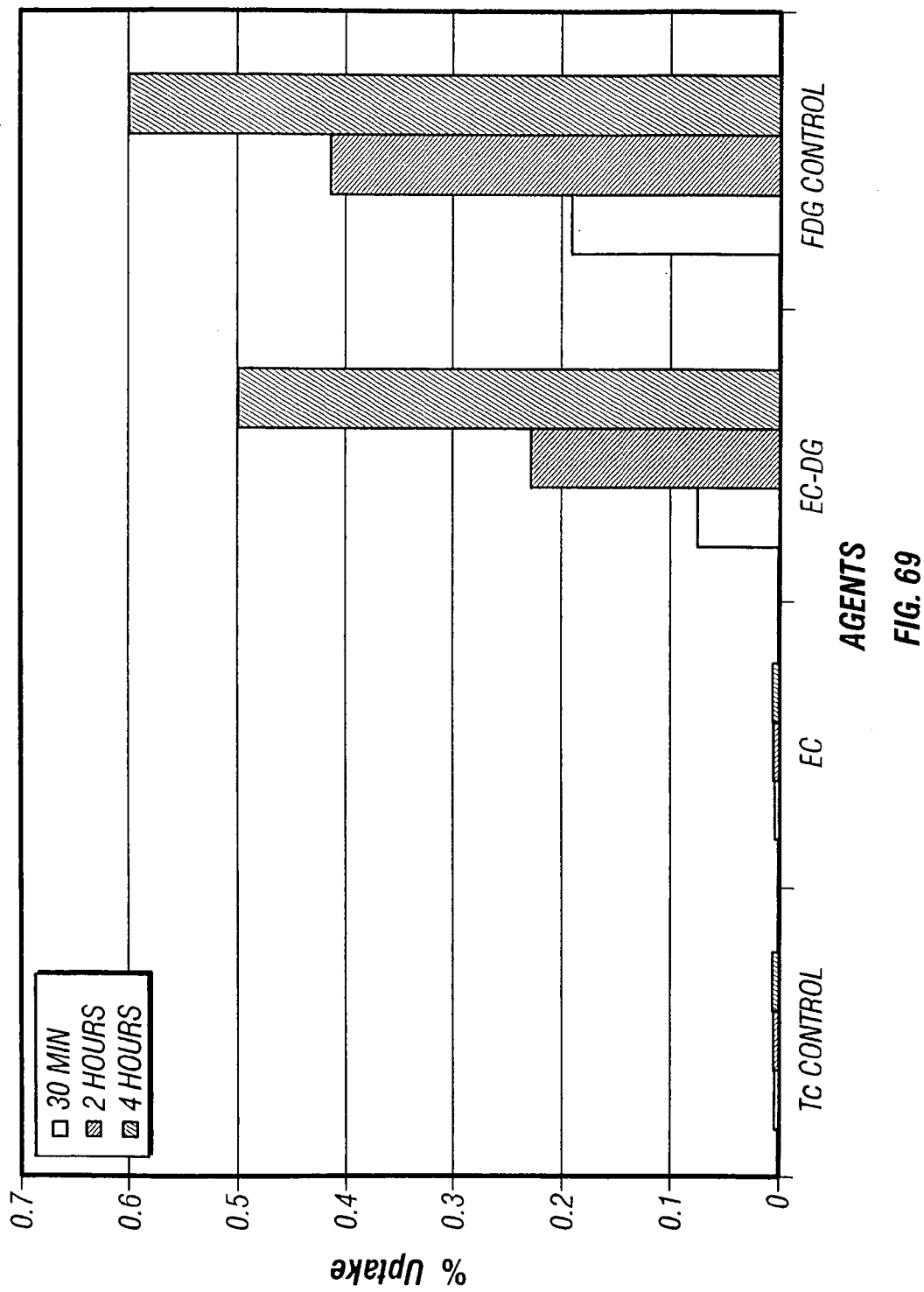
FIG. 69. In vitro cellular uptake assay of $^{99m}$Tc-EC-deoxyglucose, $^{99m}$Tc-EC and $^{18}$F-FDG in lung cancer cell line (A549). $^{99m}$Tc-EC-DG showed similar uptake compared to $^{18}$F-FDG.
Figure 70:
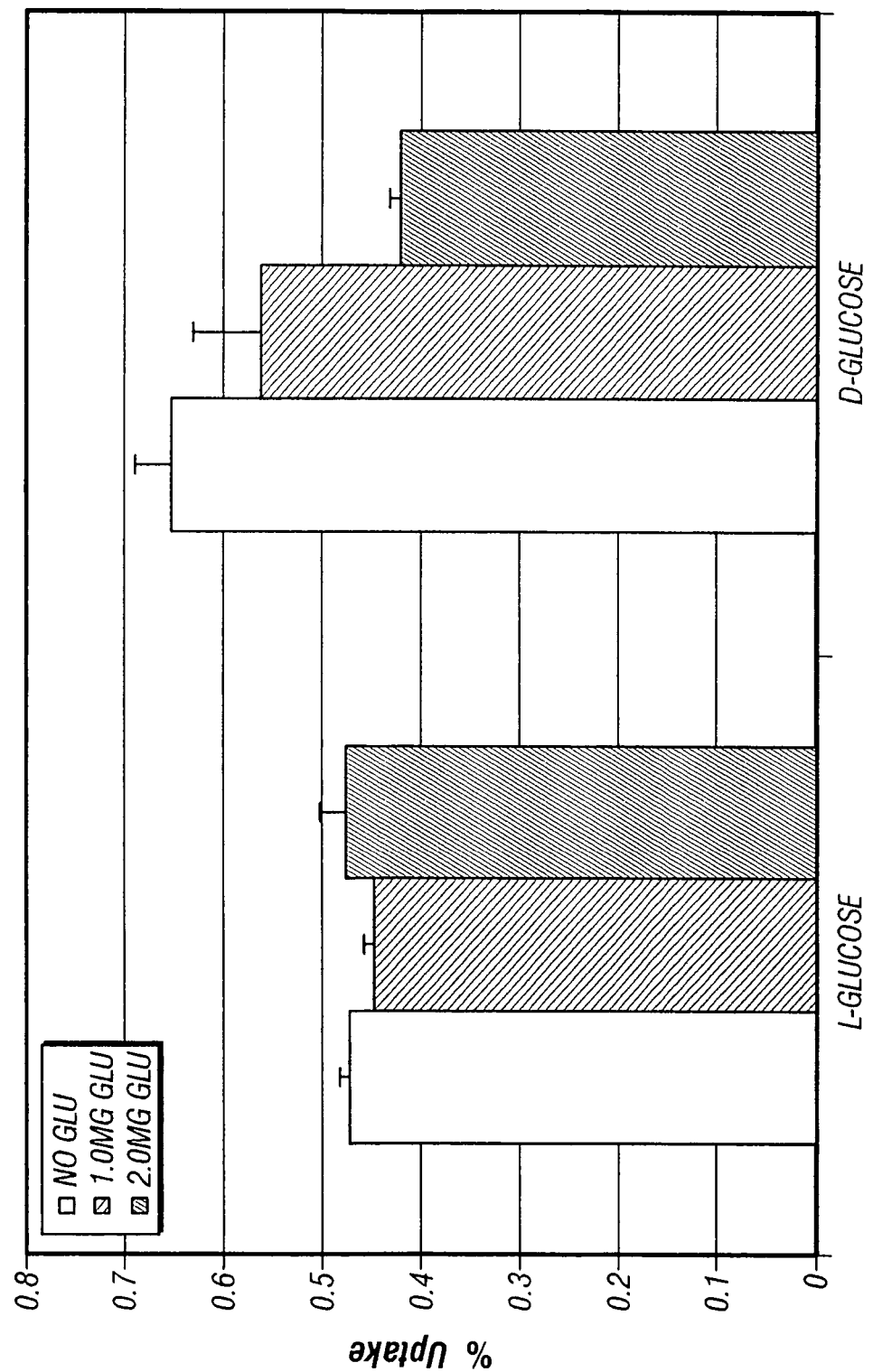
FIG. 70. Effect of d- and l-glucose on breast cellular (13762 cell line) uptake of $^{99m}$Tc-EC-DG.
Figure 71:
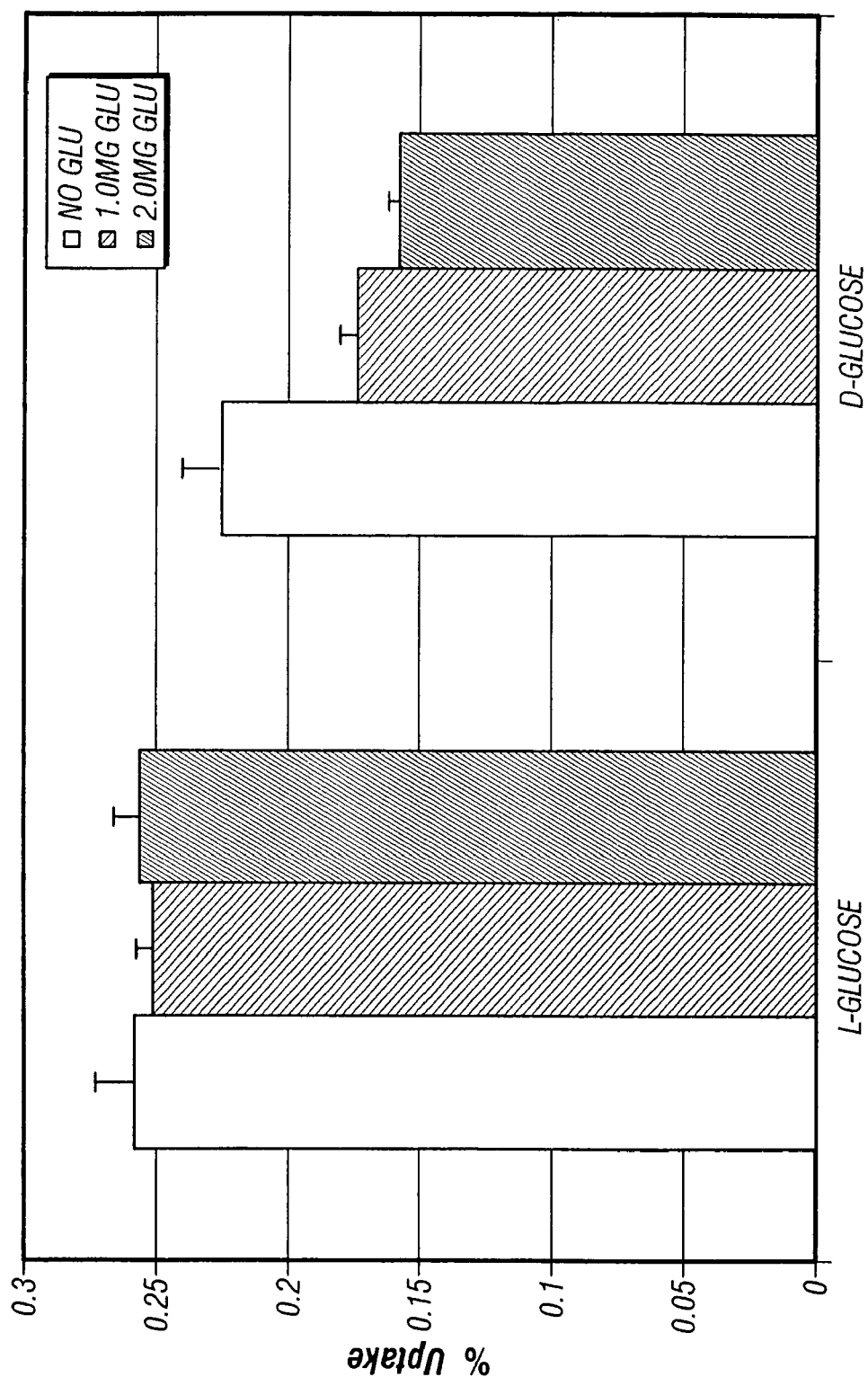
FIG. 71. Effect of d- and l-glucose on breast cellular (13762 cell line) uptake of $^{18}$F-FDG.
Figure 72:
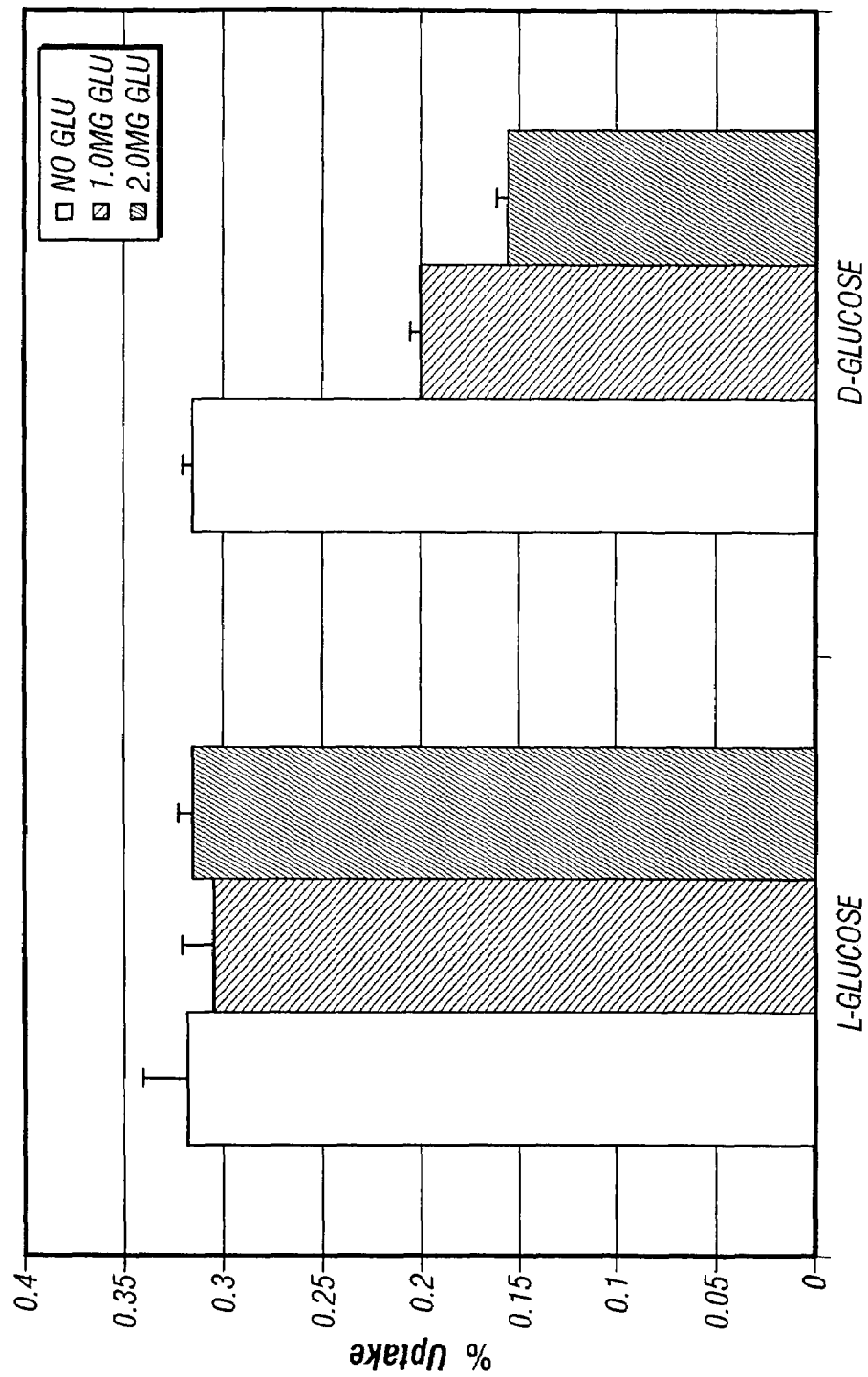
FIG. 72. Effect of d- and l-glucose on lung cellular (A549 cell line) uptake of $^{18}$F-FDG.
Figure 73:
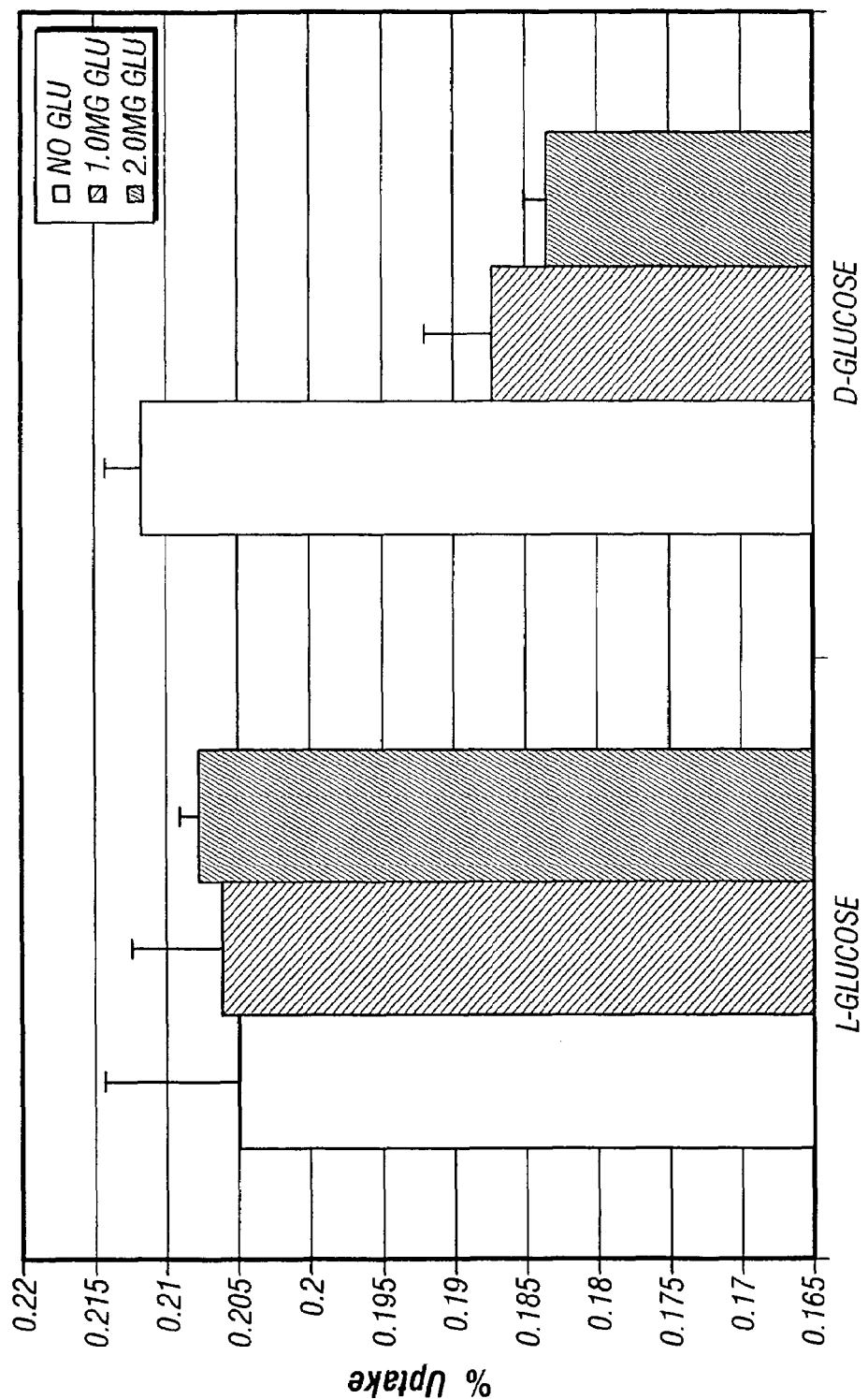
FIG. 73. Effect of d- and l-glucose on breast cellular (A549 cell line) uptake of $^{99m}$Tc-EC-DG.

In vitro cellular uptake assay was conducted by using a human lung cancer cell line (A549). Two μCi of $^{99m}$Tc-EC-DG and $^{18}$F-FDG were added to wells containing 80,000 cells each. After incubation at 0.5-4 hours, the cells were washed with phosphate buffered saline 3 times and followed by trypsin to lose the cells. The cells were then counted by a gamma counter. The uptake of $^{99m}$Tc-EC-DG was comparable to FDG (FIG. 69).

Effect of d- and l-Glucose on Cellular Uptake of $^{99m}$Tc-EC-Deoxyglucose and $^{18}$F-FDG To evaluate if the uptake of $^{99m}$Tc-EC-deoxyglucose is mediated via d-glucose mechanism, d- and l-glucose (1 mg and 2.0 mg) were added to, each well containing either breast or lung cancer cells (50,000/0.5 ml/well), along with 2 μCi of $^{99m}$Tc-EC-deoxyglucose and $^{18}$F-FDG. After 2 hours incubation, the cells were washed with phosphate buffered saline 3 times and followed by trypsin to lose the cells. The cells were counted by a gamma counter.

By adding glucose at the concentration of 1-2.0 mg/well, a decreased uptake of $^{99m}$Tc-EC-deoxyglucose and $^{18}$F-FDG by d-glucose in breast and lung cancer cells was observed. However, there was no influence on both agents by 1-glucose (FIG. 70-73). The findings suggest that the cellular uptake of $^{99m}$Tc-EC-deoxyglucose is mediated via d-glucose mechanism.

Effect of EC-Deoxyglucose Loading on Blood Glucose Level in Normal Rats

Previous experiments have shown that cellular uptake of $^{99m}$Tc-EC-deoxyglucose is similar to FDG. For instance, the hexokinase assay (glucose phosphorylation) was positive. The uptake of $^{99m}$Tc-EC-deoxyglucose is mediated via d-glucose mechanism. This study is to determine whether blood glucose level could be induced by either FDG or EC-deoxyglucose and suppressed by insulin.

Normal healthy Fischer 344 rats (weight 145-155 g) were fasting overnight prior to the experiments. The concentration of glucosamine hydrochloride, FDG and EC-deoxyglucose prepared was 60% and 164% (mg/ml). The blood glucose level (mg/dl) was determined by a glucose meter (Glucometer DEX, Bayer Corporation, Elkhart, Ind.). Prior to the study, the baseline of blood glucose level was obtained. Each rat (n=3/group) was administered 1.2 mmol/kg of glucosamine, FDG and EC-deoxyglucose. In a separate experiment, a group of rats was administered EC-deoxyglucose and FDG. Insulin (5 units) was administered after 30 minutes. Blood samples were collected from the tail vein every 30 minutes up to 6 hours post-administration.

Figure 74:
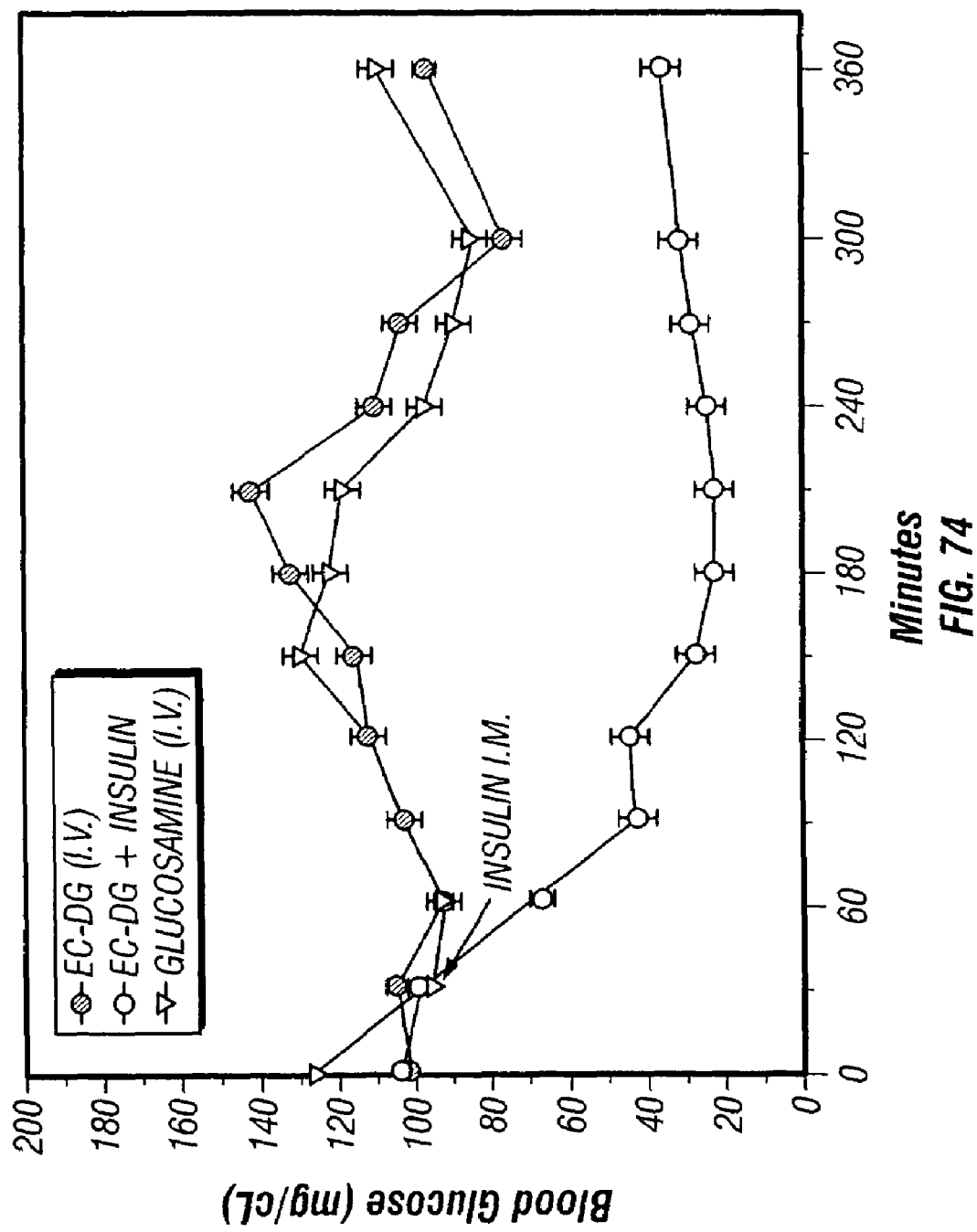
FIG. 74. Effect of in vivo blood glucose level induced by glucosamine and EC-DG (1.2 mmol/kg, i.v.).
Figure 75:
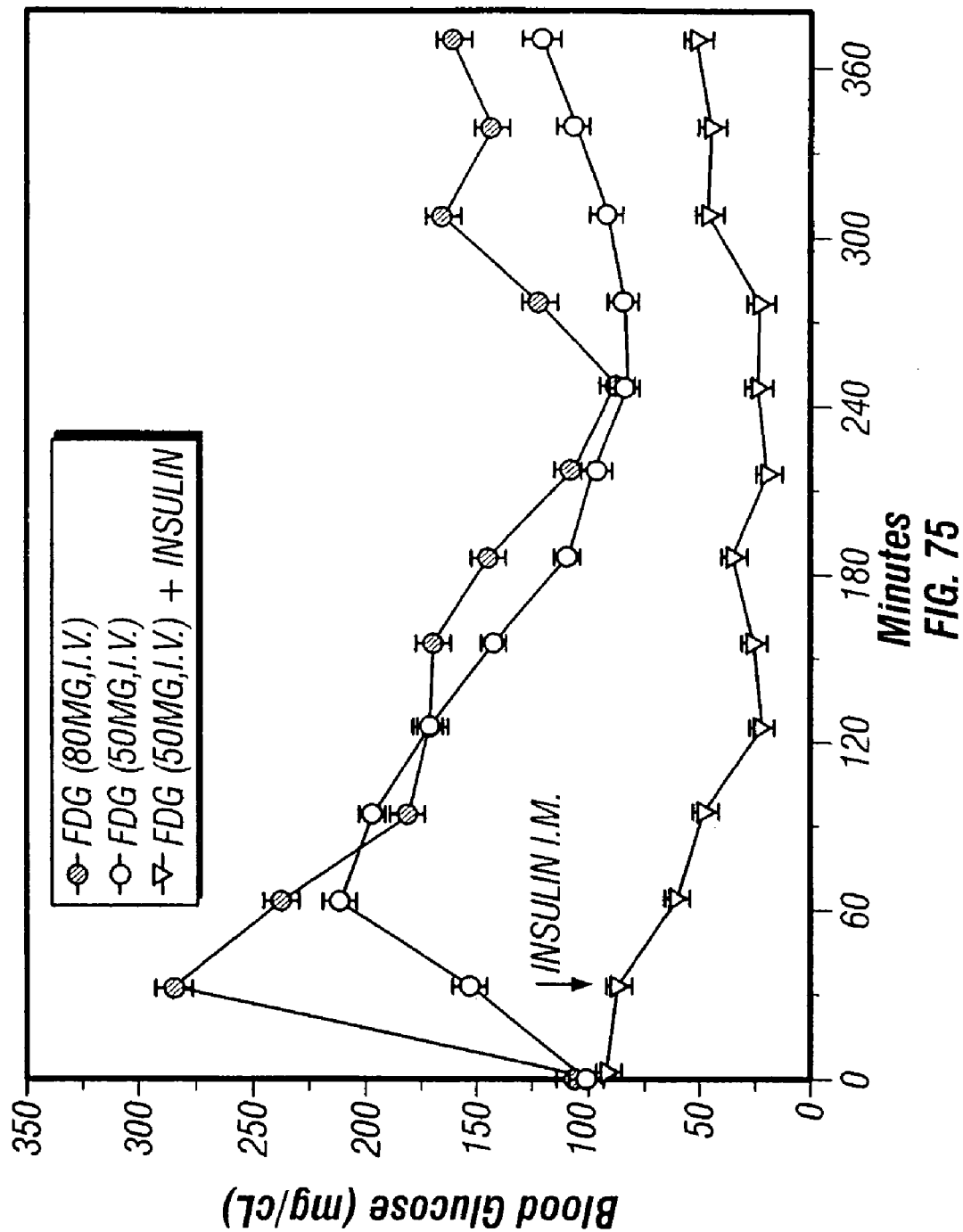
FIG. 75. Effect of in vivo blood glucose level induced by FDG (1.2 and 1.9 mmol/kg, i.v.) and insulin.
Figure 76:
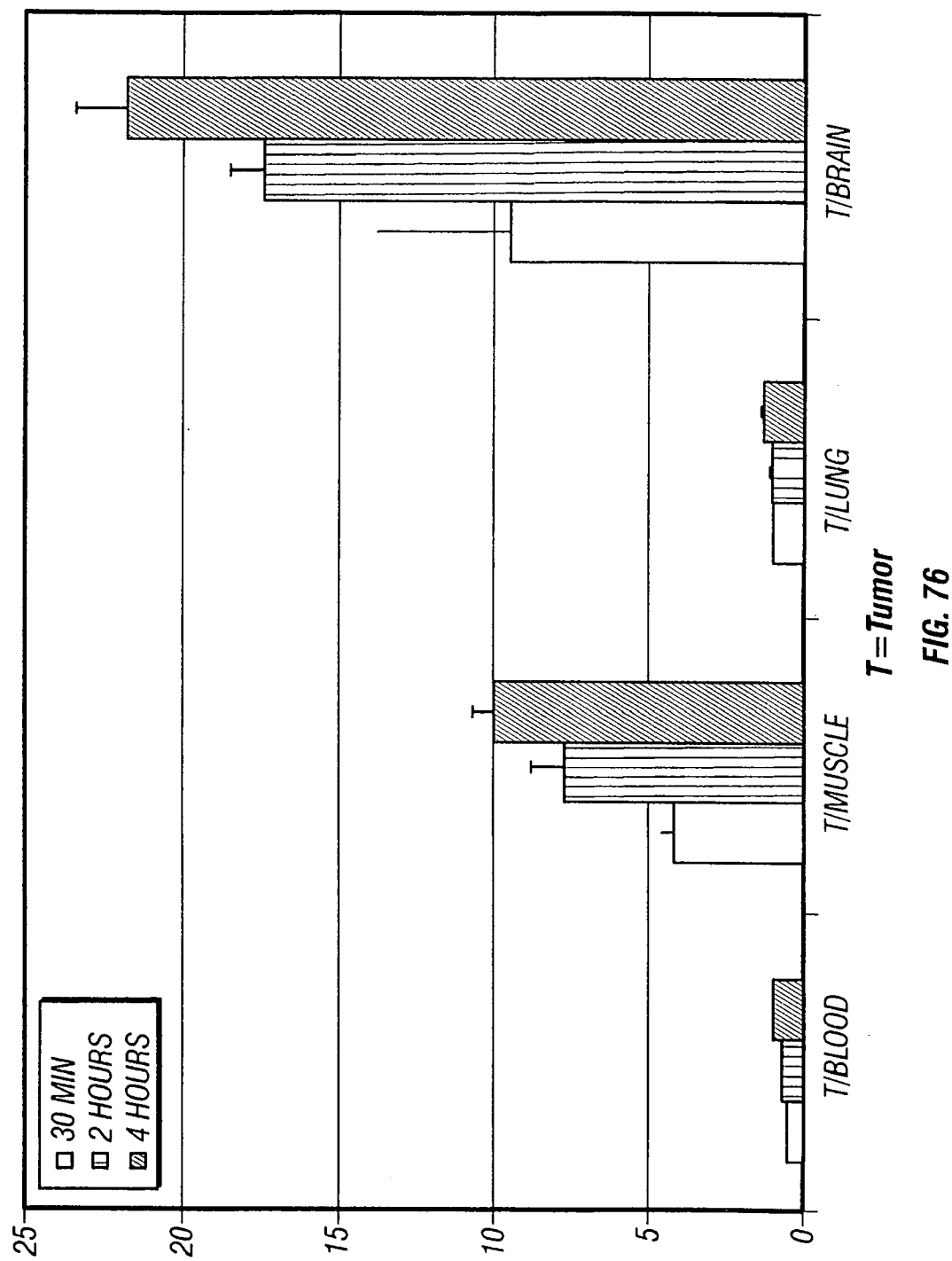
FIG. 76. Tumor-to-tissue count density ratios of $^{99m}$Tc-EC-deoxyglucose in breast tumor-bearing rats.
Figure 77:
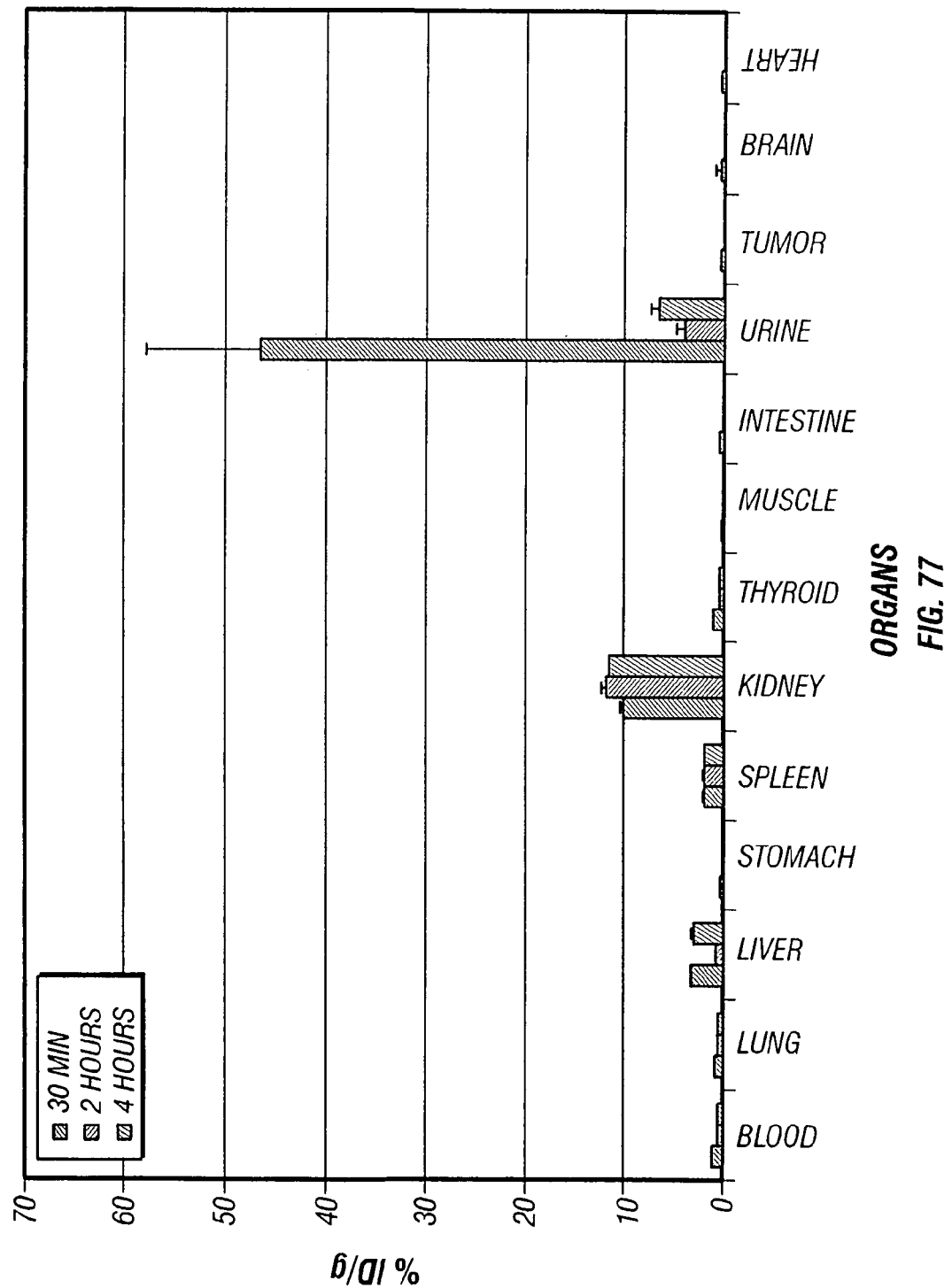
FIG. 77. In vivo biodistribution of $^{99m}$Tc-EC-deoxyglucose in breast tumor-bearing rats.
Figure 78:
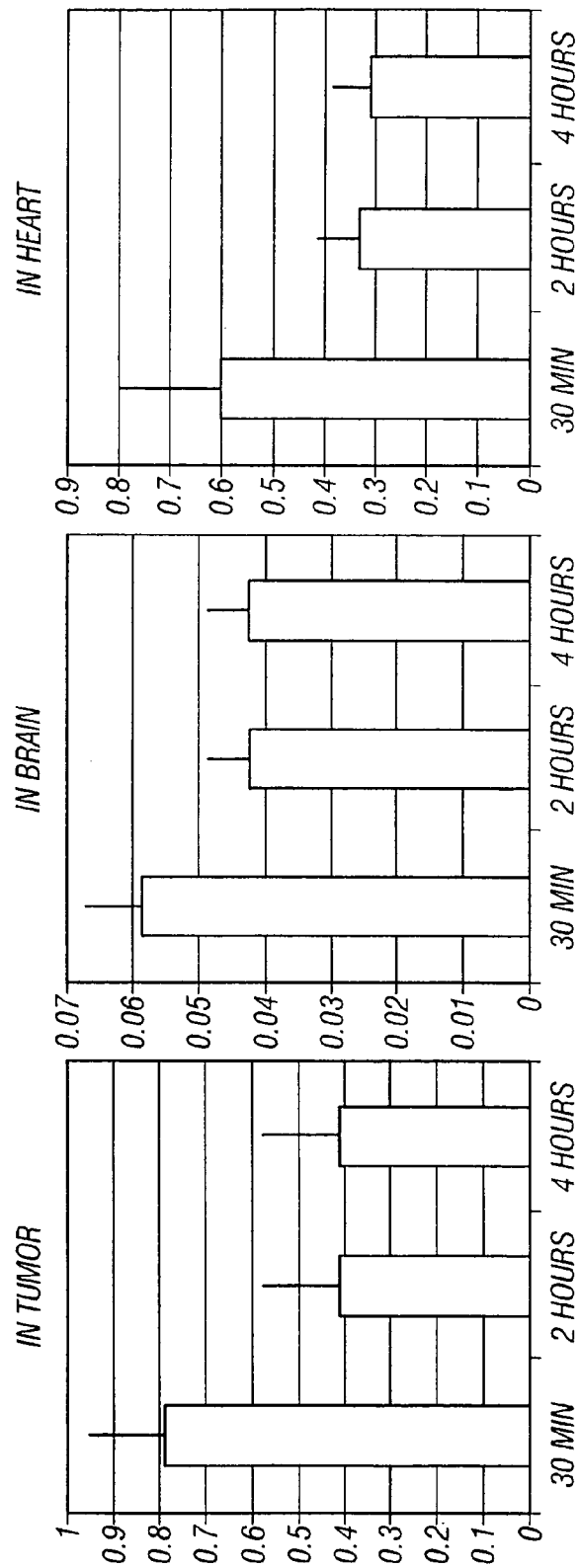
FIG. 78. In vivo tissue uptake of $^{99m}$Tc-EC-deoxyglucose in lung tumor-bearing mice.
Figure 79:
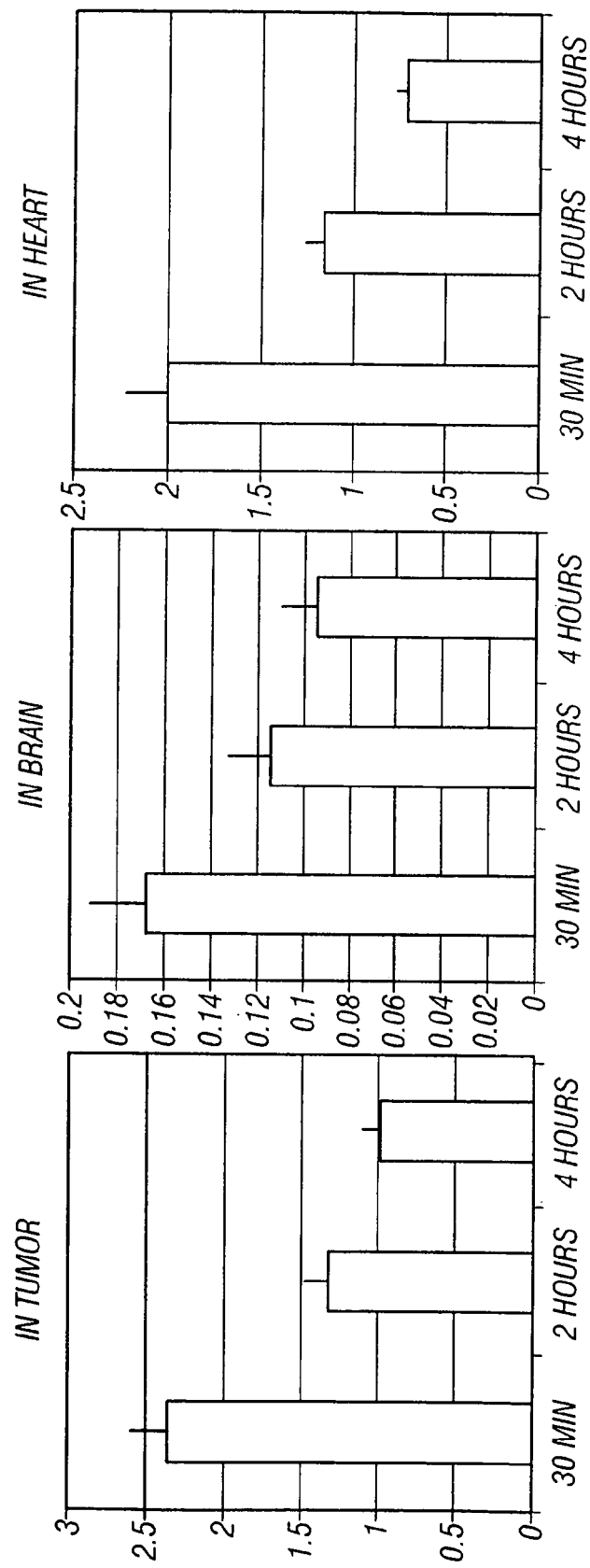
FIG. 79. In vivo tissue uptake of $^{99m}$Tc-EC-neomycin in lung tumor-bearing mice.
Figure 80:
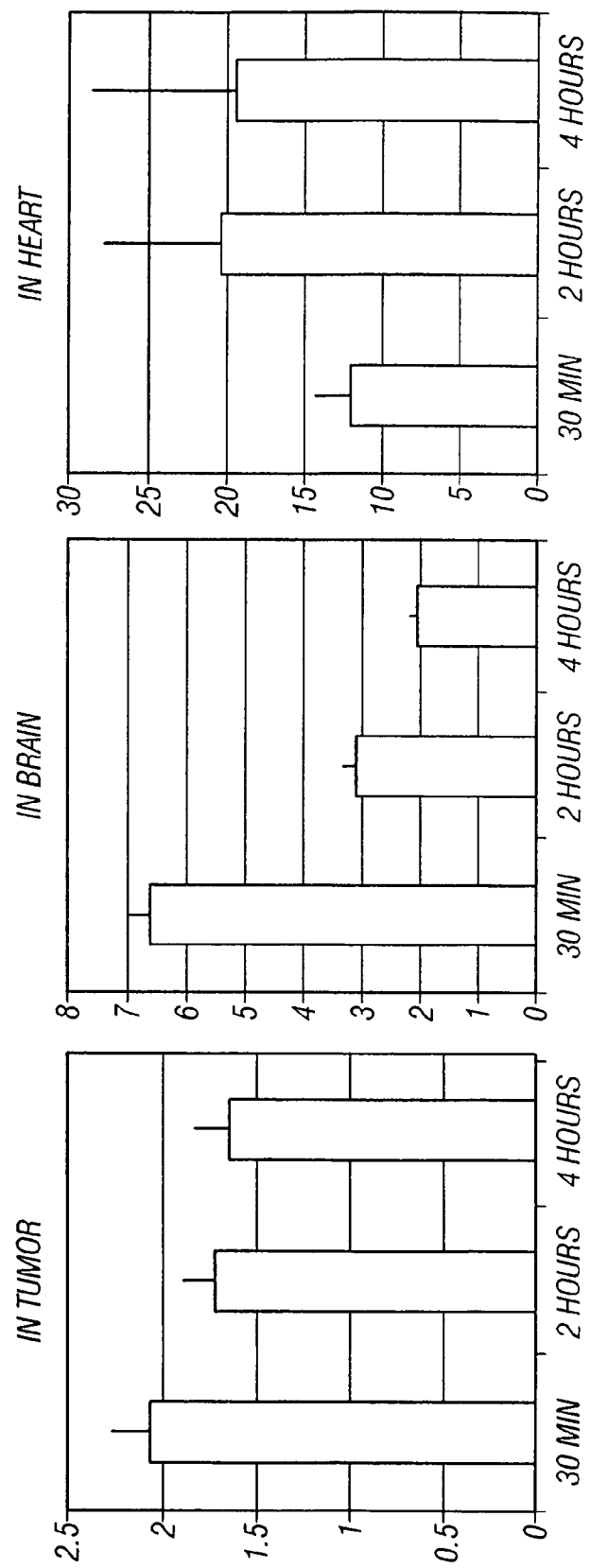
FIG. 80. In vivo tissue uptake of $^{18}$F-FDG in lung tumor-bearing mice.

Blood glucose level was induced by bolus intravenous administration of glucosamine, FDG and EC-deoxyglucose. This increased blood glucose level could be suppressed by co-administration of EC-deoxyglucose or FDG and insulin (FIGS. 74 and 75).

Tissue Distribution Studies of $^{99m}$Tc-EC-DG

For breast tumor-bearing animal model, female Fischer 344 rats (150±25 g) (Harlan Sprague-Dawley, Indianapolis, Ind.) were innoculated subcutaneously with 0.1 ml of mammary tumor cells from the 13762 tumor cell line suspension ($10^6$ cells/rat, a tumor cell line specific to Fischer rats) into the hind legs using 25-gauge needles. Studies were performed 14 to 17 days after implantation when tumors reached approximately 1 cm diameter. Rats were anesthetized with ketamine (10-15 mg/rat, intraperitoneally) before each procedure.

For lung tumor-bearing animal model, each athymic nude mouse (20-25 g) was innoculated subcutaneously with 0.1 ml of human lung tumor cells from the A549 tumor cell line suspension ($10^6$ cells/mouse) into the hind legs using 25-gauge needles. Studies were performed 17 to 21 days after implantation when tumors reached approximately 0.6 cm diameter.

In tissue distribution studies, each animal was injected intravenously with 10-20 μCi (per rat) or 1-2 μCi (per mouse) of $^{99m}$Tc-EC or $^{99m}$Tc-EC-DG (n=3/time point). The injected mass of $^{99m}$Tc-EC-DG was 1 mg per rat. At 0.5, 2 and 4 hours following administration of the radiotracers, the rodents were sacrificed and the selected tissues were excised, weighed and counted for radioactivity. The biodistribution of tracer in each sample was calculated as percentage of the injected dose per gram of tissue wet weight (% ID/g). Tumor/nontarget tissue count density ratios were calculated from the corresponding % ID/g values. When compared to $^{99m}$Tc-EC (Table 4) and free technetium (Table 9), tumor-to tissue ratios increased as a function of time in $^{99m}$Tc-EC-DG group (FIGS. 76-80).

Scintigraphic Imaging Studies

Figure 81:
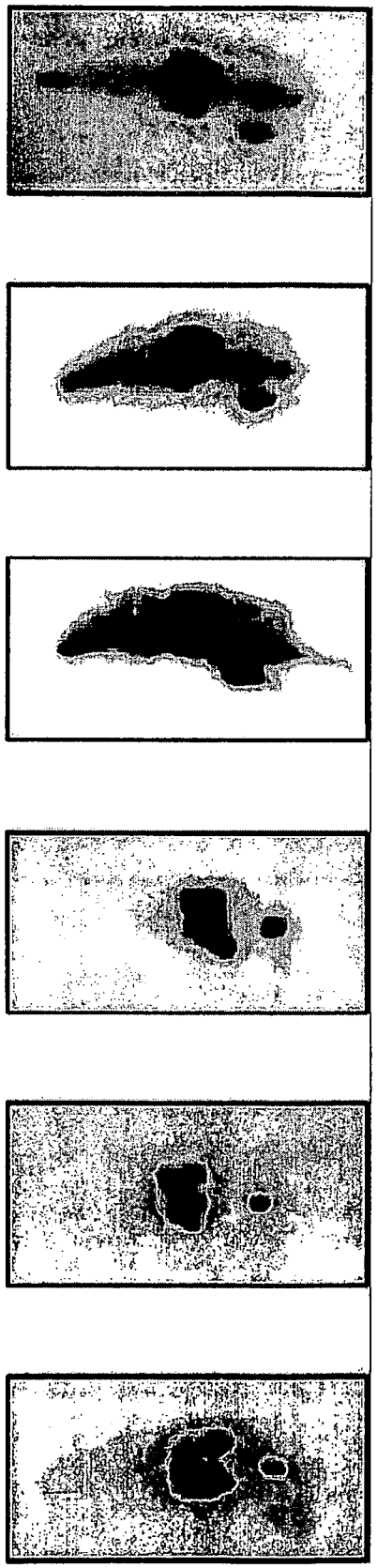
FIG. 81. Planar image of breast tumor-bearing rats after administration of $^{99m}$Tc-EC and $^{99m}$Tc-EC-deoxyglucose (100 µCi/rat, iv.) showed that the tumor could be well visualized from 0.5-4 hours postinjection.
Figure 82B:
FIG. 82B. SPECT with $^{99m}$Tc-EC-DG of a patient with malignant astrocytoma.
Figure 83A:
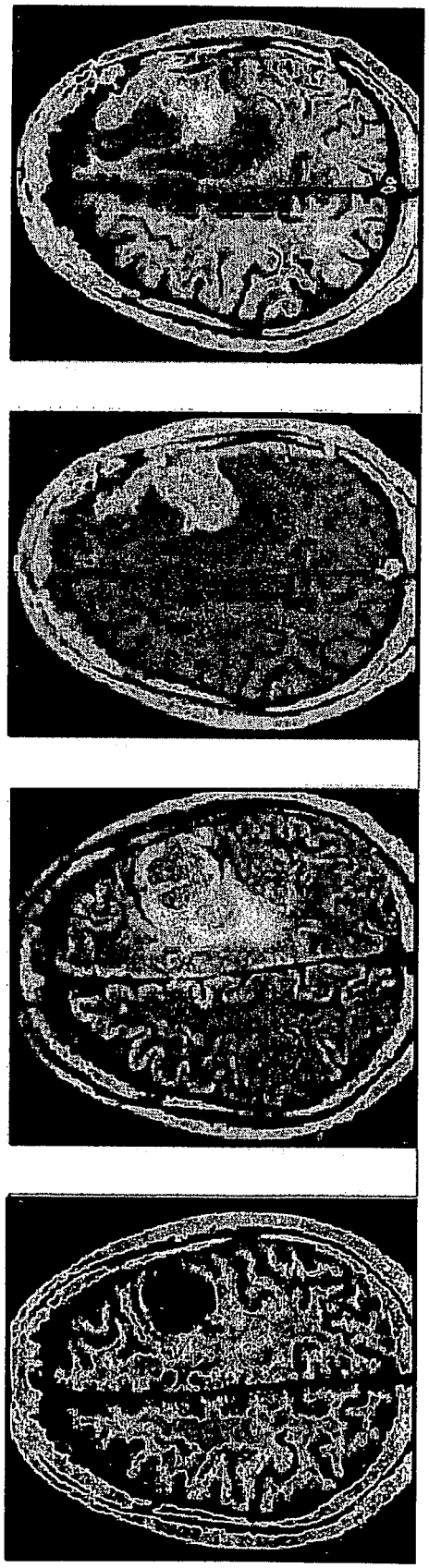
FIG. 83A. MRI of a patient with hemorrhagic astrocytoma.
Figure 83B:
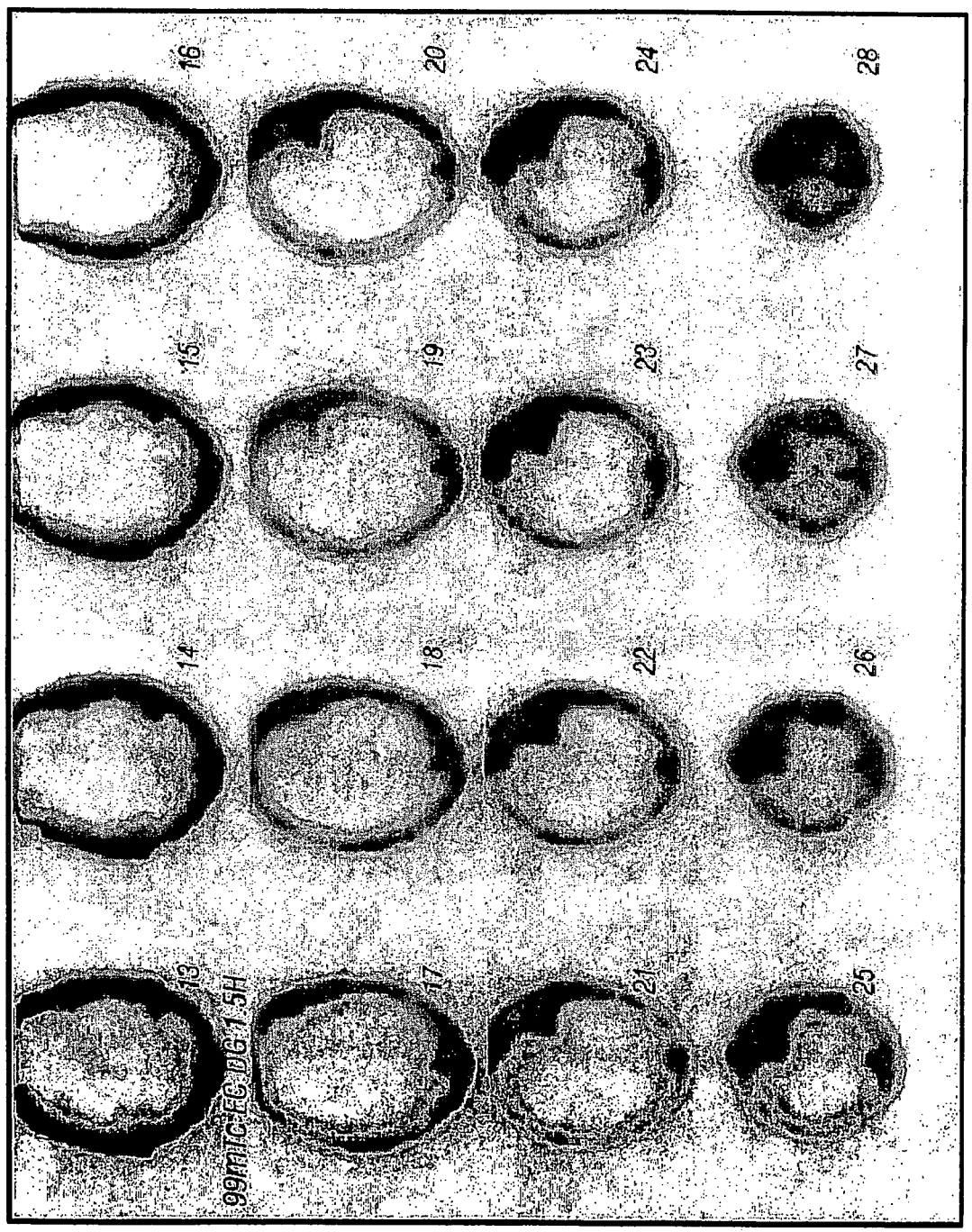
FIG. 83B. SPECT with $^{99m}$Tc-EC-DG of a patient with malignant astrocytoma.
Figure 84A:
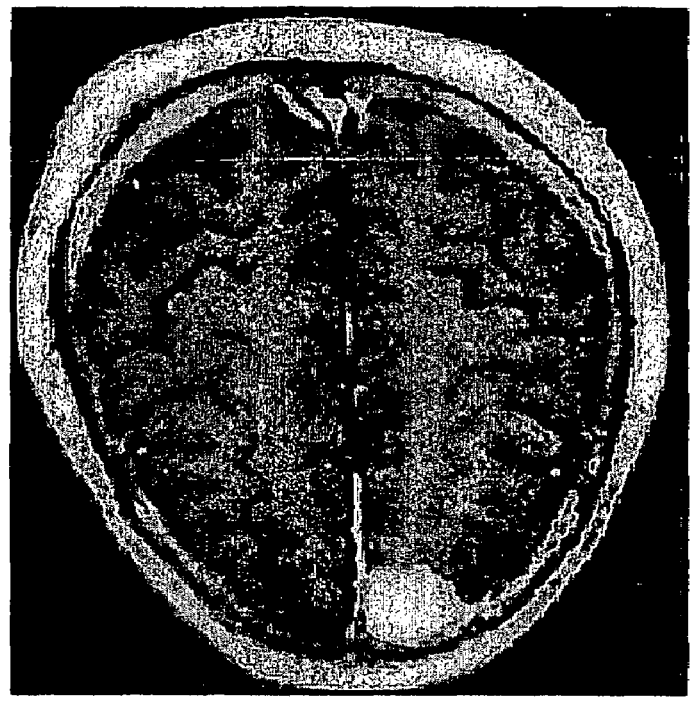
FIG. 84A. MRI of a patient with benign meningioma.
Figure 85A:
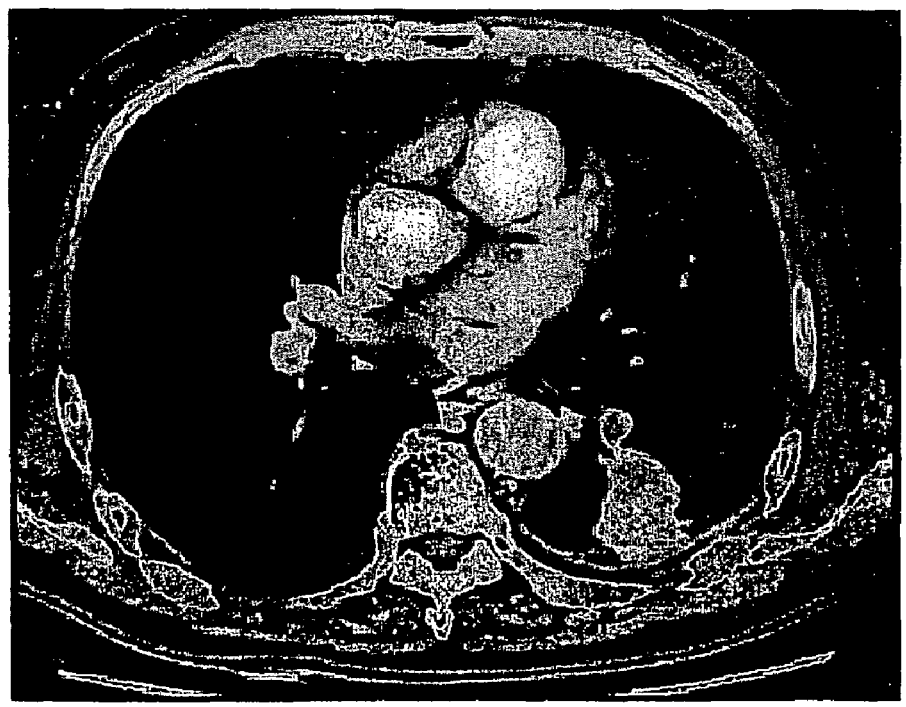
FIG. 85A. CT of a patient with TB in lung.
Figure 84B:
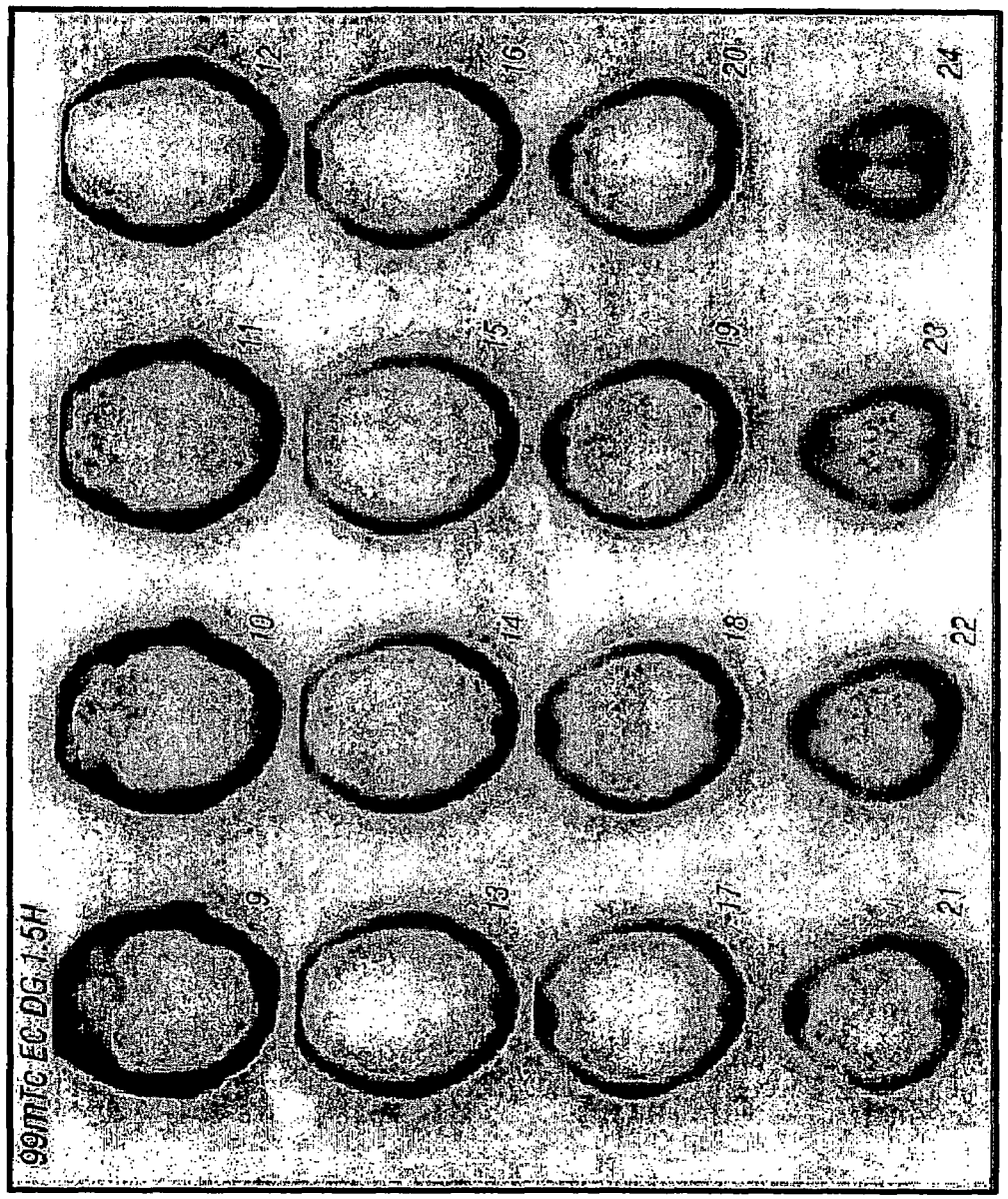
FIG. 84B. SPECT with $^{99m}$Tc-EC-DG of a patient with benign meningioma showed no focal intensed uptake.
Figure 85B:
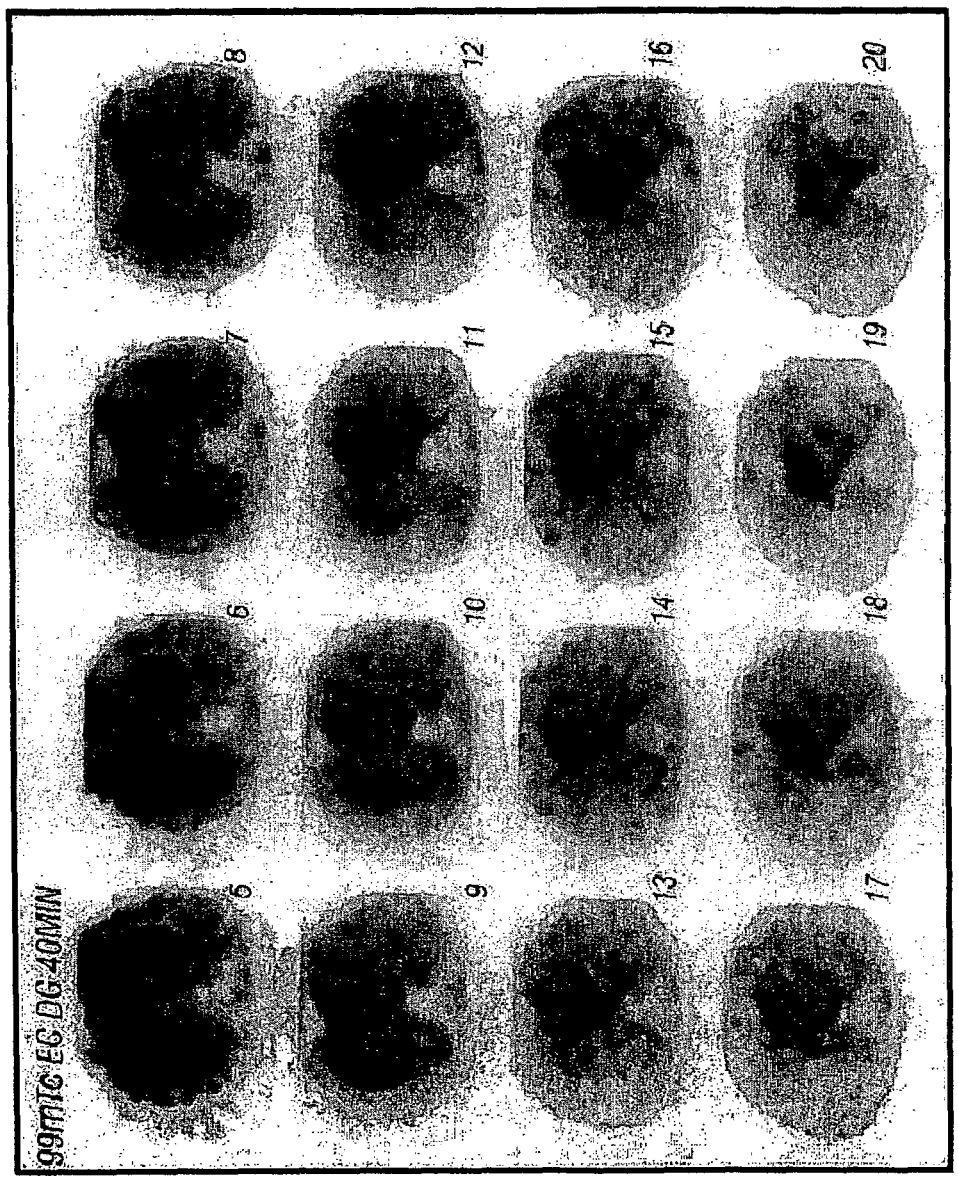
FIG. 85B. SPECT with $^{99m}$Tc-EC-DG of a patient with TB showed no focal intensed uptake.
Figure 86A:
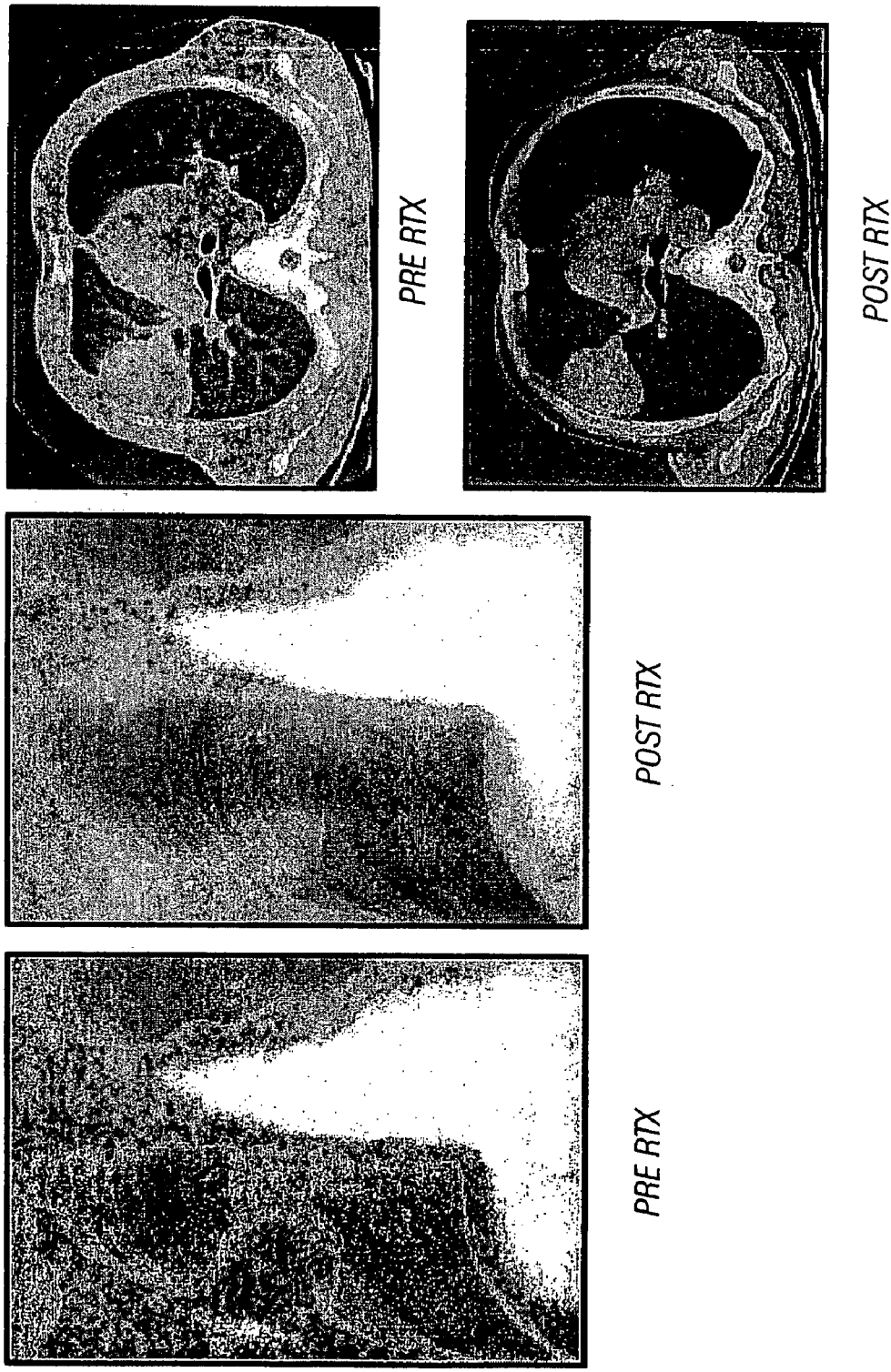
FIG. 86A. CT of patient with lung cancer.
Figure 86B:
FIG. 86B. Whole body images of $^{99m}$Tc-EC-DG of a patient with lung cancer.
Figure 86C:
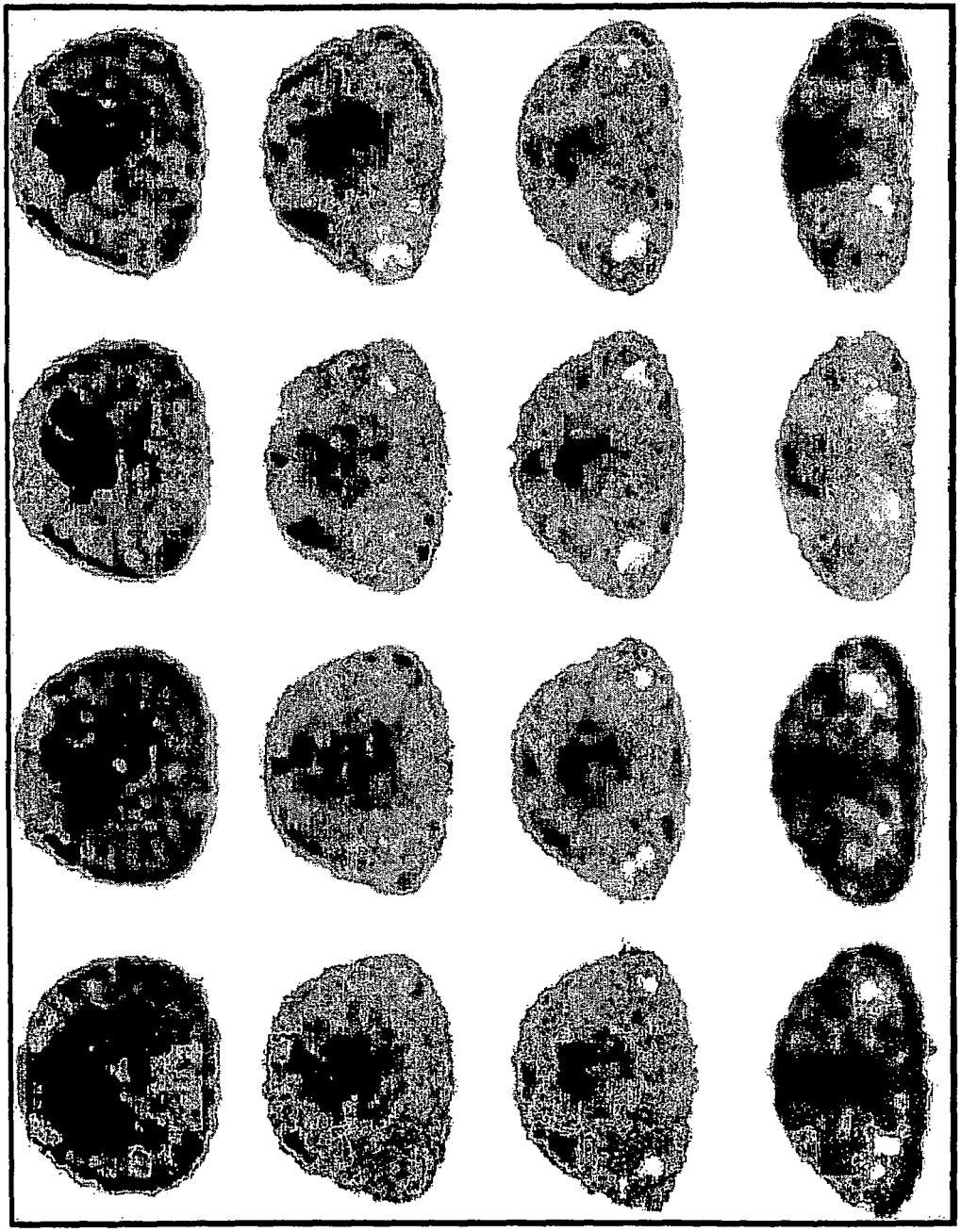
FIG. 86C. SPECT with $^{99m}$Tc-EC-DG of a patient with lung cancer, the tumor showed focal intensed uptake.

Scintigraphic images, using a gamma camera equipped with low-energy, parallel-hole collimator, were obtained 0.5, 2 and 4 hours after i.v. injection of 100 µCi of the radiotracer. The animal model used was breast tumor-bearing rats. Tumor could be visualized well when compared to $^{99m}$Tc-EC (control group) (FIG. 81). Preliminary clinical studies were conducted in 5 patients (3 brain tumors and 2 lung diseases). The images were obtained at 1-2 hours post-administration. $^{99m}$Tc-EC-DG was able to differentiate benign versus malignant tumors. For instance, malignant astrocytoma showed high uptake (FIGS. 82A, 82B, 83A and 83B). Benign meningioma showed poor uptake compared to malignant meningioma (FIGS. 84A and B). Poor uptake was observed in patient with TB (FIG. 85A and FIG. 85B), but high uptake was observed in lung tumor (FIG. 86A, FIG. 86B, and FIG. 86C).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abrams, Juweid, Tenkate, "Technetium-99m-human polyclonal IgG radiolabeled via the hydrazino nicotinamide derivative for imaging focal sites of infection in rats," *J. Nucl. Med.*, 31:2022-2028, 1990.

Bakker, Krenning, Breeman, Kiper, Kooij, Reubi, Klijn, Visser, Docter, Lamberts, "Receptor scintigraphy with a radioiodinated somatostatin analogue: radiolabeling, purification, biologic activity and in vivo application in animals," *J. Nucl. Med.*, 31:1501-1509, 1990.

Blakenberg, Katsikis, Tait et al., "In vivo detection and imaging of phosphatidylserine expression during programmed cell death," *Proc Natl. Acad. Sci USA*, 95:6349-6354, 1998.

Blakenberg, Katsikis, Tait, Davis, Naumovski, Ohtsuki, Kopiwoda, Abrams, Strauss, "Imaging of apoptosis (programmed cell death) with $^{99m}$Tc annexin V.," *J. Nucl. Med.*, 40:184-191, 1999.

Blondeau, Berse, Gravel, "Dimerization of an intermediate during the sodium in liquid ammonia reduction of L-thiazolidine-4-carboxylic acid," *Can J. Chem*, 45:49-52, 1967.

Bolhuis, Lamers, Goey et al., "Adoptive immunotherapy of ovarian carcinoma with Bs-MAb targeted lymphocytes. A multicenter study," *Int J Cancer*, 7:78-81, 1992.

Britton and Granowska, "Imaging of tumors, in tomography in nuclear medicine," *Proceedings of an International Symposium*, Vienna, Austria, IAEA, 91-105, 1996.

Bush, Jenkins, Allt, Beale, Bena, Dembo, Pringle, "Definitive evidence for hypoxic cells influencing cure in cancer therapy," *Br J Cancer*, (Suppl. III) 37:302-306, 1978.

Butterfield, Fuji, Ladd, Snow, Tan, Toner, "Segmented chelating polymers as imaging and therapeutic agents," U.S. Pat. No. 4,730,968, Mar. 24, 1998.

Campbell, Jones, Foulkes, Trowsdale, "Folate-binding protein is a marker for ovarian cancer," *Cancer Res*, 51:5329-5338, 1991.

Canevari, Miotti, Bottero, Valota, Colnaghi, "Ovarian carcinoma therapy with monoclonal antibodies," *Hybridoma*, 12:501-507, 1993.

Cherif, Yang, Tansey, Kim, Wallace, "Synthesis of [$^{18}$F]fluoromisonidazole," *Pharm Res.*, 11:466-469, 1994.

Coenen and Stocklin, "Evaluation of radiohalogenated amino acid analogues as potential tracers for PET and SPECT studies of protein synthesis," *Radioisot Klinik Forschung*, 18:402-440, 1988.

Coney, Mezzanzanica, Sanbom, Casalini, Colnaghi, Zurawski, "Chimeric munne-human antibodies directed against folate binding receptor are eff~cient mediators of ovarian carcinoma cell killing," *Cancer Res*, 54:2448-2455, 1994.

Davison, Jones, Orvig, Sohn, "A new class of oxotechnetium (+5) chelate complexes containing a TcON$_2$S$_2$ Core," *Inorg Chem*, 20:1629-1632, 1980.

Dickinson and Hiltner, "Biodegradation of poly(χ-amino acid) hydrogel. II. In vitro," *J. Biomed Mater Res.*, 15:591, 1981.

Dische, "A review of hypoxic-cell radiosensitizadon," *Int J Radiat Oncol Biol Phys*, 20:147-152, 1991.

Fanciulli, Paggi, Bruno, et al., "Glycolysis and growth rate in normal and in hexokinase-transfected NIH-3T3 cells," *Oncol Res.* 6(9):405-9, 1994.

Franklin, Waintrub, Edwards, Christensen, Prendegrast, Woods, Bunn, Kolhouse, "New anti-lung-cancer antibody cluster 12 reacts with human folate receptors present on adenocarcinoma," *Int J Cancer-Supplement*, 8:89-95, 1994.

Gatenby, Kessler, Rosenblum, Coia, Moldofsky, Hartz, Broder, "Oxygen distribution in squamous cell carcinoma metastases and its relationship to outcome of radiation therapy," *Int J Radiat Oncol Biol Phys*, 14:831-838, 1988.

Ginobbi, Geiser, Ombres, Citro, "Folic acid-polylysine carrier improves efficacy of c-myc antisense oligodeoxynucleotides on human melanoma (M14) cells," *Anticancer Res*, 17:29-35, 1997a.

Goh, Pricher, Lobie, "Growth hormone promotion of tublin polymerization stablizes the microtubule network and protects against colchicine-induced apoptosis," *Endocrinology*, 139:4364-4372, 1998.

Goldsmith, "Receptor imaging: Competitive or complementary to antibody imaging," *Sem Nucl Med.*, 27:85-93, 1997.

Goldsmith, Macapinlac, O'Brien, "Somatostatin receptor imaging in lymphoma," *Sem Nucl Med*, 25:262-271, 1995.

Gray, Conger, Elbert, Morsney, Scold, "The concentration of oxygen dissolved in tissues at the time of irradiation as a factor in radiotherapy," *Br J Radiol*, 26:638-648, 1953.

Hall, "The oxygen effect and reoxygenation," In: E. J. Hall (ed.) Radiobiology for the radiobiologist, 3rd edition J. B. Lippincott Co., Philadelphia, Pa., 137-160, 1988.

Harada, Smith, Smith et al., "Insulin-induced egr-1 and c-fos expression in 32D cells requires insulin receptor, Shc, and mitogen-activated protein kinase, but not insulin receptor substrate-1 and phosphatidylinositol 3-kinase activation," *J. Biol. Chem.* 271(47):30222-6, 1996.

Hay, Wilson, Moselen, Palmer, Denny, "Hypoxia-selective antitumor agents. Bis(nitroimidazolyl)alkanecarboxamides: a new class of hypoxia-selective cytotoxins and hypoxic cell radiosensitizers," *J Med. Chem.*, 37:381-391, 1994.

Hermann, Patel. "Adaptive recognition by nucleic acid aptamers," *Science,* 287(5454):820-5, 2000.

Holm, Hansen, Hoier-Madsen, Sondergaard, Bzorek, "Folate receptor of human mammary adenocarcinoma," *APMIS,* 102:413-419, 1994.

Hsuch and Dolnick, "Altered folate-binding protein mRNA stability in KB cells grown in folate-deficient medium," *Biochem Pharmacol,* 45:2537-2545, 1993.

Imbert, "Discovery of podophyllotoxins," *Biochimie,* 80:207-222, 1998.

Jamar, Stoffel, Van Nerom, et al., "Clinical evaluation of Tc-99m L,L-ethylenedicysteine, a new renal tracer, in transplanted patients," *J Nucl Med,* 34: 129P, 1993a.

Jamar, Van Nerom, Verbruggen, et al., "Clearance of the new tubular agent Tc-99m L,L-ethylenedicysteine: Estimation by a simplified method," *J Nucl Med,* 34:129P, 1993b.

Kabasakal. "Technetium-99m ethylene dicysteine: a new renal tubular function agent," *Eur. J Nucl. Med.* 27(3):351-7, 2000.

Kikukawa, Toyama, Katayama, et al., "Early and delayed Tc-99m ECD brain SPECT in SLE patients with CNS involvement," *Ann Nucl Med.* 14(1):25-32, 2000.

Koh, Rasey, Evans, Grierson, Lewellen, Graham, Krohn, Griffin, "Imaging of hypoxia in human tumors with [$^{18}$F] fluoromisonidazole," *Int J Radiat Oncol Biol Phys,* 22:199-212, 1992.

Kranz, Patrick, Brigle, Spinella, Roy, "Conjugates of folate and anti-T-cell-receptor antibodies specifically target folate-receptor-positive tumor cells for lysis," *Proc Natl Acad Sci,* 92:9057-9061, 1995.

Krenning, Kwokkeboom, Bakker, et al., "Somatostatin receptor scintigraphy with [In-111-DTPA-D-Phe] and [I-123-Tyr]-octretide: The Rotterdam experience with more than 1000 patients," *Eur J Nucl Med,* 7:716-731, 1995.

Lambert, Bakker, Reubi, Krenning, "Somatostatin receptor imaging in vivo localization of tumors with a radiolabeled somatostatin analog," *J. Steoid Biochem Mol Biol,* 37:1079-1082, 1990.

Leamon and Low, "Cytotoxicity of momordin-folate conjugates in cultured human cells," *J Biol Chem,* 267:24966-24971, 1992.

Leamon and Low, "Delivery of macromolecules into living cells: a method that exploits folate receptor endocytosis," *Proc Natl Acad Sci,* 88:5572-5576, 1991.

Leamon, Pastan, Low, "Cytotoxicity of folate-pseudomonas exotoxin conjugates toward tumor cells," *J Biol Chem,* 268:24847-24854, 1993.

Lee and Low, "Delivery of liposomes into cultured KB cells via folate receptor-mediated endocytosis," *J Biol Chem,* 269:3198-3204, 1994.

Lennon, Martin, Cotter. "Dose-dependent induction of apoptosis in human tumor cell lines by widely diverging stimuli," *Cell Prolif,* 24:203-214, 1991.

Lu, "Antimitotic agents," In: Foye, WO. Ed., "Cancer chemotherapeutic agents," Washington, D.C.: American Chemical Society, 345-368, 1995.

Martin, Caldwell, Rasey, Grunbaum, Cerqueia, Krohn, Enhanced binding of the hypoxic cell marker [$^{18}$F]fluoromisonidazole in ischemic myocardium," *J Nucl Med,* 30:194-201, 1989.

Mathias, Hubers, Trump, Wang, Luo, Waters, Fuchs, Low, Green, "Synthesis of Tc-99m-DTPA-folate and preliminary evaluation as a folate-receptor-targeted radiopharmaceutical (Abstract)," *J Nucl Med,* (Supplement); 38:87P, 1997a.

Mathias, Wang, Waters, Turek, Low, Green, "Indium-111-DTPA-folate as a radiopharmaceutical for targeting tumor-associated folate binding protein (Abstract)," *J Nucl Med,* (Supplement) 38:133P, 1997b.

Mathias, Wang, Lee, Waters, Low, Green, "Tumor-selective radiopharmaceudcal targeting via receptor-mediated endocytosis of Gallium-67-deferoxamine-folate," *J Nucl Med,* 37:1003-1008, 1996.

Moller, Benecke, Flier. "Biologic activities of naturally occurring human insulin receptor mutations. Evidence that metabolic effects of insulin can be mediated by a kinase-deficient insulin receptor mutant," *J Biol Chem.* 15;266 (17): 10995-1001, 1991.

Mochizuki, Inaki, Takeymoto, "Synthesis of polyglutamates containing 5-substituted uracil moieties," *Nucleic Acids Res.,* 16:121-124, 1985.

Nordsmark, Overgaard, Overgaard, "Pretreatment oxygenation predicts radiation response in advanced squamous cell carcinoma of the head and neck," *Radiother Oncol,* 41:31-39, 1996.

Offield, Jetton, Labosky, et al., "PDX-1 is required for pancreatic outgrowth and differentiation of the rostral duodenum," *Development.* 122(3):983-95, 1996.

Orr, Kreisler, Kamen, "Similarity of folate receptor expression in UMSCC 38 cells to squamous cell carcinoma differentiation markers," *J Natl Cancer Inst,* 87:299-303, 1995.

Patrick, Kranz, van Dyke, Roy, "Folate receptors as potendal therapeutic targets in choroid plexus tumors of SV40 transgenic mice," *J Neurooncol,* 32:111-123, 1997.

Piper, McCaleb, Montgomery, "A synthetic approach to poly (glutamyl) conjugates of methotrexate," *J. Med. Chem.,* 26:291-294, 1983.

Popovici, Mungiu, Trandafirescu, et al., "The influence of some antibiotics on hexokinase and pyruvate-kinase activity in the rat liver and kidney," *Arch Int Pharmacodyn Ther.* 193(1):80-6, 1971.

Raderer, Becherer, Kurtaran, Angelberger, Li, Leimer, Weinlaender, Komek, Kletter, Scheithauer, Virgolini, "Comparison of Iodine-123-vasoactive intestinal peptide receptor scintigraphy and Indium-111 CFT-102 immunoscintigraphy," *J. Nucl. Med.,* 37:1480-1487, 1996.

Raffauf, Farren, Ullyot, "Colchicine. Derivatives of trimethylcolchicinic acid," *J. Am Chem Soc,* 75:5292-5294, 1953.

Rasey, Koh, Griesohn, Grunbaum, Krohn, "Radiolabeled fluoromisonidazole as an imaging agent for tumor hypoxia," *Int. J. Radiat Oncol. Biol Phys,* 17:985-991, 1989.

Rasey, Nelson, Chin, Evans, Grunbaum, "Characterization of the binding of labeled fluoromisonidazole in cells in vitro," *Radiat Res,* 122:301-308, 1990.

Ratner and Clarke, "The action of formaldehyde upon cysteine," *J. Am Chem. Soc.,* 59:200-206, 1937.

Reubi, Krenning, Lamberts et al., "In vitro detection of somatostatin receptors in human tumors," *Metabolism,* 41:104-110 (suppl 2), 1992.

Rogers, Bachorik, Nunn. "Neomycin effects on glucose transport by rat small intestine," *Digestion.* 1(3):159-64, 1968.

Ross, Chaudhuri, Ratnam, "Differential regulation of folate receptor isoforms in normal and malignant tissue in vivo and in established cell lines," *Cancer,* 73:2432-2443, 1994.

Rowinsky, Cazenave, Donehower, "Taxol: a novel investigational antimicrotuble agent," *J. Natl. Cancer Institute,* 82(15):1247-1259, 1990.

Seabold, Gurll, Schurrer, Aktay, Kirchner, "Comparison of $^{99m}$Tc-Methoxyisobutyl Isonitrile and $^{201}$Tl Scintigraphy for Detection of Residual Thyroid Cancer After $^{131}$I Ablative Therapy," *J. Nucl. Med.,* 40(9):1434-1440, 1999.

Shankar, Zhu, Baron et al., "Glucosamine infusion in rats mimics the beta-cell dysfunction of non-insulin-dependent diabetes mellitus," *Metabolism.* 47(5):573-7, 1998.

Stella and Mathew, "Derivatives of taxol, pharmaceutical compositions thereof and methods for preparation thereof," U.S. Pat. No. 4,960,790, Oct. 2, 1990.

Surma, Wiewiora, Liniecki, "Usefulness of Tc-99m-N,N'-ethylene-1-dicysteine complex for dynamic kidney investigations," *Nucl Med Comm,* 15:628-635, 1994.

Tait and Smith, "Site-specific mutagenesis of annexin V: role of residues from Arg-200 to Lys-207 in phospholipid binding," *Arch Biochem Biophys,* 288:141-144, 1991.

Valk, Mathis, Prados, Gilbert, Budinger, "Hypoxia in human gliomas: Demonstration by PET with [$^{18}$F]fluoromisonidazole," *J Nucl Med,* 33:2133-2137, 1992.

Van Nerom, Bormans, Bauwens, Vandecruys, De Roo, Verbruggen, "Comparative evaluation of Tc-99m L,L-ethylenedicysteine and Tc-99m MAG3 in volunteers," *Eur J Nucl Med,* 16:417, 1990.

Van Nerom, Bormans, De Roo, et al., "First experience in healthy volunteers with Tc-99m-L,L-ethylenedicysteine, a new renal imaging agent," *Eur J Nucl Med,* 20:738-746, 1993.

Verbruggen, Nosco, Van Nerom et al., "Tc-99m-L,L-ethylenedicysteine: A renal imaging agent. I. Labelling and evaluation in animals," *J Nucl Med,* 33:551-557, 1992.

Verbruggen, Nosco, Van Nerom, Bormans, Adriaens, De Roo, "Evaluation of Tc-99m-L,L-ethylenedicysteine as a potential alternative to Tc-99m MAG3," *Eur J Nucl Med,* 16:429, 1990.

Villevalois-Cam, Tahiri, Chauvet, et al., "Insulin-induced redistribution of the insulin-like growth factor II/mannose 6-phosphate receptor in intact rat liver," *J Cell Biochem.* 77(2):310-22, 2000

Virgolini, Raderer, Kurtaran, "Vasoactive intestinal peptide (VIP) receptor imaging in the localization of intestinal adenocarcinomas and endocrine tumors," *N Eng J Med,* 331:1116-1121, 1994.

Wang, Lee, Mathias, Green, Low, "Synthesis, purification, and tumor cell uptake of Ga-67 deferoxamine-folate, a potential radiopharmaceutical for tumor imaging," *Bioconjugate Chem,* 7:56-62, 1996.

Wang, Luo, Lantrip, Waters, Mathias, Green, Fuchs, Low, "Design and synthesis of [$^{111}$In]DTPA-folate for use as a tumor-targeted radiopharmaceutical," *Bioconjugate Chem,* 8:673-679, 1997.

Wang, Wang, Ichijo, Giannakakou, Foster, Fojo, Wimalasena, "Microtubule-interfering agents activate c-Jun N-terminal kinasae/stress-activated protein kinase through both Ras and apoptosis signal-regulating kinase pathways," *J. Biol. Chem.,* 273:4928-4936, 1998.

Weitman, Frazier, Kamen, "The folate receptor in central nervous system malignancies of childhood," *J Neuro-Oncology,* 21:107-112, 1994.

Weitman, Lark, Coney et al., "Distribution of folate GP38 in normal and malignant cell lines and tissues," *Cancer Res,* 52:3396-3400, 1992a.

Weitman, Weinberg, Coney, Zurawski, Jennings, Kamen, "Cellular localization of the folate receptor: potential role in drug toxicity and folate homeostasis," *Cancer Res,* 52:6708-6711, 1992b.

Wester, Herz, Weber, Heiss, Schmidtke, Schwaiger, Stocklin, "Synthesis and radiopharmacology of —O(2-[$^{18}$F]fluoroethyl)-L-Tyrosine for tumor imaging," *J. Nucl. Med.,* 40:205-212, 1999.

Westerhof, Jansen, Emmerik, Kathmann, Rijksen, Jackman, Schomagel, "Membrane transport of natural folates and antifolate compounds in murine L1210 leukemia cells: Role of carrier- and receptor-mediated transport systems," *Cancer Res,* 51:5507-5513, 1991.

Yang, Wallace, Cherif, Li, Gretzer, Kim, Podoloff, "Development of F-18-labeled fluoroerythronitroimidazole as a PET agent for imaging tumor hypoxia," *Radiology,* 194: 795-800, 1995.

Yoshino, Takeda, Sugimoto, et al., "Differential effects of troglitazone and D-chiroinositol on glucosamine-induced insulin resistance in vivo in rats," *Metabolism.* 48(11): 1418-23, 1999.

What is claimed is:

1. A reagent for preparing a scintigraphic imaging agent comprising a targeting ligand covalently linked to ethylenedicysteine (EC), wherein the targeting ligand is an anticancer agent that is methotrexate, doxorubicin, tamoxifen, paclitaxel, topotecan, LHRH, mitomycin C, etoposide tomudex, podophyllotoxin, mitoxantrone, camptothecin, colchicine, endostatin, fludarabin, gemcitabine, or tomudex; an agent that mimics glucose; a folate receptor targeting ligand; or a tumor apoptotic cell targeting ligand or a tumor hypoxia targeting ligand that is annexin V, colchicine, nitroimidazole, mitomycin, or metronidazole.

2. The reagent of claim 1, wherein the targeting ligand is an agent that mimics glucose.

3. The reagent of claim 1, further comprising a linker between said targeting ligand and said ethylenedicysteine (EC).

4. A kit comprising one or more sealed containers, and a predetermined quantity of an ethylenedicysteine (EC)-targeting ligand conjugate composition in one or more of the sealed containers, wherein the targeting ligand is an anticancer agent that is methotrexate, doxorubicin, tamoxifen, paclitaxel, topotecan, LHRH, mitomycin C, etoposide tomudex, podophyllotoxin, mitoxantrone, camptothecin, colchicine, endostatin, fludarabin, gemcitabine, or tomudex; an agent that mimics glucose; a folate receptor targeting ligand; a DNA topoisomerase inhibitor; a tumor apoptotic cell targeting ligand or a tumor hypoxia targeting ligand that is annexin V, colchicine, nitroimidazole, mitomycin, or metronidazole; or glutamate pentapeptide.

5. The kit of claim 4, wherein the kit further comprises a reducing agent.

6. The kit of claim 4, wherein the targeting ligand is paclitaxel.

7. The kit of claim 4, wherein the composition further comprises a linker between said ethylenedicysteine (EC) and said targeting ligand.

8. The kit of claim 5, further defined as comprising a sealed containing comprising a reducing agent.

9. The kit of claim 8, wherein the ethylenedicysteine (EC)-targeting ligand conjugate composition and the reducing agent are comprised together in a sealed container.

10. The kit of claim 7, further defined as comprising a sealed containing comprising a linker.

11. The kit of claim 8, wherein the kit comprises a first sealed containing comprising the ethylenedicysteine (EC)-targeting ligand conjugate composition and a second sealed containing comprising a reducing agent.

12. The kit of claim 4, wherein one or more of the sealed containers is further defined as a bag.

13. The kit of claim 5, wherein the reducing agent is a dithionite ion, a stannous ion or a ferrous ion.

14. The kit of claim 4, wherein the targeting ligand is an anticancer agent that is methotrexate, doxorubicin, tamoxifen, paclitaxel, topotecan, LHRH, mitomycin C, etoposide tomudex, podophyllotoxin, mitoxantrone, camptothecin, colchicine, endostatin, fludarabin, gemcitabine, or tomudex.

15. The kit of claim 14, wherein the anticancer agent is methotrexate.

16. The kit of claim 2, wherein the agent that mimics glucose is deoxyglucose.

17. The kit of claim 2, wherein the agent that mimics glucose is glucosamine.

18. The kit of claim 4, wherein the targeting ligand is a DNA topoisomerase inhibitor.

19. The kit of claim 4, wherein the folate receptor targeting ligand is folate.

20. The kit of claim 4, wherein the folate receptor targeting ligand is tomudex.

21. The kit of claim 4, wherein the targeting ligand is a tumor apoptotic cell targeting ligand or a tumor hypoxia targeting ligand that is annexin V, colchicine, nitroimidazole, mitomycin, or metronidazole.

22. The kit of claim 21, wherein the targeting ligand is nitroimidazole.

23. The kit of claim 4, wherein the components of the kit are in a liquid form, frozen form, or dry form.

24. The kit of claim 4, wherein the components of the kit are in a lyophilized form.

25. The kit of claim 7, wherein the linker is a water soluble peptide, glutamic acid, polyglutamic acid, aspartic acid, polyaspartic acid, bromoethylacetate, ethylenediamine or lysine.

26. The kit of claim 4, wherein the kit further comprises one or more pharmaceutical adjunct materials.

27. The kit of claim 26, wherein the one or more pharmaceutical adjunct materials are selected from the group consisting of a pharmaceutically acceptable salt, a buffer, a preservative, and antioxidant, and a scavenger.

28. The kit of claim 27, wherein the kit comprises an antioxidant.

29. A kit comprising one or more sealed containers, a predetermined quantity of an ethylenedicysteine (EC)-targeting ligand conjugate composition in one or more sealed containers, and vitamin C.

30. The kit of claim 27, wherein the kit comprises a scavenger.

31. The kit of claim 30, wherein the scavenger is glucoheptonate or EDTA.

32. The kit of claim 4, wherein the kit is a home-made kit.

33. A kit comprising one or more sealed containers, a predetermined quantity of ethylenedicysteine (EC)-targeting ligand conjugate composition in one or more sealed containers, $SnCl_2$, $Na_2IPO_4$, ascorbic acid, and NaEDTA.

34. The kit of claim 33, wherein the kit comprises lyophilized EC (3 mg), $SnCl_2$ (100 µg), $Na_2IPO_4$ (13.5 mg), ascorbic acid (0.5 mg) and NaEDTA (0.5 mg) at pH 10.

35. A kit comprising one or more sealed containers, a predetermined quantity of ethylenedicysteine (EC)-folate in one or more sealed containers, $SnCl_2$, $Na_2IPO_4$, ascorbic acid, and NaEDTA.

36. The kit of claim 35, wherein the kit comprises lyophilized residue of EC-folate (3 mg), $SnCl_2$ (100 µg), $Na_2IPO_4$ (13.5 mg), ascorbic acid (0.5 mg), and NaEDTA (0.5 mg).

37. A kit comprising one or more sealed containers, a predetermined quantity of ethylenedicysteine (EC)-MN or EC-NIM, $SnCl_2$, $Na_2IPO_4$, ascorbic acid, and NaEDTA.

38. The kit of claim 37, wherein the kit comprises lyophilized residue of EC-MN or EC-NIM (3 mg), $SnCl_2$ (100 µg), $Na_2IPO_4$ (13.5 mg), ascorbic acid (0.5 mg), and NaEDTA (0.5 mg).

* * * * *